US009688668B2

(12) United States Patent
Santos et al.

(10) Patent No.: US 9,688,668 B2
(45) Date of Patent: Jun. 27, 2017

(54) LONG CHAIN BASE SPHINGOSINE KINASE INHIBITORS

(71) Applicant: UNIVERSITY OF VIRGINIA PATENT FOUNDATION, Charlottesville, VA (US)

(72) Inventors: Webster L. Santos, Blacksburg, VA (US); Kevin R. Lynch, Charlottesville, VA (US); Timothy L. Macdonald, Charlottesville, VA (US); Andrew Kennedy, Charlottesville, VA (US); Yugesh Kharel, Charlottesville, VA (US); Mithun Rajendra Raje, Baltimore, MD (US); Joseph Houck, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 4 days.

(21) Appl. No.: 14/377,300

(22) PCT Filed: Feb. 8, 2013

(86) PCT No.: PCT/US2013/025341
§ 371 (c)(1),
(2) Date: Aug. 7, 2014

(87) PCT Pub. No.: WO2013/119946
PCT Pub. Date: Aug. 15, 2013

(65) Prior Publication Data
US 2015/0210675 A1 Jul. 30, 2015

Related U.S. Application Data

(60) Provisional application No. 61/596,718, filed on Feb. 8, 2012, provisional application No. 61/639,525, filed on Apr. 27, 2012.

(51) Int. Cl.
C07D 413/04 (2006.01)
C07D 413/06 (2006.01)
C07C 257/14 (2006.01)
C07C 257/16 (2006.01)
C07C 275/70 (2006.01)
C07C 279/16 (2006.01)
C07C 279/18 (2006.01)
C07C 281/16 (2006.01)
C07C 251/02 (2006.01)
C07C 251/12 (2006.01)
C07C 271/20 (2006.01)
C07C 279/00 (2006.01)
C07D 249/08 (2006.01)
C07D 263/32 (2006.01)
C07D 271/06 (2006.01)
C07D 271/10 (2006.01)

(52) U.S. Cl.
CPC ......... *C07D 413/04* (2013.01); *C07D 413/06* (2013.01); *C07C 251/02* (2013.01); *C07C 251/12* (2013.01); *C07C 257/14* (2013.01); *C07C 257/16* (2013.01); *C07C 271/20* (2013.01); *C07C 275/70* (2013.01); *C07C 279/00* (2013.01); *C07C 279/16* (2013.01); *C07C 279/18* (2013.01); *C07C 281/16* (2013.01); *C07C 2101/02* (2013.01); *C07C 2101/14* (2013.01); *C07D 249/08* (2013.01); *C07D 263/32* (2013.01); *C07D 271/06* (2013.01); *C07D 271/10* (2013.01)

(58) Field of Classification Search
CPC ........................... C07D 413/04; C07D 413/06
See application file for complete search history.

(56) References Cited

U.S. PATENT DOCUMENTS

| 3,228,975 A | 1/1966 | Gelblum et al. |
| 3,896,125 A * | 7/1975 | Helmo ................. C07D 265/22 544/211 |
| 4,762,949 A | 8/1988 | Rinehart, Jr. et al. |
| 8,686,046 B2 * | 4/2014 | Lynch ................. C07D 409/04 514/617 |
| 2002/0052409 A1 * | 5/2002 | Ghosh ................. A61K 31/155 514/523 |
| 2006/0134056 A1 | 6/2006 | Fotsch et al. |
| 2009/0069288 A1 | 3/2009 | Breinlinger et al. |

FOREIGN PATENT DOCUMENTS

| DE | 506282 C | 9/1930 |
| EP | 2822548 A1 | 1/2015 |
| HK | 1205943 A1 | 12/2015 |
| WO | WO-9511014 A1 | 4/1995 |
| WO | WO 2009146112 A1 * | 12/2009 |
| WO | 2010/078247 A1 | 7/2010 |
| WO | 2011/020116 A1 | 2/2011 |
| WO | WO 2011020116 A1 * | 2/2011 |

(Continued)

OTHER PUBLICATIONS

Beaumont et al. Mol. Cell. Neurosci. 2007, 35, 513-524.*
CAS Registry No. 149654-96-6, which entered STN on Aug. 31, 1993.*
Kharel et al. Biochem. J. 2012, 447, 149-157.*
"European Application Serial No. 13820704.8, Extended European Search Report mailed Oct. 20, 2015", 11 pgs.
"European Application Serial No. 13820704.8, Office Action mailed Nov. 27, 2014", 3 pgs.
Bream, John B., et al., "Aralkylarninoguanidines and related compounds", Journal of Medicinal Chemistry, 13(6), (1970), 1051-1057.

(Continued)

Primary Examiner — Matthew Coughlin
(74) Attorney, Agent, or Firm — Schwegman Lundberg & Woessner, P.A.

(57) ABSTRACT

The invention relates to inhibitors of Sphingosine Kinase enzymatic activity, and methods of treating diseases and disorders by administering inhibitors of Sphingosine Kinase enzymatic activity.

6 Claims, 8 Drawing Sheets

(56) References Cited

FOREIGN PATENT DOCUMENTS

| WO | WO-2013119946 A1 | 8/2013 |
|---|---|---|
| WO | WO-2013119946 A8 | 8/2013 |

OTHER PUBLICATIONS

De Meglio, P G, "Amidoximes, guanidines, and imidazolines derived from 4-phenylpiperdine and 4-phenylcyclohexylamine with potential hypotensive activity", Farmaco, Edizone Scientifica, 25(12), (1970), 922-923.

Kharel, Yugesh, et al., "Sphingosine kinase type 2 inhibition elevates circulating sphingosine 1-phosphate", Biochemical Journal, 447, (2012), 149-157.

Kim, Keekyung, et al., "Monosubstituted guanidines from primary amines and aminoiminomethanesulfonie acid", Tetrahedron Letters, 29(26), (1988), 3183-3186.

Short, James H., et al., "Sympathetic nervous system blocking agents. V. Derivatives of isobutyl-, tert-butyl-, and neopentylguanidine", Journal of Medicinal Chemistry, 11(6), (Nov. 1968), 1129-1135.

International Search Report and Written Opinion in PCT Application No. PCT/US2013/025341 dated Apr. 24, 2013.

International Preliminary Report on Patentability in PCT Application No. PCT/US2013/025341 dated Aug. 21, 2014.

Foss, Jr. et al.: "Synthesis and Biological Evaluation of Sphingosine Kinase Substrates as Sphingosine-1-Phosphate Prodrugs," Bioorg Med Chem., vol. 17, No. 16, pp. 6123-6136, Aug. 15, 2009.

Lai et al.: "Distinct Roles of Sphingosine Kinase 1 and 2 in Murine Collagen-Induced Arthritis," J. Immunol., vol. 183, 2097-2103, Jul. 13, 2009.

"U.S. Appl. No. 14/377,300 Supplemental Preliminary Amendment Filed Mar. 30, 2016", 3 pgs.

"European Application Serial No. 13820704.8, Response filed Apr. 20, 2016 to Extended European Search Report mailed Oct. 20, 2014", 5 pgs.

\* cited by examiner

LONG CHAIN BASE SPHINGOSINE KINASE INHIBITORS

GOVERNMENT RIGHTS

This invention was made with government support under GM067958 awarded by the National Institute of Health. The government has certain rights in the invention.

FIELD OF THE INVENTION

The invention relates to inhibitors of Sphingosine Kinase enzymatic activity, and methods of treating diseases and disorders by administering inhibitors of Sphingosine Kinase enzymatic activity.

BACKGROUND

Sphingosine 1-phosphate (S1P) is a lysophospholipid mediator that evokes a variety of cellular processes, including those that result in cell proliferation, cell morphology, tumor-cell invasion, endothelial cell chemotaxis, and angiogenesis. S1P mediates its effects on cellular behavior through the S1P receptors, a family of five cell surface G protein coupled receptors called S1P(1), S1P(2), S1P(3), S1P(4), and S1P(5), which were formerly known as EDG-1, -3, -5, -6, and -8, respectively. In addition to the S1P receptors, S1P also activates various less well-defined intracellular targets. The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. Ultimately, this S1P-driven signaling results in cell survival, increased cell migration and, often, mitogenesis. The recent development of agonists targeting S1P receptors has provided insight regarding the role of this signaling system in physiologic homeostasis.

S1P is synthesized by the action of two enzymes, sphingosine kinase types 1 and 2 (SphK1, SphK2). These enzymes catalyze the transfer of a phosphate residue from adenosine triphosphate (ATP) to D-erythro sphingosine. SphK1 and SphK2 also catalyze the phosphorylation of reduced sphingosine (D-erythro sphinganine) and hydroxylated sphinganine (D-ribo phytosphingosine) to yield sphinganine 1-phosphate (dihydroS1P) and phytosphingosine 1-phosphate.

One example of a non-S1P agonist is the phosphorylated form of the immunomodulator, fingolimod (2-amino-2-[2-(4-octylphenyl)ethyl]propane 1,3-diol), which is an agonist of four of the five S1P receptors. Enhancing S1P tone at S1P(1) influences lymphocyte trafficking by decreasing lymphocyte egress from secondary lymphoid tissues. Consistent with the role of S1P(1) agonists in preventing lymphocyte egress from the vasculature, antagonists of some S1P(1) receptors cause leakage of the lung capillary endothelium, which suggests that S1P may be involved in maintaining the integrity of the endothelial barrier in some tissue beds.

Indeed, infection and tissue injury induce a cascade of biochemical changes that trigger reactions of the immune system, collectively referred to as an inflammatory response. The evolution of this response is based, at least in part, on enhancing vascular permeability and activation of the vascular endothelium, which allows white blood cells to efficiently circulate and migrate to the damaged site, thereby increasing their chances to bind to and destroy any antigens. The vascular endothelium is then thought to be activated or inflamed. Generally, inflammation is a welcomed immune response to a variety of unexpected stimuli, and as such it exhibits rapid onset and short duration (acute inflammation). Its persistent or uncontrolled activity (chronic inflammation) has, however, detrimental effects to the body and results in the pathogenesis of several immune diseases, such as: septic shock, rheumatoid arthritis, inflammatory bowel diseases, acute lung injury, pulmonary fibrosis, and congestive heart failure, for example: Furthermore, chronic inflammation resulting from persistent tissue injury can lead to organ fibrosis, and eventually, organ failure, as is the case in idiopathic pulmonary fibrosis, end-stage renal failure, and liver cirrhosis, for example.

During vascular injury and in inflammation thrombin is also released from the blood, and it activates thrombin receptors (PARs) expressed on endothelial surface. Thrombin and thrombin receptors regulate various endothelial functions and play a role in the response of endothelial cells to vascular injury, including inducing cytoskeletal changes resulting in cell rounding. Contraction of endothelial cells leads to increased permeability and compromises in the endothelial barrier. In contrast to the edemagenic effects of thrombin, S1P may enhance endothelial cell barrier properties.

S1P has also been shown to have a direct role in modulating several important effects on cells that mediate immune functions. Platelets, monocytes and mast cells secrete S1P upon activation, promoting inflammatory cascades at the site of tissue damage. Activation of SphK is required for the signaling responses since the ability of TNF-α to induce adhesion molecule expression via activation of Nuclear Factor Kappa B (NFκB) is mimicked by S1P and is blocked by DMS. Similarly, S1P mimics the ability of TNF-α to induce the expression of Cyclooxygenase-2 (COX-2) and the synthesis of prostaglandin $E_2$ ($PGE_2$), and knock-down of SphK by RNA interference blocks these responses to TNF-α. S1P is also a mediator of calcium influx during neutrophil activation by TNF-α and other stimuli, leading to the production of superoxide and other toxic radicals. Therefore, reducing the production of S1P within immune cells and their target tissues may be an effective method to treat disorders arising from oxidative stress and abnormal inflammation. Examples of such disorders include inflammatory bowel disease, arthritis, atherosclerosis, asthma, allergy, inflammatory kidney disease, circulatory shock, ischemia-reperfusion injury, post-surgical organ failure, organ transplantation, multiple sclerosis, chronic obstructive pulmonary disease, skin inflammation, periodontal disease, psoriasis and T cell-mediated diseases of immunity.

S1P also has several effects on cells that mediate immune functions. For example, platelets, monocytes, and mast cells secrete S1P upon activation, promoting inflammatory cascades. It is believed that SphK activation is required for the related signaling responses. In addition, deregulation of apoptosis in phagocytes can be an important component of chronic inflammatory diseases. S1P has been found to protect neutrophils and macrophages in response to inflammatory stresses, such as TNF-α. Additional information regarding the role of S1P and SphK in various specific inflammatory and/or autoimmune conditions can be found in U.S. Patent Application Publication No. 2008/0167352, the disclosure of which is incorporated herein. Accordingly, inhibition of the enzymatic activity of SphK (which can reduce levels of S1P) can prevent the hyperproliferation of immune cells that are important for inflammation.

S1P also has effects on vascular contractility, vascular tone, and blood pressure control. For example, the non-S1P agonist, fingolimod produces modest hypertension in patients (2-3 mmHg in 1-yr trial). In addition, it has been found that exogenous S1P elicits a marked Ca$^{2+}$- and Rho kinase-dependent pulmonary vasoconstriction in hypertensive rat lungs. Furthermore, it has been found that S1P selectively and potently constricts isolated cerebral arteries. Therefore, reducing S1P levels may be an effective method to treat disease or disorders arising from hypertension. Examples of such diseases or disorders include chronic kidney disease, pulmonary hypertension, pulmonary arterial hypertension, atherosclerosis, and stroke.

Given S1P's involvement in mediating disease pathologies associated with changes in cellular proliferation, morphology, migration, and chemotaxis, sphingosine kinases are good targets for therapeutic applications such as modulating fibrosis, tumor growth inhibition, angiogenesis, endothelial cell chemotaxis, and inflammatory and autoimmune diseases and disorders. For example, SphK1 and SphK2 have roles in affecting cell survival and proliferation. These kinases are also responsible for the equilibrium between the anti-apoptotic S1P and its pro-apoptotic metabolic precursor sphingosine and its precursor, ceramide. Thus, SphK1 and SphK2 are important drug targets.

To date, only a small number of compounds including DL-threo-dihydrosphingosine, N,N-dimethylsphingosine, and short-chain DL-erythro-sphingosine analogues, have been shown to inhibit sphingosine kinases. However, with a typical $K_I$ value of less than 10 microM, these compounds have relatively low potency. These compounds are also neither generally selective for either SphK1 or SphK2, nor are they metabolically stable in vivo. Accordingly, these compounds are not ideally suited for addressing questions concerning SphK mediated disease states.

Traditional methods of inhibiting kinases, including sphingosine kinases, have centered on targeting the ATP binding site of the kinase, a strategy that has enjoyed moderate success. However, such methods suffer from lack of selectivity across a wide array of kinases. Additionally, the amino acid sequence of the ATP binding domain of SphK1 and SphK2 is conserved across a number of diacylglycerol (DAG) kinase family members, rendering the traditional strategy problematic because it does not discriminate among kinases. By contrast, the inhibitors in the present invention are competitive with sphingosine, not with ATP, and thus are not expected to inhibit other protein and diacylglycerol kinases.

Currently, there is a need for novel, potent, and selective agents that inhibit the sphingosine substrate-binding domain of the sphingosine kinases (e.g., human SphK1 or SphK2, or both) that have enhanced potency, selectivity, and bioavailability. In addition, there is a need in the art for identification, as well as the synthesis and use, of such compounds. The present invention satisfies these needs.

SUMMARY OF THE INVENTION

The present invention provides, in one aspect, compounds that inhibit sphingosine kinase 1 and sphingosine kinase 2 (SphK1 & SphK2) enzymes. Accordingly, there are provided compounds of Formula I:

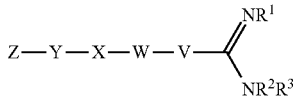

wherein:
$R^1$ is hydrogen or $R^d$;
$R^2$ and $R^3$ are each independently selected from hydrogen and $R^d$;
$R^d$ is independently selected from —O($R^{18}$), —C(O)$R^{19}$, and —C(O)$R^{20}$—O—C(O)—$R^{21}$; wherein $R^{18}$ is independently selected from hydrogen, ($C_1$-$C_6$)alkyl, ($C_6$-$C_{10}$)aryl, and ($C_6$-$C_{10}$)alkylaryl; wherein $R^{19}$ is independently selected from ($C_1$-$C_6$)alkyl, ($C_1$-$C_6$)alkoxy, ($C_1$-$C_6$)alkoxyalkyl, ($C_6$-$C_{10}$)alkoxyaryl, ($C_6$-$C_{10}$)aryl, and ($C_6$-$C_{10}$)alkylaryl; wherein $R^{20}$ is independently selected from ($C_1$-$C_6$)alkyl; and wherein $R^{21}$ is independently selected from ($C_1$-$C_6$)alkyl, ($C_6$-$C_{10}$)aryl, and ($C_6$-$C_{10}$)alkylaryl;

V is —C($R^4R^5$)—, —N($R^6$)—, —O—, —C(O)—, or —S—;
wherein $R^4$ and $R^5$ are each independently selected from hydrogen, NH$_2$, OH, and ($C_1$-$C_4$)alkyl, or $R^4$ and $R^5$, together with the atom to which they are attached form a saturated or unsaturated 3- to 8-membered ring, wherein said 3- to 8-membered ring is optionally substituted with at least one heteroatom, wherein the at least one heteroatom is independently selected from O, S, N, and N$R^7$, wherein $R^7$ is hydrogen or ($C_1$-$C_3$)alkyl, and wherein said 3- to 8-membered ring is optionally substituted by at least one substituent independently selected from OH, N($R^eR^f$), halo, ($C_1$-$C_6$) alkyl, ($C_2$-$C_6$)alkenyl, ($C_2$-$C_6$)alkynyl, ($C_1$-$C_6$)alkoxy, and ($C_1$-$C_{10}$)alkoxyalkyl; and $R^6$ is hydrogen or ($C_1$-$C_4$)alkyl;

W is present or absent, but when present, is —C($R^8R^9$)—, —N($R^{10}$)—, or —C(O)—;
wherein $R^8$ and $R^9$ are each independently present or absent, but when present, they are each independently selected from hydrogen, ($C_1$-$C_4$)alkyl, OH, and =NH, or $R^8$ or $R^9$ together with the atom to which they are attached optionally form a saturated or unsaturated 3- to 8-membered ring, wherein said 3- to 8-membered ring is optionally substituted with at least one heteroatom, wherein the at least one heteroatom is independently selected from O, S, N, and N$R^{11}$, wherein $R^{11}$ is hydrogen or ($C_1$-$C_3$)alkyl, and wherein said 3- to 8-membered ring is optionally substituted by at least one substituent independently selected from OH, N($R^eR^f$), halo, ($C_1$-$C_6$)alkyl ($C_2$-$C_6$)alkenyl, ($C_2$-$C_6$)alkynyl, ($C_1$-$C_6$)alkoxy, and ($C_1$-$C_{10}$)alkoxyalkyl; and $R^{10}$ is hydrogen or ($C_1$-$C_4$)alkyl;

wherein, when V is —C($R^4R^5$)— and W is —C($R^8R^9$)— or —N($R^{10}$)—, $R^4$ and $R^8$ or $R^{10}$, together with the atoms to which they are attached, optionally form a saturated or unsaturated 3- to 8-membered ring, wherein said 3- to 8-membered ring is optionally substituted with at least one heteroatom, wherein the at least one heteroatom is independently selected from O, S, N, and N$R^{12}$, where $R^{12}$ is hydrogen or ($C_1$-$C_3$)alkyl, and wherein said 3- to 8-membered ring is optionally substituted by at least one substituent independently selected from OH, N($R^eR^f$), halo, ($C_1$-$C_6$) alkyl ($C_2$-$C_6$)alkenyl, ($C_2$-$C_6$)alkynyl, ($C_1$-$C_6$)alkoxy, and ($C_1$-$C_{10}$)alkoxyalkyl; and $R^{10}$ is hydrogen or ($C_1$-$C_4$)alkyl;

wherein, when V is —N($R^6$)— and W is —C($R^8R^9$)—, $R^6$ and $R^8$ together with the atoms to which they are attached, optionally form a 3- to 8-membered ring, which is optionally substituted with at least one heteroatom, wherein the at least one heteroatom is independently selected from O, S, N, and N$R^{13}$, wherein $R^{13}$ is hydrogen or ($C_1$-$C_3$)alkyl, and wherein said 3- to 8-membered ring is optionally substituted by at least one substituent independently selected from OH, N($R^eR^f$), halo, ($C_1$-$C_6$)alkyl ($C_2$-$C_6$)alkenyl, ($C_2$-$C_6$)alkynyl, ($C_1$-$C_6$)alkoxy, and ($C_1$-$C_{10}$)alkoxyalkyl; and $R^{10}$ is hydrogen or ($C_1$-$C_4$)alkyl;

X and Y are each independently present or absent, but when present, they are each independently selected from —C($R^{14}R^{15}$)—, —N($R^{16}$)—, and —C(O)—;

wherein $R^{14}$ and $R^{15}$ are each independently present or absent, but when present, they are each independently selected from hydrogen, hydroxy, ($C_1$-$C_{10}$)alkyl, ($C_1$-$C_5$)alkoxy, and =NH; $R^{16}$ is hydrogen or ($C_1$-$C_4$)alkyl; or $R^{14}$ and $R^{15}$ or $R^{16}$, together with the atoms to which they are attached, form an cycloalkyl or aryl ring, or a fused aryl or arylalkyl ring structure, optionally substituted with at least one heteroatom, wherein the at least one heteroatom is independently selected from O, S, N, and $NR^{17}$, where $NR^{17}$ is hydrogen or ($C_1$-$C_3$)alkyl; and wherein said alkyl or aryl ring, or fused aryl or arylalkyl ring structure is optionally substituted by at least one substituent independently selected from OH, N($R^eR^f$), halo, ($C_1$-$C_6$)alkyl ($C_2$-$C_6$)alkenyl, ($C_2$-$C_6$)alkynyl, ($C_1$-$C_6$)alkoxy, and ($C_1$-$C_{10}$)alkoxyalkyl;

$R^e$ and $R^f$ are each independently selected from hydrogen and ($C_1$-$C_4$)alkyl; and Z is —($C_6$-$C_{14}$)alkyl, —($C_6$-$C_{14}$)alkenyl, —($C_6$-$C_{14}$)alkynyl, —($C_6$-$C_{14}$)alkoxy, —($C_6$-$C_{20}$)alkoxyalkyl, —($C_3$-$C_{12}$)cycloalkyl, —($C_6$-$C_{10}$)aryl, —($C_7$-$C_{16}$)alkylaryl, —($C_{12}$-$C_{16}$)alkoxyaryl, —($C_6$-$C_{20}$)arylalkyl, —($C_4$-$C_{10}$)heterocyclic, —($C_4$-$C_{10}$)heteroaryl, or —($C_4$-$C_{10}$)heteroaryl($C_1$-$C_{16}$)alkyl, wherein the Z groups are optionally substituted with 1, 2, 3, 4, 5, 6, or 7 substituents; wherein the substituents are each independently selected from halo, halo($C_1$-$C_7$)alkyl, ($C_1$-$C_7$)alkyl, cyano, N($R^aR^b$), ($C_1$-$C_7$)alkoxy, ($C_1$-$C_7$)alkoxyalkyl, ($C_3$-$C_{10}$)alkoxycycloalkyl, ($C_3$-$C_{10}$)cycloalkyl, ($C_6$-$C_{10}$)aryl, ($C_7$-$C_{14}$)alkylaryl, ($C_8$-$C_{16}$)acylarylalkyl, ($C_7$-$C_{14}$)heterocyclic, and ($C_7$-$C_{14}$)heteroaryl, wherein each substituent may be further optionally substituted and wherein the saturation of each ring substituent may be varied; wherein one or more of the carbon atoms in the Z alkyl groups can be independently replaced with non-peroxide oxygen, sulfur, sulfonyl, or N($R^c$); wherein each of $R^a$, $R^b$ or $R^c$ is independently hydrogen or ($C_1$-$C_7$)alkyl;

with the proviso that the atoms represented by V, W, X, Y, and Z need not be directly connected by a single bond but may be connected via any of the atoms in the ring structures described for V, W, X, and Y; and pharmaceutically acceptable salts or prodrugs thereof.

$R^1$, $R^2$, and $R^3$ are preferably hydrogen.

$R^d$ is preferably —OH or

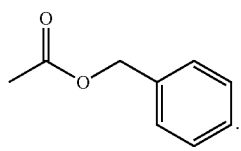

V is preferably —C($R^4R^5$)— or —N($R^6$)—, wherein $R^4$ and $R^5$ are preferably hydrogen, methyl, ethyl, or isopropyl, or $R^4$ and $R^5$ together with the atom to which they are attached form cyclopropyl or cyclobutyl, $R^6$ is hydrogen.

W is preferably present and is $CR^8R^9$, wherein $R^8$ and $R^9$ are preferably present and are hydrogen, methyl, ethyl, or isopropyl, or $R^8$ and $R^9$ together with the atom to which they are attached form cyclopropyl and cyclobutyl.

W is preferably $NR^{10}$, wherein $R^{10}$ is preferably present and is hydrogen.

Preferably, V is —C($R^4R^5$)— and W is preferably present and is $CR^8R^9$, wherein $R^4$ and $R^8$ together with the atoms to which they are attached form cyclopentyl or cyclohexyl.

Preferably, V is —N($R^6$)— and W is preferably present and is $CR^8R^9$, wherein $R^6$ and $R^8$ together with the atoms to which they are attached form azetidinyl or pyrrolidinyl.

Preferably, V is —C($R^4R^5$)— and W is preferably present and is $NR^{10}$, wherein $R^4$ and $R^{10}$ together with the atoms to which they are attached form azetidinyl or pyrrolidinyl.

Preferably, X and Y, when present, are $CR^{14}R^{15}$ and $NR^{16}$, wherein $R^{14}$ and $R^{15}$ are preferably each independently selected from hydrogen or ($C_1$-$C_6$)alkyl, or $R^{14}$ and $R^{15}$ together is =NH, and wherein $R^{16}$ is preferably hydrogen or ($C_1$-$C_6$)alkyl. In another preferred embodiment, $R^{15}$ and $R^{16}$, together with the atoms to which they are attached, are an alkyl or aryl ring structure optionally substituted with one or more heteroatoms chosen from the group azetidine, pyrrolidine, pyrrole, furan, tetrahydrofuran, thiophene, imidazolidine, imidazole, pyrazole, oxazolidine, oxazole, isoxazole, thiazole, triazole, oxadiazole, and tetrazole. In a further preferred embodiment, $R^{15}$ and $R^{16}$, together with the atoms to which they are attached, are fused alkylaryl or aryl ring structures optionally substituted with one or more heteroatoms chosen from the group indane, benzofuran, indole, indazole, benzimidazole, benzthiophene, benzoxazole, benzisoxazole, benzthiazole, purine, tetralin, and naphthalene.

Preferred values for Z include ($C_4$-$C_{12}$)alkyl, ($C_4$-$C_{12}$)alkenyl, or ($C_4$-$C_{12}$)alkylphenyl. Preferably, the alkyl chain in the alkylphenyl group of Z has 6, 7, 8, 9, 10, 11, or 12 carbon atoms.

Preferred values for

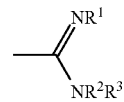

of Formula I include:

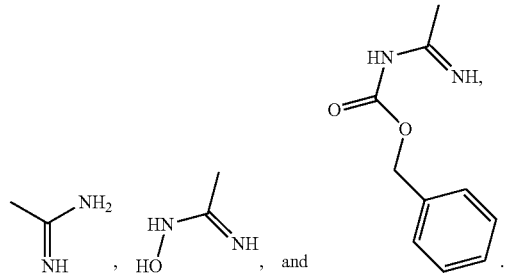

Preferred values for

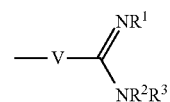

of Formula I include:

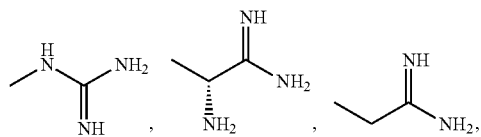

-continued
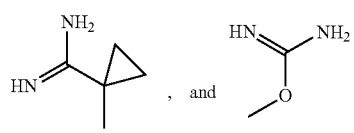, and
Preferred values for
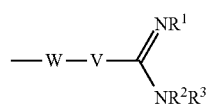
of Formula I include:
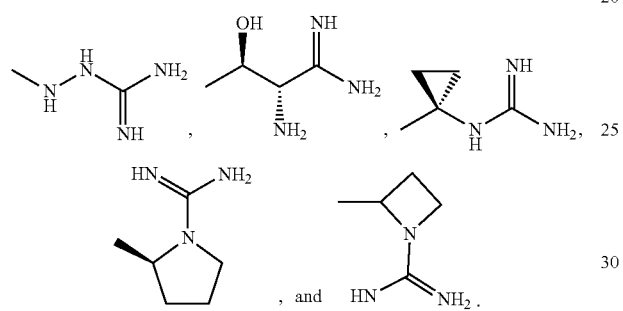
Preferred values —W—V— of Formula I include:
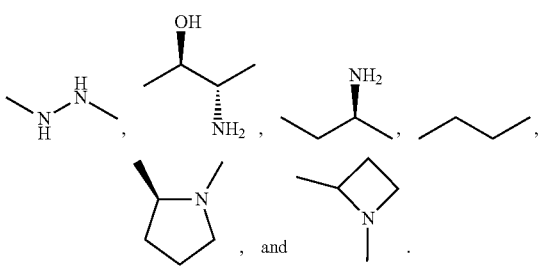
Preferred values for —Y—X—W— of Formula I include:
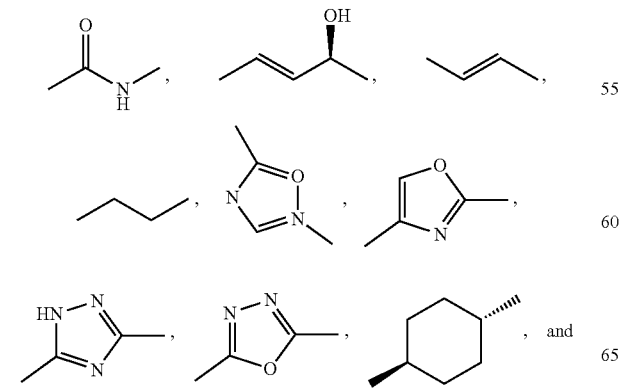
-continued
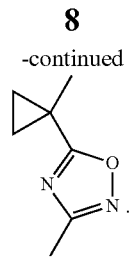
Preferred values for —Y—X—W—V— of Formula I include:
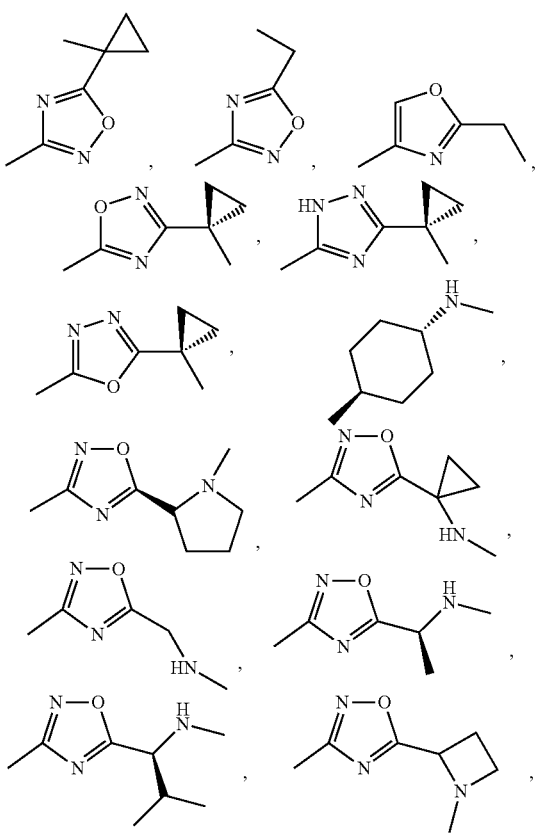
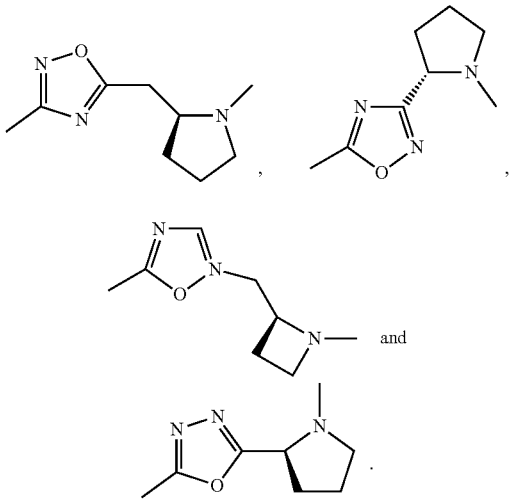

Preferred values for
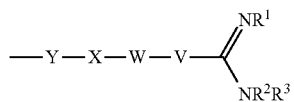
of Formula I include:
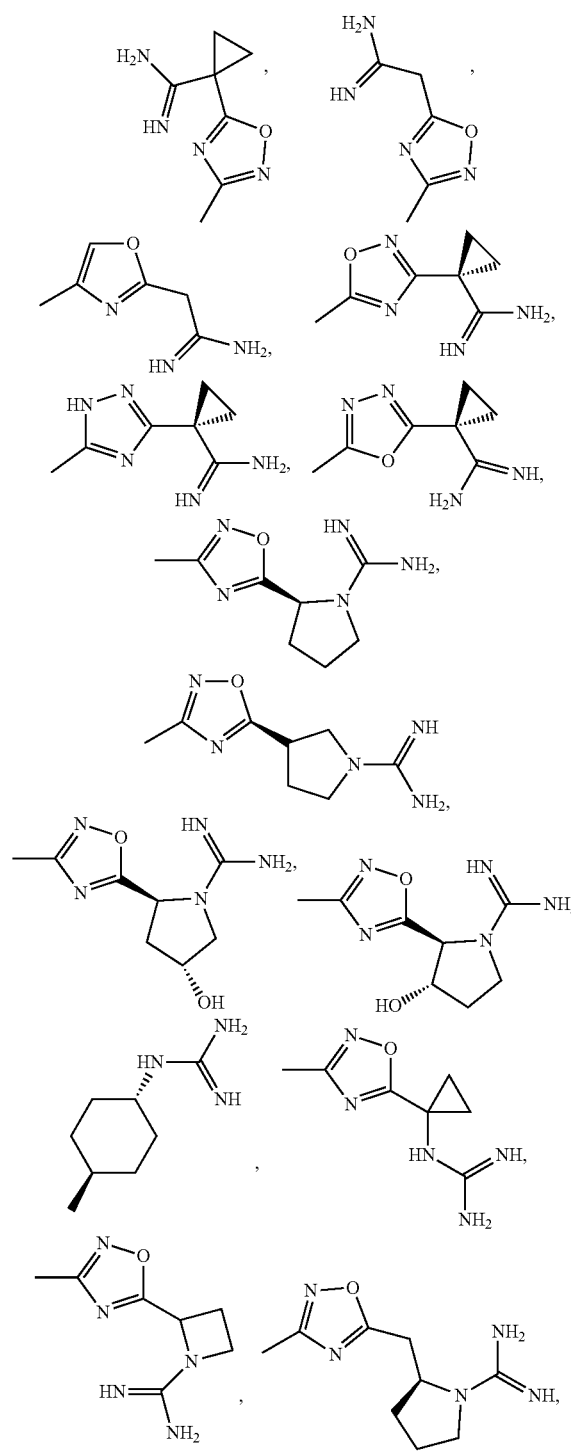
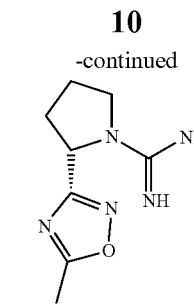
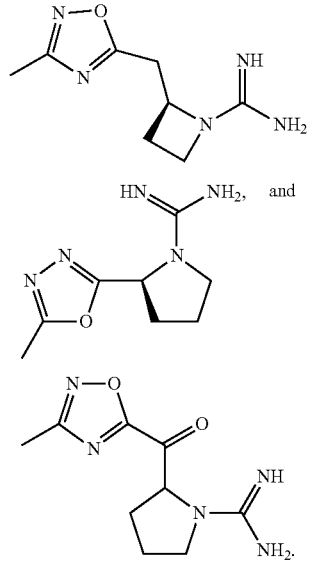
Preferred values for Z— of Formula I include:
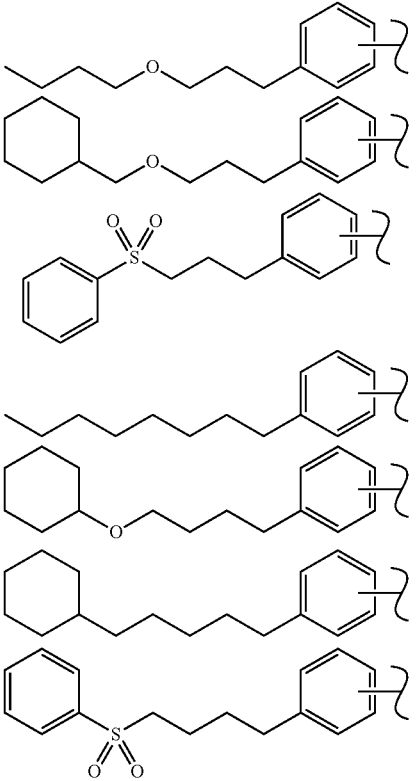

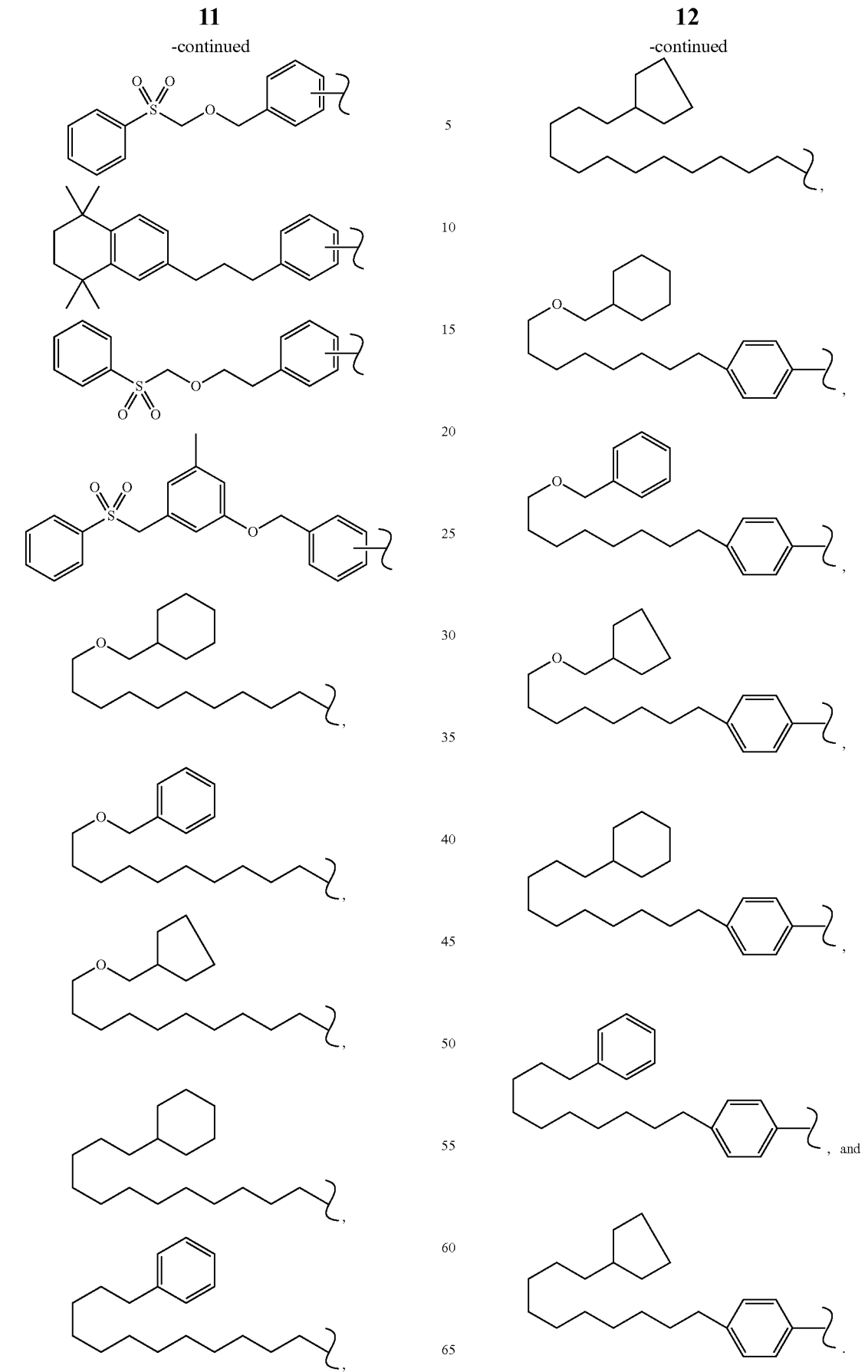

It is to be understood that the bonding can occur at any available ring atom in the values containing rings, including the preferred values above. Also, it is to be understood that the values (rings and non-rings) may encompass any racemic, optically active or stereoisomeric form, or mixtures thereof, of the compound, such as, for example, the S,R; S,S; R,R; or R,S diastereomers. Thus, by way of illustration,

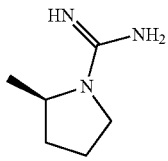

above may also be, for example,

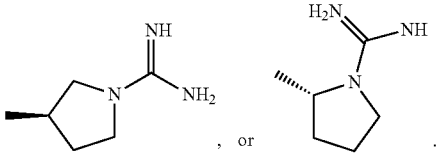

, or .

See also, e.g., Compounds listed in Table 1 below.

Preferred heteroatom groups for replacing carbon atoms in a ring or alkyl include O or $NR^{10}$. Preferred values for $R^{10}$ include hydrogen, methyl, ethyl, propyl, or isopropyl.

Preferred compounds of the invention have formulas as shown in Table 1.

TABLE 1

| Compound # | Structure | IUPAC name |
|---|---|---|
| 1 | 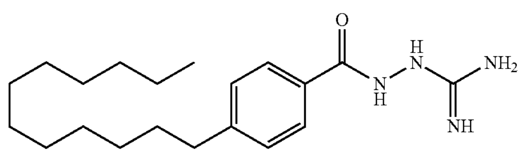 [SMILES: CCCCCCCCCCCCc1ccc(C(=O)NNC(=N)N)cc1] | 2-(4-dodecylbenzoyl)hydrazine carboximidamide |
| 2 | 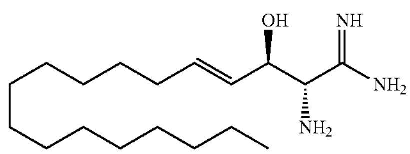 [SMILES: CCCCCCCCCCCCC/C=C/[C@@H](O)[C@@H](N)C(=N)N] | (2S,3R,E)-2-amino-3-hydroxyoctadec-4-enimidamide |
| 3 | 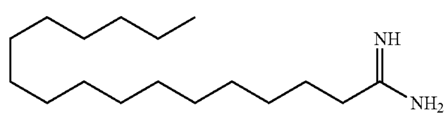 | heptadecanimidamide |
| 4 | 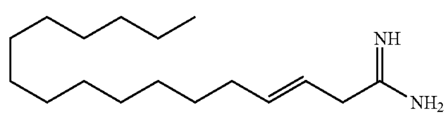 [SMILES: CCCCCCCCCCCCC/C=C/CC(=N)N] | (E)-heptadec-3-enimidamide |
| 5 | 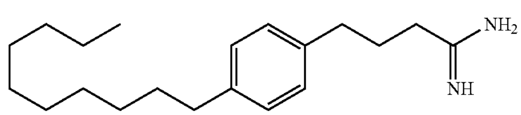 [SMILES: CCCCCCCCCCc1ccc(CCCC(=N)N)cc1] | 4-(4-decylphenyl)butanimidamide |
| 6 | 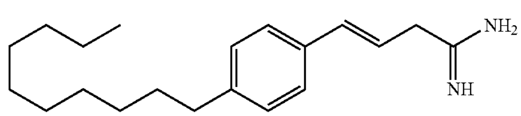 [SMILES: CCCCCCCCCCc1ccc(/C=C/CC(=N)N)cc1] | (E)-4-(4-decylphenyl)but-3-enimidamide |
| 7 | 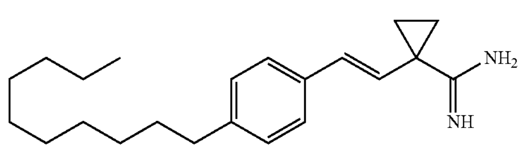 [SMILES: CCCCCCCCCCc1ccc(/C=C/C2(C(=N)N)CC2)cc1] | (E)-1-(4-decylstyryl)cyclopropanecarboximidamide |
| 8 | 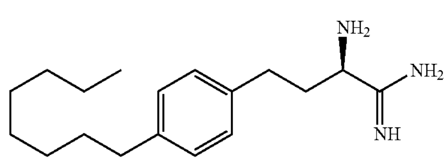 [SMILES: CCCCCCCCc1ccc(CC[C@@H](N)C(=N)N)cc1] | (R)-2-amino-4-(4-octylphenyl)butanimidamide |

TABLE 1-continued

| Compound # | Structure | IUPAC name |
|---|---|---|
| 9 | 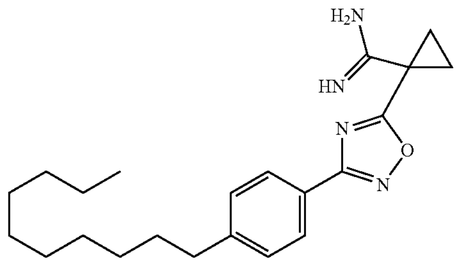 [SMILES: CCCCCCCCCCc1ccc(-c2noc(C3(C(=N)N)CC3)n2)cc1] | 1-(3-(4-decylphenyl)-1,2,4-oxadiazol-5-yl)cyclopropanecarboximidamide |
| 10 | 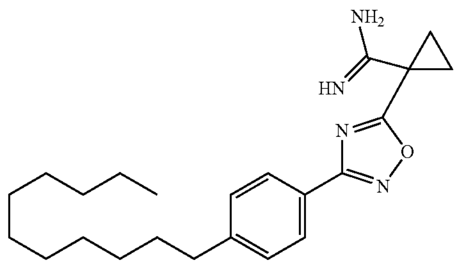 [SMILES: CCCCCCCCCCCc1ccc(-c2noc(C3(C(=N)N)CC3)n2)cc1] | 1-(3-(4-undecylphenyl)-1,2,4-oxadiazol-5-yl)cyclopropanecarboximidamide |
| 11 | 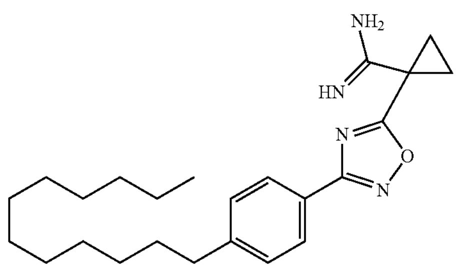 [SMILES: CCCCCCCCCCCCc1ccc(-c2noc(C3(C(=N)N)CC3)n2)cc1] | 1-(3-(4-dodecylphenyl)-1,2,4-oxadiazol-5-yl)cyclopropanecarboximidamide |
| 12 | 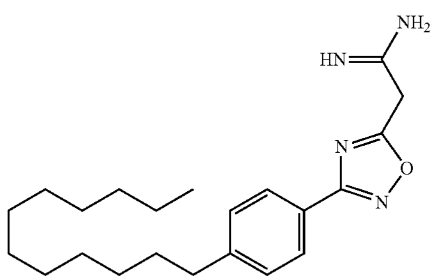 [SMILES: CCCCCCCCCCCCc1ccc(-c2noc(CC(=N)N)n2)cc1] | 2-(3-(4-dodecylphenyl)-1,2,4-oxadiazol-5-yl)acetimidamide |
| 13 | 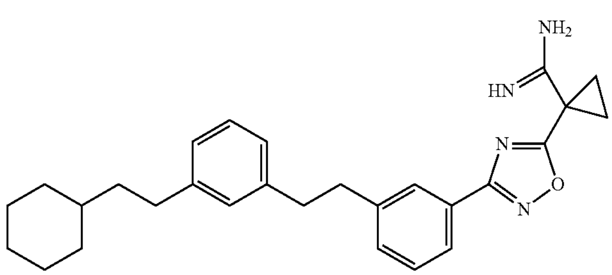 [SMILES: N=C(N)C1(c2nc(-c3cccc(CCc4cccc(CCC5CCCCC5)c4)c3)no2)CC1] | 1-(3-(3-(3-(2-cyclohexylethyl)phenethyl)phenyl)-1,2,4-oxadiazol-5-yl)cyclopropanecarboximidamide |

TABLE 1-continued

| Compound # | Structure | IUPAC name |
|---|---|---|
| 14 | 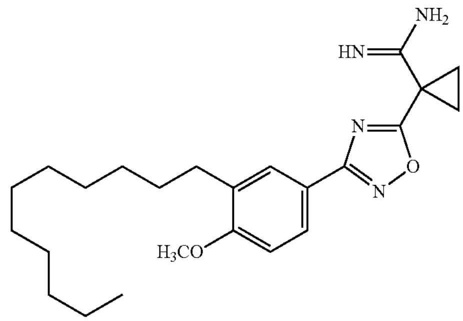 [SMILES: CCCCCCCCCCCc1cc(-c2noc(C3(C(=N)N)CC3)n2)ccc1OC] | 1-(3-(4-methoxy-3-undecylphenyl)-1,2,4-oxadiazol-5-yl)cyclopropanecarboximidamide |
| 15 | 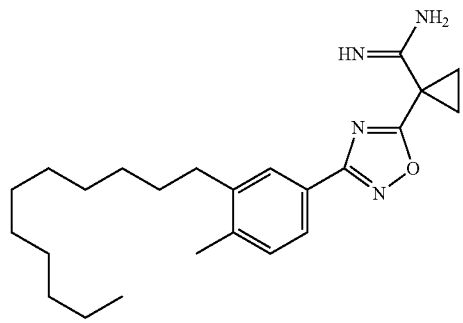 [SMILES: CCCCCCCCCCCc1cc(-c2noc(C3(C(=N)N)CC3)n2)ccc1C] | 1-(3-(4-methyl-3-undecylphenyl)-1,2,4-oxadiazol-5-yl)cyclopropanecarboximidamide |
| 16 | 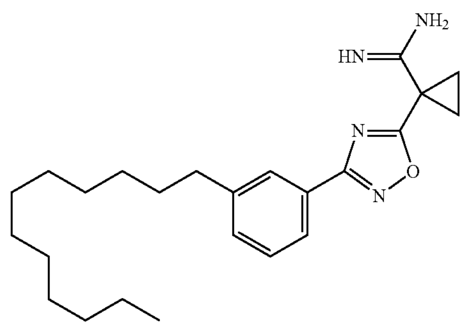 [SMILES: CCCCCCCCCCCCc1cccc(-c2noc(C3(C(=N)N)CC3)n2)c1] | 1-(3-(3-dodecylphenyl)-1,2,4-oxadiazol-5-yl)cyclopropanecarboximidamide |
| 17 | 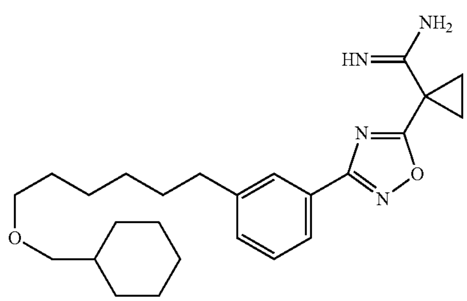 [SMILES: N=C(N)C1(c2nc(-c3cccc(CCCCCCOCC4CCCCC4)c3)no2)CC1] | 1-(3-(3-(6-(cyclohexylmethoxy)hexyl)phenyl)-1,2,4-oxadiazol-5-yl)cyclopropanecarboximidamide |
| 18 | 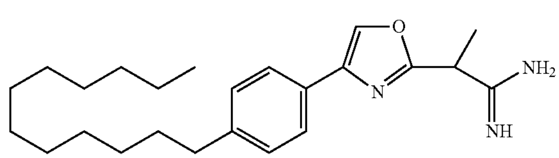 [SMILES: CCCCCCCCCCCCc1ccc(-c2coc(C(C)C(=N)N)n2)cc1] | 2-(4-(4-dodecylphenyl)oxazol-2-yl)propanimidamide |
| 19 | 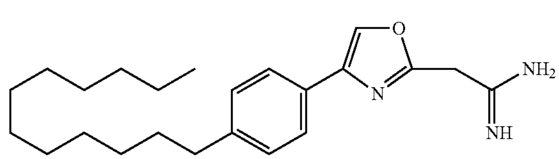 [SMILES: CCCCCCCCCCCCc1ccc(-c2coc(CC(=N)N)n2)cc1] | 2-(4-(4-dodecylphenyl)oxazol-2-yl)acetimidamide |

TABLE 1-continued

| Compound # | Structure | IUPAC name |
| --- | --- | --- |
| 20 | 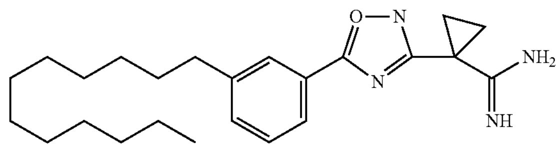 | 1-(5-(3-dodecylphenyl)-1,2,4-oxadiazol-3-yl) cyclopropanecarboximidamide |
| 21 | 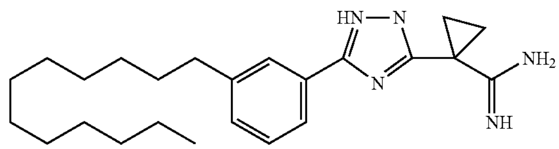 [SMILES: CCCCCCCCCCCCc1cccc(-c2n[nH]c(C3(C(=N)N)CC3)n2)c1] | 1-(5-(3-undecylphenyl)-1H-1,2,4-triazol-3-yl) cyclopropanecarboximidamide |
| 22 | 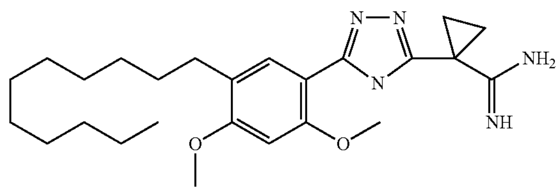 | 1-(5-(2,4-dimethoxy-5-undecylphenyl)-1,3,4-oxadiazol-2-yl)cyclopropanecarboximidamide |
| 23 | 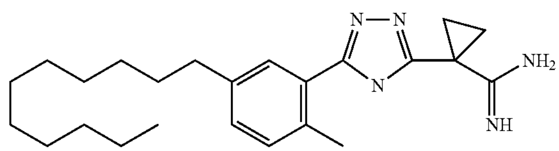 | 1-(5-(2-methyl-5-undecylphenyl)-1,3,4-oxadiazol-2-yl) cyclopropanecarboximidamide |
| 24 | 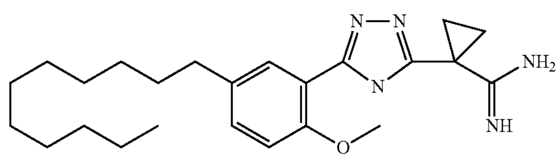 | 1-(5-(2-methoxy-5-undecylphenyl)-1,3,4-oxadiazol-2-yl)cyclopropanecarboximidamide |
| 25 | 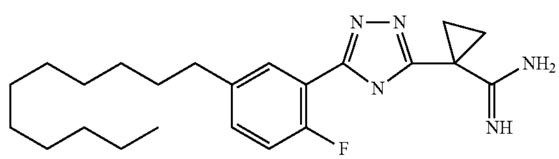 | 1-(5-(2-fluoro-5-undecylphenyl)-1,3,4-oxadiazol-2-yl) cyclopropanecarboximidamide |
| 26 | 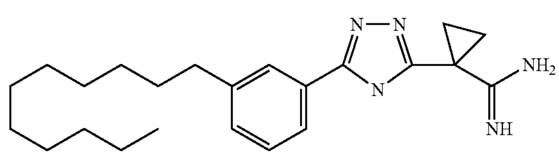 | 1-(5-(3-undecylphenyl)-1,3,4-oxadiazol-2-yl) cyclopropanecarboximidamide |
| 27 | 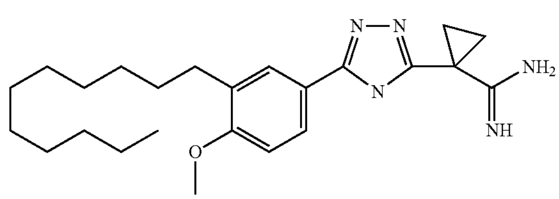 | 1-(5-(4-methoxy-3-undecylphenyl)-1,3,4-oxadiazol-2-yl)cyclopropanecarboximidamide |
| 28 | 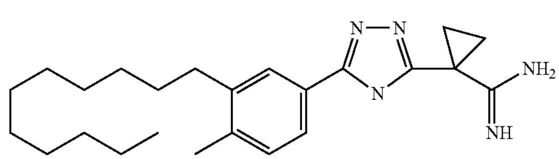 [SMILES: CCCCCCCCCCCc1cc(-c2nnc(C3(C(=N)N)CC3)[nH]2)ccc1C] | 1-(5-(4-methyl-3-undecylphenyl)-1,3,4-oxadiazol-2-yl) cyclopropanecarboximidamide |

TABLE 1-continued

| Compound # | Structure | IUPAC name |
|---|---|---|
| 29 | 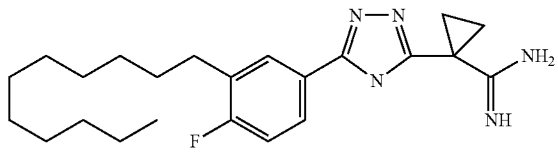 [SMILES: CCCCCCCCCCCc1cc(-c2nnc(C3(C(=N)N)CC3)[nH]2)ccc1F] | 1-(5-(4-fluoro-3-undecylphenyl)-1,3,4-oxadiazol-2-yl) cyclopropanecarboximidamide |
| 30 | 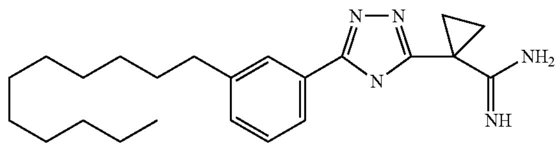 | 1-(5-(3-dodecylphenyl)-1,3,4-oxadiazol-2-yl) cyclopropanecarboximidamide |
| 31 | 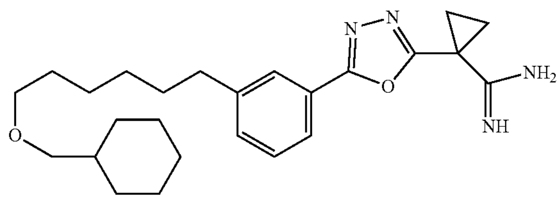 [SMILES: N=C(N)C1(c2nnc(-c3cccc(CCCCCCOCC4CCCCC4)c3)o2)CC1] | 1-(5-(3-(6-(cyclohexylmethoxy)hexyl) phenyl)-1,3,4-oxadiazol-2-yl) cyclopropanecarboximidamide |
| 32 | 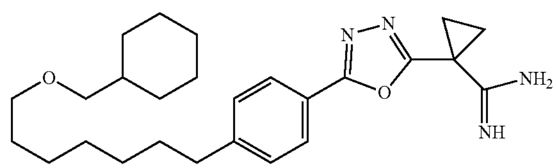 [SMILES: N=C(N)C1(c2nnc(-c3ccc(CCCCCCCOCC4CCCCC4)cc3)o2)CC1] | 1-(5-(4-(7-(cyclohexylmethoxy)heptyl) phenyl)-1,3,4-oxadiazol-2-yl) cyclopropanecarboximidamide |
| 33 | 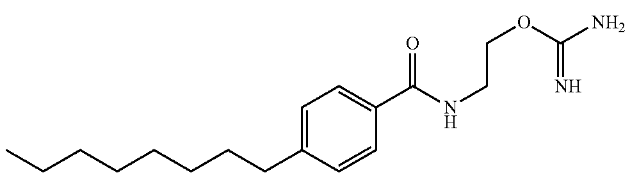 [SMILES: CCCCCCCCc1ccc(C(=O)NCCOC(=N)N)cc1] | 2-(4-octylbenzamido)ethyl carbamimidate |
| 34 | 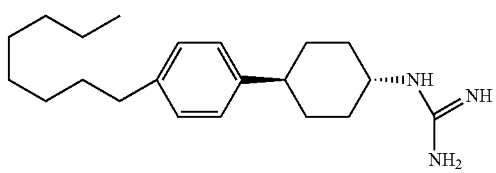 [SMILES: CCCCCCCCc1ccc([C@H]2CC[C@H](NC(=N)N)CC2)cc1] | 1-((1R,4R)-4-(4-octylphenyl)-cyclohexyl)guanidine |
| 35 | 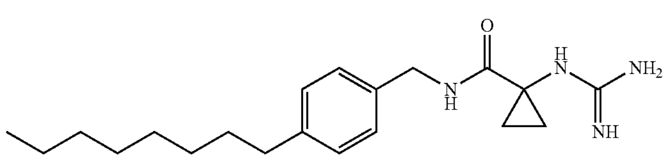 [SMILES: CCCCCCCCc1ccc(CNC(=O)C2(NC(=N)N)CC2)cc1] | 1-guanidino-N-(4-octylbenzyl) cyclopropanecarboxamide |
| 36 | 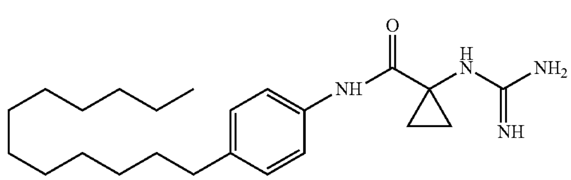 [SMILES: CCCCCCCCCCCCc1ccc(NC(=O)C2(NC(=N)N)CC2)cc1] | N-(4-dodecylphenyl)-1-guanidinocyclopropane-carboxamide |
| 37 | 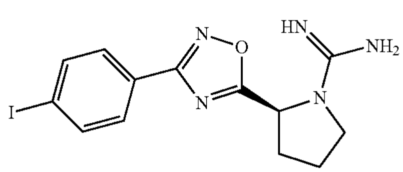 [SMILES: N=C(N)N1CCC[C@H]1c1nc(-c2ccc(I)cc2)no1] | (S)-2-(3-(4-iodophenyl)-1,2,4-oxadiazol-5-yl)pyrrolidine-1-carboximidamide |

TABLE 1-continued

| Compound # | Structure | IUPAC name |
|---|---|---|
| 38 | 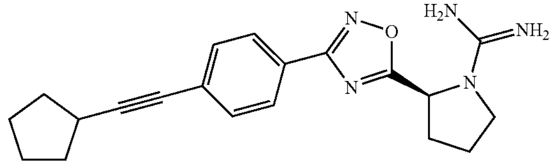 [SMILES: N=C(N)N1CCC[C@H]1c1nc(-c2ccc(C#CC3CCCC3)cc2)no1] | (S)-2-(3-(4-(cyclopentylethynyl)phenyl)-1,2,4-oxadiazol-5-yl)pyrrolidine-1-carboximidamide |
| 39 | 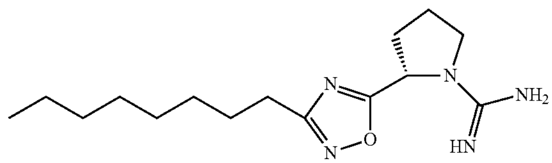 [SMILES: CCCCCCCCc1noc([C@@H]2CCCN2C(=N)N)n1] | (S)-2-(3-octyl-1,2,4-oxadiazol-5-yl)pyrrolidine-1-carboximidamide |
| 40 | 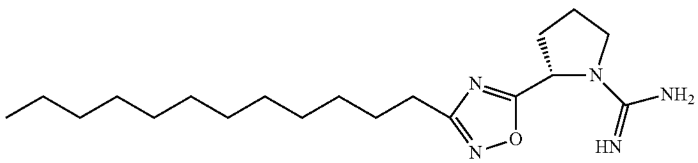 [SMILES: CCCCCCCCCCCCc1noc([C@@H]2CCCN2C(=N)N)n1] | (S)-2-(3-dodecyl-1,2,4-oxadiazol-5-yl)pyrrolidine-1-carboximidamide |
| 41 | 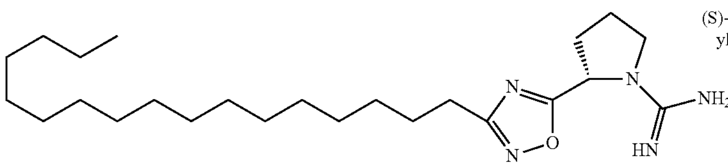 [SMILES: CCCCCCCCCCCCCCCCCc1noc([C@@H]2CCCN2C(=N)N)n1] | (S)-2-(3-hexadecyl-1,2,4-oxadiazol-5-yl)pyrrolidine-1-carboximidamide |
| 42 | 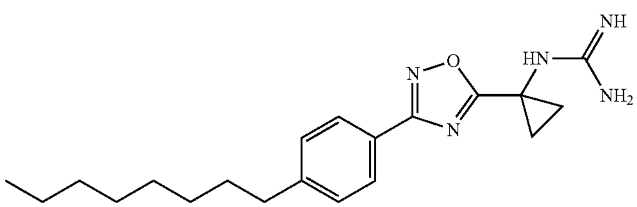 [SMILES: CCCCCCCCc1ccc(-c2noc(C3(NC(=N)N)CC3)n2)cc1] | 1-(1-(3-(4-octylphenyl)-1,2,4-oxadiazol-5-yl)cyclopropyl)guanidine |
| 43 | 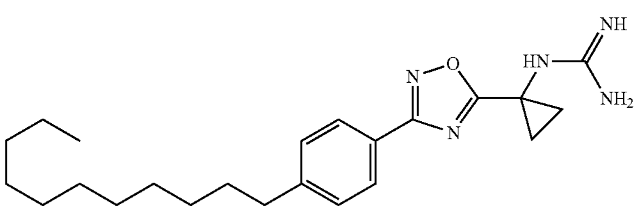 [SMILES: CCCCCCCCCCCc1ccc(-c2noc(C3(NC(=N)N)CC3)n2)cc1] | 1-(1-(3-(4-undecylphenyl)-1,2,4-oxadiazol-5-yl)cyclopropyl)guanidine |
| 44 | 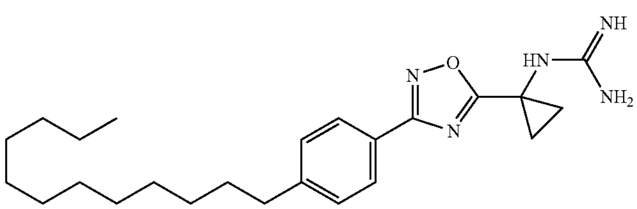 [SMILES: CCCCCCCCCCCCc1ccc(-c2noc(C3(NC(=N)N)CC3)n2)cc1] | 1-(1-(3-(4-dodecylphenyl)-1,2,4-oxadiazol-5-yl)cyclopropyl)guanidine |
| 45 | 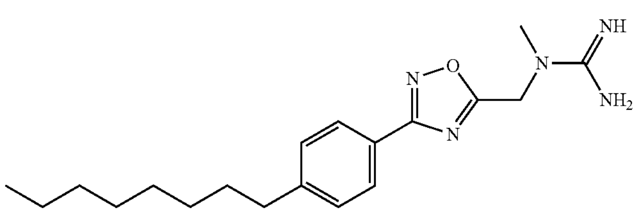 [SMILES: CCCCCCCCc1ccc(-c2noc(CN(C)C(=N)N)n2)cc1] | 1-methyl-1-((3-(4-octylphenyl)-1,2,4-oxadiazol-5-yl)methyl)guanidine |

TABLE 1-continued

| Compound # | Structure | IUPAC name |
|---|---|---|
| 46 | 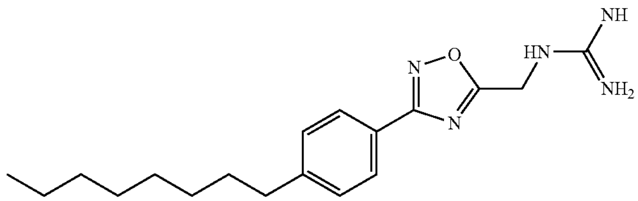 [SMILES: CCCCCCCCc1ccc(-c2noc(CNC(=N)N)n2)cc1] | 1-((3-(4-octylphenyl)-1,2,4-oxadiazol-5-yl)methyl)guanidine |
| 47 | 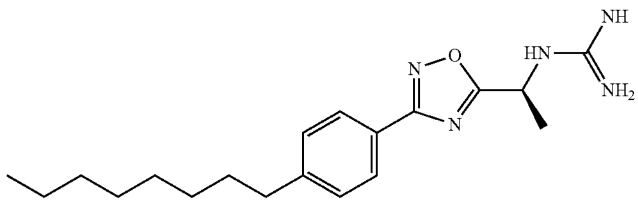 [SMILES: CCCCCCCCc1ccc(-c2noc([C@H](C)NC(=N)N)n2)cc1] | (S)-1-(1-(3-(4-octylphenyl)-1,2,4-oxadiazol-5-yl)ethyl)guanidine |
| 48 | 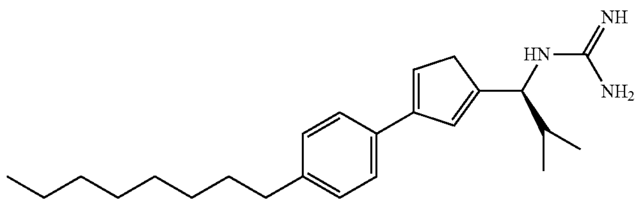 [SMILES: CCCCCCCCc1ccc(C2=CCC([C@@H](NC(=N)N)C(C)C)=C2)cc1] | (S)-1-(2-methyl-1-(3-(4-octylphenyl)-1,2,4-oxadiazol-5-yl)propyl)guanidine |
| 49 | 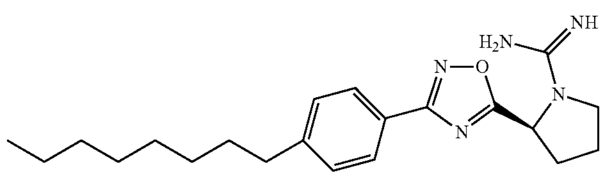 [SMILES: CCCCCCCCc1ccc(-c2noc([C@@H]3CCCN3C(=N)N)n2)cc1] | (S)-2-(3-(4-octylphenyl)-1,2,4-oxadiazol-5-yl)pyrrolidine-1-carboximidamide |
| 50 | 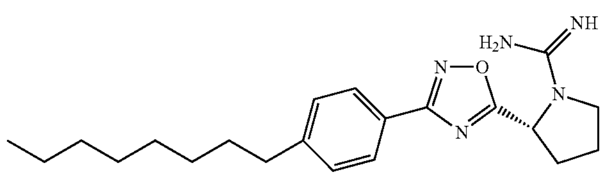 [SMILES: CCCCCCCCc1ccc(-c2noc([C@H]3CCCN3C(=N)N)n2)cc1] | (R)-2-(3-(4-octylphenyl)-1,2,4-oxadiazol-5-yl)pyrrolidine-1-carboximidamide |
| 51 | 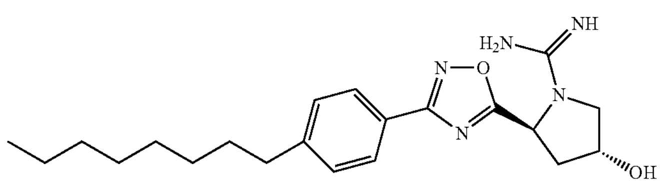 [SMILES: CCCCCCCCc1ccc(-c2noc([C@@H]3C[C@@H](O)CN3C(=N)N)n2)cc1] | (2S,4R)-4-hydroxy-2-(3-(4-octylphenyl)-1,2,4-oxadiazol-5-yl)pyrrolidine-1-carboximidamide |
| 52 | 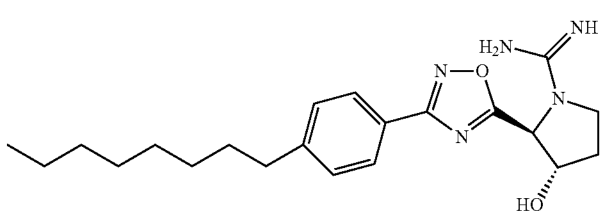 [SMILES: CCCCCCCCc1ccc(-c2noc([C@@H]3[C@@H](O)CCN3C(=N)N)n2)cc1] | (2S,3S)-3-hydroxy-2-(3-(4-octylphenyl)-1,2,4-oxadiazol-5-yl)pyrrolidine-1-carboximidamide |
| 53 | 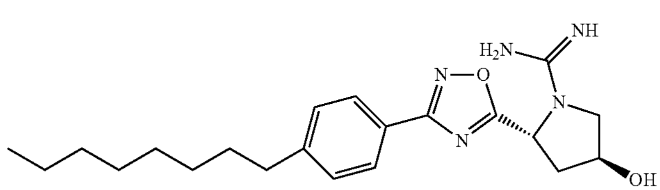 [SMILES: CCCCCCCCc1ccc(-c2noc([C@H]3C[C@H](O)CN3C(=N)N)n2)cc1] | (2R,4S)-4-hydroxy-2-(3-(4-octylphenyl)-1,2,4-oxadiazol-5-yl)pyrrolidine-1-carboximidamide |

TABLE 1-continued

| Compound # | Structure | IUPAC name |
|---|---|---|
| 54 | 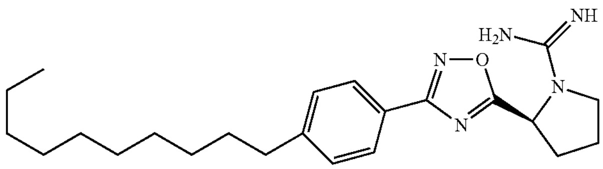 [SMILES: CCCCCCCCCCc1ccc(-c2noc([C@@H]3CCCN3C(=N)N)n2)cc1] | (S)-2-(3-(4-decylphenyl)-1,2,4-oxadiazol-5-yl)pyrrolidine-1-carboximidamide |
| 55 | 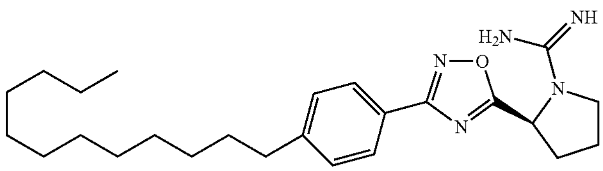 [SMILES: CCCCCCCCCCCCc1ccc(-c2noc([C@@H]3CCCN3C(=N)N)n2)cc1] | (S)-2-(3-(4-dodecylphenyl)-1,2,4-oxadiazol-5-yl)pyrrolidine-1-carboximidamide |
| 56 | 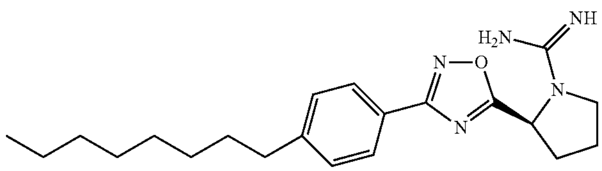 [SMILES: CCCCCCCCc1ccc(-c2noc([C@@H]3CCCN3C(=N)N)n2)cc1] | (S)-2-(3-(4-hexylphenyl)-1,2,4-oxadiazol-5-yl)pyrrolidine-1-carboximidamide |
| 57 | 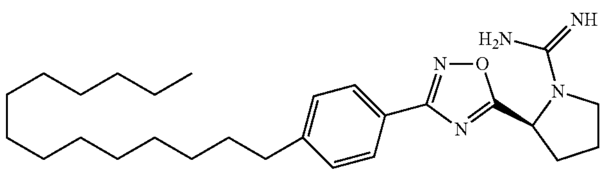 [SMILES: CCCCCCCCCCCCCCc1ccc(-c2noc([C@@H]3CCCN3C(=N)N)n2)cc1] | (S)-2-(3-(4-tetradecylphenyl)-1,2,4-oxadiazol-5-yl)pyrrolidine-1-carboximidamide |
| 58 | 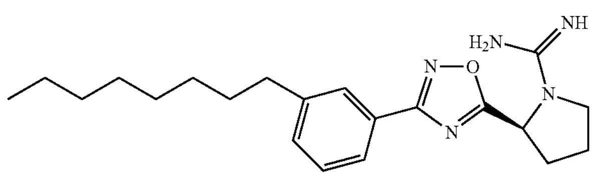 [SMILES: CCCCCCCCc1cccc(-c2noc([C@@H]3CCCN3C(=N)N)n2)c1] | (S)-2-(3-(3-octylphenyl)-1,2,4-oxadiazol-5-yl)pyrrolidine-1-carboximidamide |
| 59 | 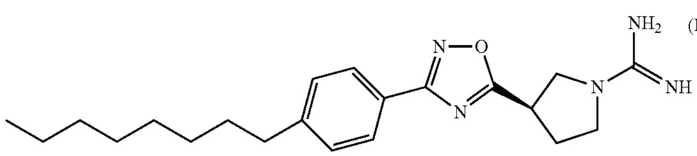 | (R)-3-(3-(4-octylphenyl)-1,2,4-oxadiazol-5-yl)pyrrolidine-1-carboximidamide |
| 60 | 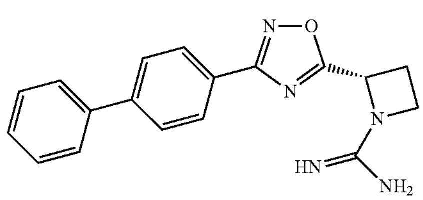 [SMILES: N=C(N)N1CC[C@H]1c1nc(-c2ccc(-c3ccccc3)cc2)no1] | (S)-2-(3-([1,1'-biphenyl]-4-yl)-1,2,4-oxadiazol-5-yl)azetidine-1-carboximidamide |
| 61 | 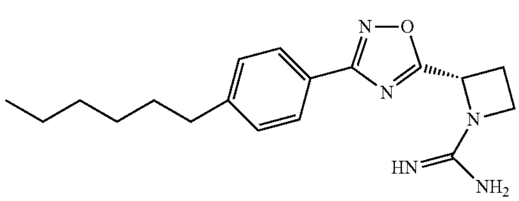 [SMILES: CCCCCCc1ccc(-c2noc([C@@H]3CCN3C(=N)N)n2)cc1] | (S)-2-(3-(4-hexylphenyl)-1,2,4-oxadiazol-5-yl)azetidine-1-carboximidamide |

TABLE 1-continued

| Compound # | Structure | IUPAC name |
|---|---|---|
| 62 | 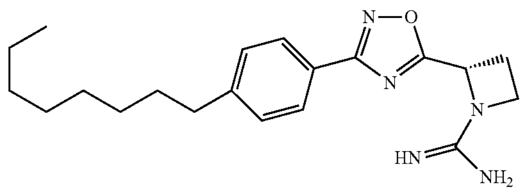 [SMILES: CCCCCCCCc1ccc(-c2noc([C@@H]3CCN3C(=N)N)n2)cc1] | (S)-2-(3-(4-octylphenyl)-1,2,4-oxadiazol-5-yl)azetidine-1-carboximidamide |
| 63 | 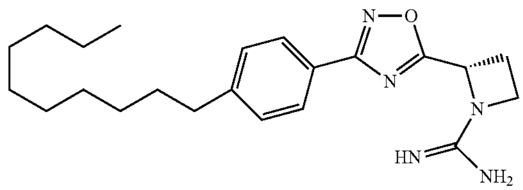 [SMILES: CCCCCCCCCCc1ccc(-c2noc([C@@H]3CCN3C(=N)N)n2)cc1] | (S)-2-(3-(4-decylphenyl)-1,2,4-oxadiazol-5-yl)azetidine-1-carboximidamide |
| 64 | 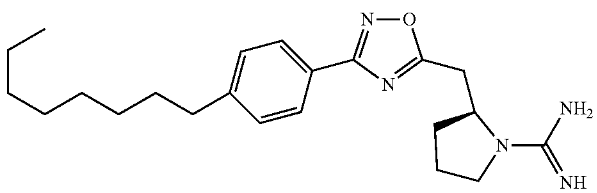 [SMILES: CCCCCCCCc1ccc(-c2noc(C[C@@H]3CCCN3C(=N)N)n2)cc1] | (S)-2-((3-(4-octylphenyl)-1,2,4-oxadiazol-5-yl)methyl)pyrrolidine-1-carboximidamide |
| 65 | 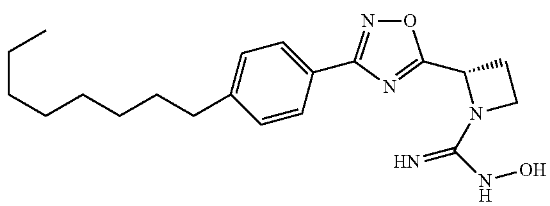 [SMILES: CCCCCCCCc1ccc(-c2noc([C@@H]3CCN3C(=N)NO)n2)cc1] | (S)-N-hydroxy-2-(3-(4-octylphenyl)-1,2,4-oxadiazol-5-yl)azetidine-1-carboximidamide |
| 66 | 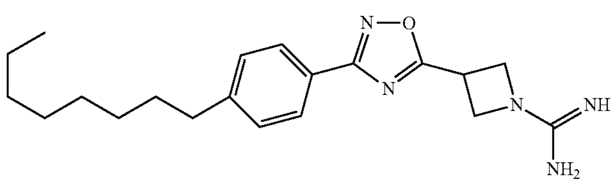 [SMILES: CCCCCCCCc1ccc(-c2noc(C3CN(C(=N)N)C3)n2)cc1] | 3-(3-(4-octylphenyl)-1,2,4-oxadiazol-5-yl)azetidine-1-carboximidamide |
| 67 | 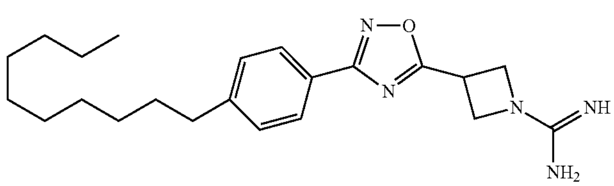 [SMILES: CCCCCCCCCCc1ccc(-c2noc(C3CN(C(=N)N)C3)n2)cc1] | 3-(3-(4-decylphenyl)-1,2,4-oxadiazol-5-yl)azetidine-1-carboximidamide |
| 68 | 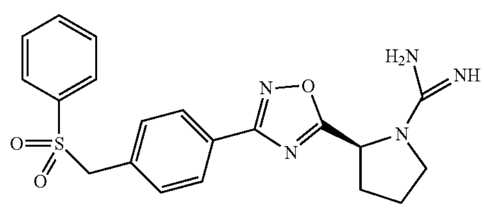 [SMILES: N=C(N)N1CCC[C@H]1c1nc(-c2ccc(CS(=O)(=O)c3ccccc3)cc2)no1] | (S)-2-(3-(4-((phenylsulfonyl)methyl)phenyl)-1,2,4-oxadiazol-5-yl)pyrrolidine-1-carboximidamide |
| 69 | 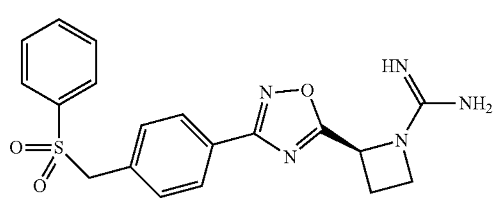 [SMILES: N=C(N)N1CC[C@H]1c1nc(-c2ccc(CS(=O)(=O)c3ccccc3)cc2)no1] | (S)-2-(3-(4-((phenylsulfonyl)methyl)phenyl)-1,2,4-oxadiazol-5-yl)azetidine-1-carboximidamide |

TABLE 1-continued

| Compound # | Structure | IUPAC name |
|---|---|---|
| 70 | 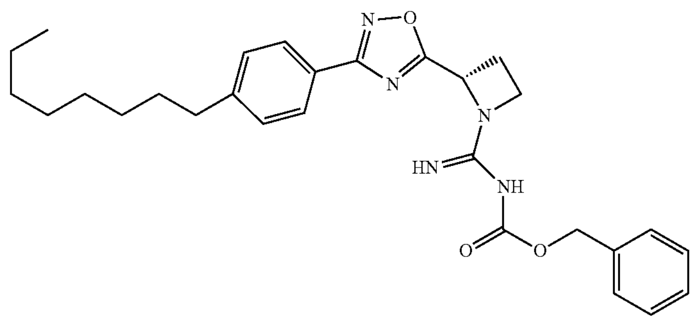 [SMILES: CCCCCCCCc1ccc(-c2noc([C@@H]3CCN3C(=N)NC(=O)OCc3ccccc3)n2)cc1] | (S)-benzyl (imino(2-(3-(4-octylphenyl)-1,2,4-oxadiazol-5-yl)azetidin-1-yl)methyl)carbamate |
| 71 | 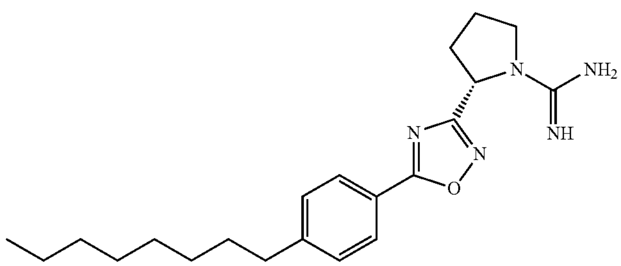 [SMILES: CCCCCCCCc1ccc(-c2nc([C@@H]3CCCN3C(=N)N)no2)cc1] | (S)-2-(5-(4-octylphenyl)-1,2,4-oxadiazol-3-yl)pyrrolidine-1-carboximidamide |
| 72 | 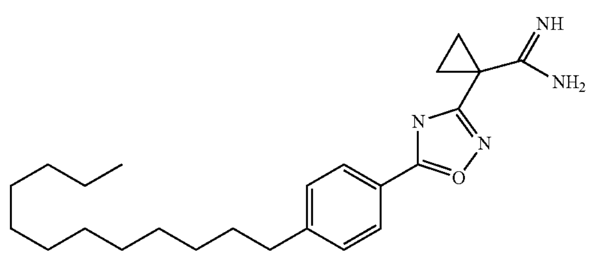 | 1-(5-(4-dodecylphenyl)-1,2,4-oxadiazol-3-yl)cyclopropanecarboximidamide |
| 73 | 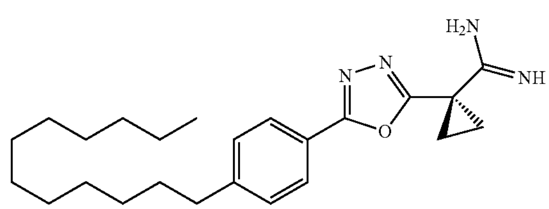 | 1-(5-(4-dodecylphenyl)-1,3,4-oxadiazol-2-yl)cyclopropanecarboximidamide |
| 74 | 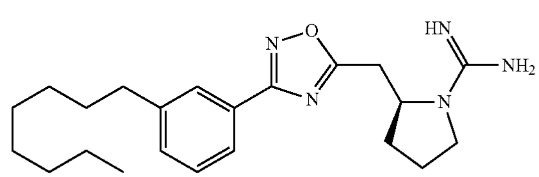 [SMILES: CCCCCCCCc1cccc(-c2noc(C[C@@H]3CCCN3C(=N)N)n2)c1] | (S)-2-((3-(3-octylphenyl)-1,2,4-oxadiazol-5-yl)methyl)pyrrolidine-1-carboximidamide |
| 75 | 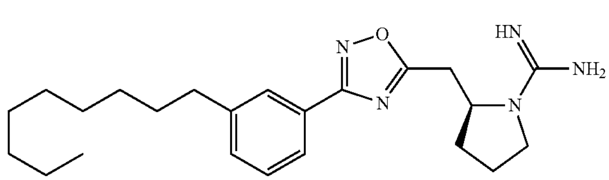 [SMILES: CCCCCCCCCc1cccc(-c2noc(C[C@@H]3CCCN3C(=N)N)n2)c1] | (S)-2-((3-(3-nonylphenyl)-1,2,4-oxadiazol-5-yl)methyl)pyrrolidine-1-carboximidamide |
| 76 | 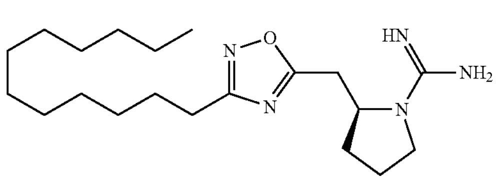 [SMILES: CCCCCCCCCCCCc1noc(C[C@@H]2CCCN2C(=N)N)n1] | (S)-2-((3-dodecyl-1,2,4-oxadiazol-5-yl)methyl)pyrrolidine-1-carboximidamide |

TABLE 1-continued

| Compound # | Structure | IUPAC name |
|---|---|---|
| 77 | 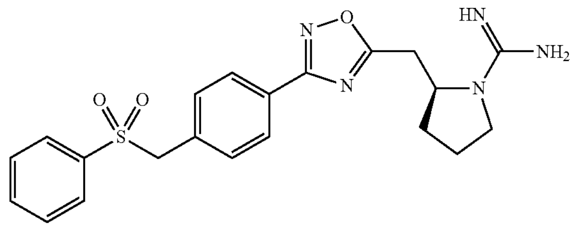 [SMILES: N=C(N)N1CCC[C@H]1Cc1nc(-c2ccc(CS(=O)(=O)c3ccccc3)cc2)no1] | (S)-2-((3-(4-((phenylsulfonyl)methyl)phenyl)-1,2,4-oxadiazol-5-yl)methyl)pyrrolidine-1-carboximidamide |
| 78 | 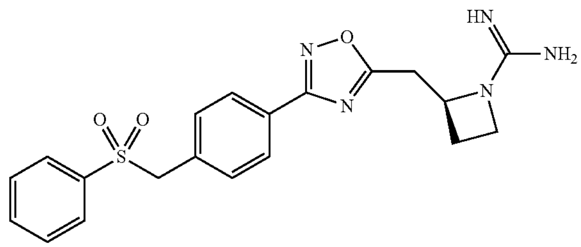 [SMILES: N=C(N)N1CC[C@H]1Cc1nc(-c2ccc(CS(=O)(=O)c3ccccc3)cc2)no1] | (S)-2-((3-(4-((phenylsulfonyl)methyl)phenyl)-1,2,4-oxadiazol-5-yl)methyl)azetidine-1-carboximidamide |
| 79 | 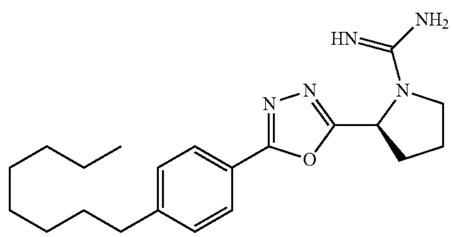 [SMILES: CCCCCCCCc1ccc(-c2nnc([C@@H]3CCCN3C(=N)N)o2)cc1] | (S)-2-(5-(4-octylphenyl)-1,3,4-oxadiazol-2-yl)pyrrolidine-1-carboximidamide |
| 80 | 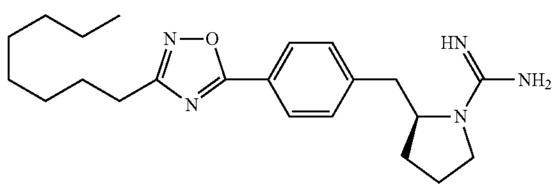 [SMILES: CCCCCCCCc1noc(-c2ccc(C[C@@H]3CCCN3C(=N)N)cc2)n1] | (S)-2-(4-(3-octyl-1,2,4-oxadiazol-5-yl)benzyl)pyrrolidine-1-carboximidamide |
| 81 | 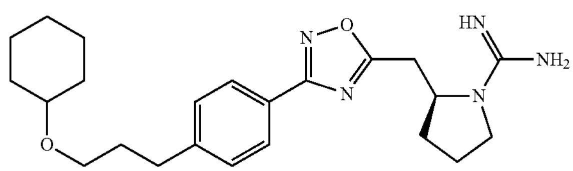 [SMILES: N=C(N)N1CCC[C@H]1Cc1nc(-c2ccc(CCCOC3CCCCC3)cc2)no1] | (S)-2-((3-(4-(3-(cyclohexyloxy)propyl)phenyl)-1,2,4-oxadiazol-5-yl)methyl)pyrrolidine-1-carboximidamide |
| 82 | 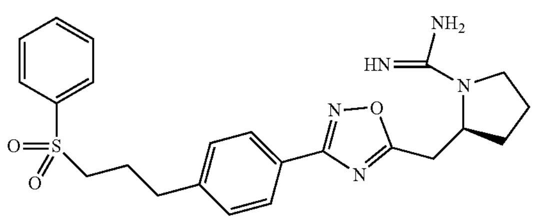 [SMILES: N=C(N)N1CCC[C@H]1Cc1nc(-c2ccc(CCCS(=O)(=O)c3ccccc3)cc2)no1] | (S)-2-((3-(4-(3-(phenylsulfonyl)propyl)phenyl)-1,2,4-oxadiazol-5-yl)methyl)pyrrolidine-1-carboximidamide |
| 83 | 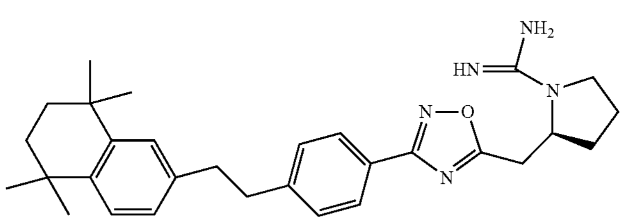 [SMILES: CC1(C)CCC(C)(C)c2cc(CCc3ccc(-c4noc(C[C@@H]5CCCN5C(=N)N)n4)cc3)ccc21] | (S)-2-((3-(4-(2-(5,5,8,8-tetramethyl-5,6,7,8-tetrahydronaphthalen-2-yl)ethyl)phenyl)-1,2,4-oxadiazol-5-yl)methyl)pyrrolidine-1-carboximidamide |

TABLE 1-continued

| Compound # | Structure | IUPAC name |
|---|---|---|
| 84 | 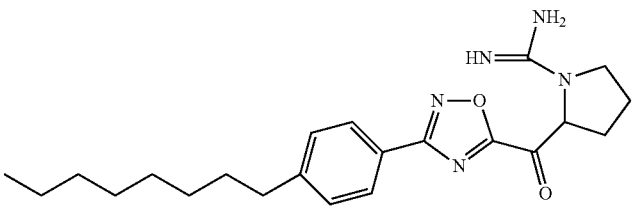 [SMILES: CCCCCCCCc1ccc(-c2noc(C(=O)C3CCCN3C(=N)N)n2)cc1] | 2-(3-(4-octylphenyl)-1,2,4-oxadiazole-5-carbonyl)pyrrolidine-1-carboximidamide |

In one aspect of the invention, the compounds of Formula I and methods of their use are directed to SphK enzyme inhibitors that have activity as selective inhibitors of the SphK1 enzyme or the SphK2 enzyme or have activity as inhibitors of both SphK1 and SphK2 enzymes.

In another aspect, the present invention provides a method for inhibiting angiogenesis in a tumor, including contacting cancerous cells with an effective amount of a compound of Formula I.

In another aspect, the present invention provides compositions and methods for the use of a compound of Formula I for the treatment of neoplastic disease. In one aspect, this treatment is effected by application of a compound of Formula I that are efficacious by virtue of their anti-angiogenic properties.

In another aspect, the present invention provides a method for preventing or treating diseases that involve excess vascular growth, e.g., retinal degenerative diseases such as macular degeneration or diabetic retinopathy, comprising contacting the affected area with an effective amount of a compound of Formula I. For example, the compound can be injected into the posterior eye in depot form.

In another aspect, the present invention provides compositions and methods for the use of a compound of formula I to prevent allergic disease for example asthma. In one aspect, the asthma could be due to over production of Th2 cytokines. In another aspect, the present invention includes a method for treating subjects suffering from an allergic disease (for example, asthma).

In another aspect, the invention provides a compound of Formula I for use in medical treatment for example treatment of inflammatory disease of the eye such as uveitis, scleritis, or vitritis.

In another aspect, the invention provides a compound of Formula I for use in medical treatment, for example, treatment of inflammatory kidney disease such as glomerulonephritis, glomerular injury, nephrotic syndrome, interstitial nephritis, lupus nephritis, Goodpasture's disease, Wegener's granulomatosis, renal vasculitis, IgA nephropathy, diabetic nephropathy, chronic allograft nephropathy and idiopathic glomerular disease.

In another aspect, the invention provides a compound of Formula I for use in medical treatment (for example, treatment of neoplastic disease).

In another aspect, the invention provides a compound of Formula I for use in medical treatment for example treatment of fibrotic disease such as pulmonary fibrosis, renal fibrosis, cardiac fibrosis, or hepatic fibrosis.

In another aspect, the invention provides a compound of Formula I for use in medical treatment of acute lung injury, sepsis, capillary leak syndrome, pneumonia, ischemia reperfusion injury, acute kidney injury, diabetic nephropathy, age-related macular degeneration, diabetic retinopathy, pulmonary fibrosis, or renal fibrosis.

In another aspect, the invention provides a compound of Formula I for use in enhancing the delivery of therapeutics by improving the integrity of vascular barriers (e.g., Blood Brain Barrier) in diseases where they are disrupted such as, but not limited to, cancer and Alzheimer's disease.

In various aspects, the invention provides a compound of Formula I for use in medical treatment wherein the treatment involves the regulation of endothelial cell barrier function as a result of the inhibition of SphK enzymatic activity by a compound of Formula I. For example, a compound of Formula I may be used to treat a disease or disorder that is associated with vascular leakage, such as acute lung injury, sepsis, capillary leak syndrome, pneumonia, ischemia reperfusion injury, acute kidney injury, diabetic nephropathy, age-related macular degeneration, diabetic retinopathy, pulmonary fibrosis, or renal fibrosis. Furthermore, a compound of Formula I that inhibits SphK2 enzymatic activity can improve the barrier function of endothelial cells by causing an increase in blood levels of S1P. In various embodiments of the invention, a compound of Formula I improves the barrier function of endothelial cells by selectively inhibiting SphK2. This improvement in endothelial cell barrier function by a compound of Formula I can also be achieved in the presence of increased levels of histamine and thrombin.

In another aspect, the invention provides a compound of Formula I for use in medical treatment for example treatment of autoimmune diseases such as multiple sclerosis, type I diabetes, inflammatory bowel diseases, Crohn's disease, ulcerative colitis, Grave's disease, Addison's disease, dermatomyositis, myasthenia gravis, systemic lupus erythematosus, scleroderma, or psoriasis.

In another aspect, the invention provides a method for the use of a compound of Formula I to prepare a medicament for inhibiting tumor growth, metastasis, or tumor angiogenesis. In another aspect, the invention provides a method for the use of a compound of Formula I to prepare a medicament for preventing or treating a fibrosis, sepsis, asthma, or an autoimmune disease in a mammalian species (for example, a human).

In another aspect, the invention provides a method for the use of a compound of Formula I for use in medical treatment of atherosclerosis.

In another aspect, the invention provides a method for the use of a compound of Formula I for use in medical treatment of hypertension for example treatment of pulmonary arterial hypertension.

The present invention also includes pharmaceutical compositions containing a compound of Formula I. More particularly, such compounds can be formulated as pharmaceutical compositions using standard pharmaceutically acceptable carriers, fillers, solubilizing agents, and stabilizers known to those skilled in the art. For example, a pharmaceutical composition including a compound of Formula I is used to administer the appropriate compound to a subject.

In another aspect, the invention provides novel intermediates and processes disclosed herein that are useful for preparing compounds of Formula I, including the generic and specific intermediates as well as the synthetic processes described herein.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

The details of one or more embodiments of the invention are set forth in the accompanying description below. Other features, objects, and advantages of the invention will be apparent from the description and drawings, and from the claims.

BRIEF DESCRIPTION OF THE TABLES

Figure 1:
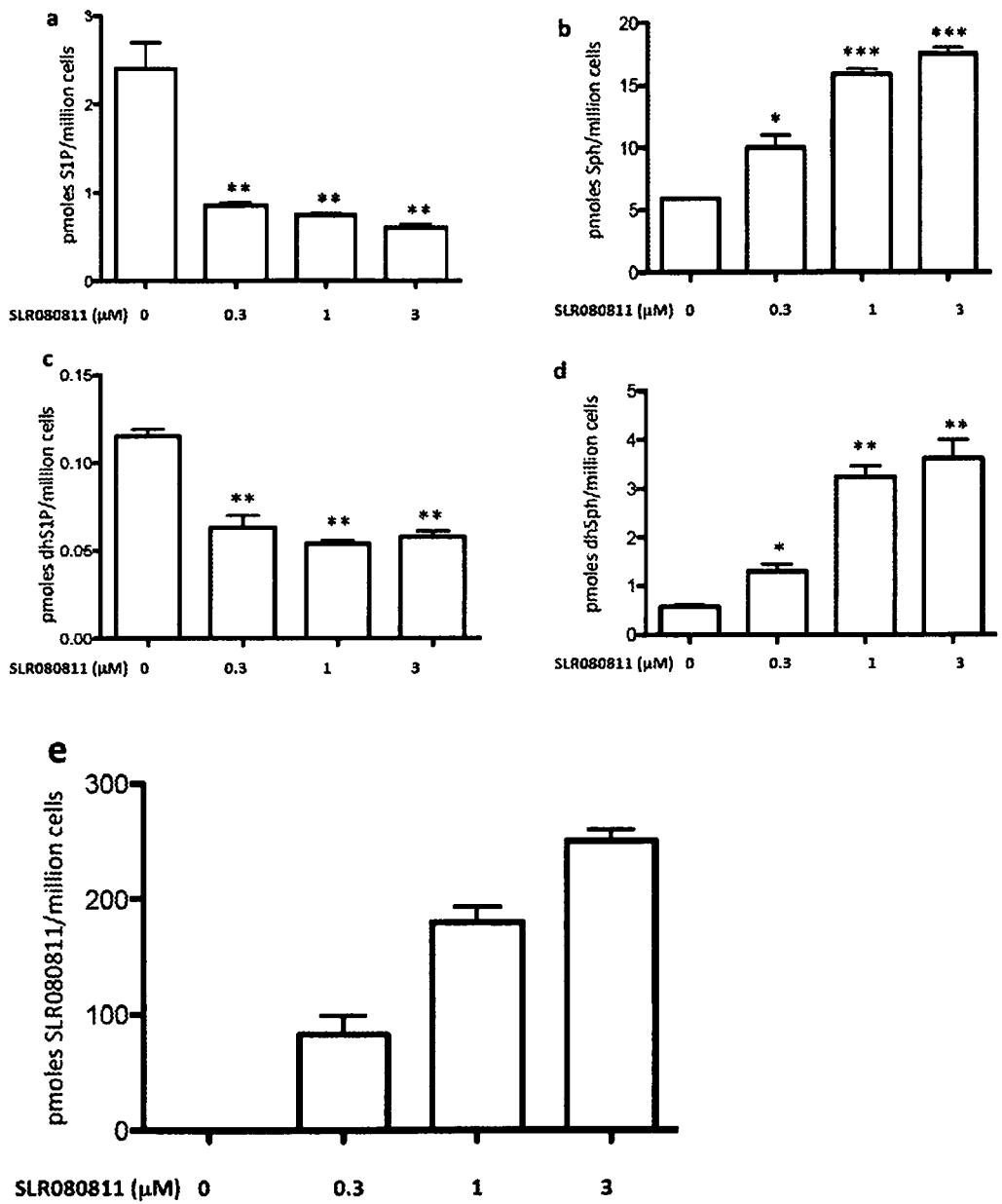
FIG. 1 exemplifies levels of sphingolipids and compound (S)-2-(3-(4-octylphenyl)-1,2,4-oxadiazol-5-YL)pyrrolidine-1-carboximidamide (SLR080811) in U937 treated with various concentrations of compound (S)-2-(3-(4-octylphenyl)-1,2,4-oxadiazol-5-YL)pyrrolidine-1-carboximidamide as indicated. After a 2 hour period of exposure, cells were harvested by centrifugation, lysed and the amounts of sphingolipids and (S)-2-(3-(4-octylphenyl)-1,2,4-oxadiazol-5-YL)pyrrolidine-1-carboximidamide in the lysates were measured by LC-MS as described in the Methods section. Amounts associated with cells are expressed as the number of pmoles per million cells. The graphs are: a: S1P, b: sphingosine, c: dihydroS1P, d: sphinganine, e: SLR080811. Data are presented as means±SD of three independent experiments. $*p<0.05$, $p<0.01$, $*p<0.001$ (one way ANOVA, and Bonferroni's Multiple Comparison Test, compared to vehicle alone).

Table 1 shows formulas of exemplary compounds of Formula I.

Table 2 includes the range of inhibitory constants ($K_I$) of test compounds determined at recombinant SphK1 and SphK2, all values in micromolar concentrations. ND not determined.

Table 3: Chemical structure and inhibitory constants of compounds (S)-2-(3-(4-octylphenyl)-1,2,4-oxadiazol-5-YL)pyrrolidine-1-carboximidamide (SLR080811) and 1a. The chemical structure of compounds (S)-2-(3-(4-octylphenyl)-

1,2,4-oxadiazol-5-YL)pyrrolidine-1-carboximidamide and 1a along with their inhibitory constants ($K_I$) for recombinant SphK1 and SphK2 are shown. Inhibitory constants were obtained by kinetic analysis of S1P production using variable concentrations of sphingosine and a fixed concentration of ATP in presence and absence of compounds. These compounds exhibit a pattern of competitive inhibition therefore KI's were calculated as $K_I=[I]/(Km'/Km-1)$, where [I] is the concentration of inhibitor, and Km' and Km are the Michaelis constants obtained in presence and absence of inhibitor. Measurements were carried out using [33P]-ATP as a tracer and a microplate-based scintillation proximity assay for the detection of [33P]-S1P as previously described. See Kharel, Y., Mathews, T. P., Kennedy, A. J., Macdonald, T. L. and Lynch, K. R. (2011) A rapid assay for assessment of sphingosine kinase inhibitors and substrates. Anal. Biochem. 411, 230-235, the disclosure of which is incorporated herein.

DETAILED DESCRIPTION

The following abbreviations are used: sphingosine kinase ("SphK"); sphingosine kinase type 1 ("SphK1"); sphingosine kinase type 2 ("SphK2"); sphingosine ("Sph"); sphingosine 1-phosphate ("S1P"); sphinganine ("dhSph" or "H2Sph"); sphinganine 1-phosphate ("dhS1P" or "H2S1P").

In describing and claiming the invention, unless otherwise defined, all technical and scientific terms used have the same meaning as commonly understood by one of ordinary skill in the art to which this invention belongs. Although any materials and methods similar or equivalent to those described here can be used in the practice or testing of the present invention, the preferred materials and methods are described below. Each of the following terms has meaning associated with it in this section. Exemplary and preferred values listed below for radicals, substituents, and ranges are for illustration purposes only; they do not exclude other defined values or other values within defined ranges for the radicals and substituents.

The terms "a," "an," "the," "at least one," and "one or more" are used interchangeably. Thus, for example, a composition that comprises "an" element means one element or more than one element.

The term "affected cell" refers to a cell of a subject afflicted with a disease or disorder, which affected cell has an altered phenotype relative to a subject not afflicted with a disease or disorder.

Cells or tissue are "affected" by a disease or disorder if the cells or tissue have an altered phenotype relative to the same cells or tissue in a subject not afflicted with a disease or disorder.

A disease or disorder is "alleviated" if the severity of a symptom of the disease or disorder, the frequency with which such a symptom is experienced by a patient, or both, is reduced.

The terms "cell," "cell line," and "cell culture" may be used interchangeably.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue is obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

A "detectable marker" or a "reporter molecule" is an atom or a molecule that permits the specific detection of a compound having the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "autoimmune disease" is a disease or disorder arising from and directed against an individual's own tissues. Examples of autoimmune diseases or disorders include, but are not limited to arthritis (rheumatoid arthritis, juvenile rheumatoid arthritis, osteoarthritis, psoriatic arthritis), Caplan's Syndrome, Felty's Syndrome, psoriasis, dermatitis, Sjorgren's Syndrome, Still's Disease, polymyositis/dermatomyositis, toxic epidermal necrolysis, systemic scleroderma and sclerosis, responses associated with inflammatory bowel disease, Crohn's disease, ulcerative colitis, respiratory distress syndrome, adult respiratory distress syndrome (ARDS), meningitis, encephalitis, uveitis, colitis, glomerulonephritis, allergic conditions, eczema, asthma, conditions involving infiltration of T cells and chronic inflammatory responses, atherosclerosis, autoimmune myocarditis, leukocyte adhesion deficiency, systemic lupus erythematosus (SLE), juvenile onset diabetes, multiple sclerosis, allergic encephalomyelitis, immune responses associated with acute and delayed hypersensitivity mediated by cytokines and T-lymphocytes, tuberculosis, sarcoidosis, granulomatosis including Wegener's granulomatosis, agranulocytosis, vasculitis (including ANCA), aplastic anemia, Diamond Blackfan anemia, immune hemolytic anemia including autoimmune hemolytic anemia (MBA), pernicious anemia, pure red cell aplasia (PRCA), Factor VIII deficiency, hemophilia A, autoimmune neutropenia, pancytopenia, leukopenia, diseases involving leukocyte diapedesis, central nervous system (CNS) inflammatory disorders, multiple organ injury syndrome, mysathenia gravis, antigen-antibody complex mediated diseases, anti-glomerular basement membrane disease, anti-phospholipid antibody syndrome, allergic neuritis, Bechet disease, Castleman's syndrome, Goodpasture's syndrome; Lambert-Eaton Myasthenic Syndrome, Reynaud's syndrome, Sjorgen's syndrome, Stevens-Johnson syndrome, solid organ transplant rejection, graft versus host disease (GVHD), pemphigoid bullous, pemphigus, autoimmune polyendocrinopathies, Reiter's disease, stiff-man syndrome, giant cell arteritis, immune complex nephritis, IgA nephropathy, IgM polyneuropathies or IgM mediated neuropathy, idiopathic thrombocytopenic purpura (ITP), thrombotic throbocytopenic purpura (TTP), autoimmune thrombocytopenia, autoimmune disease of the testis and ovary including autoimmune orchitis and oophoritis, primary hypothyroidism; autoimmune endocrine diseases including autoimmune thyroiditis, chronic thyroiditis (Hashimoto's Thyroiditis), subacute thyroiditis, idiopathic hypothyroidism, Addison's disease, Grave's disease, autoimmune polyglandular syndromes (or polyglandular endocrinopathy syndromes), Type I diabetes also referred to as insulin-dependent diabetes mellitus (IDDM) and Sheehan's syndrome; autoimmune hepatitis, lymphoid interstitial pneumonitis (HIV), bronchiolitis obliterans (non-transplant) vs NSIP, Guillain-Barre' syndrome, large vessel vasculitis (including polymyalgia rheumatica and giant cell (Takayasu's) arteritis), medium vessel vasculitis (including Kawasaki's disease and polyarteritis nodosa), ankylosing spondylitis, Berger's disease (IgA nephropathy), rapidly progressive glomerulonephritis, primary biliary cirrhosis, Celiac sprue (gluten enteropathy), cryoglobulinemia, amyotrophic lateral sclerosis (ALS), coronary artery disease etc.

An "inflammatory disease" may be any autoimmune disease, as well as include, but not be limited to: ulcerative colitis, and Crohn's disease; cardiovascular diseases such as ischemic cardiac disease and heart failure; cerebrovascular diseases; kidney diseases, including glomerulonephritis, glomerular injury, nephrotic syndrome, interstitial nephritis, lupus nephritis, Goodpasture's disease, Wegener's granulomatosis, renal vasculitis, IgA nephropathy and idiopathic glomerular disease; diabetes; diabetes complications such as retinopathy, nephropathy, nerve disease, and coronary arterial disease; skin diseases, including allergic skin disease, psoriasis, atopic dermatitis, contact sensitivity and acne; obesity; nephritis; hepatitis; cancer; Alzheimer's disease; inflammatory diseases that are caused by inflammatory cytokines; skin diseases such as allergic skin diseases; chondrocalcinosis; gout; rheumatic fever and Reiter's Disease.

The term "Immune cell(s)" include, but are not limited to, lymphocytes, (including CD4+ T cells, CD8+ T cells, Natural Killer T cells, and B cells), mast cells, basophils, macrophaged, dendritic cells, monocytes, eosinophils, neutrophils, or any other cell type that functions within the immune system.

"Vascular permeability" refers to the capacity of small molecules (e.g., ions, water, nutrients), large molecules (e.g., proteins and nucleic acids) or even whole cells (lymphocytes on their way to the site of inflammation) to pass through a blood vessel wall. Diseases and disorders characterized by undesirable vascular permeability include, for example, edema associated with brain tumors, ascites associated with malignancies, Meigs' syndrome, lung inflammation, nephrotic syndrome, pericardial effusion and pleural effusion.

A "functional" molecule is a molecule in a form in which it exhibits a property by which it is characterized. By way of example, a functional enzyme is one that exhibits the characteristic catalytic activity by which the enzyme is characterized.

The term "inhibit" refers to the ability of a disclosed compound to reduce or impede a described function. Inhibition is by at least 10%, preferably by at least 25%, more preferably by at least 50%, even more preferably by at least 75%, and most preferably, the function is inhibited by at least 95%.

The term "selective" refers to the ability of the disclosed compounds to inhibit one of the sphingosine kinase 1 or sphingosine kinase 2 (SphK1 & SphK2) enzymes and not the other enzyme. Preferably, the selective compound will have a $K_I$ value for one enzyme that is less than, by at least an order of magnitude (e.g., a ten-fold difference), the $K_I$ value for the other enzyme or in inhibition of one of the SphK enzymes over the other enzyme.

An "effective amount" means an amount sufficient to produce a selected effect. For example, an effective amount of a sphingosine kinase 1 or sphingosine kinase 2 (SphK1 & SphK2) inhibitor is an amount that inhibits substrate (sphingosine) binding of the sphingosine kinases and thereby the conversion of sphingosine to S1P and sphinganine to dhS1P.

The term "instructional material" includes a publication, a recording, a diagram, or any other medium of expression that can be used to communicate the usefulness of the disclosed compounds in the kit for effecting alleviation of the various diseases or disorders recited herein. Optionally, or alternately, the instructional material may describe one or more methods of alleviating the diseases or disorders in a cell or a tissue of a mammal. The instructional material of the kit may, for example, be affixed to a container that contains a disclosed compound or be shipped together with a container which contains the identified compound. Alternatively, the instructional material may be shipped separately from the container with the intention that the instructional material and the compound be used cooperatively by the recipient.

The term "parenteral" means not through the alimentary canal but by some other route such as subcutaneous, intramuscular, intraspinal, or intravenous.

The term "purified" and similar terms relate to the isolation of a molecule or compound in a form that is substantially free (at least 75% free, preferably 90% free, and most preferably at least 95% free) from other components normally associated with the molecule or compound in a native environment. The term "purified" does not necessarily indicate that complete purity of the particular molecules achieved during the process. A "very pure" compound refers to a compound that is greater than 90% pure. A "highly purified" compound refers to a compound that is greater than 95% pure.

A "sample" refers preferably to a biological sample from a subject, including, but not limited to, normal tissue samples, diseased tissue samples, biopsies, blood, saliva, feces, semen, tears, and urine. A sample can also be any other source of material obtained from a subject, which contains cells, tissues, or fluid of interest. A sample can also be obtained from cell or tissue culture.

The term "standard" refers to something used for comparison. For example, a standard can be a known standard agent or compound that is administered or added to a control sample and used for comparing results when measuring said compound in a test sample. Standard can also refer to an "internal standard," such as an agent or compound which is added at known amounts to a sample and is useful in determining such things as purification or recovery rates when a sample is processed or subjected to purification or extraction procedures before a marker of interest is measured.

A "subject" of analysis, diagnosis, or treatment is an animal. Such animals include mammals, preferably is a human.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The term "treating" includes prophylaxis of the specific disorder or condition, or alleviation of the symptoms associated with a specific disorder or condition or preventing or eliminating said symptoms.

The disclosed compounds are generally named according to the IUPAC or CAS nomenclature system. Abbreviations that are well known to one of ordinary skill in the art may be used (e.g., "Ph" for phenyl, "Me" for methyl, "Et" for ethyl, "h" for hour or hours, "r.t." for room temperature, "THF" for tetrahydrofuran, and "rac" for racemic mixture).

The values listed below for radicals, substituents, and ranges, are for illustration purposes only; they do not exclude other defined values or other values within defined ranges for the radicals and substituents. The disclosed compounds include compounds of Formula I having any combination of the exemplary values, preferred values, and more preferred values described herein.

The number of carbon atoms in a hydrocarbyl moiety can be indicated by the prefix "$(C_x\text{-}C_y)$," where x is the minimum and y is the maximum number of carbon atoms in the moiety(ies). Thus, for example, "$(C_1\text{-}C_6)$alkyl" refers to an alkyl substituent containing from 1 to 6 carbon atoms. Illustrating further, $(C_3\text{-}C_6)$cycloalkyl means a saturated hydrocarbyl ring containing from 3 to 6 carbon ring atoms. A single prefix attached to a multiple-component substituent applies to all of the components that follow the prefix. To illustrate, the term "arylalkyl" contains two components: aryl and alkyl. Thus, for example, $(C_6\text{-}C_{20})$arylalkyl means that the total number of carbon atoms for both the aryl and alkyl substituents ranges from 6 to 20 carbon atoms. In other words, you may have, for example, a 6 carbon aryl group appended to a 14 carbon alkyl group, or, for example, a 10 carbon aryl group appended to a 10 carbon alkyl group. In the case of multiple prefixes attached to a multiple-component substituent, each prefix applies to the component(s) that follow the prefix. To illustrate, the term "heteroarylalkyl" contains two components: heteroaryl and alkyl. Thus, for example, $(C_4\text{-}C_{10})$heteroaryl$(C_1\text{-}C_{16})$alkyl refers to a heteroaryl group containing 4 to 10 carbon atoms appended to an alkyl group containing 1 to 16 carbon atoms.

When a chemical formula is used to describe a moiety, the dash(s) indicates the portion of the moiety that has the free valence(s). If no dash(s) is included for a multiple-component substituent, the moiety is appended to the parent molecular moiety through the first listed component. For example, an arylalkyl substituent is appended to a parent molecule through the aryl group, whereas an alkylaryl substituent is appended to a parent molecule through the alkyl group.

The term "halogen" or "halo" includes bromo, chloro, fluoro, and iodo. The prefix "halo" indicates that the substituent to which the prefix is attached is substituted with one or more independently selected halogen radicals. For example, the term "haloalkyl" refers to an alkyl radical bearing at least one halogen substituent, non-limiting examples include, but are not limited to, chloromethyl, fluoroethyl, trifluoromethyl, and the like.

The term "alkyl" refers to a branched or linear hydrocarbyl group. Non-limiting examples include, but are not limited to, methyl, ethyl, n-propyl, iso-propyl, butyl, iso-butyl, sec-butyl, tert-butyl, pentyl, hexyl, heptyl, octyl, and the like. The term "alkenyl" refers to an olefinically unsaturated branched or linear hydrocarbyl group having at least one double bond. Typically, alkenyl groups refer to ethylenically unsaturated groups which may be linear or have branches and which include, but are not limited to, 1-propenyl, 2-propenyl, 1,3-butadienyl, 1-butenyl, pentenyl, hexenyl, heptenyl, octenyl, and the like. The term "alkynyl" refers to hydrocarbyl groups having at least one carbon-carbon triple bond, which group may be linear or branched and which include, but are not limited to, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and the like. The term "alkoxy" refers to an alkyl group, such as described above, attached through an oxygen atom. Examples of alkoxy can be methoxy, ethoxy, propoxy, isopropoxy, butoxy, iso-butoxy, sec-butoxy, pentoxy, 3-pentoxy, hexyloxy, heptoxy, octoxy, and the like. The term "alkoxyalkyl" can be methoxy methyl, methoxy ethyl, ethoxy methyl, ethoxy ethyl, and the like.

The term "cycloalkyl" includes groups having one ring or multiple rings. Non-limiting examples include be cyclopropyl, cyclobutyl, cyclopentyl, cyclohexyl, cycloheptyl, cyclooctyl, adamantyl, and the like.

Unless otherwise specified, the term "optionally substituted" refers to zero, one, two, three, four, five, six, seven, or more substituents, wherein the substituents are each independently selected. Each of the independently selected substituents may be the same or different than other substituents. Non-limiting examples of such substituents include halo, halo($C_1\text{-}C_{10}$)alkyl, OH, cyano, amino (—NR$^a$R$^b$), ($C_1\text{-}C_6$)alkyl, ($C_1\text{-}C_{20}$)alkoxy, ($C_2\text{-}C_{26}$)alkoxyalkyl, ($C_3\text{-}C_{12}$)cycloalkyl, ($C_6\text{-}C_{10}$)aryl, ($C_7\text{-}C_{30}$)alkylaryl, ($C_2\text{-}C_{10}$)heterocyclic, or ($C_4\text{-}C_{10}$)-heteroaryl; wherein one or more of the carbon atoms in the alkyl groups can be independently replaced with non-peroxide oxygen, sulfur, or NR$^c$; where each R$^a$, R$^b$, or R$^c$ is independently hydrogen or ($C_1\text{-}C_7$)alkyl.

The term "ring" refers to a cyclic structure of its constituent atoms. Ring sizes may vary, but typically range from 3 to 8 atoms.

The term "aryl" refers to a mono or bicyclic carbocyclic ring system having one or two aromatic rings including, but not limited to, phenyl, benzyl, benzimidazole, naphthyl, tetrahydronaphthyl, indanyl, indenyl, and the like.

The term "optionally substituted aryl" includes aryl compounds having zero, one, two, three, or four substituents, and a substituted aryl includes aryl compounds having one, two, three, or four substituents, wherein the substituents include groups such as, for example, alkyl, halo, amino, or those substituents listed herein.

The term "arylalkyl" "alkylaryl," or "aralkyl" refers to an alkyl group substituted and/or linked with at least one mono or bicyclic carbocyclic ring system having one or two aromatic rings including, but not limited to, a group such as phenyl, naphthyl, tetrahydronaphthyl, indanyl, indenyl, and the like. Non-limiting examples of arylalkyl and alkylaryl include benzyl, phenyl ethyl, and the like. The term "alkoxyaryl" can be methoxy phenyl, ethoxy phenyl, propoxy naphthyl, isopropoxy naphthyl, and the like. The term "alkoxycycloalkyl" can be methoxy cyclopropyl, ethoxy cyclopropyl, propoxy cyclobutyl, isopropoxy cyclobutyl, and the like. The term "acylarylalkyl" can be —C(O)-phenyl-methyl, —C(O)-phenyl-ethyl, and the like.

The term "heterocycle" or "heterocyclic group" refers to an optionally substituted mono- or bicyclic carbocyclic ring system containing one, two, three, or more heteroatoms (optionally in each ring) wherein the heteroatoms are non-peroxide oxygen, sulfur, and nitrogen (e.g., $NR^c$).

The term "heteroaryl" refers to an optionally substituted mono- or bicyclic carbocyclic ring system containing one, two, or three heteroatoms (optionally in each ring) wherein the heteroatoms are non-peroxide oxygen, sulfur, and nitrogen (e.g., $NR^c$). Non-limiting examples of heteroaryl groups include furyl, oxadiazolyl, thienyl, pyridyl, and the like. The term "heteroarylalkyl" can be furyl methyl, oxadiazolyl methyl, furyl ethyl, oxadiazolyl ethyl, and the like.

The term "bicyclic" represents either an unsaturated or saturated stable bridged or fused bicyclic carbon ring. The bicyclic ring may be attached at any carbon atom that affords a stable structure. Typically, a bicyclic ring system can have from about 7 to about 12 atoms in the ring system. The term includes, but is not limited to, naphthyl, dicyclohexyl, dicyclohexenyl, and the like.

The term "absent" means that the referenced variable/substituent may not be present in the structure. For example, if W is "absent" in Formula I, then W is not present in that particular structure of Formula I. In some situations, if a particular variable/substituent is "absent" in Formula I, a double bond or a triple bond may be present in that particular structure of Formula I. For example, if W and X are present and are —$C(R^8R^9)$— and —$C(R^{14}R^{15})$—, respectively, and $R^8$ and $R^{14}$, for example, are "absent," then a double bond exists between W and X (i.e., —$C(R^9)$=$C(R^{14})$—).

The proviso that "the atoms represented by V, W, X, Y, and Z in Formula I need not be directly connected by a single bond but may be connected via any of the atoms in the ring structures described for V, W, X, and Y" means that should any of V, W, X, and Y in Formula I form a ring structure with an adjacent atom or form its own ring structure than that ring structure(s) may be connected to any adjacent moieties within Formula I via any atom within that ring structure(s). By way of illustration, if V is $NR^6$ and W is $CR^8R^9$, then $R^6$ and $R^8$, together with the atoms to which they are attached, may optionally form a ring. That V-W ring, therefore, may have, for example, the following generic and exemplary structure:

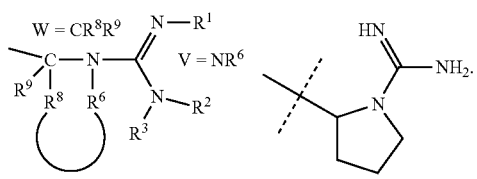

See, e.g., Compound 64. In another illustration of this proviso, if Y is $CR^{14}R^{15}$, then $R^{14}$ and $R^{15}$, together with the atoms to which they are attached, may form, for example, an aryl ring optionally substituted with at least one heteroatom selected from O, S, N, or $NR^{17}$. That Y ring, therefore, may have, for example, the following generic and exemplary structure:

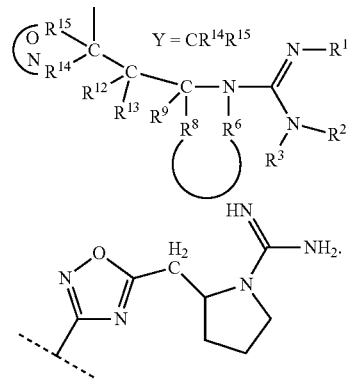

See, e.g.,

The term "pharmaceutically acceptable carrier" includes any of the standard pharmaceutical carriers, such as a phosphate buffered saline solution, hydroxypropyl beta-cyclodextrins (HO-propyl beta cyclodextrins), water, emulsions such as an oil/water or water/oil emulsion, and various types of wetting agents. The term also encompasses any of the agents approved by a regulatory agency of the U.S. Federal government or listed in the US Pharmacopeia for use in animals, including humans.

The term "pharmaceutically-acceptable salt" refers to salts which retain the biological effectiveness and properties of the disclosed compounds and which are not biologically or otherwise undesirable. In many cases, the disclosed compounds are capable of forming acid- or base-addition salts by virtue of the presence of amino or carboxyl groups or groups similar thereto. Such salts include as one example, but are not limited to, acid-addition salts from acids having the formula HA, where A is comprised of the group chloride, bromide, sulfate, acetate, benzoate, and tartrate.

The term "prodrug" refers to derivatives of the compounds of the invention which have chemically or metabolically cleavable groups and become, under physiological conditions, the compounds of the invention which are pharmaceutically active in vivo. Further, the prodrug is converted in both sufficient amounts and in a time frame that allows the active compound of the invention to accumulate in sufficient amounts to provide an efficacious effect. A prodrug of a compound may be formed in a conventional manner by reaction of a functional group of the compound (such as an amino, hydroxy or carboxy group). Prodrugs often offer advantages of solubility, tissue compatibility, or delayed release in mammals. Prodrugs include acid derivatives well known to practitioners of the art, such as, for example, esters prepared by reaction of the parent acidic compound with a suitable alcohol, or amides prepared by reaction of the parent acid compound with a suitable amine. Examples of prodrugs include, but are not limited to, acetate, formate, benzoate, carbamate, or other acylated derivatives of alcohol or amine functional groups within the compounds of the invention.

The disclosed compounds may exist in tautomeric forms and the invention includes both mixtures and separate individual tautomers. For example, the following structure:

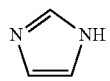

is understood to represent a mixture of the structures:

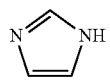

as well as

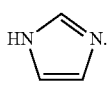

The terms 16:0, 18:0, 18:1, 20:4, or 22:6 hydrocarbon refers to a branched or straight alkyl or alkenyl group, wherein the first integer represents the total number of carbons in the group and the second integer represent the number of double bonds in the group.

The disclosed compounds can contain one or more asymmetric centers in the molecule. In accordance with the present disclosure, any structure that does not designate the stereochemistry is to be understood as embracing all the various optical isomers, as well as racemic mixtures thereof.

It will be appreciated by those skilled in the art that the disclosed compounds having chiral centers may exist, and be isolated, in optically active and racemic forms. It is to be understood that the disclosed compounds encompass any racemic; optically active or stereoisomeric form, or mixtures thereof, of the compound, which possess the useful properties described herein, such as the S,R; S,S; R,R; or R,S diastereomers. It is well known in the art how to prepare such optically active forms (for example, resolution of the racemic form by recrystallization techniques, synthesis from optically-active starting materials, chiral synthesis, or by chromatographic separation using a chiral stationary phase) and how to determine sphingosine kinase activity using the standard tests described herein, or using other similar tests which are well known in the art. In addition, some compounds may exhibit polymorphism.

Potential uses of the SphK inhibitors of the invention include, but are not limited to, anti-angiogenesis, treating neoplastic disease, treating autoimmune disorders, treating disease characterized by inflammation, treating diseases characterized by fibrosis, and treating vascular injury, such as acute lung injury, sepsis, capillary and vascular leak syndromes, pneumonia, ischemia reperfusion injury, acute kidney injury, as well as enhancing the delivery of therapeutics by improving the integrity of vascular barriers (e.g., Blood Brain Barrier) in diseases where they are disrupted such as, but not limited to cancer and Alzheimer's disease. In various embodiments of the invention, the method of treating any of the foregoing conditions may include administration of an antagonist of any one, or combination thereof, of S1P(1), S1P(2), S1P(3), S1P(4), and S1P(5).

As stated above, the SphK inhibitors of the invention may be used to treat autoimmune and inflammatory conditions, i.e., immunomodulate components of the immune system. As such, in various embodiments of the invention, the SphK inhibitors of the invention may affect the cell signaling events associated with, but not limited to, the following interleukins, cytokines, and immunomodulators: a) members of the interleukin-1 (IL-1) family; b) interleukin 2 (IL-2); c) interleukin 4 (IL-4); d) interleukin 5 (IL-5); e) interleukin-6 (IL-6); f) interleukin-12 (IL-12); g) interleukin 13 (IL-13); h) interleukin-23 (IL-23); i) tumor necrosis factor (TNF) alpha; and j) interferon gamma. For example, a SphK inhibitor of the invention may be used to treat a disease that is at least in part characterized by the overexpression or undesirable cell-signaling activities mediated by any of the above factors. Thus, in various embodiments, the presently disclosed subject matter provides a method for preventing, treating, managing, and/or ameliorating an autoimmune or inflammatory disorder or one or more symptoms thereof, said method comprising administering to a subject in need thereof a prophylactically and/or therapeutically effective amount of a compound of the presently disclosed subject matter and a prophylactically or therapeutically effective amount of one or more immunomodulatory agents.

The compounds of Formula I are also useful for the treatment of diseases or disorders that are associated with excessive vascular permeability. Thus, provided herein is a method of treating or preventing these or any other disease associated with an increase in vascular permeability or edema. For example, inhibiting edema formation should be beneficial to overall patient outcome in situations such as inflammation, allergic diseases, cancer, cerebral stroke, myocardial infarction, pulmonary and cardiac insufficiency, renal failure, and retinopathies, to name a few. Furthermore, as edema is a general consequence of tissue hypoxia, it can also be concluded that inhibition of vascular leakage represents a potential approach to the treatment of tissue hypoxia. For example, interruption of blood flow by pathologic conditions (such as thrombus formation) or medical intervention (such as cardioplegia, organ transplantation, and angioplasty) could be treated both acutely and prophylactically using inhibitors of vascular leakage.

Ischemia/reperfusion injury following stroke and myocardial infarction is also characterized by vascular permeability and edema. A deficit in tissue perfusion leads to persistent post-ischemic vasogenic edema, which develops as a result of increased vascular permeability. Tissue perfusion is a measure of oxygenated blood reaching the given tissue due to the patency of an artery and the flow of blood in an artery. Tissue vascularization may be disrupted due to blockage, or alternatively, it may result from the loss of blood flow resulting from blood vessel leakage or hemorrhage upstream of the affected site. The deficit in tissue perfusion during acute myocardial infarction, cerebral stroke, surgical revascularization procedures, and other conditions in which tissue vascularization has been disrupted, is a crucial factor in outcome of the patient's condition. Edema can cause various types of damage including vessel collapse and impaired electrical function, particularly in the heart. Subsequent reperfusion, however, can also cause similar damage in some patients, leading to a treatment paradox. While it is necessary, to unblock an occluded blood vessel or to repair or replace a damaged blood vessel, the ensuing reperfusion can, in some cases, lead to further damage. Likewise, during bypass surgery, it is necessary to stop the heart from beating and to have the patient hooked to a heart pump. Some patients who undergo bypass surgery, for example, may actually experience a worsening of condition ("post-pump syndrome"), which may be the result of ischemia during cessation of cardiac function during surgery. An arterial blockage may cause a reduction in the flow of blood, but even after the blockage is removed and the artery is opened, if tissue reperfusion fails to occur, further tissue damage may result. For example, disruption of a clot may trigger a chain of events leading to loss of tissue perfusion, rather than a gain of perfusion.

Additional diseases and disorders characterized by undesirable vascular permeability include, for example, infectious and non-infectious diseases that may result in a cytokine storm. A cytokine storm can be precipitated by a number of infectious and non-infectious diseases including, for example, graft versus host disease (GVHD), adult respiratory distress syndrome (ARDS), sepsis, avian influenza, smallpox, and systemic inflammatory response syndrome (SIRS).

When administering the compound of Formula I for treating a disease or disorder, including administering to a subject in need thereof a therapeutically acceptable amount of a compound of Formula I, or a pharmaceutical composition comprising a therapeutically effective amount of a compound of Formula I, and a pharmaceutically-acceptable carrier.

Table 2 includes: Range of inhibitory constants ($K_I$) of test compounds determined at recombinant SphK1 and SphK2, all values in micromolar concentrations. n.d. not determined.

TABLE 2

| Compound # | Structure | IUPAC name | SphK1 | SphK2 |
|---|---|---|---|---|
| 1 | 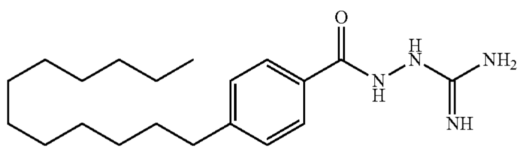 [SMILES: CCCCCCCCCCCCc1ccc(C(=O)NNC(=N)N)cc1] | 2-(4-dodecylbenzoyl)hydrazine carboximidamide | C | C |
| 2 | 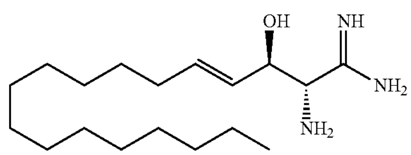 [SMILES: CCCCCCCCCCCCC/C=C/[C@@H](O)[C@@H](N)C(=N)N] | (2S,3R,E)-2-amino-3-hydroxyoctadec-4-enimidamide | C | C |
| 3 | 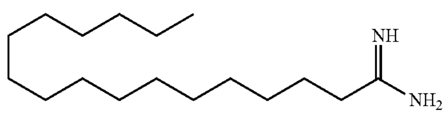 [SMILES: CCCCCCCCCCCCCCCCC(=N)N] | heptadecanimidamide | B | B |
| 4 | 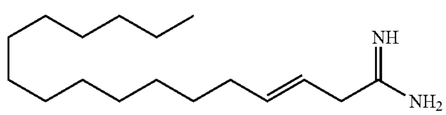 [SMILES: CCCCCCCCCCCCC/C=C/CC(=N)N] | (E)-heptadec-3-enimidamide | C | C |
| 5 | 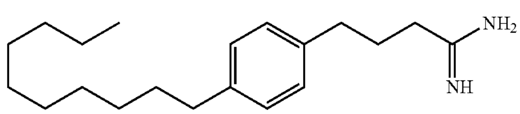 [SMILES: CCCCCCCCCCc1ccc(CCCC(=N)N)cc1] | 4-(4-decylphenyl)butanimidamide | C | C |
| 6 | 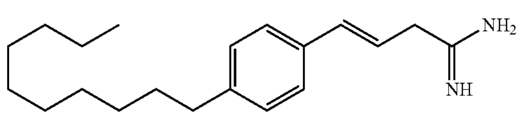 [SMILES: CCCCCCCCCCc1ccc(/C=C/CC(=N)N)cc1] | (E)-4-(4-decylphenyl)but-3-enimidamide | C | C |
| 7 | 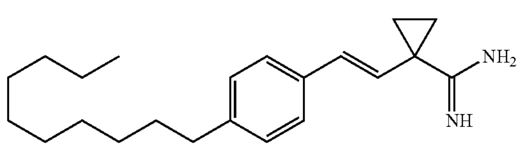 [SMILES: CCCCCCCCCCc1ccc(/C=C/C2(C(=N)N)CC2)cc1] | (E)-1-(4-decylstyryl)cyclopropanecarboximidamide | C | C |
| 8 | 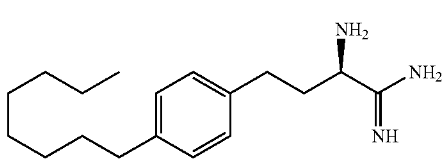 [SMILES: CCCCCCCCc1ccc(CC[C@@H](N)C(=N)N)cc1] | (R)-2-amino-4-(4-octylphenyl)butanimidamide | C | C |

TABLE 2-continued

| Compound # | Structure | IUPAC name | SphK1 | SphK2 |
|---|---|---|---|---|
| 9 | 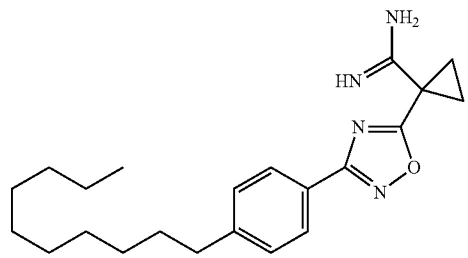 [SMILES: CCCCCCCCCCc1ccc(-c2noc(C3(C(=N)N)CC3)n2)cc1] | 1-(3-(4-decylphenyl)-1,2,4-oxadiazol-5-yl)cyclopropanecarboximidamide | B | B |
| 10 | 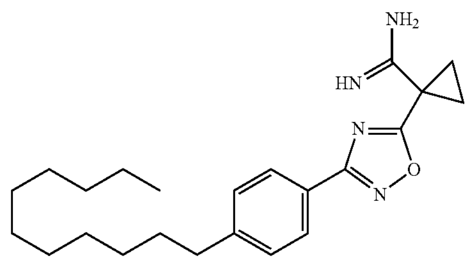 [SMILES: CCCCCCCCCCCc1ccc(-c2noc(C3(C(=N)N)CC3)n2)cc1] | 1-(3-(4-undecylphenyl)-1,2,4-oxadiazol-5-yl)cyclopropanecarboximidamide | B | B |
| 11 | 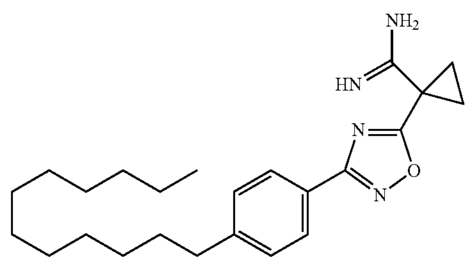 [SMILES: CCCCCCCCCCCCc1ccc(-c2noc(C3(C(=N)N)CC3)n2)cc1] | 1-(3-(4-dodecylphenyl)-1,2,4-oxadiazol-5-yl)cyclopropanecarboximidamide | B | B |
| 12 | 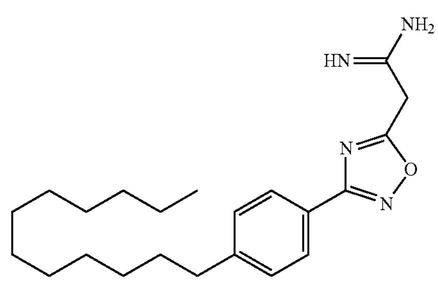 [SMILES: CCCCCCCCCCCCc1ccc(-c2noc(CC(=N)N)n2)cc1] | 2-(3-(4-dodecylphenyl)-1,2,4-oxadiazol-5-yl)acetimidamide | C | C |
| 13 | 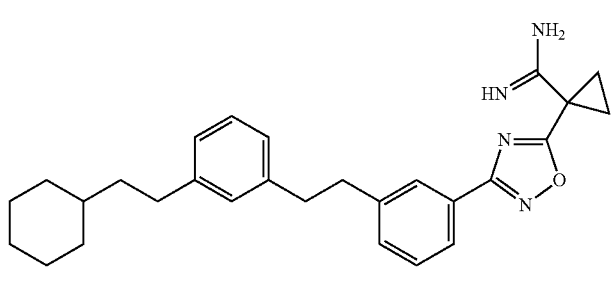 [SMILES: N=C(N)C1(c2nc(-c3cccc(CCc4cccc(CCC5CCCCC5)c4)c3)no2)CC1] | 1-(3-(3-(3-(2-cyclohexylethyl)phenethyl)phenyl)-1,2,4-oxadiazol-5-yl)cyclopropanecarboximidamide | A | B |

TABLE 2-continued

| Compound # | Structure | IUPAC name | SphK1 | SphK2 |
|---|---|---|---|---|
| 14 | 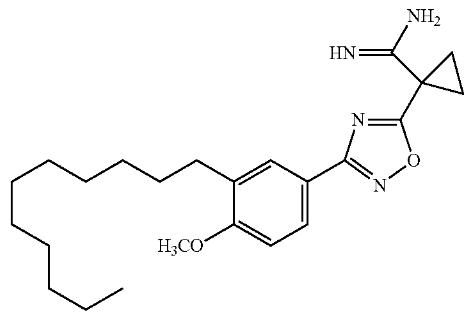 [SMILES: CCCCCCCCCCCc1cc(-c2noc(C3(C(=N)N)CC3)n2)ccc1OC] | 1-(3-(4-methoxy-3-undecylphenyl)-1,2,4-oxadiazol-5-yl)cyclopropanecarboximidamide | A | B |
| 15 | 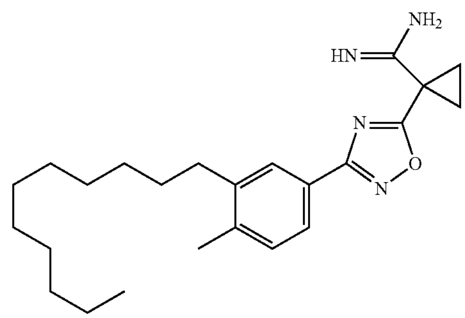 [SMILES: CCCCCCCCCCCc1cc(-c2noc(C3(C(=N)N)CC3)n2)ccc1C] | 1-(3-(4-methyl-3-undecylphenyl)-1,2,4-oxadiazol-5-yl)cyclopropanecarboximidamide | A | B |
| 16 | 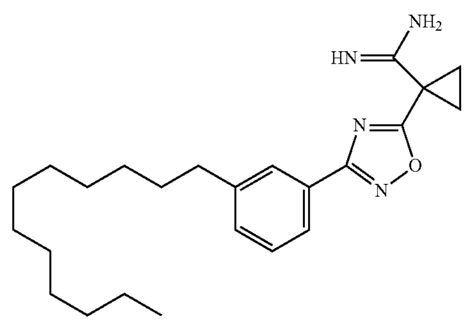 [SMILES: CCCCCCCCCCCCc1cccc(-c2noc(C3(C(=N)N)CC3)n2)c1] | 1-(3-(3-dodecylphenyl)-1,2,4-oxadiazol-5-yl)cyclopropanecarboximidamide | A | C |
| 17 | 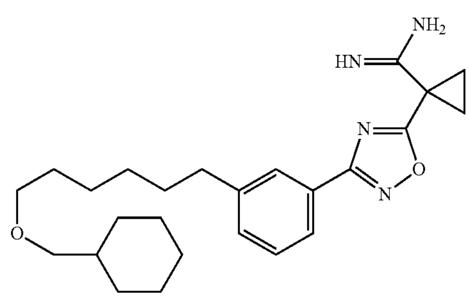 [SMILES: N=C(N)C1(c2nc(-c3cccc(CCCCCCOCC4CCCCC4)c3)no2)CC1] | 1-(3-(3-(6-(cyclohexylmethoxy)hexyl)phenyl)-1,2,4-oxadiazol-5-yl)cyclopropanecarboximidamide | A | B |
| 18 | 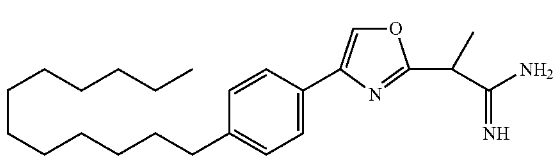 [SMILES: CCCCCCCCCCCCc1ccc(-c2coc(C(C)C(=N)N)n2)cc1] | 2-(4-(4-dodecylphenyl)oxazol-2-yl)propanimidamide | C | C |
| 19 | 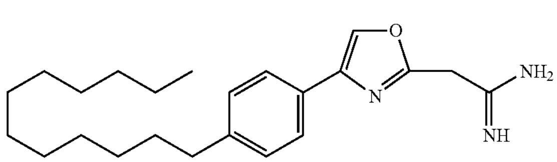 [SMILES: CCCCCCCCCCCCc1ccc(-c2coc(CC(=N)N)n2)cc1] | 2-(4-(4-dodecylphenyl)oxazol-2-yl)acetimidamide | C | C |

TABLE 2-continued

| Compound # | Structure | IUPAC name | SphK1 | SphK2 |
|---|---|---|---|---|
| 20 | 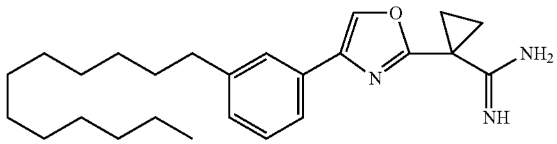 [SMILES: CCCCCCCCCCCCc1cccc(-c2coc(C3(C(=N)N)CC3)n2)c1] | 1-(5-(3-dodecylphenyl)-1,2,4-oxadiazol-3-yl)cyclopropanecarboximidamide | A | B |
| 21 | 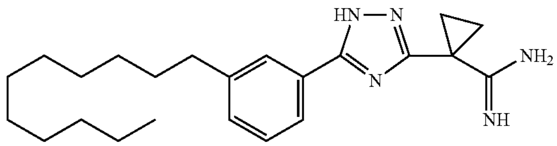 [SMILES: CCCCCCCCCCCc1cccc(-c2nc(C3(C(=N)N)CC3)n[nH]2)c1] | 1-(5-(3-undecylphenyl)-1H-1,2,4-triazol-3-yl)cyclopropanecarboximidamide | A | B |
| 22 | 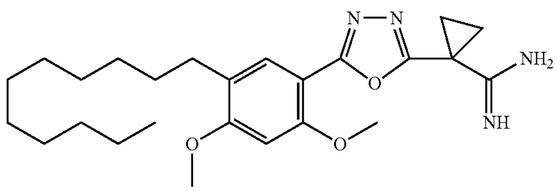 [SMILES: CCCCCCCCCCCc1cc(-c2nnc(C3(C(=N)N)CC3)o2)c(OC)cc1OC] | 1-(5-(2,4-dimethoxy-5-undecylphenyl)-1,3,4-oxadiazol-2-yl)cyclopropanecarboximidamide | A | B |
| 23 | 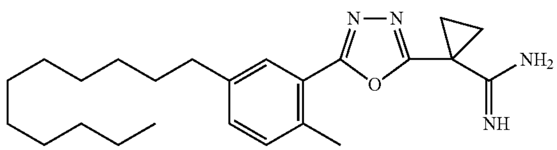 [SMILES: CCCCCCCCCCCc1ccc(C)c(-c2nnc(C3(C(=N)N)CC3)o2)c1] | 1-(5-(2-methyl-5-undecylphenyl)-1,3,4-oxadiazol-2-yl)cyclopropanecarboximidamide | A | B |
| 24 | 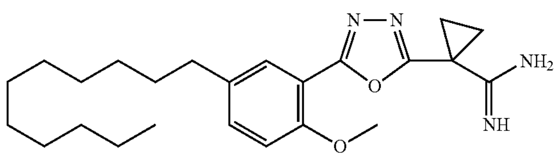 [SMILES: CCCCCCCCCCCc1ccc(OC)c(-c2nnc(C3(C(=N)N)CC3)o2)c1] | 1-(5-(2-methoxy-5-undecylphenyl)-1,3,4-oxadiazol-2-yl)cyclopropanecarboximidamide | A | B |
| 25 | 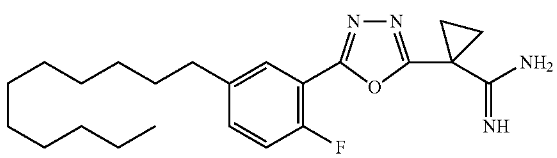 [SMILES: CCCCCCCCCCCc1ccc(F)c(-c2nnc(C3(C(=N)N)CC3)o2)c1] | 1-(5-(2-fluoro-5-undecylphenyl)-1,3,4-oxadiazol-2-yl)cyclopropanecarboximidamide | A | B |
| 26 | 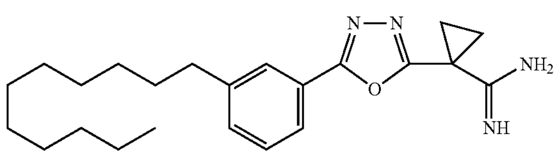 | 1-(5-(3-undecylphenyl)-1,3,4-oxadiazol-2-yl)cyclopropanecarboximidamide | A | B |
| 27 | 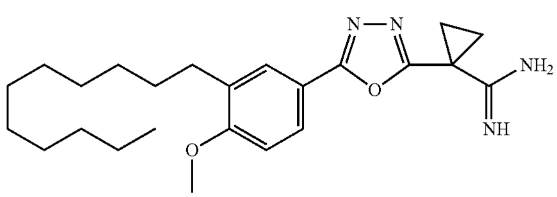 [SMILES: CCCCCCCCCCCc1cc(-c2nnc(C3(C(=N)N)CC3)o2)ccc1OC] | 1-(5-(4-methoxy-3-undecylphenyl)-1,3,4-oxadiazol-2-yl)cyclopropanecarboximidamide | A | B |
| 28 | 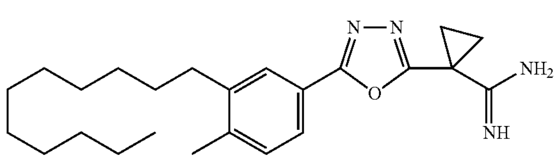 [SMILES: CCCCCCCCCCCc1cc(-c2nnc(C3(C(=N)N)CC3)o2)ccc1C] | 1-(5-(4-methyl-3-undecylphenyl)-1,3,4-oxadiazol-2-yl)cyclopropanecarboximidamide | A | B |

TABLE 2-continued

| Compound # | Structure | IUPAC name | SphK1 | SphK2 |
|---|---|---|---|---|
| 29 | 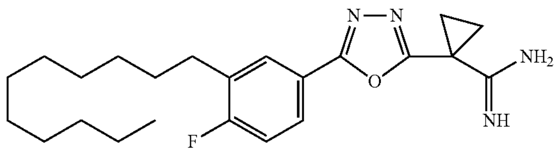 [SMILES: CCCCCCCCCCCc1cc(-c2nnc(C3(C(=N)N)CC3)o2)ccc1F] | 1-(5-(4-fluoro-3-undecylphenyl)-1,3,4-oxadiazol-2-yl)cyclopropanecarboximidamide | A | B |
| 30 | 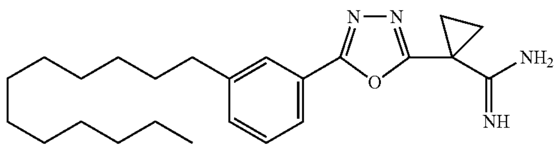 [SMILES: CCCCCCCCCCCCc1cccc(-c2nnc(C3(C(=N)N)CC3)o2)c1] | 1-(5-(3-dodecylphenyl)-1,3,4-oxadiazol-2-yl)cyclopropanecarboximidamide | A | B |
| 31 | 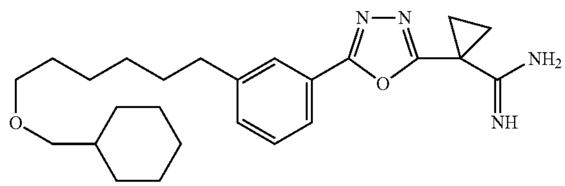 [SMILES: N=C(N)C1(c2nnc(-c3cccc(CCCCCCOCC4CCCCC4)c3)o2)CC1] | 1-(5-(3-(6-(cyclohexylmethoxy)hexyl)phenyl)-1,3,4-oxadiazol-2-yl)cyclopropanecarboximidamide | A | B |
| 32 | 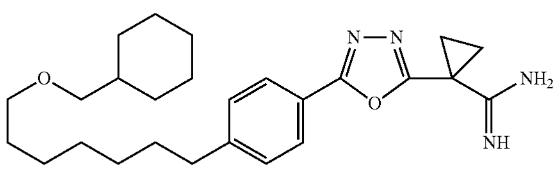 [SMILES: N=C(N)C1(c2nnc(-c3ccc(CCCCCCCOCC4CCCCC4)cc3)o2)CC1] | 1-(5-(4-(7-(cyclohexylmethoxy)heptyl)phenyl)-1,3,4-oxadiazol-2-yl)cyclopropanecarboximidamide | A | B |
| 33 | 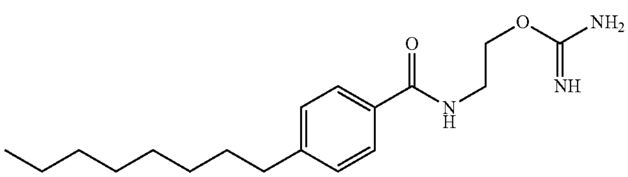 [SMILES: CCCCCCCCc1ccc(C(=O)NCCOC(=N)N)cc1] | 2-(4-octylbenzamido)ethyl carbamimidate | C | C |
| 34 | 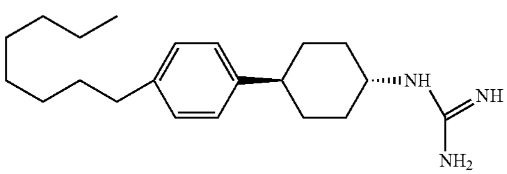 [SMILES: CCCCCCCCc1ccc([C@H]2CC[C@H](NC(=N)N)CC2)cc1] | 1-((1R,4R)-4-(4-octylphenyl)cyclohexyl)guanidine | B | C |
| 35 | 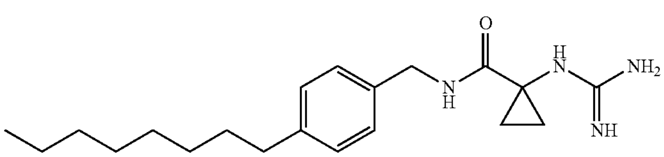 [SMILES: CCCCCCCCc1ccc(CNC(=O)C2(NC(=N)N)CC2)cc1] | 1-guanidino-N-(4-octylbenzyl)cyclopropanecarboxamide | C | C |
| 36 | 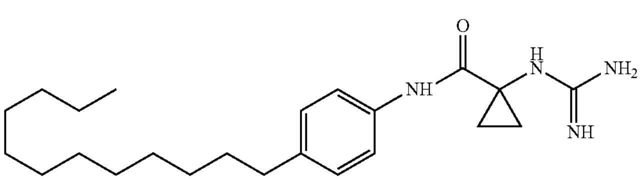 [SMILES: CCCCCCCCCCCCc1ccc(NC(=O)C2(NC(=N)N)CC2)cc1] | N-(4-dodecylphenyl)-1-guanidinocyclopropanecarboxamide | C | C |
| 37 | 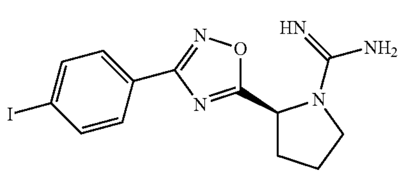 [SMILES: N=C(N)N1CCC[C@H]1c1nc(-c2ccc(I)cc2)no1] | (S)-2-(3-(4-iodophenyl)-1,2,4-oxadiazol-5-yl)pyrrolidine-1-carboximidamide | C | C |

TABLE 2-continued

| Compound # | Structure | IUPAC name | SphK1 | SphK2 |
|---|---|---|---|---|
| 38 | 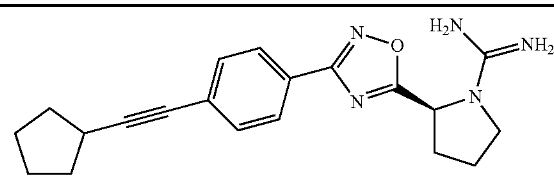 | (S)-2-(3-(4-(cyclopentylethynyl)phenyl)-1,2,4-oxadiazol-5-yl)pyrrolidine-1-carboximidamide | C | C |
| 39 | 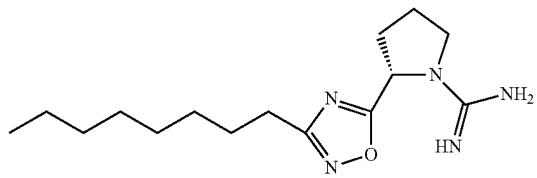 [SMILES: CCCCCCCCc1noc([C@@H]2CCCN2C(=N)N)n1] | (S)-2-(3-octyl-1,2,4-oxadiazol-5-yl)pyrrolidine-1-carboximidamide | C | C |
| 40 | 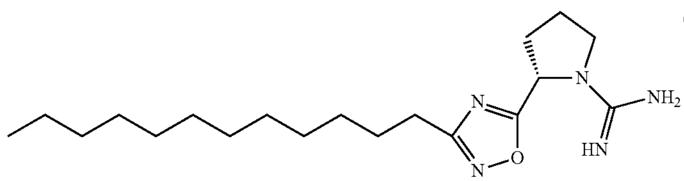 [SMILES: CCCCCCCCCCCCc1noc([C@@H]2CCCN2C(=N)N)n1] | (S)-2-(3-dodecyl-1,2,4-oxadiazol-5-yl)pyrrolidine-1-carboximidamide | C | C |
| 41 | 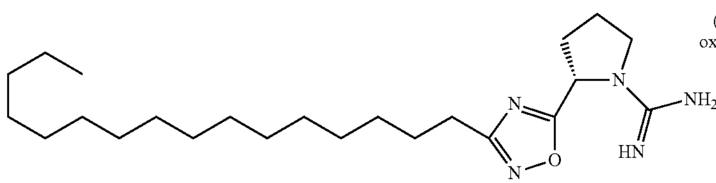 [SMILES: CCCCCCCCCCCCCCCCc1noc([C@@H]2CCCN2C(=N)N)n1] | (S)-2-(3-hexadecyl-1,2,4-oxadiazol-5-yl)pyrrolidine-1-carboximidamide | C | C |
| 42 | 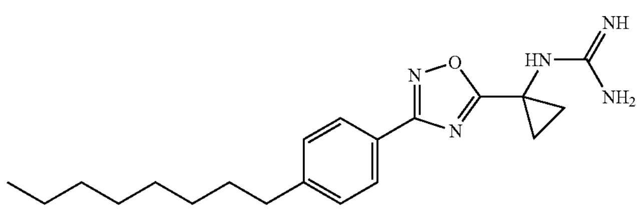 [SMILES: CCCCCCCCc1ccc(-c2noc(C3(NC(=N)N)CC3)n2)cc1] | 1-(1-(3-(4-octylphenyl)-1,2,4-oxadiazol-5-yl)cyclopropyl)guanidine | C | C |
| 43 | 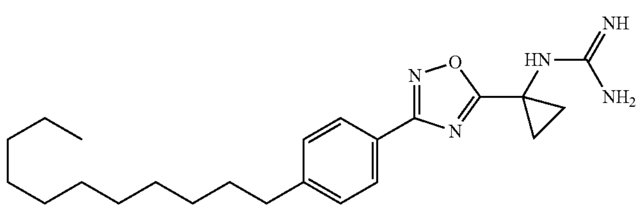 [SMILES: CCCCCCCCCCCc1ccc(-c2noc(C3(NC(=N)N)CC3)n2)cc1] | 1-(1-(3-(4-undecylphenyl)-1,2,4-oxadiazol-5-yl)cyclopropyl)guanidine | C | C |
| 44 | 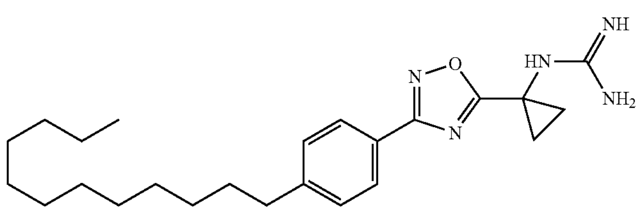 [SMILES: CCCCCCCCCCCCc1ccc(-c2noc(C3(NC(=N)N)CC3)n2)cc1] | 1-(1-(3-(4-dodecylphenyl)-1,2,4-oxadiazol-5-yl)cyclopropyl)guanidine | C | C |
| 45 | 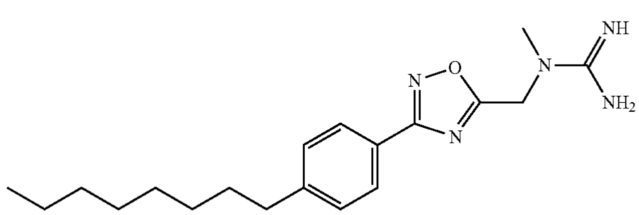 [SMILES: CCCCCCCCc1ccc(-c2noc(CN(C)C(=N)N)n2)cc1] | 1-methyl-1-((3-(4-octylphenyl)-1,2,4-oxadiazol-5-yl)methyl)guanidine | C | C |

TABLE 2-continued

| Compound # | Structure | IUPAC name | SphK1 | SphK2 |
|---|---|---|---|---|
| 46 | 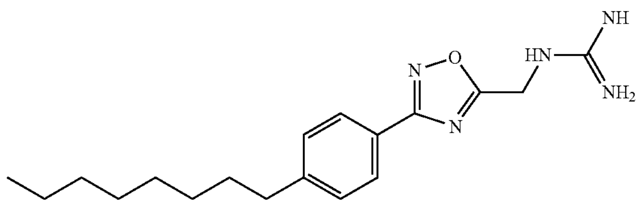 [SMILES: CCCCCCCCc1ccc(-c2noc(CNC(=N)N)n2)cc1] | 1-((3-(4-octylphenyl)-1,2,4-oxadiazol-5-yl)methyl)guanidine | B | C |
| 47 | 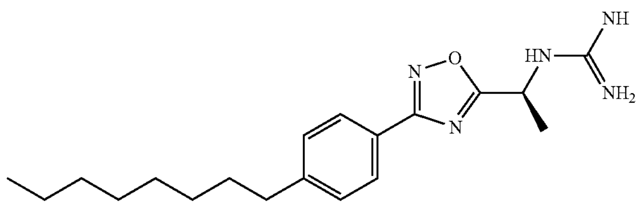 [SMILES: CCCCCCCCc1ccc(-c2noc([C@H](C)NC(=N)N)n2)cc1] | (S)-1-(1-(3-(4-octylphenyl)-1,2,4-oxadiazol-5-yl)ethyl)guanidine | B | B |
| 48 | 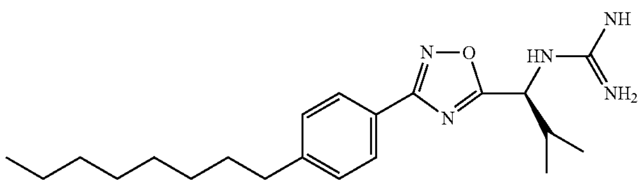 [SMILES: CCCCCCCCc1ccc(-c2noc([C@@H](NC(=N)N)C(C)C)n2)cc1] | (S)-1-(2-methyl-1-(3-(4-octylphenyl)-1,2,4-oxadiazol-5-yl)propyl)guanidine | B | B |
| 49 | 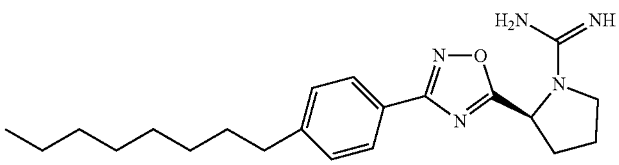 [SMILES: CCCCCCCCc1ccc(-c2noc([C@@H]3CCCN3C(=N)N)n2)cc1] | (S)-2-(3-(4-octylphenyl)-1,2,4-oxadiazol-5-yl)pyrrolidine-1-carboximidamide | C | B |
| 50 | 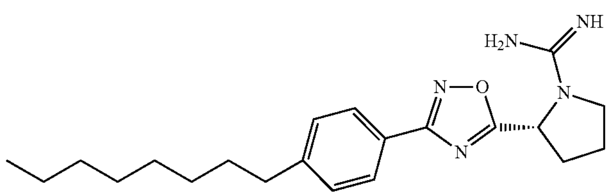 [SMILES: CCCCCCCCc1ccc(-c2noc([C@H]3CCCN3C(=N)N)n2)cc1] | (R)-2-(3-(4-octylphenyl)-1,2,4-oxadiazol-5-yl)pyrrolidine-1-carboximidamide | C | C |
| 51 | 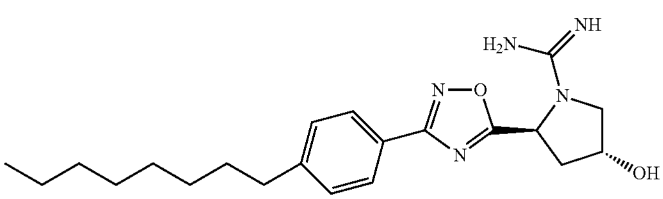 [SMILES: CCCCCCCCc1ccc(-c2noc([C@@H]3C[C@@H](O)CN3C(=N)N)n2)cc1] | (2S,4R)-4-hydroxy-2-(3-(4-octylphenyl)-1,2,4-oxadiazol-5-yl)pyrrolidine-1-carboximidamide | C | B |
| 52 | 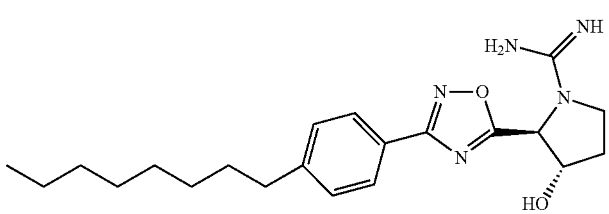 [SMILES: CCCCCCCCc1ccc(-c2noc([C@@H]3[C@@H](O)CCN3C(=N)N)n2)cc1] | (2S,3S)-3-hydroxy-2-(3-(4-octylphenyl)-1,2,4-oxadiazol-5-yl)pyrrolidine-1-carboximidamide | B | B |
| 53 | 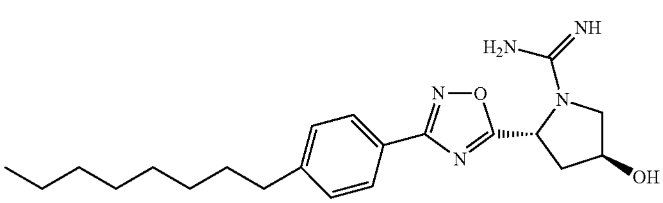 [SMILES: CCCCCCCCc1ccc(-c2noc([C@H]3C[C@H](O)CN3C(=N)N)n2)cc1] | (2R,4S)-4-hydroxy-2-(3-(4-octylphenyl)-1,2,4-oxadiazol-5-yl)pyrrolidine-1-carboximidamide | C | C |

TABLE 2-continued

| Compound # | Structure | IUPAC name | SphK1 | SphK2 |
|---|---|---|---|---|
| 54 | 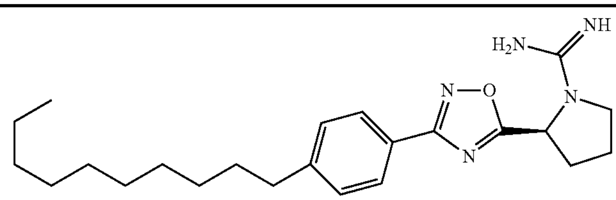 | (S)-2-(3-(4-decylphenyl)-1,2,4-oxadiazol-5-yl)pyrrolidine-1-carboximidamide | B | B |
| 55 | 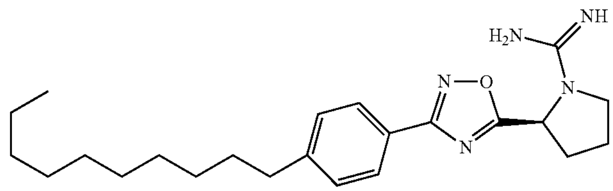 [SMILES: CCCCCCCCCCc1ccc(-c2noc([C@@H]3CCCN3C(=N)N)n2)cc1] | (S)-2-(3-(4-dodecylphenyl)-1,2,4-oxadiazol-5-yl)pyrrolidine-1-carboximidamide | C | B |
| 56 | 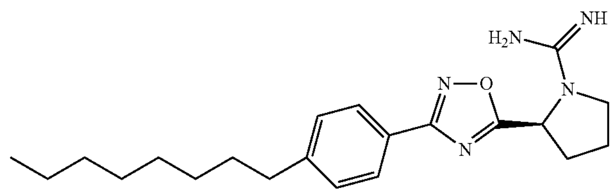 [SMILES: CCCCCCCCc1ccc(-c2noc([C@@H]3CCCN3C(=N)N)n2)cc1] | (S)-2-(3-(4-hexylphenyl)-1,2,4-oxadiazol-5-yl)pyrrolidine-1-carboximidamide | C | B |
| 57 | 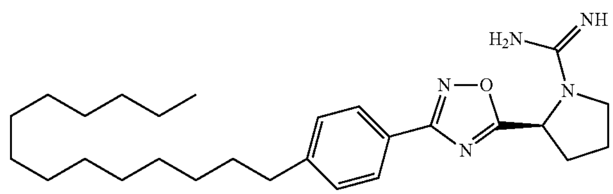 [SMILES: CCCCCCCCCCCCCCc1ccc(-c2noc([C@@H]3CCCN3C(=N)N)n2)cc1] | (S)-2-(3-(4-tetradecylphenyl)-1,2,4-oxadiazol-5-yl)pyrrolidine-1-carboximidamide | C | B |
| 58 | 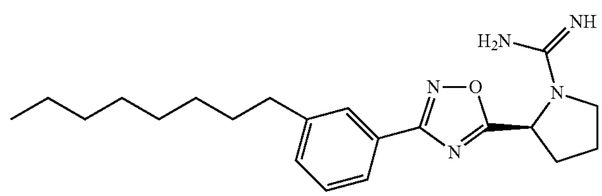 [SMILES: CCCCCCCCc1cccc(-c2noc([C@@H]3CCCN3C(=N)N)n2)c1] | (S)-2-(3-(3-octylphenyl)-1,2,4-oxadiazol-5-yl)pyrrolidine-1-carboximidamide | C | C |
| 59 | 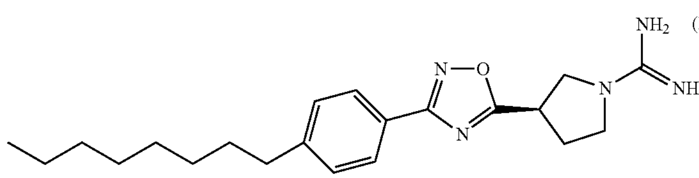 [SMILES: CCCCCCCCc1ccc(-c2noc([C@@H]3CCN(C(=N)N)C3)n2)cc1] | (R)-3-(3-(4-octylphenyl)-1,2,4-oxadiazol-5-yl)pyrrolidine-1-carboximidamide | C | C |
| 60 | 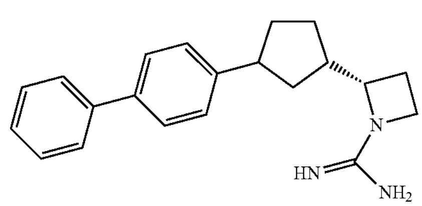 [SMILES: N=C(N)N1CC[C@H]1C1CCC(c2ccc(-c3ccccc3)cc2)C1] | (S)-2-(3-([1,1'-biphenyl]-4-yl)-1,2,4-oxadiazol-5-yl)azetidine-1-carboximidamide | C | C |
| 61 | 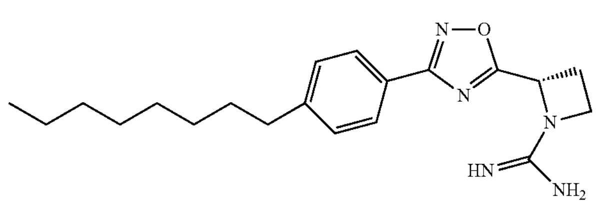 [SMILES: CCCCCCCCc1ccc(-c2noc([C@@H]3CCN3C(=N)N)n2)cc1] | (S)-2-(3-(4-hexylphenyl)-1,2,4-oxadiazol-5-yl)azetidine-1-carboximidamide | C | B |

TABLE 2-continued

| Compound # | Structure | IUPAC name | SphK1 | SphK2 |
|---|---|---|---|---|
| 62 | 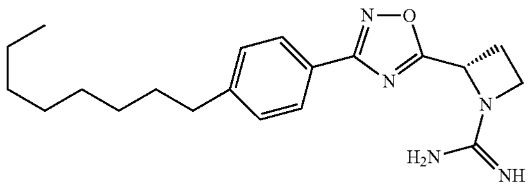 [SMILES: CCCCCCCCc1ccc(-c2noc([C@@H]3CCN3C(=N)N)n2)cc1] | (S)-2-(3-(4-octylphenyl)-1,2,4-oxadiazol-5-yl)azetidine-1-carboximidamide | C | B |
| 63 | 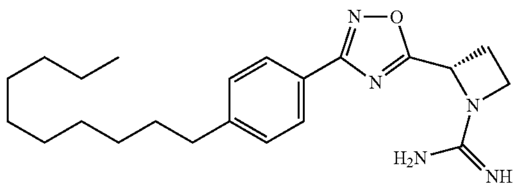 [SMILES: CCCCCCCCCCc1ccc(-c2noc([C@@H]3CCN3C(=N)N)n2)cc1] | (S)-2-(3-(4-decylphenyl)-1,2,4-oxadiazol-5-yl)azetidine-1-carboximidamide | B | B |
| 64 | 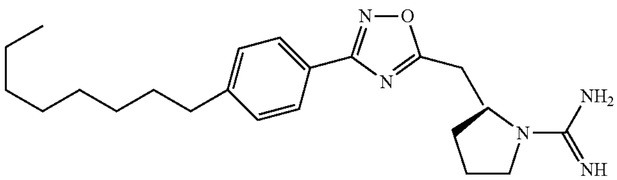 | (S)-2-((3-(4-octylphenyl)-1,2,4-oxadiazol-5-yl)methyl)pyrrolidine-1-carboximidamide | A | B |
| 65 | 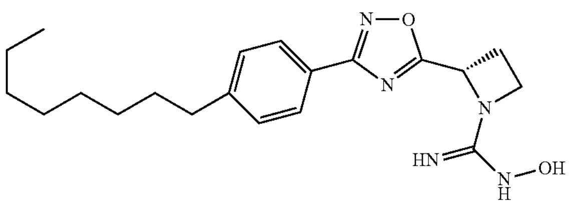 [SMILES: CCCCCCCCc1ccc(-c2noc([C@@H]3CCN3C(=N)NO)n2)cc1] | (S)-N-hydroxy-2-(3-(4-octylphenyl)-1,2,4-oxadiazol-5-yl)azetidine-1-carboximidamide | C | C |
| 66 | 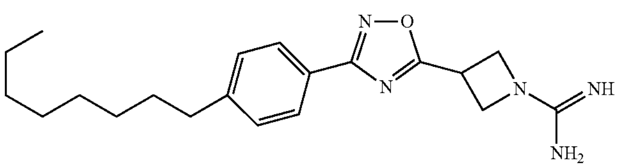 [SMILES: CCCCCCCCc1ccc(-c2noc(C3CN(C(=N)N)C3)n2)cc1] | 3-(3-(4-octylphenyl)-1,2,4-oxadiazol-5-yl)azetidine-1-carboximidamide | B | B |
| 67 | 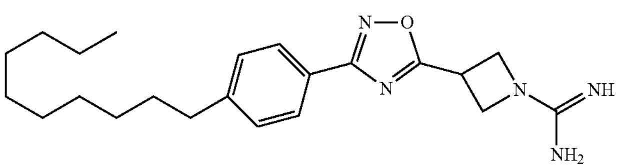 [SMILES: CCCCCCCCCCc1ccc(-c2noc(C3CN(C(=N)N)C3)n2)cc1] | 3-(3-(4-decylphenyl)-1,2,4-oxadiazol-5-yl)azetidine-1-carboximidamide | C | B |
| 68 | 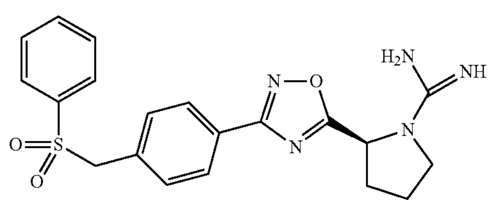 [SMILES: N=C(N)N1CCC[C@H]1c1nc(-c2ccc(CS(=O)(=O)c3ccccc3)cc2)no1] | (S)-2-(3-(4-((phenylsulfonyl)methyl)phenyl)-1,2,4-oxadiazol-5-yl)pyrrolidine-1-carboximidamide | C | C |
| 71 | 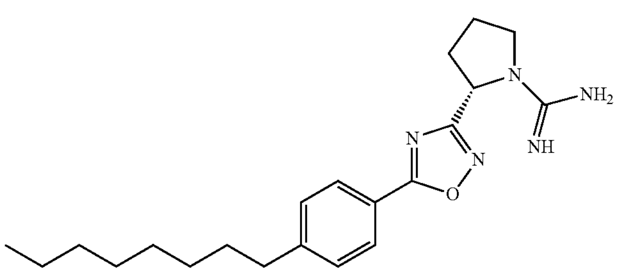 [SMILES: CCCCCCCCc1ccc(-c2nc([C@@H]3CCCN3C(=N)N)no2)cc1] | (S)-2-(5-(4-octylphenyl)-1,2,4-oxadiazol-3-yl)pyrrolidine-1-carboximidamide | C | B |

TABLE 2-continued

| Compound # | Structure | IUPAC name | SphK1 | SphK2 |
|---|---|---|---|---|
| 74 | 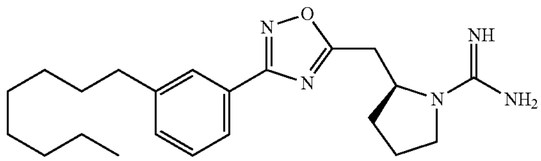 [SMILES: CCCCCCCCc1cccc(-c2noc(C[C@@H]3CCCN3C(=N)N)n2)c1] | (S)-2-((3-(3-octylphenyl)-1,2,4-oxadiazol-5-yl)methyl)pyrrolidine-1-carboximidamide | C | C |
| 75 | 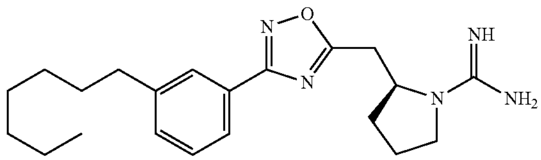 [SMILES: CCCCCCCc1cccc(-c2noc(C[C@@H]3CCCN3C(=N)N)n2)c1] | (S)-2-((3-(3-nonylphenyl)-1,2,4-oxadiazol-5-yl)methyl)pyrrolidine-1-carboximidamide | C | C |
| 76 | 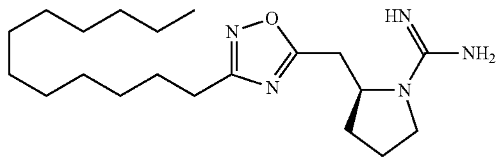 [SMILES: CCCCCCCCCCCCc1noc(C[C@@H]2CCCN2C(=N)N)n1] | (S)-2-((3-dodecyl-1,2,4-oxadiazol-5-yl)methyl)pyrrolidine-1-carboximidamide | C | C |
| 77 | 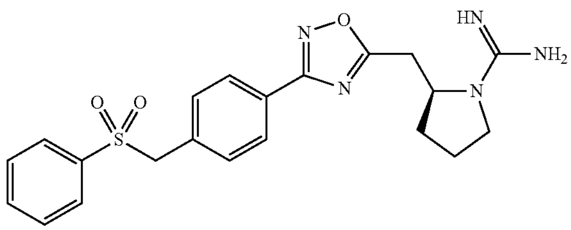 [SMILES: N=C(N)N1CCC[C@H]1Cc1nc(-c2ccc(CS(=O)(=O)c3ccccc3)cc2)no1] | (S)-2-((3-(4-((phenylsulfonyl)methyl)phenyl)-1,2,4-oxadiazol-5-yl)methyl)pyrrolidine-1-carboximidamide | C | C |

Estimated $K_i$ values at recombinant SphK1 and SphK2;
A < 1 μM, B 1-10 μM, C > 10 μM,
n.d. not determined Pharmaceutically acceptable base addition salts can be prepared from inorganic and organic bases. Salts from inorganic bases, include but are not limited to, sodium, potassium, lithium, ammonium, calcium, and magnesium salts. Salts derived from organic bases include, but are not limited to, salts of primary, secondary, and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are alkyl, substituted alkyl, alkenyl, substituted alkenyl, cycloalkyl, substituted cycloalkyl, cycloalkenyl, substituted cycloalkenyl, aryl, heteroaryl, or heterocyclic, and the like. Also included are amines where the two or three substituents, together with the amino nitrogen, form a heterocyclic or heteroaryl group. Non-limiting examples of amines include, isopropylamine, trimethyl amine, diethyl amine, tri(iso-propyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like. It should also be understood that other carboxylic acid derivatives would be useful, for example, carboxylic acid amides, including carboxamides, lower (e.g., $C_1$-$C_6$) alkyl carboxamides, dialkyl carboxamides, and the like.

In cases where compounds of Formula I are sufficiently basic or acidic to form stable nontoxic acid or base salts, preparation and administration of the compounds, as pharmaceutically acceptable salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Inorganic salts may also be formed, including hydrochloride, sulfate, nitrate, bicarbonate, and carbonate salts.

The compounds of the formulas above include all enantiomers thereof.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium, or lithium) or alkaline earth metal (for example, calcium) salts of carboxylic acids can also be made.

The compounds of Formula I can be formulated as pharmaceutical compositions and administered to a mammalian host, such as a human patient in a variety of forms adapted to the chosen route of administration, e.g., orally or parenterally, by intravenous, intramuscular, topical, or subcutaneous routes.

Thus, the compounds of Formula I may be systemically administered, e.g., orally, in combination with a pharmaceutically acceptable vehicle such as an inert diluent, or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch, gelatin, and the like; excipients such as dicalcium phosphate; a disintegrating agent such as corn starch, potato starch, alginic acid, and the like; a lubricant such as magnesium stearate; and a sweetening agent such as sucrose, fructose, lactose, or aspartame, or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain the active compound, sucrose, or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

A compound of Formula I or a pharmaceutical composition containing it may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by the use in the compositions of agents delaying absorption, for example, aluminum monostearate and gelatin.

Sterile injectable solutions are prepared by incorporating a compound of Formula I in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, a compound of Formula I may be applied in pure form, e.g., when they are liquids. However, it will generally be desirable to administer them to the skin as compositions or formulations, in combination with a dermatologically acceptable carrier, which may be a solid or a liquid.

Exemplary solid carriers include finely divided solids such as talc, clay, microcrystalline cellulose, silica, alumina, and the like. Useful liquid carriers include water, alcohols, or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of useful dermatological compositions which can be used to deliver the compounds of Formula I to the skin are known to the art; for example, see Jacquet et al. (U.S. Pat. No. 4,608,392), Geria (U.S. Pat. No. 4,992,478), Smith et al. (U.S. Pat. No. 4,559,157), and Wortzman (U.S. Pat. No. 4,820,508), the disclosures of which are incorporated herein.

Useful dosages of the compounds of Formula I can be determined by comparing their in vitro activity and in vivo activity in animal models. Methods for the extrapolation of effective dosages in mice, and other animals, to humans are known to the art; for example, see U.S. Pat. No. 4,938,949, the disclosure of which is incorporated herein.

Generally, the concentration of the compound(s) of Formula I in a liquid composition, such as a lotion, will be from about 0.1 to about 25 weight percent, preferably from about 0.5-10 weight percent. The concentration in a semi-solid or solid composition such as a gel or a powder will be about 0.1-5 weight percent, preferably about 0.5-2.5 weight percent, based on the total weight of the composition.

The amount of a compound of Formula I used in treatment will vary not only with the particular compound selected but also with the route of administration, the nature of the condition being treated, and the age and condition of the patient, and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently, 10 to 750 mg, most conveniently, 50 to 500 mg, of active ingredient per unit dosage form.

Ideally, a compound of Formula I, as the active ingredient, should be administered to achieve peak plasma concentrations of the active compound of from about 0.5 to about 75 μM, preferably, about 1 to 50 μM, most preferably, about 2 to about 30 μM. This may be achieved, for example, by the intravenous injection of a 0.05 to 5% solution of the active ingredient, optionally in saline, or orally administered as a bolus containing about 1-10 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple inhalations from an insufflator or by application of a plurality of drops into the eye.

The disclosed compounds and methods, as described above or as discussed in the Examples in the appendices, there can be employed conventional chemical, cellular, histochemical, biochemical, molecular biology, microbiology, and in vivo techniques, which are known to those of skill in the art. Such techniques are explained fully in the literature.

Without further description, it is believed that one of ordinary skill in the art can, using the preceding description and the following illustrative examples, make and utilize the disclosed compounds.

Processes for preparing compounds of Formula I or for preparing intermediates useful for preparing compounds of Formula I are provided as further embodiments of the invention. Intermediates useful for preparing compounds of Formula I are also provided as further embodiments of the invention. The compounds of the invention can be prepared using starting materials and methods known in the art. The processes are provided as further embodiments and are illustrated in the schemes herein wherein the meanings of the generic radicals are as given above unless otherwise qualified.

The invention is now described with reference to the following Examples. Without further description, it is believed that one of ordinary skill in the art can, using the preceding description and the following illustrative examples, make and utilize the disclosed compounds. The following working examples, therefore, are provided for the purpose of illustration only and specifically point out the preferred embodiments, and are not to be construed as limiting in any way the remainder of the disclosure. Therefore, the following examples should be construed to encompass any and all variations that become evident as a result of the teaching provided herein.

EXAMPLES

General Synthetic Materials and Methods:

All nonaqueous reactions were carried out in oven or flame-dried glassware under an argon or nitrogen atmosphere with dry solvents and magnetic stirring, unless otherwise stated. The argon and nitrogen were dried by passing through a tube of Drierite. Anhydrous diethyl ether ($Et_2O$), chloroform ($CHCl_3$), dimethyl sulfoxide (DMSO), toluene (PhMe), dichloromethane ($CH_2Cl_2$), methanol (MeOH), ethanol (EtOH), and tetrahydrofuran (THF) and N,N-dimethylformamide (DMF) were purchased from Aldrich or VMR Chemicals and used as received. THF was dried over activated molecular sieves (4 Å) prior to use. All other reagents were purchased from Acros chemicals and Aldrich chemicals. Except as indicated otherwise, reactions were monitored by thin layer chromatography (TLC) using 0.25 mm Whatman precoated silica gel plates. Flash chromatography was performed with the indicated solvents and Dynamic Adsorbents silica gel (particle size 0.023-0.040 mm). Proton ($^1H$) and carbon ($^{13}C$) NMR spectra were recorded on a Varian Unitylnova 500/51 or Varian Unitylnova 300/54 at 300K unless otherwise noted. Chemical shifts are reported in ppm (δ) values relative to the solvent as follows: CDCl3 (δ7.24 for proton and δ77.0 for carbon NMR), DMSO-$d_6$ (δ2.50 for proton and δ39.5 for carbon NMR) $CD_3OD$ (δ3.31 for proton and δ47.6 for carbon NMR). All high-resolution mass spectrometry was carried out by the Mass Spectrometry Laboratory in the School of Chemical Sciences at the University of Illinois Urbana-Champagne (Urbana, Ill.).

TLC Stains: $KMnO_4$; 3 g $KMnO_4$ and 20 g $K_2CO_3$ in 300 mL water and 5 mL 5% NaOH. Seebach's Dip; to a solution of 25 g phosphomolybdic acid and 7.5 g cerium (IV) sulfate in 479 mL water was added 25 mL conc. sulfuric acid dropwise. Ninhydrin; 1.5 g ninhydrin in 5 mL AcOH and 500 mL 95% EtOH. All stains required TLC development on a hot plate set to 80° C.

Other abbreviations: 1,1'-bis(diphenylphosphino)ferrocene (dppf), 4-dimethylaminopyridine (DMAP), 9-borabicyclo[3.3.1]nonane (9-BBN), acetic acid (AcOH), benzotriazol-1-yl-oxytripyrrolidinophosphonium hexafluorophosphate (PyBOP), di-tert-butyl dicarbonate ($Boc_2O$), ethyl acetate (EtOAc), N,N-diisopropylethylamine (DIEA), tert-butanol (tBuOH), tetra-n-butylammonium bromide (TBAB), triethylamine (TEA), trifluoroacetic acid (TFA), trifluoroacetic anhydride (TFAA), tetrabutylammonium fluoride (TBAF).

Liquid Chromatography and Mass Spectrometry for Evaluation of Chemical Purity.

All compounds submitted for biological evaluation were determined to be >95% pure by LCMS evaluation performed by the Mass Spectrometry Laboratory in the School of Chemical Sciences at the University of Illinois Urbana-Champagne (Urbana, Ill.). High performance liquid chromatography-mass spectrometry (LCMS) was carried out using an Agilent 2.1×50 mm C-18 column and a Micromass Q-tof Ultima mass spectrometer. Mobile phase A consisted of HPLC grade H2O and 0.01% TFA; mobile phase B consisted of MeCN and 0.01% TFA. LCMS identification and purity utilized a binary gradient starting with 90% A and 10% B and linearly increasing to 100% B over the course of 6 min, followed by an isocratic flow of 100% B for an additional 3 min. A flow rate of 0.5 mL/min was maintained throughout the HPLC method. The purity of all products was determined by integration of the total ion count (TIC) spectra and integration of the ultraviolet (UV) spectra at 214 nm. Retention times are abbreviated as $t_R$; mass to charge ratios are abbreviated as m/z.

General Procedure A: Conversion of Nitriles to Amidines.

To a solution of a nitrile (1.0 eq.) in MeOH (0.10 M) was added a 0.5 M solution of sodium methoxide in MeOH (0.50 eq.) at r.t. and then heated to 50° C. for 24 h. The intermediate imidate was detectable by TLC; however, being in equilibrium with the nitrile, full conversion does not occur. Ammonium chloride (4.0 eq.) was then added in one portion at that temperature and reacted until the imidate was completely consumed by TLC analysis. The reaction was then cooled to r.t. and evacuated to dryness to yield a crude solid. The solid was reconstituted with $CHCl_3$ and filtered through a fine glass fritted funnel in order to remove excess ammonium chloride, and the filtrate was again evacuated to dryness. The material was then recrystallized in $Et_2O$ to yield the pure amidine hydrochloride salt. The yields varied greatly depending upon substrate, because amidine formation is dependent upon the equilibrium ratio between nitrile and imidate established under the sodium methoxide conditions.

General Procedure B: PyBOP Mediated Couplings of Amines, Anilines, and Amide oximes to Carboxylic Acids.

To a suspension of an amine or aniline (1.0 eq.), carboxylic acid (1.0 eq.), and PyBOP (1.0 eq.), in $CH_2Cl_2$ at r.t. was added DIEA (4.0 eq.) and stirred for 4 h unless otherwise stated. The reaction was then evaporated to dryness and immediately purified by flash chromatography. In the case of amide oximes, a small amount of oxadiazole was formed in the reaction.

General Procedure C: Suzuki Coupling.

To a solution of alkene (1.5 eq.) at r.t. was added a 0.5 M solution of 9-BBN in THF (1.5 eq.) and stirred until consumption of the alkene was evident by TLC analysis (4 h unless otherwise stated). The reaction was then treated with 3 M NaOH, and diluted with THF (0.2 M relative to the starting alkene). The aryl halide (1.0 eq.) and $Pd(PPh_3)_4$ were then sequentially added and the reaction was heated to reflux and stirred for 4 h. The reaction was reduced to a dark oil, diluted with EtOAc and washed 1× with sat. $NaHCO_3$. The organic layer was then dried with $MgSO_4$, evaporated to a dark oil, and immediately purified by flash chromatography.

General Procedure D: Pinnick Oxidation.

To a solution of an aldehyde (1.0 eq.), $NaH_2PO_4$ (8.0 eq.), and 2-methyl-2-butene (10 eq.) in THF, water, and tBuOH (4:4:1) (0.04 M) at r.t. was added sodium chlorite (4 eq.) and stirred for 1 h. The reaction was diluted with EtOAc (10× the volume of the reaction's mixture of solvents), and washed 3× with 1 N HCl (5× the volume of the reaction's mixture of solvents). The organic layer was then dried with $MgSO_4$, and evaporated to a white solid. No further purification was necessary.

General procedure E: Deprotection of N-Boc and O-tBu Ester Protecting Groups.

To a solution of either an N-Boc or O-tBu protecting group (1.0 eq.) in $CH_2Cl_2$ (0.2 M) at r.t. was added TFA (0.2 M) and the reaction was reacted until judged complete by TLC analysis (30 min unless otherwise stated). The reaction was then evaporated to dryness and taken on crude.

General Procedure F: Conversion of Nitriles to Amide Oximes.

To a solution of nitrile (1 eq.) and hydroxylamine hydrochloride (5 eq.) in EtOH (0.2 M) was added TEA (10 eq.). The reaction was heated to 50° C. for 5 h. The EtOH was evaporated and the crude white solid was immediately purified via flash chromatography.

General Procedure G: Synthesis of 3,5-disubstituted-1,2,4-oxadiazoles Using Tetrabutylammonium Fluoride from Acylated Amide Oximes.

To a solution of O-acyl amidoxime (1.0 eq.) in THF (0.1 M) at r.t. was added a 1.0 M solution of TBAF in THF (1.0 eq.) and stirred for 1 h. The reaction was evaporated to dryness and immediately purified by flash chromatography.

General Procedure H: Coupling of Amines to N,N'-Di-Boc-1H-pyrazole-1-carboxamidine.

To a solution of amine (1.0 eq.) and N,N'-Di-Boc-1H-pyrazole-1-carboxamidine (1.1 eq.) in MeOH (0.1 M) was added a catalytic amount of DMAP followed by DIEA (3.0 eq.). The reaction was heated to 50° C. overnight, cooled to r.t., and evaporated. The resulting solid was immediately purified via flash chromatography.

General Procedure I.

Trifluoroacetic acid (15 equiv) was added to a solution of Boc-protected amine (1 equiv) in $CH_2Cl_2$ (0.2 M solution). The reaction mixture was then stirred at r.t. for 3 h. At this time, TLC showed complete conversion of starting material. The organic solvent was removed under reduced pressure. The resulting residue was partitioned between diethyl ether and water. The aqueous solution was adjusted to pH 14 by adding 10% NaOH solution. The solution was then extracted with ether and the combined organic layers were washed with brine, dried over $Na_2SO_4$, filtered, and concentrated under reduced pressure to provide the desired product.

General Procedure J.

Hydrogen chloride gas was passed through a solution of Boc-protected guanidine dissolved in methanol (0.2 M solution) for 5 min. The organic solvent was then removed under reduced pressure. The residue was washed with diethyl ether to provide the desired product.

General Procedure K.

DIEA (3 equiv) was added to a solution of amine (1 equiv) and N,N'-Di-Boc-1H-pyrazole-1-carboxamidine (0.9 equiv) in acetonitrile (0.2 M solution). The reaction mixture was then stirred at r.t. for 1-3 days. The organic solvent was removed under reduced pressure. The residue was purified by column chromatography on silica gel (85/15 hexanes/EtOAc) to provide the desired product.

General Procedure L.

DIEA (1.8 equiv) was added to a solution of 34 (1 equiv) and the appropriate Boc-protected amino acid (1.2 equiv) in DMF (0.2 M solution). HCTU (1.2 equiv) was then added to the resulting mixture at r.t. and stirred at 100° C. for 3 h. At this time, TLC showed complete conversion of starting material. The solution was partitioned between ethyl acetate and water. The organic layer was washed several times with a sat. LiBr. The aqueous solution was then extracted with ethyl acetate and the combined organic layers were washed with sat. $NaHCO_3$ and brine, dried over $Na_2SO_4$, and concentrated under reduced pressure. The residue was purified by column chromatography on silica gel (85/15 hexanes/EtOAc) to give the desired product.

General Procedure M: Coupling reaction of alkynes with aryliodide.

Alkyne (2 equiv) and TEA (5 equiv) were added to a round bottom flask containing aryl halide (1 equiv) in DMF (20 vol/wt) under nitrogen. The reaction mixture was degassed for 30 min by passing $N_2$ to remove oxygen. To the above solution were added CuI (0.03 equiv) and $PdCl_2(PPh_3)_2$ (0.05 equiv) and the reaction mixture was stirred at 80° C. for 18 hours. The reaction mixture was poured into a solution of LiBr and extracted with ethyl acetate. The combined organic solution was washed with ammonium chloride, brine, dried over $Na_2SO_4$, filtered and concentrated under reduced pressure. The resulting residue was purified by flash chromatography over silica gel to yield the product.

General Procedure N: Reduction of alkyne.

To a solution of the alkyne (1 equiv) in DME (20 vol/wt) were added 4-methylbenzenesulfonohydrazide (10 equiv) and TEA (5 equiv). The resulting reaction mixture was refluxed overnight, until complete consumption of starting alkyne was observed. The reaction was quenched by addition of water. The product was extracted using Et$_2$O, the organics were combined, dried over anhydrous sodium sulfate, and concentrated under reduced pressure.

General Procedure O: Esterification of Benzoic Acids to Methyl Benzoates.

A 2 M solution of HCl in MeOH was prepared by adding acetyl chloride dropwise to MeOH (1.0 M relative to the benzoic acid) at 0° C. This mixture was removed from the ice bath and stirred for 15 min. A benzoic acid (1 equiv) was added neat and the mixture was heated to reflux for 14 h. The mixture was then cooled to r.t. and evaporated to a yellow oil and immediately purified by flash chromatography.

General Procedure P: Benzohydrazide Formation.

To a solution of a methyl benzoate (1 equiv) in EtOH (0.6 M) at room temperature was added hydrazine (3 equiv), and the mixture was heated to reflux for 14 h. The mixture was then cooled to r.t., evaporated to a white solid, and immediately purified by flash chromatography.

General Procedure Q: Conversion of N-acylbenzohydrazides to 1,3,4-oxadiazoles.

To a solution of an N-acylbenzohydrazide (1.0 equiv) and p-toluenesulfonylchloride (2.0 equiv) in CH$_2$Cl$_2$ (0.2 M) was added TEA (3.0 equiv) dropwise. The mixture was stirred at r.t. for 12 h. The reaction was evaporated to dryness and immediately purified by flash chromatography.

Compound 1

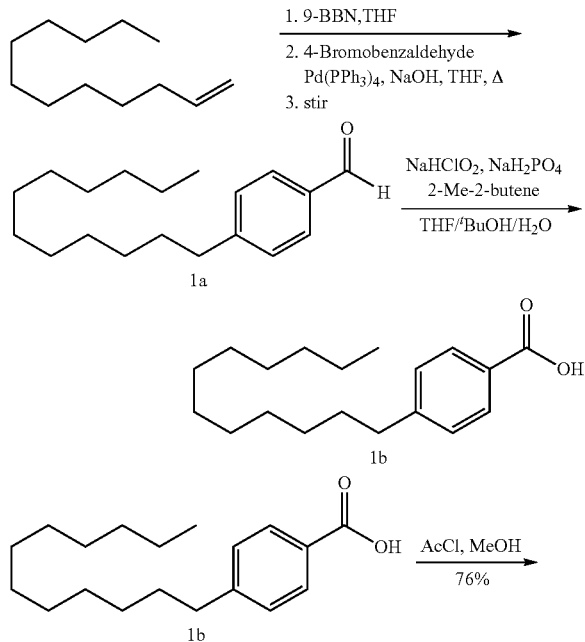

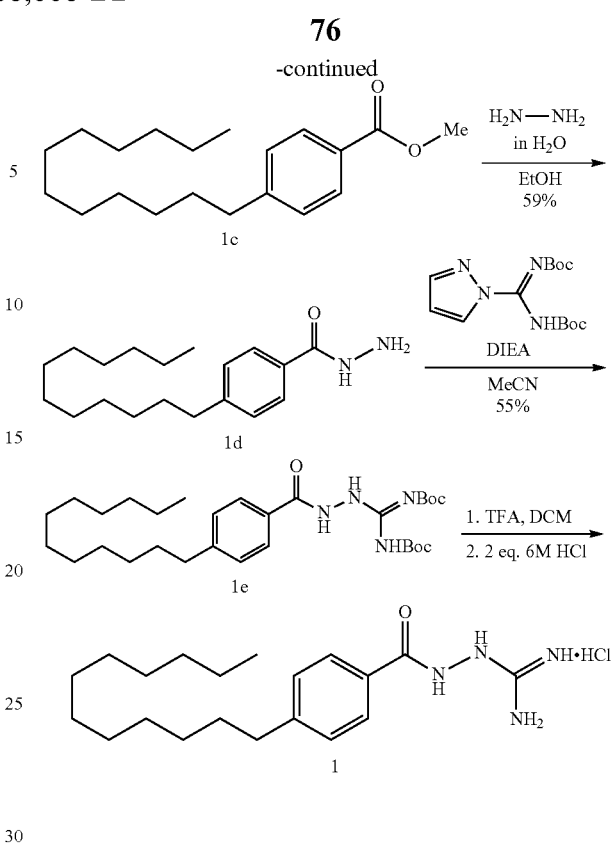

4-dodecylbenzaldehyde (1a)

General procedure C was used to convert 1-dodecene (8.1 mL, 36.50 mmol) to the title compound (5.83 g, 87%).

4-dodecylbenzoic acid (1b)

General procedure D was used to convert 1a (5.83 g, 21.24 mmol) to the title compound as white crystalline product (5.47 g, 89%).

methyl 4-dodecylbenzoate (1c)

To a stirring solution of anhydrous methanol (1.7 mL) at 0° C., acyl chloride (0.25 mL, 3.440 mmol) was added dropwise. The mixture was stirred for 10 min. at 0° C. To the mixture, acid 1b (0.500 g, 1.722 mmol) was added in one portion and stirred. The reaction was slowly heated to reflux overnight. Once complete, the reaction was concentrated under reduced pressure and purified by flash column chromatography (10% EtOAc/hexanes, R$_f$=0.66) yielding 0.398 g (1.3 mmol, 76%): $^1$H NMR (300 MHz, CDCl$_3$) δ 7.95 (d, 2H, J=8.2 Hz), 7.24 (d, 2H, J=8.1 Hz), 3.90 (s, 3H), 2.72-2.58 (m, 2H), 1.66-1.53 (m, 2H), 1.27 (m, 18H), 0.88 (t, 3H, J=6.7 Hz); $^{13}$C NMR (75 MHz, CDCl3) δ 162.66, 148.67, 129.74, 128.56, 52.09, 51.44, 36.15, 32.06, 31.29, 29.78, 29.70, 29.60, 29.50, 29.40, 22.84, 14.27.

4-dodecylbenzohydrazide (1d)

To a stirring solution of methyl ester 1c (0.398 g, 1.307 mmol) in anhydrous ethanol (2.0 mL), hydrazine (0.36 mL, 3.921 mmol) was added. The mixture was heated to reflux overnight. Once complete, the reaction was cooled, upon which a solid formed. The solvent was removed under reduced pressure and the solid washed with hexanes and filtered via a fine fritted funnel yielding 0.236 g (0.77 mmol, 59%): $^1$H NMR (300 MHz, DMSO) δ 9.68 (s, 1H), 7.72 (d, 2H, J=8.3 Hz), 7.24 (d, 2H, J=8.3 Hz), 4.51 (bs, 2H), 2.64-2.56 (m, 2H), 1.56 (m, 2H), 1.24 (m, 18H), 0.85 (t, 3H, J=6.7 Hz); $^{13}$C NMR (75 MHz, DMSO) δ 165.90, 145.69, 130.76, 128.18, 126.96, 94.88, 46.10, 34.96, 31.33, 30.74, 29.05, 28.86, 28.75, 28.67, 22.14, 14.01.

tert-butyl (((tert-butoxycarbonyl)imino)(2-(4-dodecylbenzoyl)hydrazinyl)methyl)carbamate (1e)

General procedure H was used to convert 1d (0.236 g, 0.774 mmol) to the title compound product (0.240 g, 55%). $^1$H NMR (300 MHz, CDCl3) δ 10.71 (bs, 2H), 7.88 (d, 2H, J=8.2 Hz), 7.11 (d, 2H, J=8.2 Hz), 2.71-2.39 (m, 2H), 1.52 (s, 9H), 1.50-1.45 (m, 2H), 1.40 (s, 9H), 1.23 (m, 18H), 0.85 (t, 3H, J=6.7 Hz); $^{13}$C NMR (75 MHz, CDCl3) δ 164.47, 161.20, 154.14, 150.13, 147.16, 128.68, 128.44, 127.47, 84.07, 79.15, 35.92, 31.95, 31.20, 29.67, 29.60, 29.50, 29.39, 29.22, 28.44, 28.25, 28.04, 22.72, 15.61, 14.17, 13.35.

2-(4-dodecylbenzoyl)hydrazinecarboximidamide hydrochloride (1)

To a stirring solution of 1e (0.240 g, 0.427 mmol) in CH$_2$Cl$_2$ (4.2 mL) was added TFA (4.2 mL). The reaction was stirred for 15 min. The reaction as concentrated under reduced pressure and co-evaporated with Et$_2$O (2×10 mL). The remaining residue was dissolved and stirred in 6M HCl (1.4 mL) for 5 min. The reaction was concentrated under reduced pressure and then co-evaporated with Et$_2$O (2×10 mL) to yield 0.163 g (0.43 mmol, 100%): $^1$H NMR (500 MHz, DMSO) δ 10.59 (s, 1H), 9.69 (s, 1H), 7.86 (d, 2H, J=8.1 Hz), 7.55 (s, 2H), 7.32 (d, 2H, J=8.1 Hz), 2.63 (t, 2H, J=7.6 Hz), 1.77-1.45 (m, 2H), 1.25 (m, 18H), 0.85 (t, 3H, J=6.9 Hz); $^{13}$C NMR (126 MHz, DMSO) δ 166.47, 158.84, 147.14, 129.23, 128.27, 128.03, 35.02, 31.34, 30.77, 29.06, 28.88, 28.76, 28.63, 22.15, 14.02.

Compound 2

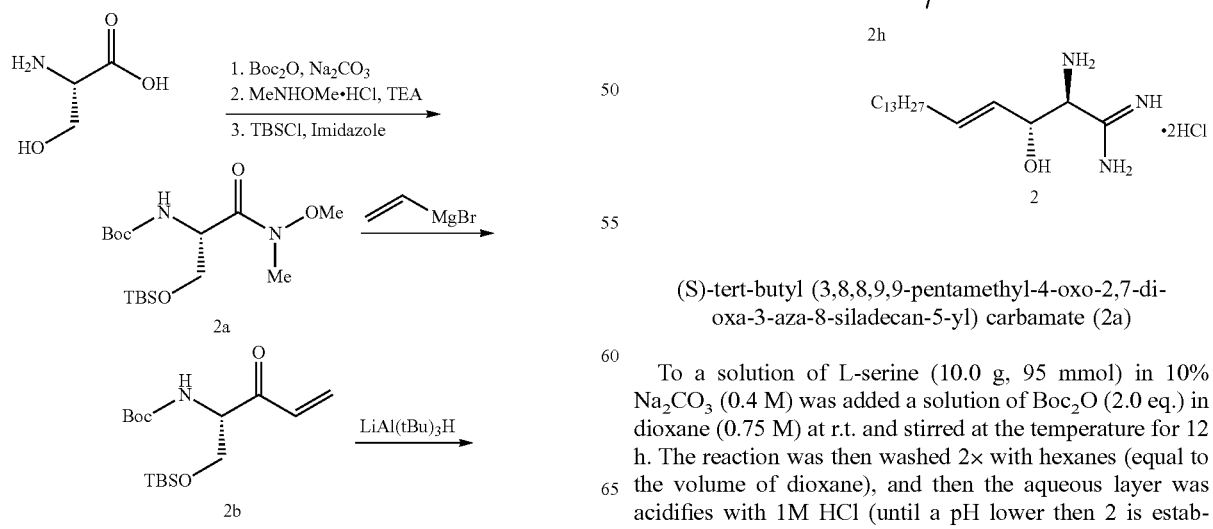

(S)-tert-butyl (3,8,8,9,9-pentamethyl-4-oxo-2,7-dioxa-3-aza-8-siladecan-5-yl) carbamate (2a)

To a solution of L-serine (10.0 g, 95 mmol) in 10% Na$_2$CO$_3$ (0.4 M) was added a solution of Boc$_2$O (2.0 eq.) in dioxane (0.75 M) at r.t. and stirred at the temperature for 12 h. The reaction was then washed 2× with hexanes (equal to the volume of dioxane), and then the aqueous layer was acidifies with 1M HCl (until a pH lower then 2 is established). The acidic aqueous solution was then extracted 3× with EtOAc (equal to the volume of the aqueous layer), dried with Na$_2$SO$_4$, and concentrated to white solid. The N-Boc serine, PyBOP (1.1 eq.), and Weinreb salt (1.1 eq.) were dissolved in CH$_2$Cl$_2$ (0.6 M) at 0° C. and TEA (1.1 eq.) was added. The reaction was warmed to r.t. and stirred for 4 h. The reaction was then quenched with 1 M HCl (10× the volume of CH$_2$Cl$_2$) and extracted 3× into EtOAc (10× the volume of CH$_2$Cl$_2$). The organic layers were dried with Na$_2$SO$_4$ and concentrated to a solid. The serine derivative and imidazole (1.2 eq.) were dissolved in CH$_2$Cl$_2$ (0.6 M) at r.t. and TBSCl (1.1 eq.) was added in one portion. The reaction turned cloudy and would clear over time. The reaction was stirred for 6 h and then diluted with EtOAc (20× the volume of CH$_2$Cl$_2$) before being washed 3× washed with 1 M HCl (20× the volume of CH$_2$Cl$_2$). The organic layers were dried with Na$_2$SO$_4$, concentrated, and purified by column chromatography to yield the title compound. 92% over 3 steps. Clear and colorless oil. R$_f$=0.36 (20% EtOAc in hexanes; KMnO$_4$). $^1$H NMR (300 MHz, CDCl$_3$) δ 5.31 (d, J=8.8 Hz, 1H), 4.68 (dt, J=8.6, 4.4 Hz, 1H), 3.75 (ddd, J=15.4, 5.0 Hz, 2H), 3.69 (s, 3H), 3.14 (s, 3H), 1.36 (s, 9H), 0.79 (s, 9H), −0.04 (s, 6H). $^{13}$C NMR (75 MHz, CDCl$_3$) δ 170.91, 155.55, 79.64, 63.65, 61.60, 52.63, 32.28, 28.51, 25.94, 18.41, −5.36.

(S)-tert-butyl (1-((tert-butyldimethylsilyl)oxy)-3-oxopent-4-en-2-yl)carbamate (2b)

To a solution of Weinreb amide 2a (5.00 g, 13.8 mmol) in THF (0.3 M) at 0° C. was added 0.7 M vinylmagnesium bromide in THF dropwise over 20 min. After the addition the reaction was stirred for 10 min at 0° C. before being slowly quenched with 1 M HCl over 20 min. The slurry of salt and ice was warmed to r.t. and extracted 3× into EtOAc (10× the volume of THF). The organic layers were dried with Na$_2$SO$_4$, concentrated, and purified by column chromatography to yield the title compound. 96%. Clear and colorless oil. R$_f$=0.69 (20% EtOAc in hexanes; KMnO$_4$). $^1$H NMR (300 MHz, CDCl$_3$) δ 6.55 (dd, J=17.4, 10.5 Hz, 1H), 6.34 (dd, J=17.4, 1.4 Hz, 1H), 5.83 (d, J=10.5 Hz, 1H), 5.52 (d, J=7.3 Hz, 1H), 4.59 (dt, J=7.7, 3.9 Hz, 1H), 4.00 (dd, J=10.3, 3.3 Hz, 1H), 3.85 (dd, J=10.3, 4.4 Hz, 1H), 1.44 (s, 9H), 0.83 (s, 9H), 0.00 (s, 3H), −0.01 (s, 3H). $^{13}$C NMR (75 MHz, CDCl$_3$) δ 196.62, 155.54, 133.34, 129.67, 80.00, 63.66, 59.75, 28.56, 25.95, 18.41, −5.39.

tert-butyl ((2S,3R)-1-((tert-butyldimethylsilyl)oxy)-3-hydroxypent-4-en-2-yl) carbamate (2c)

A solution of enone 2b (2.95 g, 8.95 mmol) in EtOH (0.5 M) was cooled to −78° C. and a 1.0 M solution of LiAl(tBu)$_3$H in THF (2.1 eq.) was slowly added down the side of the flask as to not affect the temperature of the reaction. After the addition was complete, the reaction was warmed to r.t. in the acetone dry ice bath as the dry ice was slowly consumed over time. Once the reaction reacted at r.t. after 2 h, the reaction was quenched with 1 M HCl (10× the volume of EtOH) and extracted 3× into EtOAc (30× the volume of EtOH). The organic layers were dried with Na$_2$SO$_4$, concentrated, and purified by column chromatography to yield the title compound. 96%. Clear and colorless oil. R$_f$=0.58 (20% EtOAc in hexanes; KMnO$_4$). $^1$H NMR (300 MHz, CDCl$_3$) δ 5.89 (dddd, J=16.9, 10.5, 4.9, 1.2 Hz, 1H), 5.39-5.15 (m, 3H), 4.27-4.17 (m, 1H), 3.89 (ddd, J=10.3, 3.0, 1.4 Hz, 1H), 3.74 (dd, J=20.0, 10.5 Hz, 2H), 3.59 (dd, J=7.5, 3.2 Hz, 1H), 3.58 (br s, 1H), 1.41 (s, 9H), 0.86 (s, 9H), 0.03 (s, 6H). $^{13}$C NMR (75 MHz, CDCl$_3$) δ 155.98, 138.12, 116.01, 79.70, 74.93, 63.54, 54.30, 28.57, 26.00, 18.31, −5.46.

(4S,5R)-tert-butyl 4-(hydroxymethyl)-2,2-dimethyl-5-vinyloxazolidine-3-carboxylate (2d)

To a solution of alcohol 2c (1.60 g, 4.83 mmol) in a 2:1 solvent mixture of acetone and 2,2-dimethoxy propane (0.3 M) at r.t. was added K10 clay (20 w/w %) in one portion. The reaction was stirred for 30 min, diluted with CHCl$_3$ and filtered through a fine fritted funnel, and the filtrate was concentrated to a clear oil. The crude oil was then dissolved in THF (0.3 M) at r.t. and treated with a 1.0 M solution of TBAF in THF (1.5 eq.) and stirred for 2 h, when the solvent was removed by evaporation. The crude reaction was then purified by column chromatography to yield the title compound. 99% over 2 steps. Clear and colorless oil. R$_f$=0.32 (20% EtOAc in hexanes; KMnO$_4$). $^1$H NMR (300 MHz, CDCl$_3$) δ 5.82 (ddd, J=16.9, 10.5, 6.6 Hz, 1H), 5.47-5.17 (m, 2H), 4.53 (t, J=5.9 Hz, 1H), 4.10-3.35 (m, 4H), 1.51 (s, 3H), 1.46 (s; 3H), 1.41 (s, 9H). $^{13}$C NMR (126 MHz, CDCl$_3$) δ 153.81, 131.84, 118.93, 92.93, 81.00, 76.34, 62.60, 60.91, 28.28, 24.62, 21.97.

(4S,5R)-tert-butyl 4-cyano-2,2-dimethyl-5-vinyloxazolidine-3-carboxylate (2e)

To a solution of alcohol 2d (1.33 g, 5.18) in DMSO (0.2 M) and 2,4,6-collidine (8.0 eq.) was added IBX (3.0 eq.) in one portion and the reaction was heated to 35° C. for ~1.3 h. After full conversion of the alcohol to the aldehyde by TLC, NH$_4$Cl (2.0 eq.) was added in one portion at 35° C. and the reaction was held at that temperature for 6 h. The reaction was then cooled to r.t., quenched with Na$_2$SO$_3$ (10× the volume of DMSO), and extracted 3× into EtOAc (20× the volume of DMSO). The organic layers were dried with Na$_2$SO$_4$, concentrated, and purified by column chromatography to yield the title compound. 52%. White solid. R$_f$=0.65 (20% EtOAc in hexanes; Ninhydrin). $^1$H NMR (300 MHz, CDCl$_3$) δ 5.97 (ddd, J=10.0, 9.4, 5.8 Hz, 1H), 5.61-5.44 (m, 2H), 4.70-4.52 (m, 2H), 1.63 (s, 3H), 1.51 (s, 3H), 1.47 (s, 9H). $^{13}$C NMR (75 MHz, CDCl$_3$) δ 150.49, 130.93, 122.52, 116.03, 95.46, 82.18, 76.15, 52.43, 28.45, 26.32, 24.63.

(4S,5R)-tert-butyl 4-cyano-2,2-dimethyl-5-((E)-pentadec-1-en-1-yl)oxazolidine-3-carboxylate (2f)

To a solution of the alkene 2e (382 mg, 1:51 mmol) and 1-pentadecene (4.0 eq.) in CH$_2$Cl$_2$ (0.1 M) was added Grubbs 2$^{nd}$ generation catalyst (0.03 eq.) and the reaction was heated to reflux for 3.5 h. The reaction was then cooled to r.t., evaporated to dryness, and purified by column chromatography to yield the title compound. 78%. Clear and colorless oil. R$_f$=0.65 (20% EtOAc in hexanes; Ninhydrin). $^1$H NMR (300 MHz, CDCl$_3$) δ 5.99 (dt, J=15.2, 6.7 Hz, 1H), 5.65 (dd, J=15.3, 7.1 Hz, 1H), 4.65-4.47 (m, 2H), 2.10 (dt, J=6.9, 6.9 Hz, 2H), 1.68-1.60 (m, 3H), 1.55-1.46 (m, 12H), 1.45-1.34 (m, J=13.0, 6.6 Hz, 2H), 1.33-1.20 (m, J=19.9 Hz, 20H), 0.86 (t, J=6.7 Hz, 3H). $^{13}$C NMR (75 MHz, CDCl$_3$) δ 150.57, 140.71, 122.49, 116.25, 95.19, 82.09, 76.26, 52.60, 32.56, 32.13, 29.86, 29.76, 29.64, 29.57, 29.38, 28.84, 28.47, 27.31, 26.36, 25.45, 24.63, 22.90, 14.33.

(4S,5R)-tert-butyl 4-((Z)—N'-hydroxycarbamimidoyl)-2,2-dimethyl-5-((E)-pentadec-1-en-1-yl)oxazolidine-3-carboxylate (2g)

To a solution of nitrile 2f (470 mg, 1.08 mmol) and hydroxylamine (5.0 eq.) in EtOH (0.1 M) was added TEA (10 eq.) and heated to 50° C. for 5 h. The reaction was then cooled to r.t., evaporated to dryness, and purified by column chromatography to yield the title compound. 92%. Clear and colorless oil. $R_f$=0.49 (35% EtOAc in hexanes; Seebach's Dip). $^1$H NMR (500 MHz, CDCl$_3$) δ 8.90 (s, 1H), 6.91 (s, 1H), 6.40 (s, 1H), 5.81 (dt, J=14.8, 7.1 Hz, 1H), 5.38 (dd, J=15.5, 7.4 Hz, 1H), 4.65-4.41 (m, 2H), 2.02-1.92 (m, 2H), 1.72-1.56 (m, 3H), 1.55-1.25 (m, 14H), 1.26-1.09 (m, 20H), 0.80 (t, J=6.8 Hz, 3H). $^{13}$C NMR (126 MHz, CDCl$_3$) δ 151.76, 150.62, 138.38, 122.90, 93.33, 80.30, 76.87, 60.87, 31.84, 29.62, 29.54, 29.41, 29.29, 28.81, 28.22, 22.61, 14.05.

(4S,5R)-tert-butyl 4-(N'-(tert-butoxycarbonyl)carbamimidoyl)-2,2-dimethyl-5-((E)-pentadec-1-en-1-yl)oxazolidine-3-carboxylate (2h)

A 0.1 M solution of samarium (II) iodide in THF (3.0 eq.) was added to amide oxime 2g (386 mg, 0.825 mmol) at 0° C. and warmed to r.t. The reaction was stirred at r.t. for 8 h and then quenched by opening the flask to the atmosphere and turned form the dark blue of samarium (II) to the pale yellow of samarium (I). The reaction was then treated with TEA (5.0 eq.) and Boc$_2$O (3.0 eq.) and stirred for 30 min. The reaction was then filtered through Celite™ with EtOAc (10× the volume of the reaction), concentrated, and purified by column chromatography to yield the title compound. 53%. Atropisomer A: $R_f$=0.74 (20% EtOAc in hexanes; Seebach's Dip). $^1$H NMR (500 MHz, CDCl$_3$) δ 10.27 (s, 1H), 10.03 (s, 1H), 5.93 (dt, J=15.1, 6.9 Hz, 1H), 5.70-5.07 (m, 1H), 4.78 (t, J=7.4 Hz, 1H), 1.98 (dt, J=6.7 Hz, 2H), 1.84-1.75 (m, 3H), 1.56-1.15 (m, 43H), 0.86 (t, J=6.9 Hz, 3H). $^{13}$C NMR (126 MHz, CDCl$_3$) δ 151.95, 151.05, 149.98, 138.01, 122.93, 94.22, 82.47, 80.69, 77.01, 60.96, 32.33, 31.91, 29.66, 29.54, 29.47, 29.34, 28.15, 27.97, 27.87, 22.67, 14.11. Atropisomer B: $R_f$=0.55 (20% EtOAc in hexanes; Seebach's Dip). $^1$H NMR (500 MHz, CDCl$_3$) δ 7.87 (s, 1H), 7.67 (s, 1H), 5.92 (dt, J=14.8, 6.7 Hz, 1H), 5.77-5.01 (m, 1H), 4.73 (t, J=7.2 Hz, 1H), 2.04-1.93 (m, 2H), 1.78-1.67 (m, 3H), 1.58-1.15 (m, 43H), 0.85 (t, J=7.0 Hz, 3H). $^{13}$C NMR (126 MHz, CDCl$_3$) δ 151.99, 151.00, 149.90, 137.86, 122.83, 94.22, 82.54, 80.78, 76.78, 63.09, 32.23, 31.89, 29.64, 29.54, 29.44, 29.33, 28.13, 27.85, 22.65, 14.09. Atropisomer A: B=3.4:1 by yield.

(2S,3R,E)-2-amino-3-hydroxyoctadec-4-enimidamide dihydrochloride (2)

To a flask containing the di-Boc protected 2h was added 2 M dry HCl in ether at 0° C. and warmed to r.t. The reaction was stirred for 3 h and then evaporated to dryness to yield the title compound. 99%. White solid. $^1$H NMR (500 MHz, DMSO) δ 8.01 (s, 3H), 7.81 (s, 2H), 7.54 (s, 2H), 5.66 (dt, J=16.8, 5.0 Hz, 1H), 5.39 (dd, J=15.5, 6.9 Hz, 1H), 4.41-4.35 (m, 1H), 3.73 (dd, J=9.9, 5.1 Hz, 1H), 2.39 (s, 1H), 1.95 (dt, J=13.7, 6.7 Hz, 2H), 1.37-1.27 (m, 2H), 1.27-1.16 (m, 20H), 0.83 (t, J=6.9 Hz, 3H). $^{13}$C NMR (126 MHz, DMSO) δ 168.10, 134.48, 126.87, 70.26, 57.67, 32.20, 31.74, 29.53, 29.17, 29.13, 28.88, 22.55, 14.42.

Compound 3

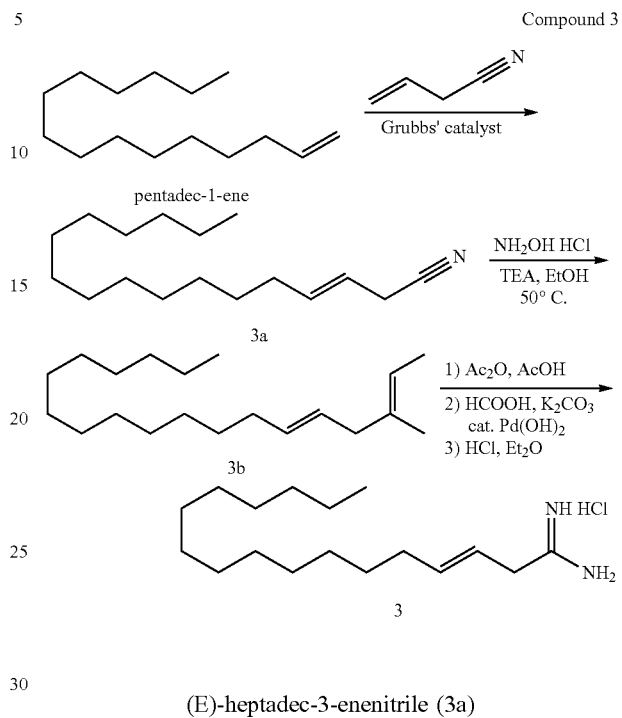

(E)-heptadec-3-enenitrile (3a)

To a solution of 1-pentadecene (1.2 mL, 4.4 mmol) and allyl cyanide (0.1 mL, 1.1 mmol) in DCM (18.0 mL) was added Grubbs' second-generation catalyst (5 mol %). The reaction mixture was stirred for 2.5 h at reflux. After cooling to r.t., the solution was concentrated under reduced pressure. The yellow oil was loaded onto silica gel and purified via flash chromatography (10% EtOAc in hexanes) to yield 168 mg (0.67 mmol, 56%) of 1 as a colorless oil. $R_f$=0.59 (15% EtOAc/hexanes); $^1$H NMR (300 MHz, CDCl$_3$) δ 5.92-5.70 (m, 1H), 5.36 (m, 1H), 3.06 (d, J=5.6, 2H), 2.04 (s, 2H), 1.34 (m, 22H), 0.88 (t, J=6.6, 3H).

(1Z,3E)-N'-hydroxyheptadec-3-enimidamide (3b)

General procedure F was used to convert 3a (379 mg, 1.52 mmol) to the title product. 50%. Purple oil. $R_f$=0.24 (50% EtOAc in hexanes). $^1$H NMR (300 MHz, CDCl$_3$) δ 5.72-5.55 (m, 1H), 5.50-5.34 (m, 1H), 4.56 (s, 1H), 2.83 (d, J=6.9, 2H), 2.14-1.95 (m, 2H), 1.25 (m, 22H), 0.87 (t, J=6.7, 3H).

heptadecanimidamide hydrochloride (3)

Potassium formate was prepared in situ from HCOOH (0.29 mL, 7.58 mmol) and K$_2$CO$_3$ (520 mg, 3.79 mmol) in MeOH (2.0 mL). The parent amide oxime (214 mg, 0.76 mmol) was dissolved in AcOH (1 mL) and Ac$_2$O (0.1 mL, 0.83 mmol) was added at r.t. After 5 min, the potassium formate solution in MeOH was added, followed by a catalytic amount of Pd(OH)$_2$. The mixture was stirred at r.t. overnight. The solution was filtered through Celite, washed with EtOH, and the filtrate was evaporated. The residue was dissolved in anhydrous EtOH and 5 M HCl in EtOH (12 eq.) was then added. After evaporation, the material was recrystallized in Et$_2$O to yield the pure amidine hydrochloride salt. $^1$H NMR (500 MHz, DMSO) δ 9.02 (s, 1H), 8.73 (s, 1H), 2.37-2.31 (m, 2H), 1.57 (m, 2H), 1.22 (m, 26H), 0.83 (t, J=6.9, 3H). $^{13}$C NMR (126 MHz, DMSO) δ 171.50, 32.11, 31.74, 29.51, 29.30, 29.16, 28.93, 28.63, 26.72, 22.54, 14.41.

Compound 4

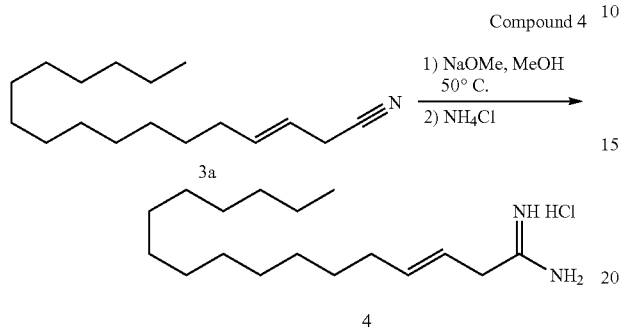

(E)-heptadec-3-enimidamide hydrochloride (4)

General procedure A was used to convert 3a (170 mg, 0.7 mmol) to the title compound as white solid (4%). $^1$H NMR (500 MHz, DMSO) δ 5.74-5.62 (m, 1H), 5.51-5.40 (m, 1H), 3.06 (d, J=7.0 Hz, 2H), 1.98 (q, J=6.9 Hz, 2H), 1.22 (s, 22H), 0.84 (t, J=6.9 Hz, 3H); $^{13}$C NMR (126 MHz, DMSO) δ 136.6, 121.8, 35.5, 32.2, 31.7, 29.49, 29.46, 29.3, 29.2, 29.0, 28.9, 22.5, 14.4; $t_R$=11.31 min.; m/z=267.29.

Compound 5

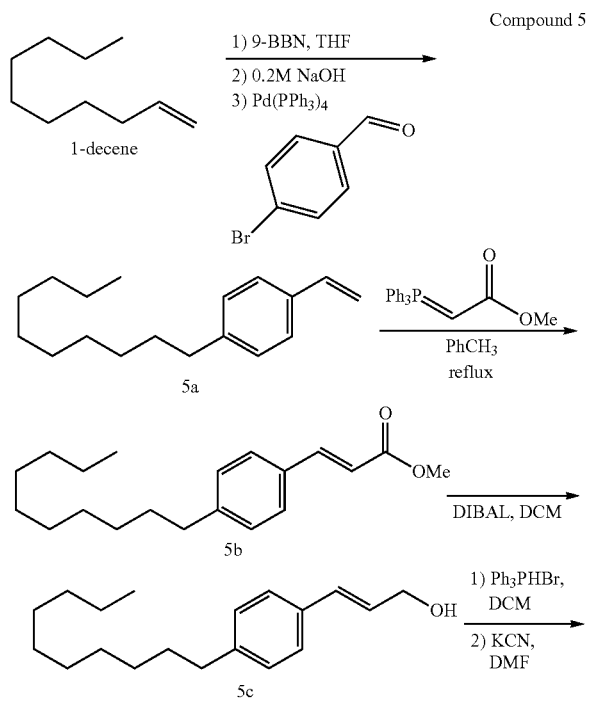

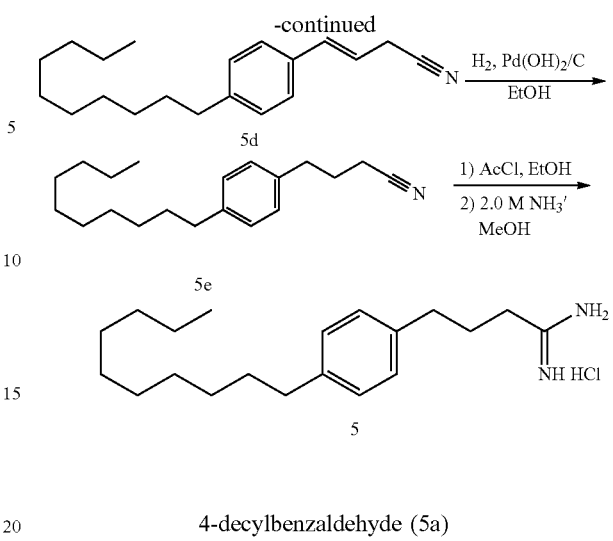

4-decylbenzaldehyde (5a)

General procedure C was used to couple 1-decene (5.0 mL, 26.5 mmol) and 4-bromobenzaldehyde (3.3, 17.7 mmol) to yield the title compound as yellow oil (88% yield). $R_f$=0.70 (20% EtOAc/hexanes); $^1$H NMR (300 MHz, CDCl$_3$) δ 7.79 (d, J=8.1, 2H), 7.33 (d, J=8.0, 2H), 2.68 (t, J=7.5, 2H), 1.71-1.56 (m, 2H), 1.28 (m, 14H), 0.87 (t, J=6.7, 3H); $^{13}$C NMR (75 MHz, CDCl$_3$) δ 192.4, 150.9, 134.7, 130.2, 129.4, 36.6, 32.2, 31.4, 29.9, 29.8, 29.7, 29.6, 23.0, 14.5.

(E)-methyl 3-(4-decylphenyl)acrylate (5b)

To a solution of 4-decylbenzaldehyde (5a) (1.0 g, 4.2 mmol) in toluene (21.0 mL) was added methyl (triphenylphosphorylidene)acetate (2.8 g, 8.4 mmol). The reaction mixture was stirred for 2 h at reflux. After cooling to r.t., the solution was concentrated. The white solid was loaded onto silica gel and purified via flash chromatography (10% EtOAc in hexanes) to yield 1.08 g (3.57 mmol, 85%) of the title product as a white solid. $R_f$=0.69 (15% EtOAc/hexanes); $^1$H NMR (300 MHz, CDCl$_3$) δ 7.68 (d, J=16.0, 1H), 7.44 (d, J=8.1, 2H), 7.19 (d, J=8.1, 2H), 6.40 (d, J=16.0, 1H), 3.80 (s, 3H), 2.61 (t, J=7.5, 2H), 1.68-1.53 (m, 2H), 1.38-1.17 (m, 14H), 0.88 (t, J=6.7, 3H); $^{13}$C NMR (75 MHz, CDCl$_3$) δ 167.7, 145.9, 145.0, 131.9, 129.1, 128.2, 116.8, 51.7, 36.0, 32.0, 31.4, 29.7, 29.7, 29.6, 29.4, 29.4, 22.8, 14.2.

(E)-3-(4-decylphenyl)prop-2-en-1-ol (5c)

To a solution of 5b (1.1 g, 3.6 mmol) in dichloromethane (7.5 mL) stirring at −78° C. was added a 1.2 M solution of diisobutylaliminum hydride (8.9 mL, 10.7 mmol) in toluene dropwise via syringe. The reaction mixture was warmed to ambient temperature slowly and stirred overnight. The mixture was subsequently cooled to 0° C. and quenched with 1 M HCl. The solution was extracted three times with 15 mL portions of EtOAc. The organic layer was washed with 10 mL of brine, dried over MgSO$_4$ and concentrated to yield 960 mg (3.17 mmol, 98%) of the title product as a white solid. $R_f$=0.22 (15% EtOAc/hexanes); $^1$H NMR (300 MHz, CDCl$_3$) δ 7.31 (d, J=8.1, 2H), 7.15 (d, J=8.1, 2H), 6.60 (d, J=15.9, 1H), 6.33 (dt, J=5.8, 15.9, 1H), 4.31 (d, J=5.7, 2H), 2.61 (t, J=7.5, 2H), 1.70-1.55 (m, 2H), 1.44-1.19 (m, 14H), 0.91 (t, J=6.7, 3H); $^{13}$C NMR (75 MHz, CDCl$_3$) δ 142.9, 134.4, 131.4, 128.9, 127.8, 126.7, 64.1, 36.0, 32.2, 31.8, 29.9, 29.8, 29.6, 23.0, 21.8, 14.4.

(E)-4-(4-decylphenyl)but-3-enenitrile (5d)

To a solution of triphenylphosphonium bromide (1.3 g, 3.2 mmol) in dichloromethane (2.6 mL) stirring at 0° C. was added 5c (430 mg, 1.6 mmol) in dichloromethane (2.6 mL), also cooled to 0° C. The reaction mixture was warmed to ambient temperature and stirred for another 2.5 h. The mixture was then quenched with a saturated sodium bicarbonate solution. The resulting aqueous layer was extracted two times with 10 mL portions of diethyl ether. The organic layer was collected and washed with 10 mL of brine, dried over $MgSO_4$ and concentrated. The resulting solid was taken up in DMF (5.3 mL) and cooled to 0° C. Potassium cyanide (200 mg, 3.2 mmol) was added while stirring and left overnight. The reaction mixture was diluted with 50 mL ethyl acetate and washed 10 times with 1.0 M NaOH. The organic layer was washed with brine, dried with $MgSO_4$ and evaporated. The residue was loaded onto silica in dichloromethane and purified via flash chromatography (15% EtOAc in hexanes) to yield 133 mg (0.47 mmol, 30%) of the title product as an oil. $R_f$=0.50 (15% EtOAc/hexanes); $^1$H NMR (300 MHz, $CDCl_3$) δ 7.29 (d, J=7.9, 2H), 7.16 (d, J=7.9, 2H), 6.71 (d, J=15.8, 1H), 6.01 (dt, J=5.4, 15.7, 1H), 3.27 (d, J=5.7, 2H), 2.60 (t, J=7.5, 2H), 1.70-1.53 (m, 2H), 1.30 (m, 14H), 0.90 (t, J=6.4, 3H). $^{13}$C NMR (75 MHz, $CDCl_3$) δ 143.6, 134.8, 133.3, 129.0, 126.6, 117.7, 115.9, 35.9, 32.2, 31.6, 29.9, 29.8, 29.6, 23.0, 21.0, 14.4.

4-(4-decylphenyl)butanenitrile (5e)

To a solution of 5d (210 mg, 0.8 mmol) in EtOH (7.6 mL) was added Pearlman's catalyst (50 mg, 5 mol %). The apparatus was flushed with hydrogen, equipped with a balloon, and stirred for 2 h. The reaction was filtered through Celite, washed with EtOH, and concentrated to 200 mg (0.70 mmol, 93%) of a yellow oil. $R_f$=0.42 (10% EtOAc/hexanes); $^1$H NMR (300 MHz, $CDCl_3$) δ 7.11 (s, 4H), 2.75 (t, J=7.4, 2H), 2.58 (t, J=7.8, 2H), 2.32 (t, J=7.1, 2H), 2.07-1.91 (m, 2H), 1.58 (m, 2H), 1.28 (m, 14H), 0.88 (t, J=6.7, 3H); $^{13}$C NMR (75 MHz, $CDCl_3$) δ 141.5, 137.1, 129.0, 128.7, 120.0, 35.9, 34.3, 32.2, 31.9, 29.94, 29.85, 29.7, 27.3, 23.0, 16.7, 14.5.

4-(4-decylphenyl)butanimidamide hydrochloride (5)

To dry EtOH (3.5 mL) at 0° C. was added acetyl chloride (1.0 mL, 14.0 mmol). After 10 min, nitrile 5d (200 mg, 0.7 mmol) in EtOH (3.5 mL) was added dropwise via syringe. The color of the solution changed from brown to yellow-orange. The mixture was slowly warmed to ambient temperature overnight. The EtOH was evaporated under reduced pressure and the residue was coevaporated with ether two times. The residue was placed in vacuo for 2 h. A 2.0 M solution of ammonia in MeOH (7.0 mL) was added to the reaction flask dropwise. The solution was stirred overnight. The reaction mixture was evaporated to dryness, diluted in $CHCl_3$, and filtered through a fine fritted funnel. The eluent was evaporated to dryness and the residue was diluted with ether and triturated to give 12.7 mg (0.037 mmol, 5.5%) of a brown solid. $^1$H NMR (300 MHz, DMSO-$d_6$) δ 8.98 (s, 2H), 8.65 (s, 2H), 7.08 (s, 4H), 2.62-2.43 (m, 2H), 2.38 (t, J=7.5, 2H), 1.96-1.78 (m, 2H), 1.60-1.44 (m, 2H), 1.21 (s, 14H), 0.83 (t, J=6.4, 3H); $^{13}$C NMR (126 MHz, DMSO-$d_6$) δ 170.7, 140.0, 137.9, 128.3, 128.1, 34.7, 34.0, 31.6, 31.3, 31.0, 28.99, 28.85, 28.7, 27.9, 22.1, 14.0.

Compound 6

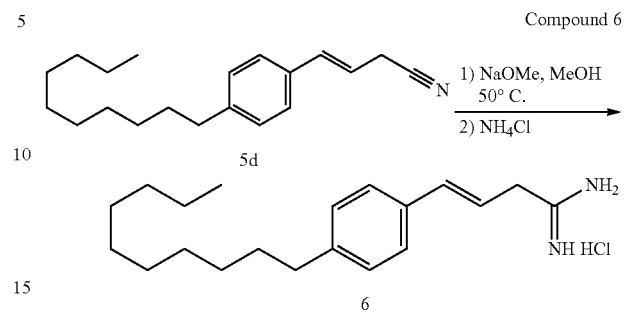

(E)-4-(4-decylphenyl)but-3-enimidamide hydrochloride (6)

General procedure A was used to convert 5d (130 mg, 0.5 mmol) to the title product as white solid (1.3% yield). $^1$H NMR (500 MHz, DMSO) δ 8.44 (s, 2H), 7.36 (d, J=8.0, 2H), 7.18 (d, J=8.1, 2H), 6.59 (d, J=16.0, 1H), 6.27 (d, J=16.0, 1H), 3.29 (d, J=7.0, 2H), 2.56 (t, 2H), 1.60-1.51 (m, 2H), 1.32-1.19 (m, 14H), 0.87 (t, J=6.7, 3H); $^{13}$C NMR (126 MHz, DMSO) δ 134.7, 129.1, 126.7, 120.8, 36.0, 35.3, 31.7, 31.3, 29.4, 29.3, 29.1, 29.0, 22.5, 14.4; $t_R$=10.83 min; m/z=301.31.

Compound 7

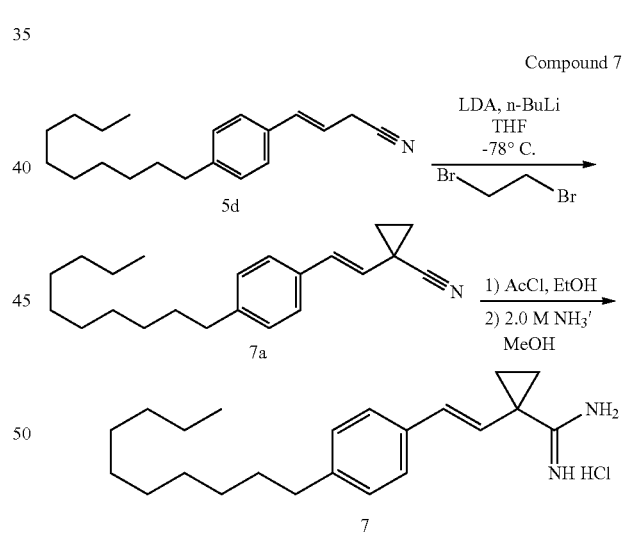

(E)-1-(4-decylstyryl)cyclopropanecarbonitrile (7a)

To a solution of diisopropylamine (0.3 mL, 1.9 mmol) in THF (0.9 mL) at −78° C. was added a 2.2 M solution of n-butyl lithium in hexanes (0.8 mL, 1.8 mmol). The mixture was stirred for 30 min while the temperature was maintained at −78° C. DMPU (53 μL, 0.4 mmol) was added to the reaction flask and stirred for 15 min. Next, nitrile 5d (0.2 g, 0.7 mmol) was added as a solution in THF (0.85 mL). The color of the reaction mixture changed from a pale yellow to a deep red. The solution was stirred at −78° C. for 30 min and subsequently warmed to −30° C. for an additional 30 min. The mixture was cooled to −78° C. and 1,2-dibromoethane (0.3 mL, 3.53 mmol) was added dropwise over 3 min. The mixture was warmed to ambient temperature slowly overnight. The reaction was quenched with saturated ammonium chloride, extracted three times with 15 mL portions of diethyl ether. The ether layer was washed with 1 M HCl, water, saturated sodium bicarbonate, and brine and dried over MgSO$_4$. The solvent was evaporated in vacuo, loaded onto silica gel in DCM, and purified via flash chromatography (10% EtOAc/hexanes) to yield 94 mg (0.30 mmol, 43%) of a brown oil. $R_f$=0.40 (10% EtOAc/hexanes); $^1$H NMR (300 MHz, CDCl$_3$) δ 7.24 (d, J=8.3, 2H), 7.12 (d, J=8.1, 2H), 6.79 (d, J=15.9, 1H), 5.49 (d, J=15.8, 1H), 2.58 (t, J=7.2, 2H), 1.65-1.53 (m, 4H), 1.36-1.22 (m, 14H), 1.19 (dd, J=5.1, 7.8, 2H), 0.88 (t, J=6.7, 3H); $^{13}$C NMR (75 MHz, CDCl$_3$) δ 143.5, 131.1, 129.1, 126.4, 125.5, 115.4, 36.0, 33.0, 32.2, 31.7, 29.9, 29.8, 29.7, 29.6, 23.0, 17.1, 14.5, 12.8.

(E)-1-(4-decylstyryl)cyclopropanecarboximidamide hydrochloride (7)

To dry EtOH (1.5 mL) at 0° C. was added acetyl chloride (0.5 mL, 6.0 mmol). After 10 min, nitrile 7a (90 mg, 0.3 mmol) in EtOH (1.5 mL) was added dropwise via syringe. The color of the solution changed from brown to yellow-orange. The mixture was slowly warmed to ambient temperature overnight. The EtOH was evaporated under reduced pressure and the residue was coevaporated with ether two times. The residue was placed in vacuo for 2 h. A 2.0 M solution of ammonia in MeOH (3.0 mL) was added to the reaction flask dropwise. The solution was stirred overnight. The solvent was evaporated to dryness, diluted in CHCl$_3$ and filtered through a fine fritted funnel. The eluent was evaporated to dryness and the residue was triturated with diethyl ether to give 4.1 mg (0.013 mmol, 4.2%) of a brown solid. $t_R$=11.67 min.; m/z=327.23. $^1$H NMR (500 MHz, DMSO) δ 8.86 (d, J=64.9, 4H), 7.32 (d, J=7.6, 2H), 7.13 (d, J=7.9, 2H), 6.41 (d, J=16.0, 1H), 6.28 (d, J=16.6, 1H), 2.66-2.41 (m, 2H), 1.54 (m, 2H), 1.43-1.04 (m, 20H), 0.83 (t, J=6.6, 3H).

Compound 8

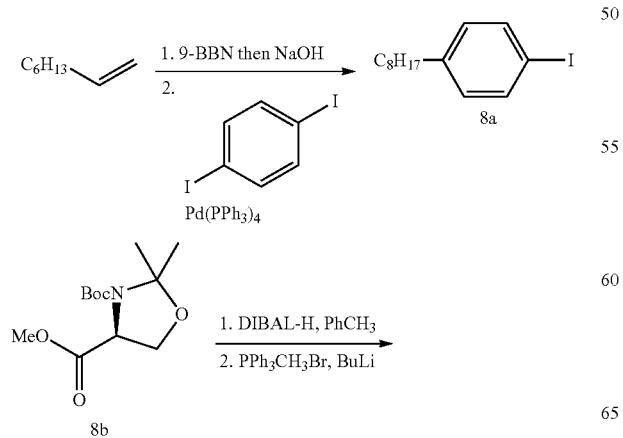

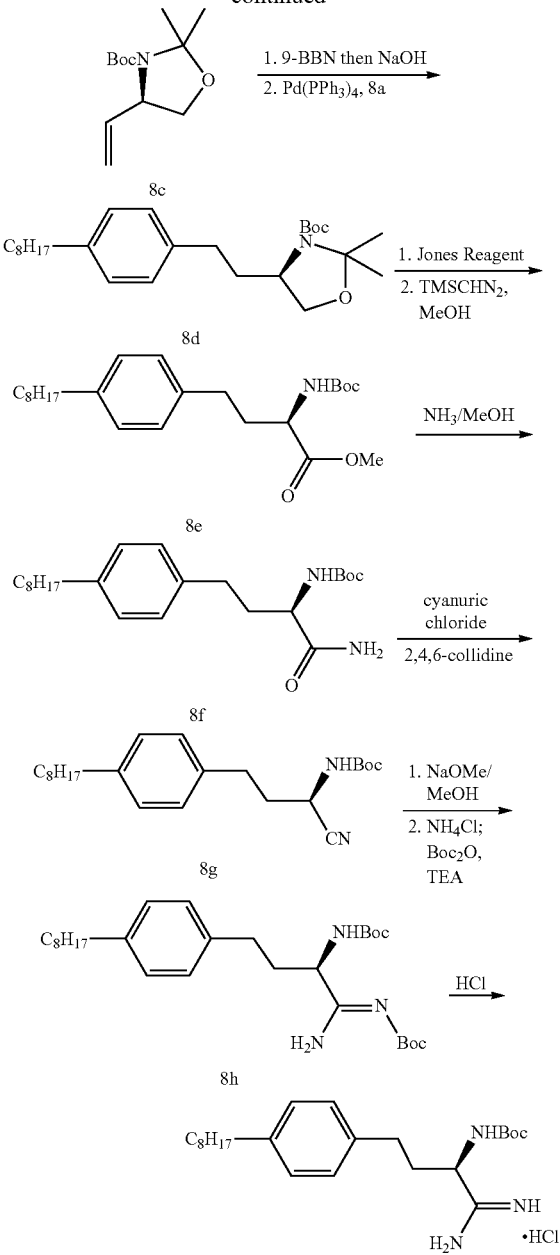

1-iodo-4-octylbenzene (8a)

To a 0.5 M solution of 9-BBN (2.0 eq.) was added 1-octene (4.28 mL, 27.3 mmol, 2.0 eq.) and stirred for 12 h. The reaction was then treated with 3N NaOH$_{(aq)}$ (2.2 eq.), followed by the solid additions of 1,4-diiodobenzene (6.00 g, 18.19 mmol, 1.0 eq.) and Pd(PPh$_3$)$_4$ sequentially. The reaction was then heated to reflux for 1 h, then cooled to r.t., and extracted 2× into EtOAc (500 mL). The organic layer was then dried with Na$_2$SO$_4$, evaporated to a black oil, and immediately purified by flash chromatography to yield the title solution. 95%. Clear and colorless oil. $R_f$=0.76 (hexanes; Seebach's Dip). $^1$H NMR (500 MHz, CDCl$_3$) δ 7.70 (d, J=8.0 Hz, 2H), 7.21 (s, 4H), 7.02 (d, J=8.0 Hz, 1H), 2.67 (t, J=7.8 Hz, 6H), 1.76-1.67 (m, 6H), 1.40 (s, 30H), 1.01 (t, J=7.0 Hz, 9H). $^{13}$C NMR (126 MHz, CDCl$_3$) δ 142.50, 140.09, 137.34, 130.61, 128.33, 90.67, 35.75, 32.08, 32.05, 31.79, 29.70, 29.59, 29.47, 29.44, 29.39, 22.84, 14.27.

(R)-tert-butyl 2,2-dimethyl-4-vinyloxazolidine-3-carboxylate (8c)

To a solution of 8b (1.41 g, 5.43 mmol) in PhMe (0.27 M) at −78° C. was added 20% DIBAL-H in PhMe dropwise down the side of the flask as to not raise the temperature of the reaction, and the reaction was held at −78° C. for 45 min. The reaction was then slowly quenched with anhydrous MeOH with a vent needle to relieve any pressure formed by hydrogen gas formation. The slurry was then warmed to r.t. and partitioned between EtOAc (30× the volume of PhMe) and 1 M HCl (20× the volume of PhMe), and the aqueous layer was extracted twice more with EtOAc (30× the volume of PhMe). The organic layers were combined, dried with Na$_2$SO$_4$, and concentrated to a clear and colorless oil. The crude Garner's aldehyde was immediately taken on without further purification. To a solution of triphenylmethylphosphonium bromide (2.0 eq.) in THF (0.1 M) at −78° C. was added a 2.1 M solution of n-BuLi in hexanes (1.9 eq.). The reaction was warmed to r.t. for 30 m before cooling back to −78° C., when the neat aldehyde was added to the reaction dropwise. The reaction was then warmed to r.t. and stirred for 12 h. The reaction was then diluted with Et$_2$O (8× the volume of THF) and immediately filtered through a pad of silica gel and purified by column chromatography to yield the title compound. 63% over 2 steps. Clear and colorless oil. R$_f$=0.54 (10% EtOAc in hexanes; KMnO$_4$). Rotamer A: $^1$H NMR (300 MHz, CDCl$_3$) δ 5.71 (ddd, J=8.8, 8.2 Hz, 1H), 5.21-4.95 (m, J=20.1 Hz, 2H), 4.23-4.08 (m, 1H), 3.94 (dd, J=8.8, 6.2 Hz, 1H), 3.64 (dd, J=8.8, 2.3 Hz, 1H), 1.55-1.45 (m, J=17.0 Hz, 3H), 1.44-1.29 (m, J=22.9 Hz, 12H). $^{13}$C NMR (75 MHz, CDCl$_3$) δ 152.06, 137.53, 115.86, 94.04, 79.64, 68.21, 59.82, 28.52, 26.66, 23.78. Rotamer B: $^1$H NMR (300 MHz, CDCl$_3$) δ 5.71 (ddd, J=8.8, 8.2 Hz, 1H), 5.21-4.95 (m, J=20.1 Hz, 2H), 4.34-4.21 (m, 1H), 3.94 (dd, J=8.8, 6.2 Hz, 1H), 3.64 (dd, J=8.8, 2.3 Hz, 1H), 1.55-1.45 (m, J=17.0 Hz, 3H), 1.44-1.29 (m, J=22.9 Hz, 12H). $^{13}$C NMR (75 MHz, CDCl$_3$) δ 152.06, 136.93, 115.86, 94.04, 80.21, 68.21, 59.82, 28.52, 24.95. Rotamer A: B=1.3:1 by $^1$H NMR.

(R)-tert-butyl 2,2-dimethyl-4-(4-octylphenethyl)oxazolidine-3-carboxylate (8d)

General procedure C was used to couple alkene 8c (702 mg, 3.09 mmol) and aryl iodide 9 (1.00 eq.) to yield the title compound. 71%. Tan oil. R$_f$=0.58 (10% EtOAc in hexanes; Seebach's Dip). Rotamer A: $^1$H NMR (500 MHz, CDCl$_3$) δ 7.11 (s, 4H), 4.02-3.86 (m, 2H), 3.80 (t, J=8.7 Hz, 2H), 2.70-2.43 (m, 4H), 2.22-2.07 (m, 1H), 1.85-1.69 (m, 1H), 1.64-1.52 (m, 8H), 1.49 (s, 9H), 1.36-1.20 (m, 10H), 0.89 (t, J=7.1 Hz, 3H). $^{13}$C NMR (126 MHz, CDCl$_3$) δ 151.76, 140.57, 138.43, 128.17, 93.64, 79.41, 66.77, 56.96, 35.55, 35.31, 32.37, 31.61, 29.36, 28.47, 26.79, 22.67, 14.12. Rotamer B: $^1$H NMR (500 MHz, CDCl$_3$) δ 7.11 (s, 4H), 4.02-3.86 (m, 2H), 3.80 (t, J=8.7 Hz, 2H), 2.70-2.43 (m, 4H), 2.06-2.00 (m, 1H), 1.85-1.69 (m, 1H), 1.64-1.52 (m, 8H), 1.43 (s, 9H), 1.36-1.20 (m, 10H), 0.89 (t, J=7.1 Hz, 3H). $^{13}$C NMR (126 MHz, CDCl$_3$) δ 152.13, 140.42, 138.71, 93.11, 79.93, 66.67, 57.64, 35.55, 32.37, 31.89, 29.49, 29.27, 28.47, 27.57, 24.56, 22.67, 14.12. IR (CHCl$_3$) 2926 (m), 1698 (s), 1387 (s). [α]$^{20}_D$=−32.4 (c=1.00, CHCl$_3$) Rotamer A: B=1.3:1 by $^1$H NMR.

(R)-methyl 2-((tert-butoxycarbonyl)amino)-4-(4-octylphenyl)butanoate (8e)

To a solution of oxizolidine 8d (734 mg, 1.76 mmol) in acetone (0.05M) at 0° C. was added 2.67 M Jones reagent (26.7 g CrO$_3$ and 22 mL H$_2$SO$_4$ diluted to 100 mL with H$_2$O) (3.0 eq.) dropwise. The reaction turned orange and was warmed to r.t. and stirred for 1.5 h. The reaction was quenched with 2-propanol (2 mL) and partitioned between EtOAc (20× the volume of acetone) and 1 M HCl (10× the volume of acetone) and the aqueous layer was washed 2× with equal volume of EtOAc. The organic layers were combined, dried with Na$_2$SO$_4$, and concentrated to a clear and colorless oil. The N-Boc protected amino acid was then taken on crude. To a solution of the crude carboxylic acid in a 5:1 solvent mixture of PhMe and MeOH (0.2 M) was added 2.0 M TMSCHN$_2$ in hexanes (1.05 eq.) and stirred for 1 h. The reaction was quenched with AcOH until the yellow reaction color cleared (~1 mL) and then partitioned between sat. NaHCO$_3$ (5× the reaction solvent mixture) and EtOAc (10× the reaction solvent mixture). The organic layer was isolated and the remaining aqueous solution was washed 2× with the same volume of EtOAc. The combined organic layers were then dried with Na$_2$SO$_4$, concentrated to a clear and colorless oil, and immediately purified by column chromatography to yield the title compound. 79% over 2 steps. Clear and colorless oil. R$_f$=0.30 (10% EtOAc in hexanes; Seebach's Dip). $^1$H NMR (300 MHz, CDCl$_3$) δ 7.08 (s, 4H), 5.05 (d, J=7.9 Hz, 1H), 4.35 (dd, J=7.5, 5.3 Hz, 1H), 3.71 (s, 3H), 2.63 (t, J=7.3 Hz, 2H), 2.59-2.51 (m, 2H), 2.13 (td, J=13.8, 7.7 Hz, 1H), 1.92 (dt, J=14.9, 7.8 Hz, 1H), 1.64-1.51 (m, 2H), 1.46 (s, 9H), 1.27 (d, J=7.4 Hz, 10H), 0.87 (t, J=6.7 Hz, 3H). $^{13}$C NMR (75 MHz, CDCl$_3$) δ 173.52, 155.46, 140.85, 138.06, 128.70, 128.45, 80.37, 53.49, 52.48, 35.78, 34.66, 32.12, 31.81, 31.42, 29.71, 29.59, 29.49, 28.54, 22.90, 14.34. IR (CHCl$_3$) 2926 (s), 2855 (w), 1719 (m), 1513 (w), 1366 (w), 1166 (m). [α]$^{20}_D$=−26.2 (c=1.00, CHCl$_3$)

(R)-tert-butyl (1-amino-4-(4-octylphenyl)-1-oxobutan-2-yl)carbamate (8f)

To a solution of methyl ester 8e (560 mg, 1.38 mmol) in MeOH (0.3 M) at 0° C. was added 7 M ammonia in MeOH (3× the volume of MeOH), warmed to r.t., and stir for 3 d. The reaction was quenched with 1 N HCl (10× the volume of the reaction) and extracted 3× into CHCl$_3$ (10× the volume of the reaction). The combined organic layers were then dried with Na$_2$SO$_4$, concentrated to a clear and colorless oil, and immediately purified by column chromatography to yield the title compound. 87%. White solid. R$_f$=0.32 (50% EtOAc in hexanes; Seebach's Dip). $^1$H NMR (300 MHz, CDCl$_3$) δ 7.07 (s, 4H), 6.44 (s, 1H), 6.06 (s, 1H), 5.32 (d, J=7.6 Hz, 1H), 4.19 (dd, J=5.9 Hz, 1H), 2.66 (t, J=7.8 Hz, 2H), 2.58-2.51 (m, 2H), 2.11 (ddt, J=14.7, 7.3 Hz, 1H), 1.91 (td, J=15.6, 7.9 Hz, 1H), 1.58 (dt, J=7.2 Hz, 2H), 1.44 (s, 9H), 1.36-1.18 (m, J=6.9 Hz, 10H), 0.88 (t, J=6.7 Hz, 3H). $^{13}$C NMR (75 MHz, CDCl$_3$) δ 175.08, 156.03, 140.94, 138.19, 128.73, 128.47, 80.32, 53.98, 35.79, 34.41, 32.13, 31.82, 31.63, 29.72, 29.62, 29.50, 28.56, 27.90, 14.35. IR (CHCl$_3$) 3325 (br w), 2926 (s), 2854 (w), 1678 (m), 1514 (w), 1455 (w), 1168 (m). [α]$^{20}$=+9.77 (c=1.00, CHCl$_3$)

(R)-tert-butyl (1-cyano-3-(4-octylphenyl)propyl) carbamate (8g)

To a solution of cyanuric chloride (0.5 eq.) in 2,4,6-collidine (4.0 eq.) was added amide 8f (380 mg, 0.973 mmol) in DMF (0.05M) at r.t. The reaction turned yellow and then deep red and was stirred for 3.5 h. The reaction was then quenched with 1 M HCl (20× the volume of DMF) and extracted 3× into EtOAc (30× the volume of DMF), the organic layers were dried with $Na_2SO_4$, concentrated to a solid, and immediately purified by column chromatography to yield the title compound. 95%. White solid. $R_f$=0.85 (20% EtOAc in hexanes; Ninhydrin). $^1$H NMR (500 MHz, $CDCl_3$) δ 7.15-7.08 (m, J=8.2 Hz, 4H), 5.07 (d, J=6.2 Hz, 1H), 4.62-4.41 (m, J=5.5 Hz, 1H), 2.85-2.69 (m, 2H), 2.61-2.55 (m, 2H), 2.10 (dt, J=7.1, 6.8 Hz, 2H), 1.65-1.55 (m, 2H), 1.47 (s, 9H), 1.38-1.22 (m, 10H), 0.90 (t, J=7.0 Hz, 3H). $^{13}$C NMR (126 MHz, $CDCl_3$) δ 154.34, 141.31, 136.33, 128.77, 128.26, 118.87, 81.08, 41.88, 35.56, 34.95, 31.90, 31.56, 31.10, 29.49, 29.37, 29.27, 28.23, 22.68, 14.13. IR ($CHCl_3$) 3350 (w), 2920 (m), 2850 (w), 2278 (w), 1687 (m), 1514 (w), 1455 (m), 1164 (w). $[\alpha]^{20}_D$=+12.6 (C=1.00, $CHCl_3$) mp=73.1-74.5° C. (uncorrected).

(R)-tert-butyl (1-amino-1-((tert-butoxycarbonyl) imino)-4-(4-octylphenyl)butan-2-yl) carbamate (8h)

To a solution of a nitrile 14 (161 mg, 0.432 mmol) in MeOH (0.10 M) was added a 0.5 M solution of sodium methoxide in MeOH (0.50 eq.) at r.t. and stirred for 24 h. The intermediate imidate was detectable by TLC; however, being in equilibrium with the nitrile, full conversion does not occur. Ammonium chloride (2.0 eq.) was then added in one portion at that temperature and reacted until the imidate was completely consumed by TLC analysis. The reaction was then cooled to r.t. and evacuated to dryness to yield a crude solid. The solid was reconstituted with $CHCl_3$ and filtered through a fine glass fritted funnel in order to remove excess ammonium chloride, and the filtrate was again evacuated to dryness. The crude amidine was then dissolved in THF (0.1 M) and the solution was treated with TEA (2.5 eq.) and $Boc_2O$ (2.0 eq.) and stirred for 2 h. The reaction was then evaporated to dryness and purified by column chromatography to yield the title compound. 50% over 2 steps. White solid. $R_f$=0.33 (20% EtOAc in hexanes; Seebach's Dip). $^1$H NMR (300 MHz, $CDCl_3$) δ 8.10 (s, 1H), 7.09 (s, 4H), 5.22 (d, J=7.9 Hz, 1H), 4.64 (s, 1H), 2.69 (t, J=8.0 Hz, 2H), 2.59-2.51 (m, 2H), 2.15 (ddt, J=8.0, 4.8 Hz, 1H), 1.84 (ddt, J=16.1, 8.1 Hz, 1H), 1.64-1.53 (m, 2H), 1.48 (s, 9H), 1.45 (s, 9H), 1.35-1.21 (m, J=7.4 Hz, 10H), 0.87 (t, J=6.7 Hz, 3H). $^{13}$C NMR (75 MHz, $CDCl_3$) δ 172.72, 156.13, 149.75, 140.98, 138.16, 128.73, 128.43, 82.96, 80.53, 54.53, 35.78, 34.14, 32.11, 31.81, 31.67, 29.71, 29.60, 29.48, 28.53, 28.18, 22.90, 14.34. IR ($CHCl_3$) 3299 (br, w), 2927 (s), 2855 (m), 1767 (s), 1715 (s), 1513 (s), 1367 (m), 1146 (s). $[\alpha]^{20}_D$=+13.1 (c=1.00, $CHCl_3$)

(R)-2-amino-4-(4-octylphenyl)butanimidamide dihydrochloride (8)

To a flask containing the di-Boc protected 8h was added 2 M dry HCl in ether at 0° C. and warmed to r.t. The reaction was stirred for 3 h and then evaporated to dryness to yield the title compound. 99%. White solid. $^1$H NMR (300 MHz, $CD_3OD$) δ 7.10 (s, 4H), 3.93 (t, J=5.9 Hz, 1H), 2.66 (t, J=8.3 Hz, 2H), 2.55 (t, J=7.9 Hz, 2H), 2.23-1.98 (m, 2H), 1.59 (tt, J=6.2 Hz, 2H), 1.38-1.19 (m, J=7.2 Hz, 10H), 0.88 (t, J=6.7 Hz, 3H). $^{13}$C NMR (75 MHz, $CD_3OD$) δ 170.98, 141.06, 137.34, 128.56, 127.97, 53.06, 35.31, 33.59, 31.83, 31.60, 30.41, 29.39, 29.22, 29.13, 27.01, 22.53, 13.24. IR (pellet) 3228 (br, w), 3167 (br, w), 2923 (s), 2853 (m), 1754 (w), 1682 (s), 1614 (m), 1486 (m), 1151 (s). $[\alpha]^{20}_D$=+26.0 (c=1.00, MeOH).

Compounds 9-11

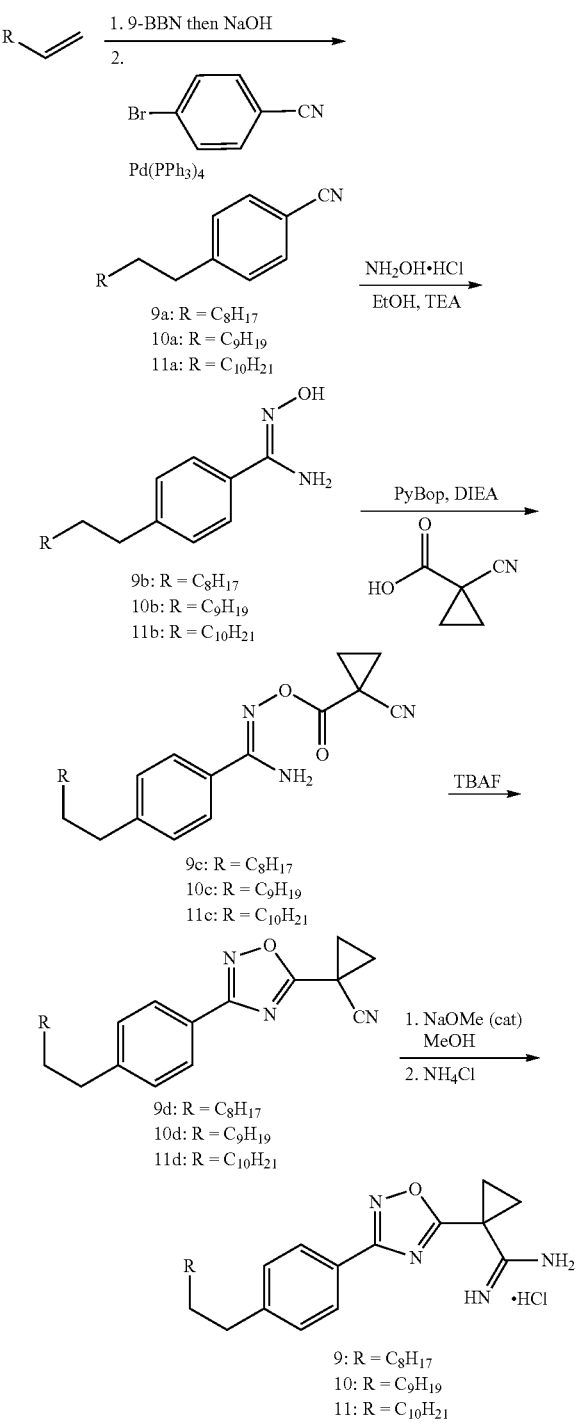

Compound 9

4-decylbenzonitrile (9a)

General procedure C was used to couple 1-decene (1.20 mL, 6.16 mmol) and 4-bromobenzonitrile (750 mg, 4.11 mmol) to yield the title product as clear colorless oil (98% yield). $R_f$=0.47 (5% EtOAc in hexanes). $^1$H NMR (300 MHz, CDCl$_3$) δ 7.51 (d, J=8.1, 2H), 7.24 (d, J=8.0, 2H), 2.62 (t, J=7.6, 2H), 1.68-1.48 (m, 2H), 1.37-1.13 (m, 14H), 0.85 (t, J=6.6, 3H). $^{13}$C NMR (75 MHz, CDCl$_3$) δ 148.77, 132.24, 129.38, 119.31, 109.68, 36.31, 32.12, 31.20, 29.81, 29.77, 29.65, 29.55, 29.40, 22.91, 14.33.

(Z)-4-decyl-N'-hydroxybenzimidamide (9b)

General procedure F was used to convert 9a (0.98 g, 4.03 mmol) to the title product (90% yield). $R_f$=0.48 (50% EtOAc in hexanes). $^1$H NMR (300 MHz, CDCl$_3$) δ 7.54 (d, J=8.3, 2H), 7.20 (d, J=8.3, 2H), 4.93 (s, 2H), 2.62 (t, J=7.5, 2H), 1.72-1.50 (m, 2H), 1.42-1.14 (m, 14H), 0.88 (t, J=6.6, 3H). $^{13}$C NMR (75 MHz, CDCl$_3$) δ 152.94, 145.42, 129.82, 128.91, 126.00, 36.00, 32.13, 31.54, 29.82, 29.72, 29.56, 29.51, 22:92, 14.36.

(Z)—N'-((1-cyanocyclopropanecarbonyl)oxy)-4-decylbenzimidamide (9c)

General procedure B was used to couple 9b (150 mg, 0.54 mmol) and 1-cyano-1-cyclopropanecarboxylic acid (60 mg, 0.54 mmol) to yield the title product as white solid (91%). $R_f$=0.32 (25% EtOAc in hexanes). $^1$H NMR (300 MHz, CDCl$_3$) δ 7.57 (d, J=8.1, 2H), 7.19 (d, J=8.1, 2H), 5.31 (s, 2H), 2.61 (t, J=7.7, 2H), 1.78 (dd, J=4.7, 8.3, 2H), 1.66 (dd, J=4.7, 8.3, 2H), 1.58 (m, 2H), 1.24 (m, 14H), 0.86 (t, J=6.2, 3H). $^{13}$C NMR (75 MHz, CDCl$_3$) δ 164.82, 157.95, 146.89, 129.04, 127.88, 126.92, 118.98, 36.02, 32.11, 31.45, 29.80, 29.68, 29.54, 29.43, 22.91, 19.38, 14.36, 12.65.

1-(3-(4-decylphenyl)-1,2,4-oxadiazol-5-yl)cyclopropanecarbonitrile (9d)

General procedure G was used to convert 9c (182 mg, 0.49 mmol) to the title product as white solid (73% yield). $R_f$=0.43 (25% EtOAc in hexanes). $^1$H NMR (300 MHz, CDCl$_3$) δ 7.93 (d, J=8.2, 2H), 7.27 (d, J=8.1, 2H), 2.65 (t, J=7.5, 2H), 2.01 (s, 4H), 1.63 (m, 2H), 1.25 (m, 18H), 0.88 (t, J=6.7, 3H). $^{13}$C NMR (75 MHz, CDCl$_3$) δ 174.84, 169.02, 147.23, 129.19, 127.70, 123.48, 117.79, 36.21, 32.15, 31.43, 29.88, 29.71, 29.60, 29.50, 23.33, 22.94, 19.50, 14.38, 9.10.

1-(3-(4-decylphenyl)-1,2,4-oxadiazol-5-yl)cyclopropanecarboximidamide hydrochloride (9)

General procedure A was used to convert 9d (126 mg, 0.36 mmol) to the title product. In this example, the solid was purified via flash chromatography. The hydrochloride salt was prepared by the dropwise addition of 2 M HCl in ether to the purified amidine. The ether was evaporated, reconstituted in ether, and again evacuated to dryness to yield the title product as tan solid (66% yield). $R_f$=0.42 (15% MeOH in CHCl$_3$). $^1$H NMR (500 MHz, DMSO) δ 9.54 (s, 2H), 9.39 (s, 2H), 7.87 (d, J=5.8, 2H), 7.36 (d, J=5.9, 2H), 2.62 (s, 2H), 1.94 (s, 2H), 1.83 (s, 2H), 1.56 (s, 2H), 1.23 (m, 14H), 0.83 (s, 3H). $^{13}$C NMR (126 MHz, DMSO) δ 177.73, 168.18, 166.02, 147.06, 129.70, 127.50, 123.50, 35.50, 31.74, 31.09, 29.43, 29.27, 29.14, 29.08, 22.61, 22.56, 18.67, 14.44.

Compound 10

4-undecylbenzonitrile (10a)

General procedure C was used to couple undecene (2.40 mL, 11.66 mmol) and 4-bromobenzonitrile (1.40 g, 7.70 mmol) to yield the title product as colorless oil (99% yield). $R_f$=0.50 (10% EtOAc in hexanes). $^1$H NMR (300 MHz, CDCl$_3$) δ 7.48 (d, J=8.2, 2H), 7.21 (d, J=8.1, 2H), 2.60 (t, J=7.5, 2H), 1.57 (m, 2H), 1.22 (m, 16H), 0.84 (t, J=6.3, 3H). $^{13}$C NMR (75 MHz, CDCl$_3$) δ 148.67, 132.17, 129.35, 119.15, 109.75, 36.28, 32.14, 31.19, 29.86, 29.78, 29.65, 29.58, 29.42, 22.91, 14.30.

(Z)—N'-hydroxy-4-undecylbenzimidamide (10b)

General procedure F was used to convert 12a (2.00 g, 7.77 mmol) to the title product as white solid (95% yield). $R_f$=0.51 (50% EtOAc in hexanes). $^1$H NMR (300 MHz, CDCl$_3$) δ 7.54 (d, J=8.2, 2H), 7.19 (d, J=8.2, 2H), 4.93 (s, 2H), 2.61 (t, J=7.5 1H), 1.73-1.50 (m, 2H), 1.45-1.19 (m, 16H), 0.89 (t, J=6.7, 3H). $^{13}$C NMR (75 MHz, CDCl$_3$) δ 152.90, 145.36, 129.91, 128.90, 126.01, 36.00, 32.16, 31.55, 29.84, 29.75, 29.59, 29.53, 22.93, 14.37.

(Z)—N'-((1-cyanocyclopropanecarbonyl)oxy)-4-undecylbenzimidamide (10c)

General procedure B was used to couple 10b (150 mg, 0.52 mmol) and 1-cyano-1-cyclopropanecarboxylic acid (57 mg, 0.52 mmol) to yield the title product as white solid (82% yield). $R_f$=0.63 (50% EtOAc in hexanes). $^1$H NMR (300 MHz, CDCl$_3$) δ 7.58 (d, J=8.2, 2H), 7.20 (d, J=8.1, 2H), 5.29 (s, 2H), 2.61 (t, J=7.5, 2H), 1.79 (dd, J=4.6, 8.4, 2H), 1.67 (dd, J=4.8, 8.3, 2H), 1.58 (m, 2H), 1.24 (m, 16H), 0.87 (t, J=6.5, 3H). $^{13}$C NMR (75 MHz, CDCl$_3$) δ 164.81, 157.94, 146.92, 130.21, 129.06, 127.88, 126.92, 118.99, 36.03, 32.14, 31.46, 29.85, 29.80, 29.69, 29.57, 29.43, 22.92, 19.39, 14.37, 12.66.

1-(3-(4-undecylphenyl)-1,2,4-oxadiazol-5-yl)cyclopropanecarbonitrile (10d)

General procedure G was used to convert 10c (163 mg, 0.43 mmol) to the title product as white solid (81% yield). $R_f$=0.64 (25% EtOAc in hexanes). $^1$H NMR (300 MHz, CDCl$_3$) δ 7.93 (d, J=8.3, 2H), 7.27 (d, J=8.3, 2H), 2.65 (t, J=7.5, 2H), 2.02 (d, J=7.9, 4H), 1.63 (m, 2H), 1.28 (m, 16H), 0.88 (t, J=6.7, 3H). $^{13}$C NMR (75 MHz, CDCl$_3$) δ 174.85, 169.01, 147.24, 129.18, 127.69, 123.51, 117.78, 36.20, 32.15, 31.43, 29.87, 29.71, 29.58, 29.50, 22.93, 20.89, 18.90, 14.37, 9.08.

1-(3-(4-undecylphenyl)-1,2,4-oxadiazol-5-yl)cyclopropanecarboximidamide hydrochloride (10)

General procedure A was used to convert 10d (127 mg, 0.35 mmol) to the title product. In this example, the solid was purified via flash chromatography. The hydrochloride salt was prepared by the dropwise addition of 2 M HCl in ether to the purified amidine. The ether was evaporated, reconstituted in ether, and again evacuated to dryness to yield the title product as tan solid (32% yield). $R_f$=0.49 (15%

MeOH in CHCl$_3$). $^1$H NMR (500 MHz, DMSO) δ 9.56 (s, 2H), 9.42 (s, 2H), 7.88 (d, J=7.5, 2H), 7.37 (d, J=7.5, 2H), 2.62 (t, J=7.1, 3H), 1.95 (s, 2H), 1.85 (s, 2H), 1.57 (s, 2H), 1.24 (m, 16H), 0.83 (t, J=6.4, 3H). $^{13}$C NMR (126 MHz, DMSO) δ 177.72, 168.18, 166.04, 147.05, 129.68, 127.50, 123.50, 35.49, 31.74, 31.08, 29.44, 29.27, 29.16, 29.07, 22.60, 22.55, 18.66, 14.42.

Compound 11

4-dodecylbenzonitrile (11a)

General procedure C was used to couple 1-dodecene (3.64 mL, 16.4 mmol) and 4-iodobenzonitrile (2.5 g, 10.9 mmol) to yield the title product as colorless oil (99% yield). R$_f$=0.52 (10% EtOAc in hexanes). $^1$H NMR (300 MHz, CDCl$_3$) δ 7.56 (d, J=8.1, 2H), 7.26 (d, J=8.1, 2H), 2.71-2.59 (m, 2H), 1.60 (m, 2H), 1.38-1.16 (m, 18H), 0.88 (t, J=6.7, 3H).

(Z)-4-dodecyl-N'-hydroxybenzimidamide (11b)

General procedure F was used to convert 11a (1.17 g, 4.31 mmol) to the title product as white solid (86% yield). R$_f$=0.52 (50% EtOAc in hexanes). $^1$H NMR (300 MHz, CDCl$_3$) δ 7.53 (d, J=8.3, 2H), 7.20 (d, J=8.3, 2H), 4.88 (s, 2H), 2.61 (t, J=7.5, 2H), 1.60 (m, 2H), 1.25 (m, 18H), 0.88 (t, J=6.7, 3H).

(Z)—N'-((1-cyanocyclopropanecarbonyl)oxy)-4-dodecylbenzimidamide (11c)

General procedure B was used to couple 13b (200 mg, 0.66 mmol) and 1-cyano-1-cyclopropanecarboxylic acid (311 mg, 0.60 mmol) to yield the title product as white solid (80% yield). R$_f$=0.21 (25% EtOAc in hexanes). $^1$H NMR (300 MHz, CDCl$_3$) δ 7.58 (d, J=8.0, 2H), 7.21 (d, J=7.9, 2H), 5.28 (s, 2H), 2.62 (t, J=7.6, 2H), 1.80 (dd, J=4.8, 8.2, 2H), 1.68 (dd, J=4.6, 8.4, 2H), 1.64-1.52 (m, 2H), 1.25 (m, 18H), 0.87 (t, J=6.5, 3H). $^{13}$C NMR (75 MHz, CDCl$_3$) δ 164.81, 157.93, 146.98, 129.09, 127.85, 126.93, 118.99, 36.03, 32.14, 31.47, 29.87, 29.81, 29.69, 29.58, 29.43, 22.92, 19.41, 14.37, 12.65.

1-(3-(4-dodecylphenyl)-1,2,4-oxadiazol-5-yl)cyclopropanecarbonitrile (11d)

General procedure G was used to convert 11c (190 mg, 0.48 mmol) to the title product as white solid (99% yield). R$_f$=0.56 (25% EtOAc in hexanes). $^1$H NMR (300 MHz, CDCl$_3$) δ 7.94 (d, J=8.2, 2H), 7.27 (d, J=8.1, 2H), 2.65 (t, J=7.5, 2H), 2.01 (s, 4H), 1.63 (m, 2H), 1.25 (m, 18H), 0.88 (t, J=0.6.7, 3H). $^{13}$C NMR (75 MHz, CDCl$_3$) δ 174.83, 169.02, 147.25, 129.19, 127.70, 123.48, 117.80, 36.21, 32.15, 31.45, 29.88, 29.71, 29.60, 29.50, 23.33, 22.94, 20.90, 14.38, 9.10.

1-(3-(4-dodecylphenyl)-1,2,4-oxadiazol-5-yl)cyclopropanecarboximidamide hydrochloride (11)

General procedure A was used to convert 11d (190 mg, 0.50 mmol) to the title product as yellow solid (50% yield). R$_f$=0.28 (15% MeOH in CHCl$_3$). $^1$H NMR (500 MHz, DMSO) δ 9.56 (s, 1H), 9.43 (s, 1H), 7.88 (d, J=7.1, 2H), 7.37 (d, J=7.2, 2H), 2.62 (m, 2H), 1.96 (s, 2H), 1.84 (s, 2H), 1.57 (s, 2H), 1.24 (m, 18H), 0.83 (t, J=5.9, 2H). $^{13}$C NMR (126 MHz, DMSO) δ 177.73, 168.17, 166.03, 147.04, 129.67, 127.50, 123.51, 35.50, 31.75, 31.09, 29.46, 29.27, 29.17, 29.08, 22.60, 22.56, 18.66, 14.42.

Compound 12

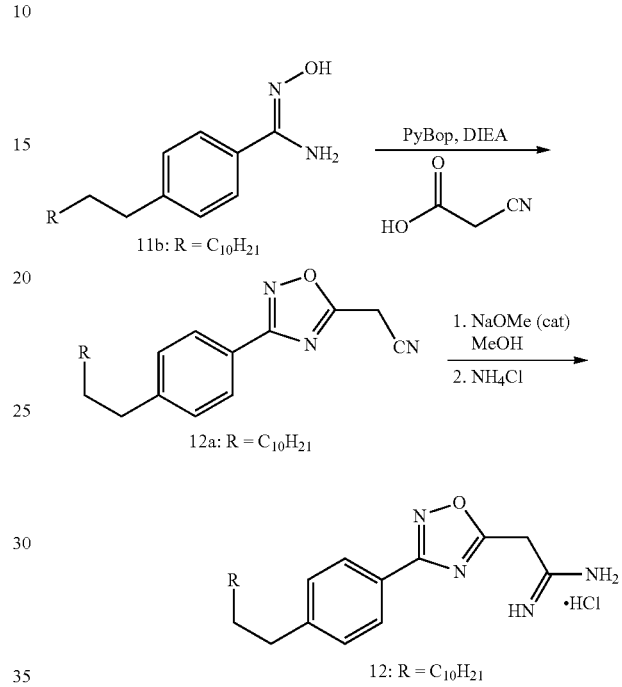

2-(3-(4-dodecylphenyl)-1,2,4-oxadiazol-5-yl)acetonitrile (12a)

General procedure B was used to couple 11b (200 mg, 0.66 mmol) and cyanoacetic acid (51 mg, 0.60 mmol) to yield the oxadiazole product as white solid (27% yield). R$_f$=0.50 (25% EtOAc in hexanes). $^1$H NMR (300 MHz, CDCl$_3$) δ 7.97 (d, J=8.2, 2H), 7.30 (d, J=8.2, 2H), 4.12 (s, 2H), 2.64 (t, J=7.6, 2H), 1.63 (m, 2H), 1.28 (m, 18H), 0.87 (t, J=6.6, 3H). $^{13}$C NMR (75 MHz, CDCl$_3$) δ 169.33, 168.94, 147.50, 129.30, 127.71, 123.23, 115.45, 67.39, 36.22, 32.15, 31.44, 29.89, 29.81, 29.71, 29.60, 29.51, 22.94, 17.38, 14.37.

2-(3-(4-dodecylphenyl)-1,2,4-oxadiazol-5-yl)acetimidamide hydrochloride (12)

General procedure A was used to convert 12a (61 mg, 0.16 mmol) to the title product as tan solid (40% yield). R$_f$=0.25 (15% MeOH in CHCl$_3$). $^1$H NMR (500 MHz, DMSO) δ 9.47 (s, 2H), 9.15 (s, 2H), 7.90 (s, 2H), 7.37 (s, 2H), 4.38 (s, 2H), 2.63 (s, 2H), 1.57 (s, 2H), 1.21 (s, 18H), 0.82 (s, 3H). $^{13}$C NMR (126 MHz, DMSO) δ 173.81, 168.25, 163.97, 147.06, 129.72, 127.48, 123.56, 35.50, 31.75, 31.09, 30.63, 29.46, 29.27, 29.16, 29.08, 22.56, 14.43.

Compound 13:

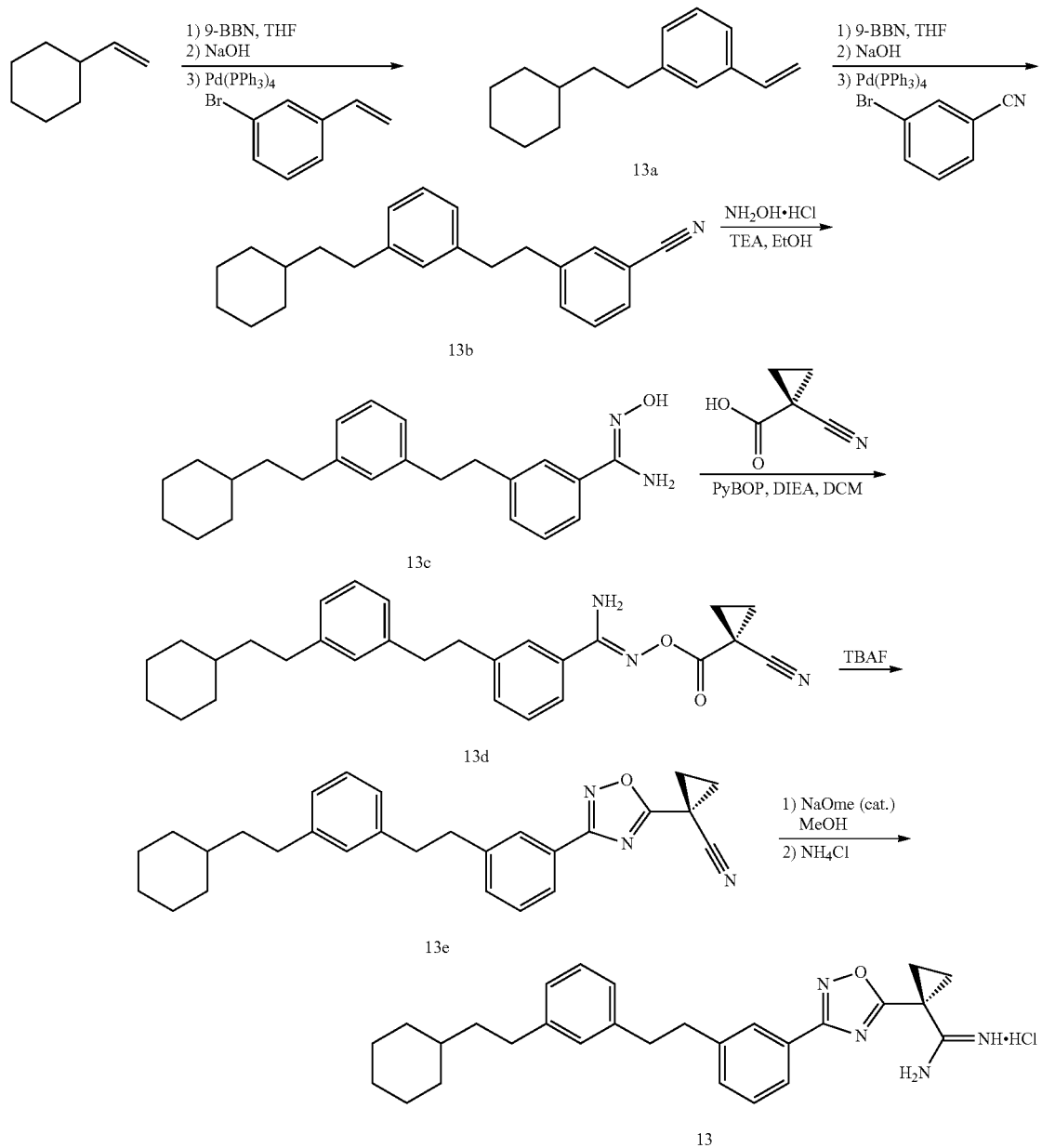

1-(2-cyclohexylethyl)-3-vinylbenzene (13a)

General procedure C was used to couple vinylcyclohexane (1.12 mL, 8.19 mmol) and 3-bromostyrene (0.71 mL, 5.46 mmol) to yield the title product as clear and colorless oil (92% yield). $R_f$=0.76 (5% EtOAc in hexanes, KMnO$_4$). $^1$H NMR (300 MHz, CDCl$_3$) δ 7.29-7.24 (m, 3H), 7.18-7.06 (m, 1H), 6.75 (dd, J=10.9, 17.6, 1H), 5.78 (dd, J=1.0, 17.6, 1H), 5.26 (dd, J=0.9, 10.9, 1H), 2.71-2.61 (m, 2H), 2.00-0.87 (m, 13H). $^{13}$C NMR (75 MHz, CDCl$_3$) δ 143.58, 137.64, 137.21, 130.79, 128.54, 128.05, 126.43, 123.60, 113.60, 39.53, 37.49, 33.45, 33.36, 26.83, 26.47.

3-(3-(2-cyclohexylethyl)phenethyl)benzonitrile (13b)

General procedure C was used to couple 13a (980 mg, 4.57 mmol) and 2-bromobenzonitrile (690 mg, 3.81 mmol) to yield the title product. 28%. Clear and colorless oil. $R_f$=0.57 (5% EtOAc in hexanes). $^1$H NMR (300 MHz, CDCl$_3$) δ 7.87-6.80 (m, 8H), 3.02-2.82 (m, 2H), 2.67-2.51 (m, 2H), 2.38-2.23 (m, 2H), 1.87-1.06 (m, 11H), 1.05-0.81 (m, 2H). $^{13}$C NMR (75 MHz, CDCl$_3$) δ 143.61, 137.64, 137.20, 130.80, 130.16, 129.26, 128.55, 128.06, 126.43, 125.02, 123.61, 115.51, 113.63, 39.55, 37.50, 33.46, 33.36, 26.85, 26.48.

(Z)-3-(3-(2-cyclohexylethyl)phenethyl)-N'-hydroxy-benzimidamide (13c)

General procedure F was used to convert 13b (83 mg, 0.26 mmol) to the title product as white solid (52% yield). $R_f$=0.35 (40% EtOAc in hexanes). $^1$H NMR (300 MHz, CDCl$_3$) δ 7.52-7.40 (m, 2H), 7.39-7.12 (m, 4H), 7.08-6.93 (m, 2H), 4.92 (s, 2H), 3.05-2.81 (m, 2H), 2.72-2.51 (m, 2H), 1.97-1.08 (m, 15H), 1.08-0.84 (m, 2H). $^{13}$C NMR (75 MHz, CDCl$_3$) δ 153.02, 143.70, 142.45, 141.51, 132.46, 130.29, 128.95, 128.72, 128.35, 127.50, 126.13, 125.79; 124.09, 39.61, 38.03, 37.97, 37.52, 33.42, 33.36, 30.00, 29.48, 28.48, 27.55, 26.99, 26.81, 26.46, 26.21.

(Z)—N'-((1-cyanocyclopropanecarbonyl)oxy)-3-(3-(2-cyclohexylethyl)phenethyl)benzimidamide (13d)

General procedure B was used to couple 13c (48 mg, 0.14 mmol) and 1-cyano-1-cyclopropanecarboxylic acid (18 mg, 0.16 mmol) to yield the title product as white solid (30% yield). $R_f$=0.26 (25% EtOAc in hexanes). $^1$H NMR (300 MHz, CDCl$_3$) δ 7.65-6.84 (m, 8H), 5.19 (s, 2H), 3.02-2.80 (m, 4H), 2.67-2.49 (m, 2H), 1.94-0.79 (m, 13H). $^{13}$C NMR (75 MHz, CDCl$_3$) δ 164.68, 157.85, 143.54, 142.75, 141.32, 131.71, 130.44, 128.93, 128.78, 128.37, 127.09, 126.19, 125.84, 124.48, 118.85, 39.62, 37.94, 37.51, 33.42, 33.35, 26.81, 26.46, 19.32, 12.54.

1-(3-(3-(2-cyclohexylethyl)phenethyl)phenyl)-1,2,4-oxadiazol-5-yl)cyclopropanecarbonitrile (13e)

General procedure G was used to convert 13d (18 mg, 0.04 mmol) to the title product as white solid (99% yield). $R_f$=0.58 (25% EtOAc in hexanes). $^1$H NMR (600 MHz, CDCl$_3$) δ 7.91-7.86 (m, 2H), 7.43-7.36 (m, 2H), 7.33-7.29 (m, 1H), 7.20 (t, J=7.5, 1H), 7.05-6.97 (m, 2H), 3.03-2.88 (m, 4H), 2.62-2.54 (m, 2H), 2.06 (s, 4H), 1.83-1.08 (m, 11H), 0.99-0.84 (m, 2H). $^{13}$C NMR (151 MHz, CDCl$_3$) δ 174.85, 169.02, 143.50, 142.91, 141.33, 132.02, 129.01, 128.70, 128.42, 127.63, 126.21, 126.02, 125.73, 125.32, 117.65, 39.61, 37.98, 37.94, 37.54, 33.47, 33.45, 33.38, 26.84, 26.47, 20.78, 9.00.

1-(3-(3-(2-cyclohexylethyl)phenethyl)phenyl)-1,2,4-oxadiazol-5-yl)cyclopropanecarboximidamide hydrochloride (13)

General procedure A was used to convert 13e (27 mg, 0.06 mmol) to the title product as yellow solid (17% yield). $R_f$=0.29 (15% MeOH in CHCl$_3$).

Compound 14

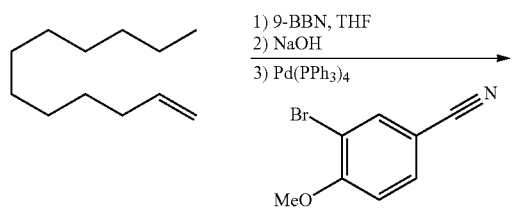

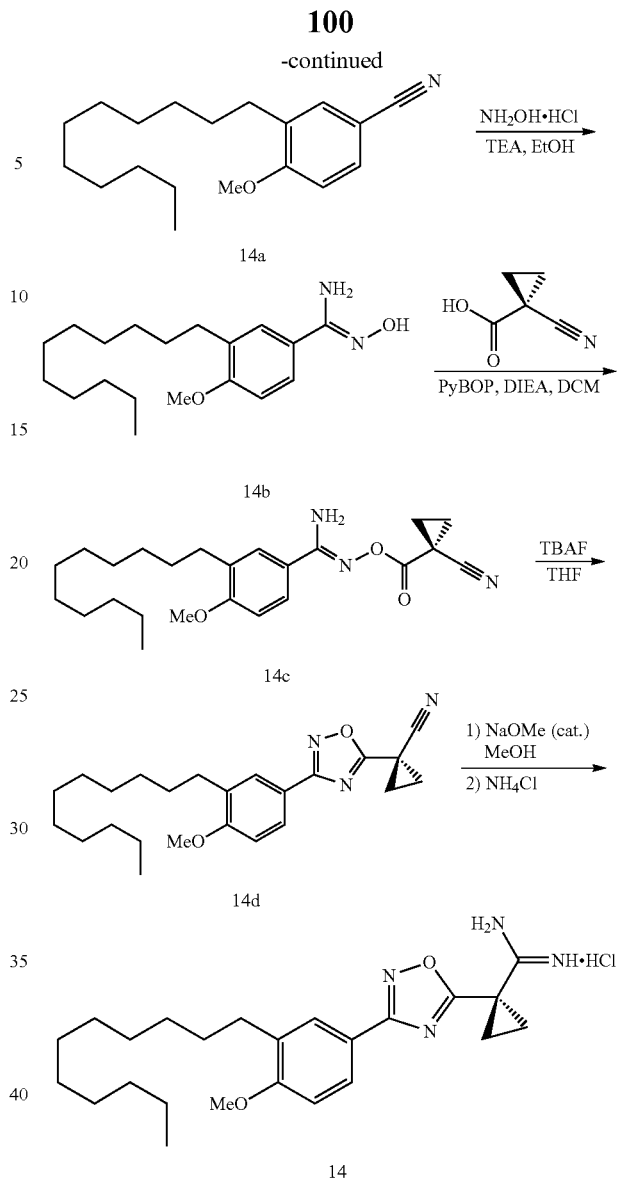

4-methoxy-3-undecylbenzonitrile (14a)

General procedure C was used to couple 1-undecene (0.63 mL, 13.23 mmol) and 3-bromo-4-methoxybenzonitrile (240 mg, 1.13 mmol) to yield the title product as clear and colorless oil (52% yield). $R_f$=0.26 (5% EtOAc in hexanes). $^1$H NMR (300 MHz, CDCl$_3$) δ 7.47 (dd, J=1.9, 8.5, 1H), 7.37 (d, J=1.8, 1H), 6.85 (d, J=8.5, 1H), 3.86 (s, 3H), 2.57 (t, J=7.7, 2H), 1.60-1.45 (m, 2H), 1.37-1.15 (m, 16H), 0.87 (t, J=6.6, 3H). $^{13}$C NMR (75 MHz, CDCl$_3$) δ 160.87, 133.15, 132.81, 131.86, 119.67, 110.47, 103.48, 55.58, 31.99, 29.82, 29.72, 29.65, 29.50, 29.42, 29.28, 22.76, 14.19.

(Z)—N'-hydroxy-4-methoxy-3-undecylbenzimidamide (14b)

General procedure F was used to convert 14a (170 mg, 0.59 mmol) to the title product as white solid (85% yield). $R_f$=0.27 (40% EtOAc in hexanes). $^1$H NMR (300 MHz, CDCl$_3$) δ 7.50-7.36 (m, 2H), 6.83 (d, J=8.3, 1H), 4.85 (s, 2H), 3.83 (s, 3H), 2.48 (t, J=7.7, 2H), 1.63-1.49 (m, 2H), 1.43-1.08 (m, 16H), 0.88 (t, J=6.1, 3H). $^{13}$C NMR (75 MHz, CDCl$_3$) δ 158.99, 152.82, 131.78, 127.44, 124.67, 124.53, 110.13, 55.51, 32.06, 30.32, 29.77, 29.69, 29.50, 22.83, 14.27.

(Z)—N'-((1-cyanocyclopropanecarbonyl)oxy)-4-methoxy-3-undecylbenzimidamide (14c)

General procedure B was used to couple 14b (161 mg, 0.50 mmol) and 1-cyano-1-cyclopropanecarboxylic acid (61 mg, 0.55 mmol) to yield the title product as white solid (80% yield). R$_f$=0.16 (25% EtOAc in hexanes). $^1$H NMR (300 MHz, CDCl$_3$) δ 7.50-7.40 (m, 2H), 6.78 (d, J=8.5, 1H), 5.30 (s, 2H), 3.80 (s, 3H), 2.65-2.47 (m, 2H), 1.75 (dd, J=4.7, 8.3, 2H), 1.63 (dd, J=4.6, 8.3, 2H), 1.57-1.45 (m, 2H), 1.37-1.15 (m, 16H), 0.86 (t, J=6.5, 3H). $^{13}$C NMR (75 MHz, CDCl$_3$) δ 164.69, 159.87, 157.76, 131.92, 128.15, 125.67, 122.02, 118.76, 109.99, 55.37, 31.92, 30.17, 29.64, 29.51, 29.36, 22.69, 19.11, 14.14, 12.44.

1-(3-(4-methoxy-3-undecylphenyl)-1,2,4-oxadiazol-5-yl)cyclopropanecarbonitrile (14d)

General procedure G was used to convert 14c (167 mg, 0.40 mmol) to the title product as white solid (50% yield). R$_f$=0.54 (25% EtOAc in hexanes). $^1$H NMR (300 MHz, CDCl$_3$) δ 7.85 (dd, J=2.0, 8.5, 1H), 7.79 (d, J=2.0, 1H), 6.89 (d, J=8.5, 1H), 3.87 (s, 3H), 2.56 (t, J=7.8, 2H), 2.02 (s, 4H), 1.67-1.49 (m, 2H), 1.44-1.14 (m, 16H), 0.87 (t, J=6.6, 3H). $^{13}$C NMR (75 MHz, CDCl$_3$) δ 174.40, 168.82, 160.26, 132.24, 128.97, 126.90, 117.88, 117.79, 110.30, 55.53, 32.03, 30.23, 29.74, 29.64, 29.48, 22.82, 20.65, 14.25, 8.95.

1-(3-(4-methoxy-3-undecylphenyl)-1,2,4-oxadiazol-5-yl)cyclopropanecarboximidamide hydrochloride (14)

General procedure A was used to convert 14d (91 mg, 0.23 mmol) to the title product as yellow solid (52% yield). $^1$H NMR (600 MHz, DMSO) δ 9.51 (s, 2H), 9.38 (s, 2H), 7.84-7.55 (m, 2H), 7.14-6.93 (m, 1H), 3.81 (s, 2H), 2.62-2.35 (m, 2H), 2.00-1.66 (m, 4H), 1.57-1.35 (m, 2H), 1.34-1.03 (m, 16H), 0.80 (t, J=6.6, 3H). $^{13}$C NMR (151 MHz, DMSO) δ 176.26, 166.88, 165.05, 159.07, 130.56, 127.42, 126.05, 116.78, 110.67, 55.44, 30.68, 28.88, 28.60, 28.41, 28.38, 28.24, 28.21, 28.09, 21.51, 21:41, 17.75, 13.46.

Compound 15

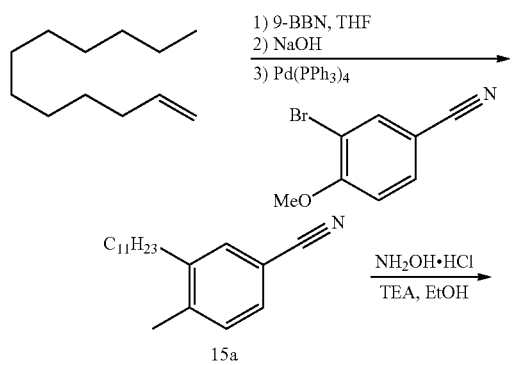

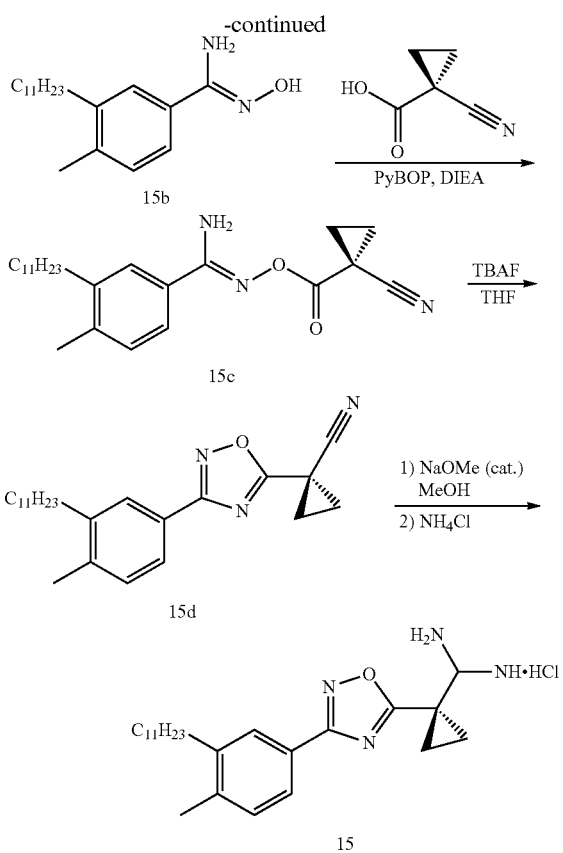

4-methyl-3-undecylbenzonitrile (15a)

General procedure C was used to couple 1-undecene (0.31 mL, 1.51 mmol) and 3-bromo-4-methylbenzonitrile (198 mg, 1.01 mmol) to yield the title product as clear and colorless oil (66% yield). R$_f$=0.36 (5% EtOAc in hexanes). $^1$H NMR (300 MHz, CDCl$_3$) δ 7.40 (s, 1H), 7.37 (d, J=7.8, 1H), 7.20 (d, J=7.8, 1H), 2.59 (t, J=7.8, 2H), 2.35 (s, 3H), 1.65-1.48 (m, 2H), 1.45-1.21 (m, 16H), 0.87 (t, J=6.0, 3H). $^{13}$C NMR (75 MHz, CDCl$_3$) δ 142.53, 141.94, 132.26, 130.88, 129.53, 109.69, 33.05, 32.05, 29.91, 29.76, 29.65, 29.48, 22.82, 19.83, 14.27.

(Z)—N'-hydroxy-4-methyl-3-undecylbenzimidamide (15b)

General procedure F was used to convert 15a (179 mg, 0.66 mmol) to the title product as white solid (58% yield). R$_f$=0.37 (40% EtOAc in hexanes). $^1$H NMR (300 MHz, CDCl$_3$) δ 7.43 (d, J=1.7, 1H), 7.37 (dd, J=1.9, 7.8, 1H), 7.15 (d, J=7.9, 1H), 4.93 (s, 2H), 2.60 (t, J=7.9, 2H), 2.32 (d, J=6.3, 3H), 1.66-1.50 (m, 2H), 1.47-1.20 (m, 16H), 0.90 (t, J=6.7, 3H). $^{13}$C NMR (75 MHz, CDCl$_3$) δ 152.84, 141.59, 138.06, 130.39, 130.07, 126.33, 123.26, 33.48, 32.03, 30.39, 29.85, 29.76, 29.69, 29.47, 22.81, 19.32, 14.24.

(Z)—N'-((1-cyanocyclopropanecarbonyl)oxy)-4-methyl-3-undecylbenzimidamide (15c)

General procedure B was used to couple 15b (115 mg, 0.38 mmol) and 1-cyano-1-cyclopropanecarboxylic acid (46 mg, 0.42 mmol) to yield the title product as white solid (65% yield). $R_f$=0.25 (40% EtOAc in hexanes). $^1$H NMR (300 MHz, CDCl$_3$) δ 7.48-7.33 (m, 2H), 7.14 (d, J=7.9, 1H), 5.29 (s, 2H), 2.62-2.47 (m, 2H), 2.31 (s, 2H), 1.83-1.70 (m, 2H), 1.69-1.61 (m, 2H), 1.56-1.41 (m, 2H), 1.38-1.15 (m, 16H), 0.86 (t, J=7.3, 3H). $^{13}$C NMR (75 MHz, CDCl$_3$) δ 164.69, 157.94, 141.98, 139.71, 130.52, 127.89, 127.14, 123.99, 118.81, 33.38, 31.97, 30.33, 29.67, 29.40, 22.75, 19.36, 19.20, 14.20, 12.45.

1-(3-(4-methyl-3-undecylphenyl)-1,2,4-oxadiazol-5-yl)cyclopropanecarbonitrile (15d)

General procedure G was used to convert 15c (97 mg, 0.25 mmol) to the title product as white solid (87% yield). $R_f$=0.61 (25% EtOAc in hexanes). $^1$H NMR (300 MHz, CDCl$_3$) δ 7.80 (d, J=1.7, 1H), 7.75 (dd, J=1.8, 7.8, 1H), 7.22 (d, J=7.9, 1H), 2.63 (t, J=7.9, 2H), 2.35 (s, 3H), 2.02 (s, 4H), 1.66-1.51 (m, 2H), 1.46-1.13 (m, 16H), 0.88 (t, J=6.7, 3H). $^{13}$C NMR (75 MHz, CDCl$_3$) δ 169.06, 142.14, 140.19, 130.78, 127.85, 125.03, 123.54, 117.75, 33.42, 32.04, 30.36, 29.84, 29.75, 29.67, 29.47, 22.82, 20.73, 19.62, 14.26, 8.98.

1-(3-(4-methyl-3-undecylphenyl)-1,2,4-oxadiazol-5-yl)cyclopropanecarboximidamide hydrochloride (15)

General procedure A was used to convert 15d (81 mg, 0.21 mmol) to the title product as yellow solid (57% yield). $^1$H NMR (600 MHz, DMSO) δ 9.49 (d, J=59.0, 4H), 7.79-7.55 (m, 2H), 7.28 (d, J=7.9, 1H), 2.66-2.52 (m, 2H), 2.28 (s, 3H), 2.03-1.69 (m, 4H), 1.56-1.38 (m, 2H), 1.38-1.05 (m, 16H), 0.80 (t, J=6.6, 3H). $^{13}$C NMR (151 MHz, DMSO) δ 176.59, 167.19, 165.11, 141.18, 139.31, 130.47, 126.45, 124.04, 122.66, 32.01, 30.78, 29.21, 28.49, 28.36, 28.20, 21.62, 21.52, 18.68, 17.90, 13.57.

Compound 16

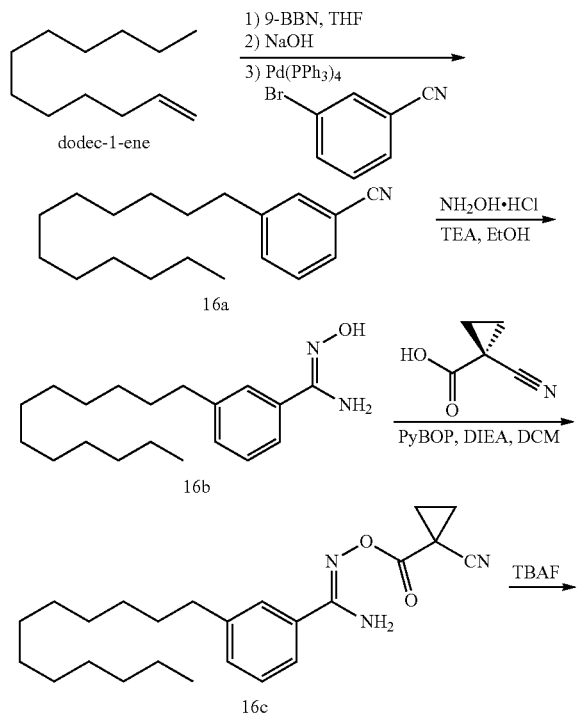

3-dodecylbenzonitrile (16a)

General Procedure C was used to couple 1-dodecene (1.83 mL, 8.24 mmol) and 3-bromobenzonitrile (1.0 g, 5.49 mmol) to yield the title product as clear and colorless oil (98% yield). $R_f$=0.40 (5% EtOAc in hexanes). $^1$H NMR (300 MHz, CDCl$_3$) δ 7.50-7.44 (m, 2H), 7.43-7.32 (m, 2H), 2.63 (t, J=6.0, 7.5, 2H), 1.73-1.48 (m, 2H), 1.41-1.13 (m, 18H), 0.88 (t, J=6.7, 3H). $^{13}$C NMR (75 MHz, CDCl$_3$) δ 144.42, 133.21, 132.14, 129.64, 129.18, 119.34, 112.41, 77.65, 77.23, 76.81, 35.72, 32.12, 31.31, 29.84, 29.73, 29.62, 29.55, 29.32, 22.90, 14.34.

3-dodecyl-N'-hydroxybenzimidamide (16b)

General Procedure F was used to convert 16a (1.4 g, 5.16 mmol) to the title product as white solid (25% yield). $R_f$=0.60 (50% EtOAc in hexanes). $^1$H NMR (300 MHz, CDCl$_3$) δ 7.51-7.39 (m, 2H), 7.35-7.19 (m, 2H), 4.92 (s, 2H), 2.62 (t, J=7.5, 2H), 1.71-1.55 (m, 2H), 1.44-1.20 (m, 18H), 0.89 (t, J=6.7, 3H). $^{13}$C NMR (75 MHz, CDCl$_3$) δ 152.97, 143.63, 132.56, 130.27, 128.69, 126.12, 123.39, 36.12, 32.11, 31.66, 29.87, 29.71, 29.55, 22.89, 14.33.

(Z)—N'-((1-cyanocyclopropanecarbonyl)oxy)-3-dodecylbenzimidamide (16c)

General Procedure B was used to couple 16b (438 mg, 1.43 mmol) and 1-cyano-1-cyclpropanecarboxylic acid (159 mg, 1.43 mmol) to yield the title product as white solid (25% yield). $R_f$=0.25 (25% EtOAc in hexanes). $^1$H NMR (300 MHz, CDCl$_3$) δ 7.55-7.43 (m, 2H), 7.38-7.27 (m, 2H), 5.25 (s, 2H), 2.62 (t, J=7.5, 2H), 1.82 (dd, J=3.1, 6.5, 2H), 1.69 (dd, J=4.6, 8.4, 2H), 1.66-1.53 (m, 2H), 1.41-1.14 (m, 18H), 0.87 (t, J=6.6, 3H). $^{13}$C NMR (75 MHz, CDCl$_3$) δ 161.88, 158.08, 144.06, 131.71, 130.54, 128.92, 127.07, 124.21, 118.94, 36.01, 32.11, 31.60, 29.85, 29.77, 29.67, 29.51, 22.88, 19.38, 14.32, 12.62.

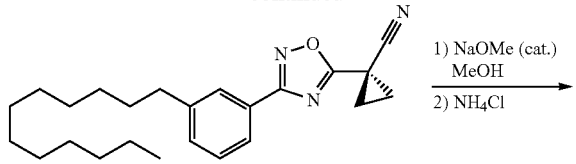

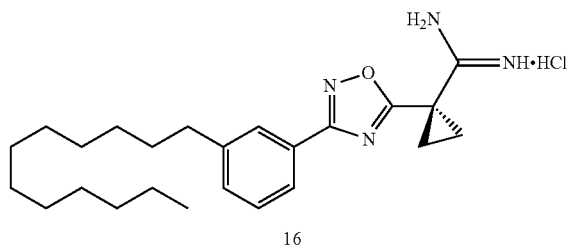

1-(3-(3-dodecylphenyl)-1,2,4-oxadiazol-5-yl)cyclopropanecarbonitrile (16d)

General Procedure G was used to convert 16c (100 mg, 0.25 mmol) to the title product (69% yield). $R_f$=0.64 (25% EtOAc in hexanes). $^1$H NMR (300 MHz, CDCl$_3$) δ 7.95-7.81 (m, 2H), 7.45-7.29 (m, 2H), 2.83-0.2.46 (m, 2H), 2.03

(s, 4H), 1.64 (bs, 2H), 1.41-1.19 (m, 18H), 0.88 (t, J=6.5, 3H). $^{13}$C NMR (75 MHz, CDCl$_3$) δ 172.21, 169.36, 144.15, 132.18, 131.97, 129.09, 127.65, 125.11, 117.74, 36.02, 34.95, 33.36, 32.93, 32.65, 32.38, 32.11, 31.62, 29.85, 29.68, 29.54, 27.76, 27.06, 25.91, 24.53, 24.24, 22.88, 20.85, 20.03, 18.76, 14.32, 9.05.

1-(3-(3-dodecylphenyl)-1,2,4-oxadiazol-5-yl)cyclopropanecarboximidamide hydrochloride (16)

General procedure A was used to convert 16d (66 mg, 0.17 mmol) to the title product as yellow solid (19% yield). $^1$H NMR (600 MHz, DMSO) δ 9.54 (s, 2H), 9.41 (s, 2H), 7.88-7.74 (m, 2H), 7.52-7.39 (m, 2H), 2.66 (s, 2H), 1.97 (s, 2H), 1.86 (s, 2H), 1.58 (s, 2H), 1.41-1.09 (m, 18H), 0.84 (s, 3H). $^{13}$C NMR (151 MHz, DMSO) δ 177.79, 168.30, 166.11, 144.09, 132.31, 129.77, 127.19, 126.06, 125.01, 35.38, 31.77, 31.46, 29.51, 29.50, 29.48, 29.46, 29.31, 29.18, 29.10, 22.58, 18.77, 14.45.

Compound 17

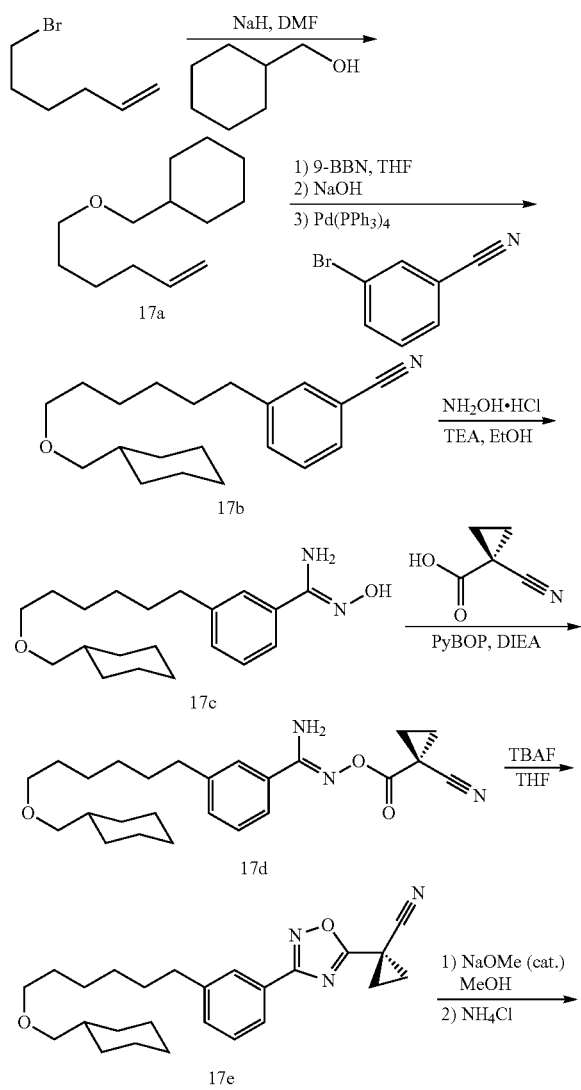

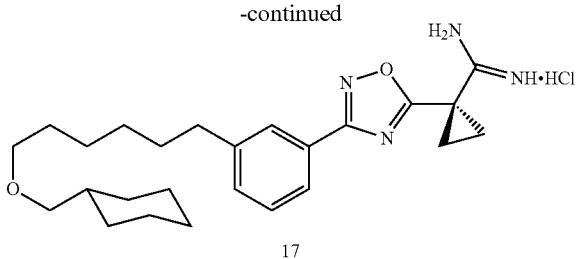

((hex-5-en-1-yloxy)methyl)cyclohexane (17a)

To a solution of cyclohexylmethanol (2.46 mL, 20.0 mmol) in DMF (0.1 M) was added 60% sodium hydride dispersed in mineral oil (800 mg, 20.0 mmol) at 0° C. Then the mixture was warmed to r.t. and then reacted for 2 h. 6-bromohexene (1.34 mL, 10.0 mmol) was added in one portion, and the mixture stirred for 12 h. The reaction was quenched with 1.0 M HCl (100 mL) at 0° C. The mixture was diluted with EtOAc and washed 5× with water (250 mL), dried with MgSO$_4$, evaporated to a yellow oil, and immediately purified by flash chromatography (5% EtOAc in hexanes). 49% yield. Rt=0.29 (5% EtOAc in hexanes, KMnO$_4$). $^1$H NMR (300 MHz, CDCl$_3$) δ 5.80 (ddt, J=6.7, 10.2, 16.9, 1H), 5.06-4.89 (m, 2H), 3.38 (t, J=6.5, 2H), 3.19 (d, J=6.6, 2H), 2.12-2.01 (m, 2H), 1.83-1.09 (m, 13H), 1.02-0.80 (m, 2H). $^{13}$C NMR (75 MHz, CDCl$_3$) δ 139.00, 114.56, 76.99, 71.00, 38.18, 33.73, 30.30, 29.34, 26.81, 26.03, 25.65.

3-(6-(cyclohexylmethoxy)hexyl)benzonitrile (17b)

General procedure C was used to couple 17a (0.40 g, 2.06 mmol) and 3-bromobenzonitrile (0.25 g, 1.37 mmol) to yield the title product. (98% yield). R$_f$=0.37 (10% EtOAc in hexanes). $^1$H NMR (300 MHz, CDCl$_3$) δ 7.51-7.25 (m, 4H), 3.37 (t, J=6.0, 2H), 3.18 (d, J=6.6, 2H), 2.63 (t, J=7.7, 2H), 1.85-1.09 (m, 17H), 1.00-0.79 (m, 2H). $^{13}$C NMR (75 MHz, CDCl$_3$) δ 144.24, 133.15, 132.06, 129.61, 129.13, 112.35, 76.99, 71.04, 38.16, 35.55, 31.16, 30.29, 29.73, 29.05, 26.79, 26.12, 26.01.

(Z)-3-(6-(cyclohexylmethoxy)hexyl)-N'-hydroxybenzimidamide (17c)

General procedure F was used to convert 17b (411 mg, 1.37 mmol) to the title product as white solid (88% yield). R$_f$=0.34 (40% EtOAc in hexanes). $^1$H NMR (300 MHz, CDCl$_3$) δ 7.49-7.41 (m, 2H), 7.35-7.20 (m, 3H), 4.90 (s, 2H), 3.37 (t, J=6.6, 2H), 3.19 (d, J=6.6, 2H), 2.69 (t, J=7.7, 2H), 1.87-1.03 (m, 17H), 1.04-0.81 (m, 2H). $^{13}$C NMR (75 MHz, CDCl$_3$) δ 152.96, 143.47, 130.24, 128.66, 126.01, 123.29, 76.96, 71.14, 38.15, 35.95, 31.50, 30.30, 29.76, 29.23, 26.81, 26.16, 26.02.

(Z)—N'-((1-cyanocyclopropanecarbonyl)oxy)-3-(6-(cyclohexylmethoxy)hexyl)benzimidamide (17d)

General procedure B was used to couple 17c (400 mg, 1.21 mmol) and 1-cyano-1-cyclopropanecarboxylic acid (134 mg, 1.21 mmol) to yield the title product as white solid (75% yield). R$_f$=0.21 (25% EtOAc in hexanes). $^1$H NMR (300 MHz, CDCl$_3$) δ 7.53-7.38 (m, 2H), 7.31-7.22 (m, 2H), 5.36 (s, 2H), 3.33 (t, J=6.5, 2H), 3.15 (d, J=6.6, 2H), 2.52 (t, J=7.7, 2H), 1.85-1.03 (m, 21H), 0.98-0.76 (m, 2H). $^{13}$C NMR (75 MHz, CDCl$_3$) δ 164.62, 157.95, 143.57, 131.40, 130.32, 128.64, 126.86, 124.07, 118.71, 76.78, 70.93, 37.98, 35.67, 31.29, 30.13, 29.58, 29.05, 26.64, 25.97, 25.86, 19.17, 12.40.

1-(3-(3-(6-(cyclohexylmethoxy)hexyl)phenyl)-1,2,4-oxadiazol-5-yl)cyclopropanecarbonitrile (17e)

General procedure G was used to convert 17d (386 mg, 0.91 mmol) to the title product as white solid (81% yield). R$_f$=0.60 (25% EtOAc in hexanes). $^1$H NMR (300 MHz, CDCl$_3$) δ 7.88-7.80 (m, 2H), 7.42-7.28 (m, 2H), 3.36 (t, J=6.5, 2H), 3.18 (d, J=6.6, 2H), 2.61 (t, J=7.8, 2H), 2.02 (s, 4H), 1.81-1.04 (m, 17H), 1.00-0.79 (m, 2H). $^{13}$C NMR (75 MHz, CDCl$_3$) δ 174.79, 169.01, 143.80, 131.86, 128.91, 127.51, 125.86, 124.99, 117.65, 76.93, 71.08, 38.12, 35.83, 31.43, 30.26, 29.73, 29.19, 26.76, 26.12, 25.98, 20.79, 8.95.

1-(3-(3-(6-(cyclohexylmethoxy)hexyl)phenyl)-1,2,4-oxadiazol-5-yl)cyclopropanecarboximidamide hydrochloride (17)

General procedure A was used to convert 17e (352 mg, 0.87 mmol) to the title product as yellow solid (16% yield). $^1$H NMR (600 MHz, DMSO) δ 9.53 (s, 2H), 9.38 (s, 2H), 7.87-7.67 (m, 2H), 7.54-7.27 (m, 2H), 3.18 (t, J=6.5, 2H), 3.02 (d, J=6.6, 2H), 2.58 (t, J=7.7, 2H), 2.05-1.79 (m, 4H), 1.75-0.99 (m, 17H), 0.95-0.78 (m, 2H). $^{13}$C NMR (151 MHz, DMSO) δ 177.15, 167.67, 165.37, 143.44, 131.71, 129.17, 126.55, 125.40, 124.37, 75.59, 69.93, 37.35, 34.70, 30.77, 29.42, 28.95, 28.24, 26.02, 25.37, 25.21, 21.98, 18.10.

Compounds 18-19

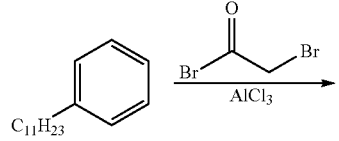

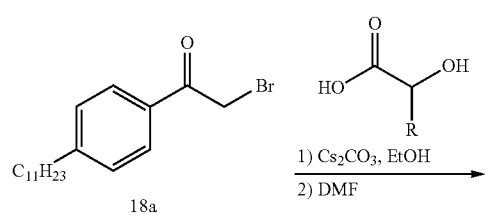

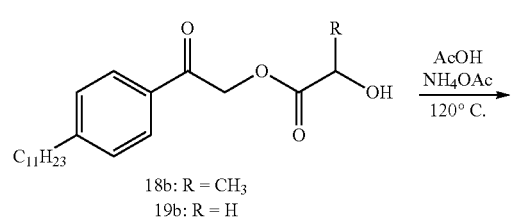

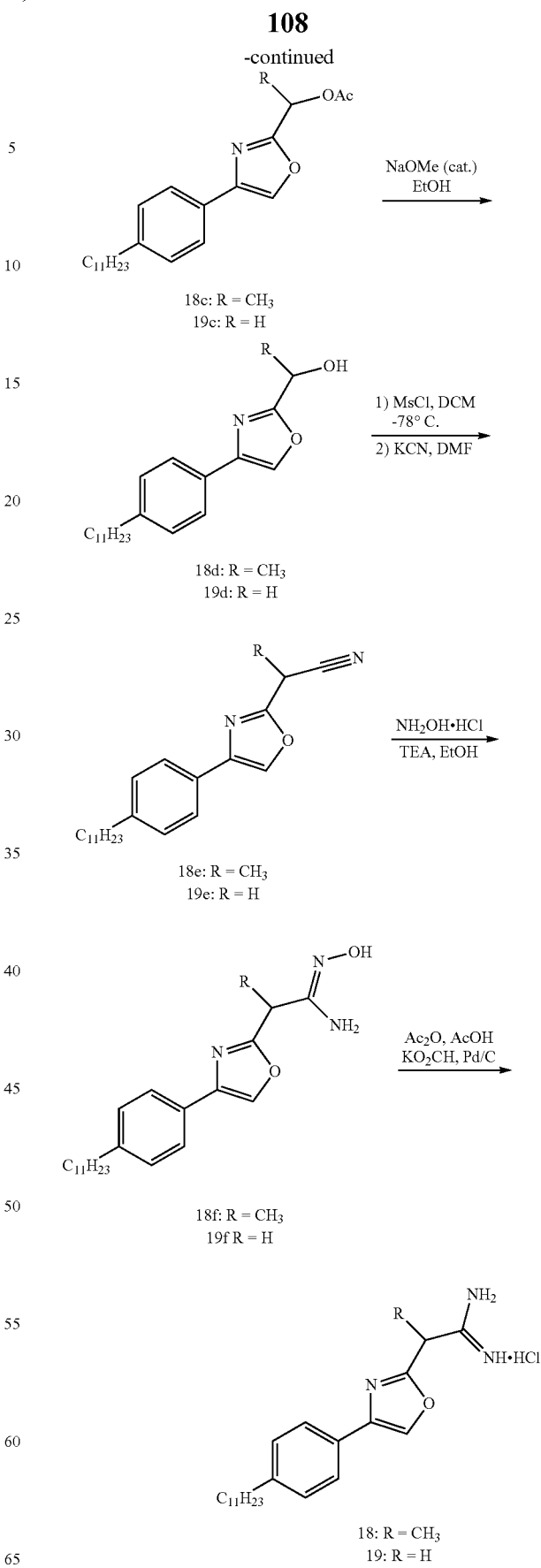

Compound 18

2-bromo-1-(4-dodecylphenyl)ethanone (18a)

To a solution of AlCl$_3$ (3.13 g, 23.5 mmol) in dichloroethane (2.0 M) was added bromoacetyl bromide (2.13 mL, 24.5 mmol) and phenyldodecane (5.89 g, 20.4 mmol) sequentially at 0° C. The mixture was warmed slowly to r.t. over 4 hours. The reaction was then cooled to 0° C. and the additional aluminum chloride was quenched with water. The solution was extracted three times into EtOAc, dried over MgSO$_4$, and evaporated. The crude material was purified via flash chromatography to yield the title product as yellow oil (91% yield). R$_f$=0.55 (10% EtOAc in hexanes). $^1$H NMR (300 MHz, CDCl$_3$) δ 7.89 (d, J=8.1, 2H), 7.28 (d, J=8.1, 2H), 4.42 (s, 2H), 2.66 (t, J=7.7, 2H), 1.63 (m, 2H), 1.28 (m, 18H), 0.88 (t, J=6.5, 3H). $^{13}$C NMR (75 MHz, CDCl$_3$) δ 190.69, 149.76, 131.49, 128.94, 128.75, 35.97, 31.83, 30.97, 29.56, 29.47, 29.36, 29.28, 29.18, 22.61, 14.05.

2-(4-dodecylphenyl)-2-oxoethyl 2-hydroxypropanoate (18b)

A solution of DL-lactic acid (0.54 mL, 5.44 mmol) and Cs$_2$CO$_3$ (0.51 eq.) in EtOH (18 mL, 0.3 M) was sonicated for 6 m at r.t. The solvent was then evaporated and dried under vacuum for 20 min. The cesium carboxylate salt was then solvated in DMF (30 mL) and 18a (1 eq.) was transferred by cannula in DMF (6 mL) at r.t. The reaction was stirred for 12 h before being diluted with EtOAc (200 mL) and washed 3× with neat water (50 mL). The organic layer was then dried with MgSO$_4$, evaporated to a white solid, and immediately purified by flash chromatography to yield the title compound as white solid (70% yield). Rf=0.21 (25% EtOAc in hexanes). $^1$H NMR (3.00 MHz, CDCl$_3$) δ 7.78 (d, 8.0, 2H), 7.25 (d, J=8.1, 2H), 5.38 (q, J=16.3, 1H), 2.71-2.54 (m, 2H), 2.00 (s, 2H), 1.63-1.49 (m, 5H), 1.39-1.11 (m, 18H), 0.84 (t, J=6.6, 3H).

1-(4-(4-dodecylphenyl)oxazol-2-yl)ethyl acetate (18c)

To a round bottom flask containing 18b (1.10 g, 2.44 mmol) and ammonium acetate (10 eq.) was added AcOH (20 mL, 0.12 M). The reaction was then heated to reflux for 16 h. The reaction was then cooled to r.t., evaporated to dryness, and immediately purified by flash chromatography to yield the title compound as white solid (24% yield). R$_f$=0.61 (15% EtOAc in hexanes). $^1$H NMR (300 MHz, CDCl$_3$) δ 7.83 (s, 1H), 7.63 (d, J=8.2, 2H), 7.20 (d, J=8.2, 3H), 6.02 (q, J=6.7, 1H), 2.61 (t, J=7.7, 2H), 2.12 (s, 3H), 1.70 (d, J=6.7, 3H), 1.67-1.55 (m, 2H), 1.44-1.21 (m, 18H), 0.88 (t, J=6.7, 3H). $^{13}$C NMR (75 MHz, CDCl$_3$) δ 169.95, 162.32, 143.17, 141.11, 133.48, 128.82, 128.14, 125.60, 65.13, 35.83, 32.01, 31.48, 29.75, 29.60, 29.45, 29.35, 22.78, 21.01, 18.43, 14.21.

1-(4-(4-dodecylphenyl)oxazol-2-yl)ethanol (18d)

To a solution of 18c (367 mg, 0.9 mmol) in EtOH was added a 0.5 M solution of sodium methoxide in methanol (0.37 mL, 0.18 mmol). The mixture was stirred at r.t. for 1 h, evaporated, and immediately purified by flash chromatography as white solid (75% yield). R$_f$=0.19 (15% EtOAc in hexanes). $^1$H NMR (300 MHz, CDCl$_3$) δ 7.76 (s, 1H), 7.59 (d, J=8.1, 2H), 7.19 (d, J=8.1, 2H), 5.01 (q, J=6.2, 1H), 4.63 (s, 1H), 2.61 (t, J=7.7, 2H), 1.62 (d, J=6.7, 5H), 1.44-1:18 (m, 18H), 0.90 (t, J=6.6, 3H). $^{13}$C NMR (75 MHz, CDCl$_3$) δ 166.72, 143.10, 140.54, 133.15, 128.82, 128.04, 125.52, 63.61, 35.82, 32.01, 31.47, 29.77, 29.61, 29.46, 22.78, 21.20, 14.20.

2-(4-(4-dodecylphenyl)oxazol-2-yl)propanenitrile (18e)

To a solution of 18d (0.24 g, 0.67 mmol) in CH$_2$Cl$_2$ (3 mL, 0.3 M) at −78° C. was added TEA (1.2 eq.) then methanesulfonylchloride (1.1 eq.). After 30 min, the reaction was diluted with DMF (3 mL, 0.3 M) and KCN (2 eq.) was added neat. The reaction was warmed to r.t. and stirred overnight. After being diluted with EtOAc (100 mL), the organic layer was washed 3× with water (50 mL), once with brine, dried over MgSO$_4$ and evaporated. The crude material was immediately purified by flash chromatography to yield the title product as white solid (57% yield). R$_f$=0.58 (10% EtOAc in hexanes). $^1$H NMR (300 MHz, CDCl$_3$) δ 7.86 (s, 1H), 7.64 (d, J=8.1, 2H), 7.22 (d, J=8.1, 2H), 5.17 (q, J=6.9, 1H), 2.57 (t, J=7.7, 2H), 1.98 (d, J=6.9, 3H), 1.72-1.54 (m, 2H), 1.45-1.16 (m, 18H), 0.89 (t, J=6.6, 3H). $^{13}$C NMR (75 MHz, CDCl$_3$) δ 162.61, 143.40, 141.35, 133.82, 128.94, 128.03, 125.64, 48.61, 35.88, 32.05, 31.53, 29.79, 29.73, 29.64, 29.50, 29.40, 22.83, 22.69, 14.26.

(Z)-2-(4-(4-dodecylphenyl)oxazol-2-yl)-N'-hydroxypropanimidamide (18f)

General procedure F was used to convert 18e (140 mg, 0.38 mmol) to the title product as white solid (22% yield). R$_f$=0.33 (50% EtOAc in hexanes). $^1$H NMR (300 MHz, CDCl$_3$) δ 7.81 (s, 1H), 7.61 (d, J=8.0, 2H), 7.20 (d, J=8.0, 2H), 4.38 (q, J=6.9, 1H), 2.54 (t, J=7.7, 2H), 1.71-1.55 (m, 2H), 1.51 (d, J=6.9, 3H), 1.45-1.15 (m, 18H), 0.88 (t, J=6.5, 3H). $^{13}$C NMR (75 MHz, CDCl$_3$) δ 165.21, 156.45, 145.62, 142.27, 140.89, 138.20, 128.90, 128.22, 125.64, 56.00, 35.88, 33.95, 32.05, 31.53, 29.77, 29.64, 29.49, 29.42, 29.29, 29.13, 29.04, 22.82, 14.26.

2-(4-(4-dodecylphenyl)oxazol-2-yl)propanimidamide hydrochloride (18)

Potassium formate was prepared in situ from HCOOH (2.1 mmol) and K$_2$CO$_3$ (1.1 mmol) in MeOH (1.0 mL). The parent amideoxime, 18f (81 mg, 0.21 mmol) was dissolved in AcOH (1 mL) and Ac$_2$O (0.02 mL, 0.2 mmol) was added at r.t. After 5 min, the potassium formate solution in MeOH was added, followed by 10% Pd/C. The mixture was stirred at r.t. overnight. The solution was filtered through Celite, washed with EtOH, and the filtrate was evaporated. The residue was dissolved in anhydrous EtOH and 5 M HCl in EtOH (12 eq.) was then added. After evaporation, the material was recrystallized in Et$_2$O to yield the pure amidine hydrochloride salt.

Compound 19

2-(4-dodecylphenyl)-2-oxoethyl 2-hydroxyacetate (19b)

A solution of glycolic acid (1.41 g, 18.5 mmol) and $Cs_2CO_3$ (0.51 eq.) in EtOH (61 mL, 0.3 M) was sonicated for 6 m at r.t. The solvent was then evaporated and dried under vacuum for 20 min. The cesium carboxylate salt was then solvated in DMF (100 mL) and 18a (1 eq.) was transferred by cannula in DMF (20 mL) at r.t. The reaction was stirred for 12 h before being diluted with EtOAc (400 mL) and washed 3× with neat water (100 mL). The organic layer was then dried with $MgSO_4$, evaporated to a white solid, and immediately purified by flash chromatography to yield the title compound as white solid (86% yield). Rf=0.18 (25% EtOAc in hexanes). $^1$H NMR (300 MHz, $CDCl_3$) δ 7.82 (d, J=8.4, 2H), 7.29 (d, J=8.4, 2H), 5.44 (s, 2H), 4.39 (d, J=5.8, 2H), 2.67 (t, J=7.8, 2H), 2.50 (t, J=5.8, 2H), 1.62 (m, 2H), 1.25 (m, 18H), 0.87 (t, J=6.7, 3H).

(4-(4-dodecylphenyl)oxazol-2-yl)methyl acetate (19c)

To a round bottom flask containing 19b (1.10 g, 2.44 mmol) and ammonium acetate (10 eq.) was added AcOH (20 mL, 0.12 M). The reaction was then heated to reflux for 16 h. The reaction was then cooled to r.t., evaporated to dryness, and immediately purified by flash chromatography to yield the title compound as white solid (30% yield). Rf=0.51 (10% EtOAc in hexanes). $^1$H NMR (300 MHz, $CDCl_3$) δ 7.88 (s, 1H), 7.63 (d, J=8.1, 2H), 7.21 (d, J=8.1, 2H), 5.21 (s, 2H), 2.61 (t, J=7.8, 2H), 2.16 (s, 3H), 1.61 (m, 2H), 1.27 (m, 18H), 0.88 (t, J=6.7, 3H). $^{13}$C NMR (75 MHz, $CDCl_3$) δ 170.14, 158.74, 143.24, 141.35, 133.92, 128.78, 127.80, 125.44, 57.87, 35.72, 31.89, 31.37, 29.64, 29.48, 29.33, 29.26, 22.67, 20.60, 14.11.

(4-(4-dodecylphenyl)oxazol-2-yl)methanol (19d)

To a solution of 19c (334 mg, 0.87 mmol) in EtOH was added a 0.5 M solution of sodium methoxide in methanol (0.35 mL, 0.17 mmol). The mixture was stirred at r.t. for 1 h, evaporated, and immediately purified by flash chromatography as white solid (97% yield). Rf=0.17 (15% EtOAc in hexanes). $^1$H NMR (300 MHz, $CDCl_3$) δ 7.79 (s, 1H), 7.59 (d, J=8.0, 2H), 7.21 (d, J=8.0, 2 H), 4.93 (s, 1H), 4.77 (s, 2H), 2.68 (t, J=7.7, 3H), 1.70-1.53 (m, 2H), 1.46-1.13 (m, J=12.5, 18H), 0.97 (t, J=6.6, 3H). $^{13}$C NMR (75 MHz, $CDCl_3$) δ 164.22, 143.33, 140.79, 133.47, 128.96, 127.88, 125.50, 57.22, 35.86, 32.04, 31.51, 29.80, 29.64, 29.48, 22.81, 14.25.

2-(4-(4-dodecylphenyl)oxazol-2-yl)acetonitrile (19e)

To a solution of 19d (0.25 g, 0.73 mmol) in $CH_2Cl_2$ (2.5 mL, 0.3 M) at −78° C. was added TEA (1.2 eq.) then methanesulfonylchloride (1.1 eq.). After 30 min, the reaction was diluted with DMF (2.5 mL, 0.3 M) and KCN (2 eq.) was added neat. The reaction was warmed to r.t. and stirred overnight. After being diluted with EtOAc (100 mL), the organic layer was washed 3× with water (50 mL), once with brine, dried over $MgSO_4$, and evaporated. The crude material was immediately purified by flash chromatography to yield the title product as white solid (91% yield). Rf=0.18 (15% EtOAc in hexanes). $^1$H NMR (300 MHz, $CDCl_3$) δ 7.88 (s, 1H), 7.63 (d, J=8.2, 2H), 7.22 (d, J=8.2, 2H), 4.66 (s, 2H), 2.62 (t, J=7.7, 2H), 1.69-1.55 (m, 2H), 1.28 (m, 18H), 0.88 (t, J=6.7, 3H). $^{13}$C NMR (75 MHz, $CDCl_3$) δ 159.12, 143.36, 141.57, 134.27, 128.82, 127.68, 125.42, 35.87, 35.73, 31.90, 31.37, 29.64, 29.48, 29.34, 29.26, 22.67, 14.11.

(Z)-2-(4-(4-dodecylphenyl)oxazol-2-yl)-N'-hydroxyacetimidamide (19f)

General procedure F was used to convert 19e (164 mg, 0.47 mmol) to the title product as white solid (45% yield). Rf=0.20 (50% EtOAc in hexanes). $^1$H NMR (300 MHz, $CDCl_3$) δ 7.84 (s, 1H), 7.62 (d, J=8.2, 2H), 7.21 (d, J=8.1, 2H), 4.25 (s, 2H), 2.54 (t, J=7.7, 2H), 2.04 (s, 2H), 1.72-1.50 (m, 2H), 1.47-1.12 (m, 18H), 0.87 (t, J=6.6, 3H). $^{13}$C NMR (75 MHz, $CDCl_3$) δ 163.25, 159.29, 143.52, 141.74, 134.42, 129.13, 128.98, 125.58, 60.51, 36.01, 35.89, 31.73, 31.52, 29.79, 29.63, 29.49, 29.41, 22.79, 21.15, 14.24.

2-(4-(4-dodecylphenyl)oxazol-2-yl)acetimidamide hydrochloride (19)

Potassium formate was prepared in situ from HCOOH (2.1 mmol) and $K_2CO_3$ (1.1 mmol) in MeOH (1.0 mL). The parent amideoxime, 19f (81 mg, 0.21 mmol) was dissolved in AcOH (1 mL) and $Ac_2O$ (0.02 mL, 0.2 mmol) was added at r.t. After 5 min, the potassium formate solution in MeOH was added, followed by 10% Pd/C. The mixture was stirred at r.t. overnight. The solution was filtered through Celite, washed with EtOH, and the filtrate was evaporated. The residue was dissolved in anhydrous EtOH and 5 M HCl in EtOH (12 eq.) was then added. After evaporation, the material was recrystallized in $Et_2O$ to yield the pure amidine hydrochloride salt. $^1$H NMR (500 MHz, DMSO) δ 8.67 (s, 1H), 7.68 (d, J=8.0, 2H), 7.26 (d, J=8.0, 2H), 2.58 (t, J=7.6, 2H), 2.05 (s, J=0.8, 2H), 1.62-1.52 (m, 2H), 1.34-1.15 (m, 18H), 0.84 (t, J=6.8, 3H). $^{13}$C NMR (126 MHz, DMSO) δ 146.49, 142.51, 141.96, 136.04, 128.79, 126.71, 125.13, 45.25, 34.91, 31.31, 30.84, 30.73, 29.02, 28.86, 28.72, 28.67, 22.11, 13.98, 8.41.

Compound 20

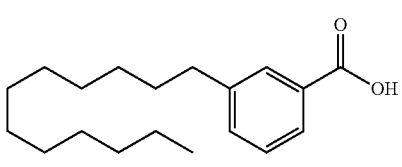

20a

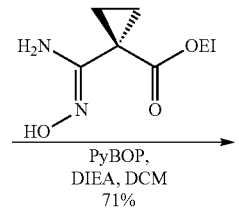

PyBOP, DIEA, DCM
71%

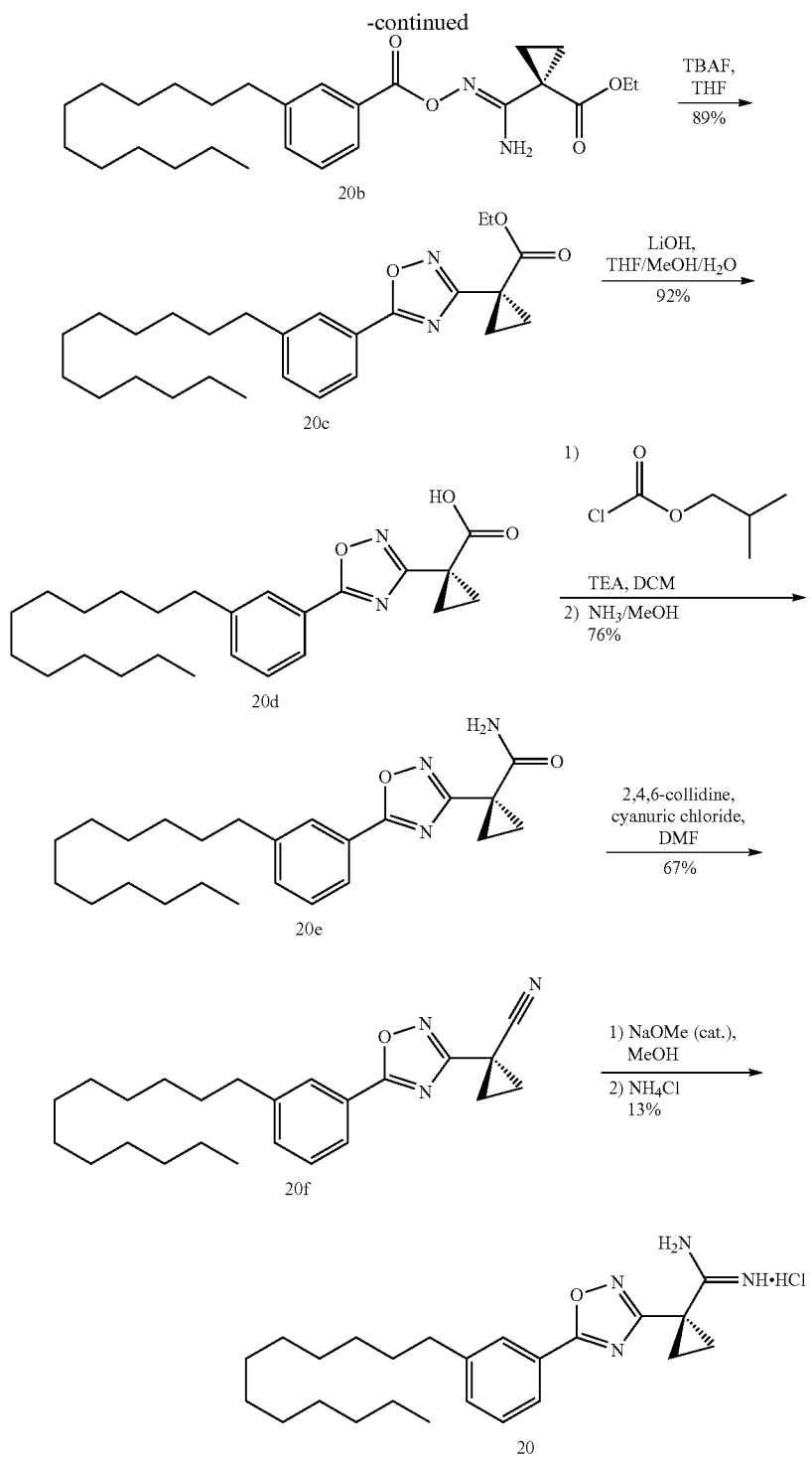

(Z)-ethyl 1-(N'-((3-dodecylbenzoyl)oxy)carbamim-idoyl)cyclopropanecarboxylate (20b)

General procedure B was used to couple 1.4 mmol of the amide oxime to 1.4 mmol of the acid 20a. Following purification, 1.01 mmol of 20b were isolated. ¹H NMR (600 MHz, Chloroform-d) δ 7.89-7.77 (m, 2H), 7.45-7.31 (m, 2H), 5.59 (s, 2H), 4.18 (q, J=3 Hz, 2H), 2.65 (t, J=3 Hz, 2H), 1.65-1.60 (m, 2H), 1.34-1.21 (m, 25H), 0.88 (t, 3H).

Ethyl 1-(5-(3-dodecylphenyl)-1,2,4-oxadiazol-3-yl) cyclopropanecarboxylate (20c)

General procedure G was used to convert 20b (164 mg, 0.47 mmol) to the title product (89% yield). ¹H NMR (300 MHz, Chloroform-d) δ 7.98-7.90 (m, 2H), 7.45-7.37 (m, 2H), 4.21 (q, J=7.1 Hz, 2H), 2.68 (t, 2H), 1.70-1.60 (m, 2H), 1.37-1.18 (m, 25H), 0.87 (t, J=6.7 Hz, 3H).

1-(5-(3-dodecylphenyl)-1,2,4-oxadiazol-3-yl)cyclopropanecarboxylic acid (20d)

To a solution containing 0.90 mmol 20c in 1.65 mL each of MeOH, THF, and H$_2$O were added 2.7 mmol LiOH. This mixture was stirred 15 h. at r.t. At this point, the mixture was taken up in 100 mL EtOAc, washed with three 10 mL portions of 1 N HCl, one portion of 10 mL of brine, and then dried over Na$_2$SO$_4$. Following solvent evaporation, 0.83 mmol of the product were isolated.

1-(5-(3-dodecylphenyl)-1,2,4-oxadiazol-3-yl)cyclopropanecarboxamide (20e)

To a solution of 0.83 mmol 20d in 1.66 mL DCM was added 0.91 mmol i-butylchloroformate and 0.35 mL TEA (0.726 g/mL). After this solution stirred 1 h., 1.25 mL of NH$_3$ in MeOH (2 M) were added dropwise, and the mixture stirred an additional 15 h. at r.t. At this time, the solvent was evaporated and the crude product purified by flash chromatography (silica gel, 20% EtOAc/Hexanes). 0.63 mmol of the product were isolated. $^1$H NMR (600 MHz, Chloroform-d) δ 8.23 (s, 2H), 7.96-7.89 (m, 2H), 7.47-7.39 (m, 2H), 2.69 (t, J=4.5 Hz, 2H), 1.69-1.62 (m, 2H), 1.38-1.21 (m, 22H), 0.88 (t, J=7.1 Hz, 3H).

1-(5-(3-dodecylphenyl)-1,2,4-oxadiazol-3-yl)cyclopropanecarbonitrile (20f)

To an ice-cold stirring solution of 5.03 mmol 2,4,6-collidine and 1.98 mmol cyanuric chloride in 6.3 mL DMF was added 0.63 mmol 20e. This mixture was warmed to r.t. and stirred for 15 h. At this time, the reaction was slowly quenched with a saturated NaHCO$_3$ solution and then extracted with three portions of 25 mL EtOAc. The combined organic layers were then washed with three 10 mL portions of 1 N HCl and one 10 mL portion of brine, and then dried over Na$_2$SO$_4$. The crude product was then purified using flash chromatography to yield 0.42 mmol 20f. $^1$H NMR (300 MHz, Chloroform-d) δ 7.98-7.87 (m, 2H), 7.47-7.38 (m, 2H), 2.74-2.64 (m, 2H), 1.70-1.60 (m, 2H), 1.37-1.16 (m 22H), 0.88 (t, J=6.7 Hz, 3H).

1-(5-(3-dodecylphenyl)-1,2,4-oxadiazol-3-yl)cyclopropanecarboximidamide hydrochloride (20)

General procedure A was used to yield 0.054 mmol of the amidine hydrochloride salt 20 from 0.42 mmol of the nitrile 2f. Additional purification through flash chromatography was required (silica gel, 15% CHCl$_3$/MeOH). $^1$H NMR (600 MHz, DMSO-d6) δ 9.32 (s, 2H), 9.11 (s, 2H), 7.94-7.90 (m, 2H), 7.60-7.54 (m, 2H), 2.52 (t, J=1.8 Hz, 2H), 1.64-1.56 (m, 2H), 1.33-1.18 (m, 22H), 0.86 (t, J=9 Hz, 3H). $^{13}$C NMR (151 MHz, DMSO) δ 176.08, 170.09, 168.54, 167.40, 166.01, 144.60, 134.16, 130.11, 127.97, 125.83, 123.35, 65.39, 35.19, 31.76, 31.34, 29.48, 29.47, 22.57, 21.69, 16.44, 15.65, 14.44.

Compound 21

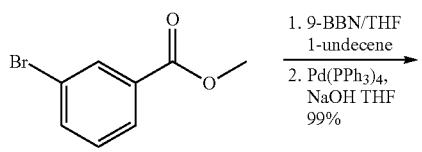

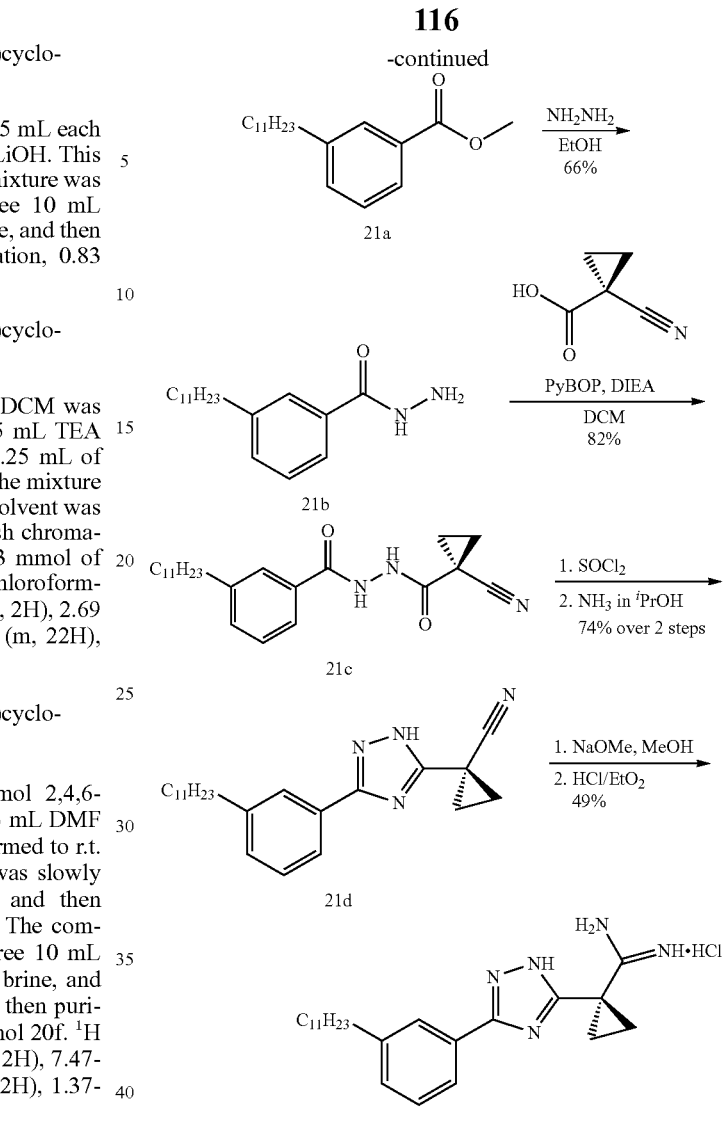

methyl 3-undecylbenzoate (21a)

General procedure C was used to couple 1-undecene (1.076 g, 6.975 mmol) and 3-bromo-4-methylbenzonitrile (1.00 g, 4.650 mmol) to yield the title product as an oil (99% yield). R$_f$=0.81 (10% EtOAc in hexanes). $^1$H NMR (300 MHz, CDCl$_3$) δ 7.86 (d, J=1.8 Hz, 1H), 7.85-7.82 (m, 1H), 7.36 (t, J=1.8 Hz, 1H), 7.33 (s, 1H), 3.91 (s, 2H), 2.69-2.61 (t, J=7.6, 2H), 1.62 (m, 2H), 1.30 (m, 2H), 1.25 (s, 12H), 0.88 (t, J=6.7 Hz, 3H). $^{13}$C NMR (75 MHz, CDCl$_3$) δ 167.53, 143.38, 133.23, 129.64, 128.38, 127.05, 52.20, 51.42, 35.90, 32.06, 31.55, 29.78, 29.71, 29.62, 29.49, 29.39, 22.84, 14.28.

3-undecylbenzohydrazide (21b)

21a (0.560 g, 1.938 mmol) was dissolved in anhydrous ethanol (0.6M). To the stirring solution, anhydrous hydrazine (0.185 g, 5.784 mmol, 0.2 mL) was added and the reaction mixture was heated to reflux for 24 hours. The reaction mixture was cooled, the volume reduced under pressure, and then purified via flash chromatography (silica gel, 50% EtOAc in hexanes to 75% EtOAc in hexanes) to afford an oil (0.369 g, 66%): $R_f$=0.32 (75% EtOAc in hexanes).

N'-(1-cyanocyclopropanecarbonyl)-3-undecylbenzohydrazide (21c)

General procedure B was used to convert 21b (0.369 g, 1.269 mmol) to the title product as an oil (82% yield). $R_f$=0.62 (50% EtOAc in hexanes). $^1$H NMR (300 MHz, CDCl3) δ 9.27 (NH, s, 1H), 9.00 (NH, s, 1H), 7.65 (s, J=5.3 Hz, 1H), 7.64-7.59 (m, 1H), 7.33 (s, 1H), 7.30 (s, 1H), 2.67-2.52 (m, 2H), 1.63 (qd, J=9.0, 5.3 Hz, 6H), 1.24 (m, 16H), 0.87 (t, J=6.7 Hz, 3H). $^{13}$C NMR (75 MHz, CDCl3) δ 165.77, 164.48, 143.89, 132.89, 131.02, 128.73, 127.63, 124.68, 118.89, 51.38, 35.89, 32.03, 31.46, 29.78, 29.75, 29.70, 29.59, 29.46, 29.42, 22.80, 18.62, 14.26, 12.64.

1-(3-(3-undecylphenyl)-1H-1,2,4-triazol-5-yl)cyclopropanecarbonitrile (21d)

21c (0.398 g, 1.039 mmol) was dissolved in thionyl chloride (2.472 g, 20.776 mmol, 1.5 mL) and heated to reflux for 4 hours. Excess thionyl chloride was removed under reduced pressure and co-evaporated twice with Et$_2$O to a yellow solid and carried on crude. The crude material (0.437 g, 1.039 mmol) was dissolved in anhydrous iso-propanol saturated in ammonia (0.02 M). The reaction was equipped with a balloon of gaseous ammonia and the reaction stirred overnight followed by heating to reflux for 30 h. The reaction transformed from yellow to purple. The reaction was cooled, the solvent removed under reduced pressure, and purified via flash chromatography (silica gel, 15% EtOAc in hexane to 25% EtOAc in hexane) to yield an oil (0.280 g, 74%). $^1$H NMR (300 MHz, Acetone) δ 7.87 (s, 1H), 7.85-7.80 (m, 1H), 7.50 (t, J=5.7 Hz, 1H), 7.47 (d, J=2.1 Hz, 1H), 2.77-2.63 (m, 2H), 2.03 (qd, J=3.5, 2.2 Hz, 4H), 1.73-1.59 (m, 2H), 1.40-1.22 (m, 16H), 0.86 (t, J=6.7 Hz, 3H). $^{13}$C NMR (75 MHz, Acetone) δ 165.93, 163.61, 145.16, 133.08, 130.18, 127.46, 125.09, 124.57, 118.97, 47.08, 36.33, 32.74, 32.32, 30.48, 30.28, 30.03, 23.44, 19.26, 14.48, −2.97, −6.84.

1-(3-(3-undecylphenyl)-1H-1,2,4-triazol-5-yl)cyclopropanecarboximidamide hydrochloride (21)

General procedure A was used to convert 21d (0.280 g, 0.766 mmol) to the title product as an oil. $R_f$=0.24 (10% MeOH in CHCl$_3$). The oil was dissolved in Et$_2$O and a few drops of 12.1 M HCl was added and swirled. The ether was removed under reduced pressure and co-evaporated twice with Et$_2$O to afford a white solid (0.156 g, 49%). $^1$H NMR (600 MHz, DMSO) δ 9.44 (d, J=33.7 Hz, 2H), 7.80 (d, J=6.0 Hz, 1H), 7.47 (dd, J=24.6, 7.3 Hz, 1H), 2.65 (t, J=6.9 Hz, 2H), 1.90 (dd, J=62.8, 4.5 Hz, 4H), 1.58 (m, 2H), 1.25 (m, 16H), 0.83 (t, J=7.0 Hz, 3H). $^{13}$C NMR (151 MHz, DMSO) δ 166.90, 164.22, 163.87, 143.71, 132.04, 129.29, 126.19, 124.06, 123.12, 34.81, 31.25, 30.84, 28.99, 28.95, 28.80, 28.66, 28.57, 22.05, 20.27, 16.93, 13.89.

Compound 22

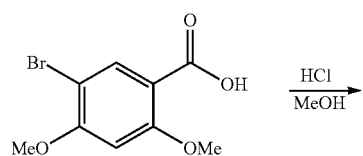

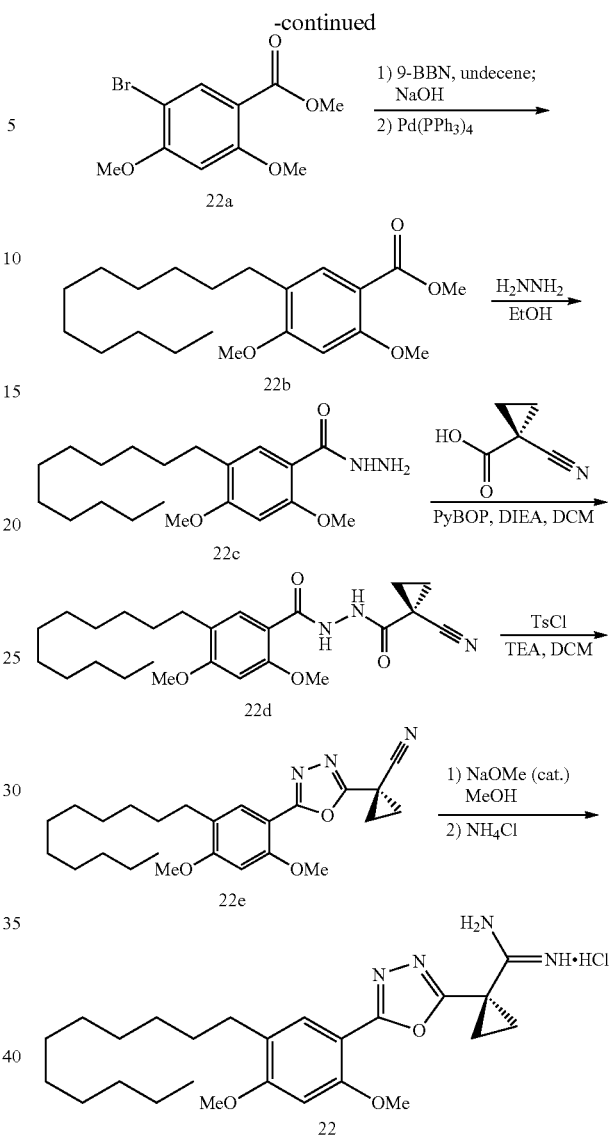

methyl 5-bromo-2,4-dimethoxybenzoate (22a)

General Procedure O was used to convert 5-bromo-2,4-dimethoxybenzoic acid (500 mg, 1.91 mmol) to the title product as white solid (87% yield). $R_f$=0.43 (50% EtOAc in hexanes). $^1$H NMR (300 MHz, CDCl$_3$) δ 8.01 (s, 1H), 6.43 (s, 1H), 3.91 (s, 3H), 3.89 (s, 3H), 3.82 (s, 3H). $^{13}$C NMR (75 MHz, CDCl$_3$) δ 164.85, 160.87, 159.92, 136.26, 112.81, 101.57, 96.48, 56.36, 51.92.

methyl 2,4-dimethoxy-5-undecylbenzoate (22b)

General Procedure C was used to couple 1-undecene (0.59 mL, 2.87 mmol) and 22a (460 mg, 1.67 mmol) to yield the title product as clear and colorless oil (86% yield). $R_f$=0.49 (50% EtOAc in hexanes). $^1$H NMR (600 MHz, CDCl$_3$) δ 7.60 (s, 1H), 6.38 (s, 1H), 3.84 (s, 3H), 3.81 (s, 3H), 3.78 (s, 3H), 2.46 (t, J=3.9, 2H), 1.50-1.45 (m, 2H), 1.22-1.19 (m, 16H), 0.82 (t, J=7.1, 3H). $^{13}$C NMR (151 MHz, CDCl$_3$) δ 166.17, 161.74, 159.85, 133.02, 122.99, 110.80, 95.21, 56.08, 55.23, 32.01, 29.76, 29.62, 29.58, 29.57, 29.55, 29.45, 29.43, 29.30, 29.28, 29.18, 27.37, 26.43, 26.41, 26.21, 22.84, 14.06

2,4-dimethoxy-5-undecylbenzohydrazide (22c)

General Procedure P was used to convert 22b (502 mg, 1.44 mmol) to the title product as clear and colorless oil (36% yield). $R_f$=0.12 (75% EtOAc in hexanes). $^1$H NMR (300 MHz, CDCl$_3$) δ 8.82 (s, 1H), 7.91 (s, 1H), 6.37 (s, 1H), 3.91 (s, 3H), 3.83 (s, 3H), 2.51 (t, J=7.6, 2H), 1.59-1.43 (m, 2H), 1.36-1.14 (m, 16H), 0.84 (t, J=6.6, 3H). $^{13}$C NMR (75 MHz, CDCl$_3$) δ 166.80, 161.13, 157.21, 132.89, 124.29, 111.40, 94.32, 55.97, 55.51, 31.96, 29.90, 29.68, 29.58, 29.40, 29.32, 22.73, 14.18.

N'-(1-cyanocyclopropanecarbonyl)-2,4-dimethoxy-5-undecylbenzohydrazde (22d)

General procedure B was used to couple 22c (180 mg, 0.51 mmol) and 1-cyano-1-cyclopropanecarboxylic acid (63 mg, 0.57 mmol) to yield the title product as white solid (63% yield). $R_f$=0.22 (50% EtOAc in hexanes). $^1$H NMR (300 MHz, CDCl$_3$) δ 10.12 (s, 1H), 7.92 (s, 1H), 6.39 (s, 1H), 3.97 (s, 3H), 3.86 (s, 3H), 2.52 (t, J=7.7, 2H), 1.76 (dd, J=4.2, 8.6, 2H), 1.59 (dd, J=4.5, 8.3, 2H), 1.56-1.46 (m, 2H), 1.37-1.16 (m, 16H), 0.86 (t, J=6.5, 3H). $^{13}$C NMR (75 MHz, CDCl$_3$) δ 162.54, 161.99, 157.61, 133.08, 124.73, 119.07, 110.09, 94.35, 56.32, 55.63, 32.01, 29.73, 29.61, 29.45, 29.33, 22.78, 18.21, 14.23, 12.54.

1-(5-(2,4-dimethoxy-5-undecylphenyl)-1,3,4-oxadi-azol-2-yl)cyclopropanecarbonitrile (22e)

General procedure Q was used to convert 22d (144 mg, 0.33 mmol) to the title product as white solid (74% yield). $R_f$=0.63 (40% EtOAc in hexanes). $^1$H NMR (300 MHz, CDCl$_3$) δ 7.63 (s, 1H), 6.49 (s, 1H), 3.95 (s, 3H), 3.89 (s, 3H), 2.54 (t, J=7.7, 2H), 1.91 (q, J=3.4, 4H), 1.61-1.45 (m, 2H), 1.36-1.16 (m, 16H), 0.86 (t, J=6.6, 3H). $^{13}$C NMR (75 MHz, CDCl$_3$) δ 164.63, 161.65, 157.98, 130.91, 124.33, 118.26, 103.87, 95.32, 56.30, 55.58, 32.01, 29.96, 29.73, 29.61, 29.44, 22.78, 19.01, 18.19, 14.22, 7.16.

1-(5-(2,4-dimethoxy-5-undecylphenyl)-1,3,4-oxadi-azol-2-yl)cyclopropanecarboximidamide hydrochloride (22)

General procedure A was used to convert 22e (102 mg, 0.24 mmol) to the title product as yellow solid (21% yield). $^1$H NMR (600 MHz, DMSO) δ 9.56 (s, 2H), 9.35 (s, 2H), 7.55 (s, 1H), 6.77 (s, 1H), 3.98-3.73 (m, 6H), 2.53 (m, 2H), 1.90-1.69 (m, 4H), 1.56-1.39 (m, 2H), 1.33-1.05 (m, 16H), 0.83 (t, J=6.6, 3H). $^{13}$C NMR (151 MHz, DMSO) δ 165.99, 163.45, 162.92, 162.66, 160.99, 160.92, 157.29, 157.19, 122.58, 122.53, 103.10, 102.89, 96.31, 56.25, 55.83, 39.50, 37.85, 31.03, 29.10, 28.77, 28.73, 28.59, 28.53, 28.44, 21.85, 20.18, 16.47, 13.75.

Compounds 23-24

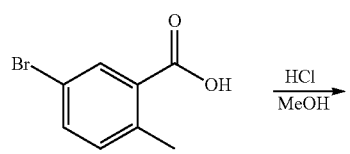

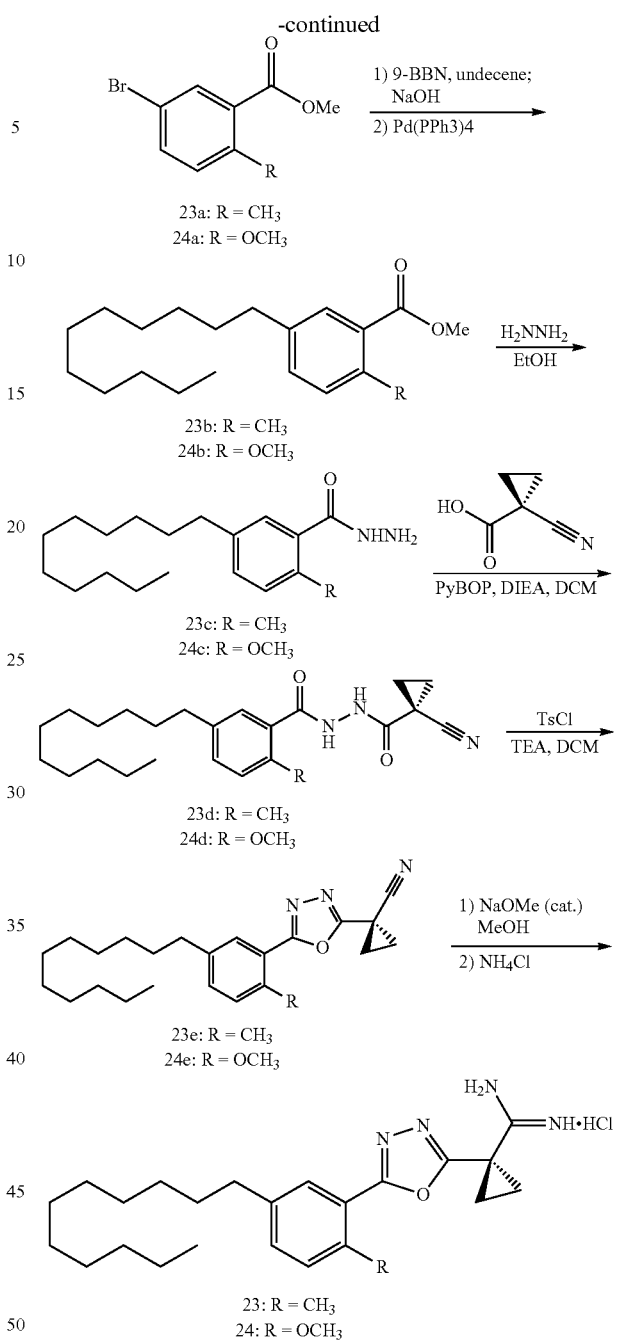

Compound 23 methyl 5-bromo-2-methylbenzoate (23a)

General procedure O was used to convert 5-bromo-2-methylbenzoic acid (500 mg, 2.33 mmol) to the title product as white solid (93% yield). $R_f$=0.56 (10% EtOAc in hexanes). $^1$H NMR (300 MHz, CDCl$_3$) δ 7.95 (d, J=2.2, 1H), 7.40 (dd, J=2.2, 8.2, 1H), 7.01 (d, J=8.1, 1H), 3.82 (s, 3H), 2.46 (s, 3H). $^{13}$C NMR (75 MHz, CDCl$_3$) δ 166.38, 139.13, 134.68, 133.21, 130.94, 119.02, 77.58, 77.16, 76.74, 51.98, 21.18.

methyl 2-methyl-5-undecylbenzoate (23b)

General procedure C was used to couple 1-undecene (0.67 mL, 3.26 mmol) with 23a (498 mg, 2.17 mmol) to yield the title product as clear and colorless oil (99% yield). $R_f$=0.40 (5% EtOAc in hexanes). $^1$H NMR (600 MHz, CDCl$_3$) δ 7.72 (d, J=1.9, 1H), 7.21 (dd, J=1.9, 7.8, 1H), 7.14 (d, J=7.8, 1H), 3.90 (s, 3H), 2.59 (t, J=3.9, 2H), 2.55 (s, 3H), 1.66-1.55 (m, 2H), 1.37-1.20 (m, 16H), 0.88 (t, J=7.1, 3H). $^{13}$C NMR (151 MHz, CDCl$_3$) δ 168.43, 140.50, 137.39, 132.23, 131.73, 130.55, 51.87, 35.45, 32.06, 31.58, 29.81, 29.77, 29.72, 29.64, 29.49, 29.41, 22.84, 21.43, 14.27.

2-methyl-5-undecylbenzohydrazide (23c)

General procedure P was used to convert 23b (660 mg, 2.12 mmol) to the title product as white solid (16% yield). $R_f$=0.34 (75% EtOAc in hexanes). $^1$H NMR (600 MHz, CDCl$_3$) δ 7.16-7.10 (m, 3H), 2.59 (t, J=3.9, 2H), 2.38 (s, 3H), 1.60-1.53 (m, 2H), 1.32-1.22 (m, 16H), 0.87 (t, J=7.0, 3H). $^{13}$C NMR (151 MHz, CDCl$_3$) δ 171.23, 140.67, 133.97, 133.68, 131.14, 130.58, 127.08, 35.42, 32.04, 31.52, 29.79, 29.75, 29.70, 29.61, 29.46, 29.38, 22.81, 19.44, 14.25.

N'-(1-cyanocyclopropanecarbonyl)-2-methyl-5-undecylbenzohydrazide (23d)

General procedure B was used to couple 23c (103 mg, 0.03 mmol) and 1-cyano-1-cyclopropanecarboxylic acid (41 mg, 0.04 mmol) to yield the title product as white solid (64% yield). $R_f$=0.60 (50% EtOAc in hexanes). $^1$H NMR (300 MHz, CDCl$_3$) δ 9.12 (s, 1H), 8.28 (s, 1H), 7.26 (s, 1H), 7.14 (m, 1H), 2.54 (t, J=7.7, 2H), 2.40 (s, 3H), 1.72 (dd, J=4.6; 8.2, 2H), 1.63-1.48 (m, 4H), 1.36-1.14 (m, 16H), 0.86 (t, J=6.6, 3H). $^{13}$C NMR (75 MHz, CDCl$_3$) δ 167.97, 164.35, 140.74, 134.42, 132.26, 131.29, 131.21, 127.34, 118.98, 35.39, 32.01, 31.55, 29.68, 29.58, 29.44, 29.40, 22.78, 21.13, 19.45, 18.60, 14.23, 12.56.

1-(5-(2-methyl-5-undecylphenyl)-1,3,4-oxadiazol-2-yl)cyclopropanecarbonitrile (23e)

General procedure Q was used to convert 23d to the title product as white solid (83% yield). $R_f$=0.40 (50% EtOAc in hexanes). $^1$H NMR (600 MHz, CDCl$_3$) δ 7.72 (s, 1H), 7.24 (d, J=1.1, 2H), 2.65-2.61 (m, 5H), 1.98-1.94 (m, 4H), 1.62 (dt, J=7.6, 15.5, 2H), 1.35-1.22 (m, 16H), 0.87 (t, J=7.0, 3H). $^{13}$C NMR (151 MHz, CDCl$_3$) δ 166.05, 161.96, 141.19, 135.74, 131.93, 131.90, 129.68, 128.89, 127.12, 118.02, 35.41, 32.01, 31.58, 29.75, 29.72, 29.69, 29.59, 29.44, 29.37, 22.79, 21.65, 19.29, 14.24, 7.18.

1-(5-(2-methyl-5-undecylphenyl)-1,3,4-oxadiazol-2-yl)cyclopropanecarboximidamide hydrochloride (23)

General procedure A was used to convert 23e (68 mg, 0.18 mmol) to the title product (37% yield). $^1$H NMR (600 MHz, DMSO) δ 9.32 (s, 4H), 7.64 (s, 1H), 7.29 (s, 2H), 3.30 (s, 3H), 2.63-2.53 (m, 2H), 1.99-1.73 (m, 4H), 1.66-1.43 (m, 2H), 1.37-1.04 (m, 16H), 0.80 (t, J=7.1, 3H). $^{13}$C NMR (151 MHz, DMSO) δ 166.35, 164.04, 163.25, 140.22, 134.38, 131.46, 131.29, 128.10, 121.73, 34.07, 30.95, 30.58, 28.69, 28.64, 28.50, 28.36, 28.26, 21.77, 20.64, 19.97, 16.67, 13.69.

Compound 24 methyl 5-bromo-2-methoxybenzoate (24a)

General procedure O was used to convert 5-bromo-2-methoxybenzoic acid (500 mg, 2.16 mmol) to the title product. 90%. White solid. $R_f$=0.21 (10% EtOAc in hexanes). $^1$H NMR (300 MHz, CDCl$_3$) δ 7.89 (d, J=2.6, 1H), 7.54 (dd, J=2.6, 8.9, 1H), 6.85 (d, J=8.9, 1H), 3.88 (s, 6H). $^{13}$C NMR (75 MHz, CDCl$_3$) δ 165.40, 158.35, 136.21, 134.34, 121.69, 113.94, 112.30, 56.37, 52.40.

methyl 2-methoxy-5-undecylbenzoate (24b)

General procedure C was used to couple 1-undecene (0.67 mL, 3.2 mmol) and 24a (390 mg, 1.59 mmol) to yield the title product as clear and colorless oil (88% yield). $R_f$=0.27 (10% EtOAc in hexanes). $^1$H NMR (300 MHz, CDCl$_3$) δ 7.59 (d, J=2.2, 1H), 7.25 (dd, J=2.9, 7.9, 1H), 6.88 (d, J=8.5, 1H), 3.90-3.84 (m, 6H), 2.54 (t, J=7.8, 2H), 1.63-1.46 (m, 2H), 1.33-1.17 (m, 16H), 0.86 (t, J=6.6, 3H). $^{13}$C NMR (75 MHz, CDCl$_3$) δ 171.26, 157.32, 134.73, 133.49, 131.48, 119.68, 112.08, 56.20, 52.09, 34.90, 32.02, 31.64, 29.73, 29.59, 29.45, 29.32, 22.80, 14.24.

2-methoxy-5-undecylbenzohydrazide (24c)

General procedure P was used to convert 24b (450 mg, 1.40 mmol) to the title product as white solid (44% yield). $R_f$=0.23 (75% EtOAc in hexanes). $^1$H NMR (300 MHz, CDCl$_3$) δ 8.96 (s, 1H), 7.97 (d, J=2.2, 1H), 7.21 (dd, J=2.3, 8.4, 1H), 6.84 (d, J=8.4, 1H), 3.88 (s, 3H), 2.54 (t, J=7.8, 2H), 1.68-1.46 (m, 2H), 1.36-1.07 (m, 16H), 0.84 (t, J=6.6, 3H). $^{13}$C NMR (75 MHz, CDCl$_3$) δ 166.68, 155.54; 135.88, 132.86, 131.72, 119.36, 111.19, 55.92, 34.89, 31.94, 31.57, 29.65, 29.52, 29.37, 29.25, 22.72, 14.16.

N'-(1-cyanocyclopropanecarbonyl)-2-methoxy-5-undecylbenzohydrazide (24d)

General procedure B was used to couple 24c (200 mg, 0.62 mmol) and 1-cyano-1-cyclopropanecarboxylic acid (69 mg, 0.62 mmol) to yield the title product as white solid (60% yield). $R_f$=0.51 (50% EtOAc in hexanes). $^1$H NMR (300 MHz, CDCl$_3$) δ 10.27 (s, 1H), 9.41 (s, 1H), 7.98 (d, J=2.3, 1H), 7.34-7.16 (m, 1H), 6.86 (d, J=8.5, 1H), 3.92 (s, 3H), 2.54 (t, J=7.8, 2H), 1.83 (dd, J=4.5, 8.3, 2H), 1.63 (dd, J=4.6, 8.2, 4H), 1.39-1.11 (m, 16H), 0.85 (t, J=6.6, 3H). $^{13}$C NMR (75 MHz, CDCl$_3$) δ 162.68, 162.53, 155.73, 136.02, 133.78, 131.92, 118.99, 118.05, 111.33, 56.21, 34.81, 31.92, 31.49, 29.64, 29.51, 29.36, 29.22, 22.71, 18.21, 14.15, 12.50.

1-(5-(2-methoxy-5-undecylphenyl)-1,3,4-oxadiazol-2-yl)cyclopropanecarbonitrile (24e)

General procedure Q was used to convert 24d (155 mg, 0.37 mmol) to the title product as white solid (38% yield). $R_f$=0.28 (25% EtOAc in hexanes). $^1$H NMR (300 MHz, CDCl$_3$) δ 7.70 (dd, J=5.3, 8.8, 2H), 7.33-7.27 (m, 1H), 6.95 (d, J=8.6, 1H), 3.91 (s, 3H), 2.58 (t, J=7.7, 2H), 1.93 (q, J=3.7, 4H), 1.67-1.51 (m, 2H), 1.35-1.17 (m, 16H), 0.86 (t, J=6.7, 3H).

1-(5-(2-methoxy-5-undecylphenyl)-1,3,4-oxadiazol-2-yl)cyclopropanecarboximidamide hydrochloride (24)

General procedure A was used to convert 24e (56 mg, 0.14 mmol) to the title product as brown solid (47% yield). $^1$H NMR (600 MHz, DMSO) δ 9.34 (s, 4H), 7.69-7.56 (m, 1H), 7.49-7.34 (m, 1H), 7.23-7.08 (m, 1H), 3.84 (s, 3H), 2.63-2.53 (m, 2H), 1.95-1.71 (m, 4H), 1.59-1.44 (m, 2H), 1.38-1.08 (m, 16H), 0.83 (t, J=6.6, 3H). $^{13}$C NMR (151 MHz, DMSO) δ 166.28, 163.67, 162.59, 155.30, 134.47, 133.22, 129.30, 112.64, 111.41, 56.07, 33.68, 31.09, 30.86, 28.83, 28.80, 28.78, 28.65, 28.50, 28.34, 21.90, 20.28, 16.63, 13.81.

Compound 25

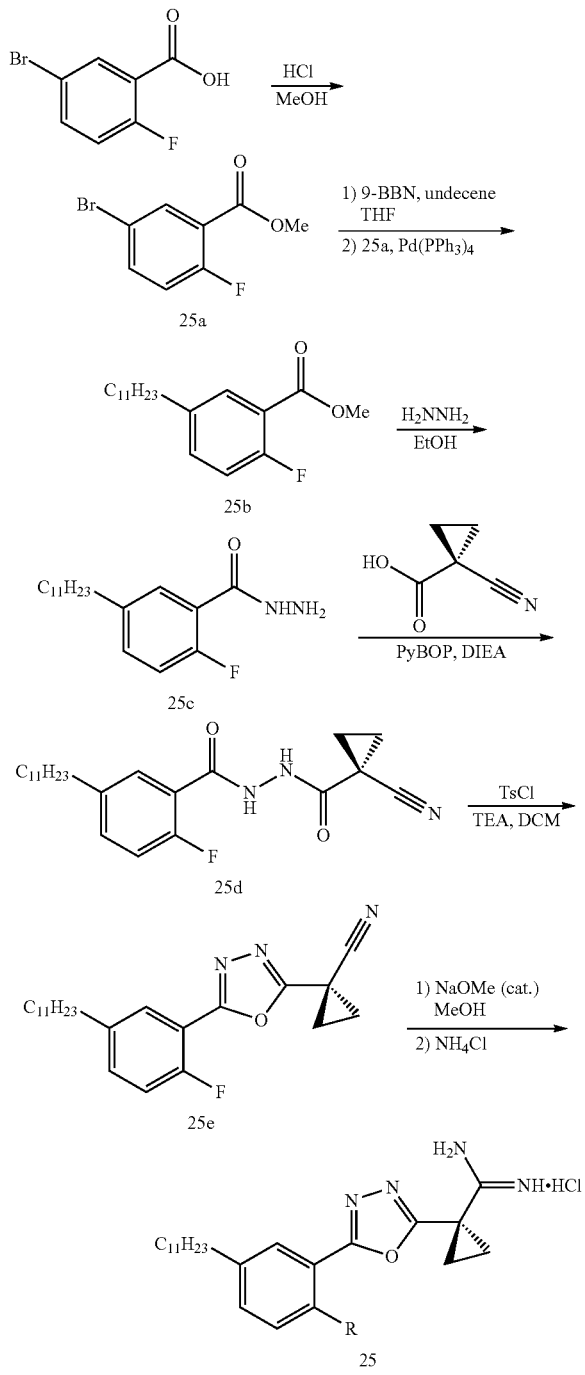

methyl 5-bromo-2-fluorobenzoate (25a)

General procedure O was use to convert 5-bromo-2-fluorobenzoic acid (700 mg, 3.2 mmol) to the title product as white solid (90% yield). $R_f$=0.32 (10% EtOAc in hexanes). $^1$H NMR (300 MHz, CDCl$_3$) δ 8.05 (dd, J=2.6, 6.3, 1H), 7.61 (ddd, J=2.6, 4.2, 8.8, 1H), 7.03 (dd, J=8.9, 10.0, 1H), 3.93 (s, J=0.8, 3H). $^{13}$C NMR (75 MHz, CDCl$_3$) δ 168.30, 161.06 (d, J=260.9), 137.37 (d, J=8.7), 134.86, 119.01 (d, J=24.0), 116.55 (d, J=3.6), 52.78.

methyl 2-fluoro-5-undecylbenzoate (25b)

General procedure C was used to couple 1-undecene (0.88 mL, 4.3 mmol) with 25a (668 mg, 2.87 mmol) to yield the title product as clear and colorless oil (61% yield). $R_f$=0.40 (10% EtOAc in hexanes). $^1$H NMR (300 MHz, CDCl$_3$) δ 7.72 (dd, J=2.3, 7.0, 1H), 7.34-7.27 (m, 1H), 7.03 (dd, J=8.5, 10.6, 1H), 3.92 (s, 3H), 2.52 (t, J=7.7, 2H), 1.71-1.46 (m, 2H), 1.41-1.14 (m, 16H), 0.87 (t, J=6.6, 3H). $^{13}$C NMR (75 MHz, CDCl$_3$) δ 168.88, 160.35 (d, J=256.9), 138.78 (d, J=3.5), 134.51 (d, J=8.6), 131.71, 116.78 (d, J=22.5), 52.41, 35.07, 32.05, 31.53, 29.76, 29.69, 29.57, 29.48, 29.28, 22.82, 14.26.

2-fluoro-5-undecylbenzohydrazide (25c)

General procedure P was used to convert 25b (310 mg, 1.01 mmol) to the title product as white solid (90% yield). $R_f$=0.52 (75% EtOAc in hexanes). $^1$H NMR (300 MHz, CDCl$_3$) δ 7.87 (dd, J=2.4, 7.4, 1H), 7.25 (ddd, J=2.4, 5.4, 9.6, 1H), 7.00 (dd, J=8.4, 11.7, 1H), 3.99 (s, 2H), 2.67 (t, J=7.7, 2H), 1.67-1.48 (m, 2H), 1.36-1.12 (m, 16H), 0.86 (t, J=6.7, 3H). $^{13}$C NMR (75 MHz, CDCl$_3$) δ 164.95, 159.00 (d, J=245.2), 139.81 (d, J=1.8), 133.57 (d, J=9.0), 131.37, 118.76 (d, J=13.0), 115.87 (d, J=24.7), 35.11, 32.02, 31.49, 29.73, 29.67, 29.55, 29.45, 29.27, 22.80, 14.24.

N'-(1-cyanocyclopropanecarbonyl)-2-fluoro-5-undecylbenzohydrazide (25d)

General procedure B was used to couple 25c (278 mg, 0.90 mmol) to 1-cyano-1-cyclopropanecarboxylic acid (100 mg, 0.90 mmol) to yield the title product as white solid (68% yield). $R_f$=0.70 (50% EtOAc in hexanes). $^1$H NMR (300 MHz, CDCl$_3$) δ 9.15 (s, 1H), 8.93 (d, J=15.1, 1H), 7.87 (dd, J=2.3, 7.3, 1H), 7.36-7.21 (m, 1H), 7.03 (dd, J=8.4, 11.7, 1H), 2.59 (t, J=7.7, 2H), 1.77 (dd, J=4.6, 8.3, 2H), 1.66-1.50 (m, 4H), 1.40-1.13 (m, 16H), 0.86 (t, J=6.6, 3H). $^{13}$C NMR (75 MHz, CDCl$_3$) δ 163.87, 161.53, 159.06 (d, J=247.0), 139.97, 134.47 (d, J=9.0), 131.59, 119.00, 117.58 (d, J=12.2), 115.97 (d, J=24.4), 35.03, 31.99, 31.42, 29.72, 29.64, 29.52, 29.42, 29.24, 22.77, 18.60, 14.22, 12.56.

1-(5-(2-fluoro-5-undecylphenyl)-1,3,4-oxadiazol-2-yl)cyclopropanecarbonitrile (25e)

General procedure Q was used to convert 25d (246 mg, 0.61 mmol) to the title product as white solid (65% yield). $R_f$=0.61 (25% EtOAc in hexanes). $^1$H NMR (300 MHz, CDCl$_3$) δ 7.78 (dd, J=2.3, 6.7, 1H), 7.31 (ddd, J=2.3, 4.8, 8.4, 1H), 7.11 (dd, J=8.5, 10.3, 1H), 2.61 (t, J=7.7, 2H), 1.95 (s, 4H), 1.66-1.51 (m, 2H), 1.36-1.17 (m, 16H), 0.84 (t, J=6.7, 3H). $^{13}$C NMR (75 MHz, CDCl3) δ 162.64, 162.47, 158.31 (d, J=256.4), 139.63 (d, J=3.5, OH), 133.95 (d, J=8.0, 1H), 116.75 (d, J=20.6, 1H), 111.08 (d, J=11.5, OH). $^{13}$C NMR (75 MHz, CDCl3) δ 134.00, 133.89, 129.61, 129.10, 127.03, 117.77, 116.89, 116.62, 111.16, 111.01, 34.99, 31.93, 31.44, 29.64, 29.59, 29.46, 29.37, 29.18, 22.71, 19.27, 14.16, 7.21.

1-(5-(2-fluoro-5-undecylphenyl)-1,3,4-oxadiazol-2-yl)cyclopropanecarboximidamide hydrochloride (25)

General procedure A was used to convert 25e (152 mg, 0.40 mmol) to the title product as yellow solid (38% yield). $^{13}$C NMR (151 MHz, DMSO) δ 166.48, 163.92, 160.60, 157.31 (d, J=253.5, 1H), 139.31, 133.90 (d, J=6.5, 1H), 128.61, 116.75 (d, J=21.3, 1H), 110.81 (d, J=11.6, 1H), 33.79, 31.09, 30.75, 28.82, 28.79, 28.62, 28.51, 28.34, 21.90, 20.05, 16.86, 13.80. LCMS: $t_R$=4.86; m/z=401.3. HRMS m/z calcd for $C_{23}H_{34}N_4OF$ (M+H), 401.2717. found 401.2712.

Compound 26

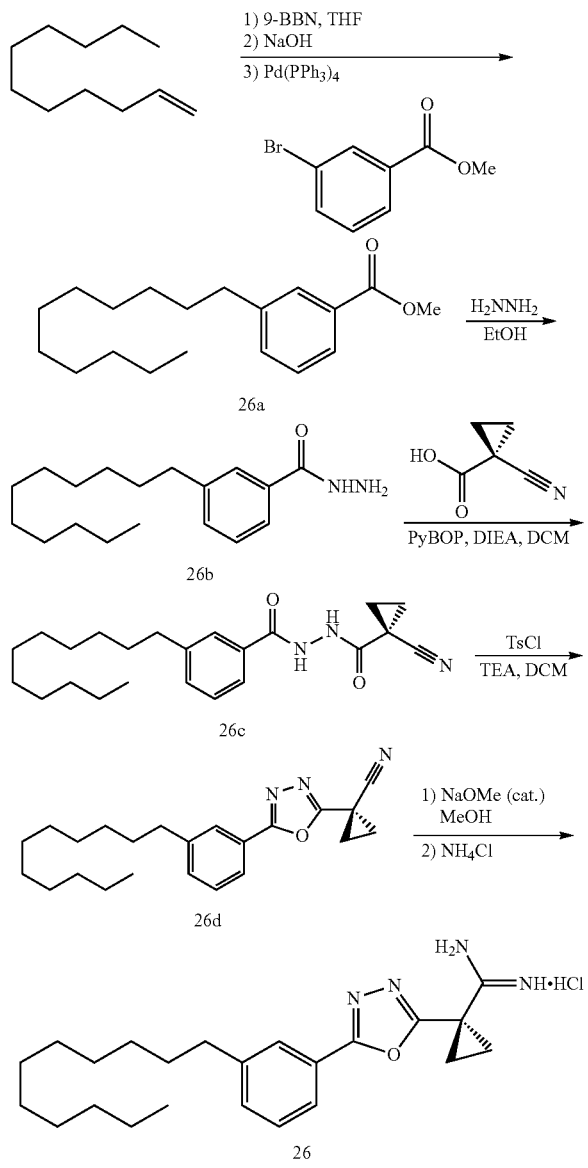

methyl 3-undecylbenzoate (26a)

General procedure C was used to couple 1-undecene (2.87 mL, 13.95 mmol) to methyl 3-bromobenzoate (2.0 g, 9.3 mmol) to yield the title product as clear and colorless oil (99% yield). $R_f$=0.51 (10% EtOAc in hexanes). $^1$H NMR (300 MHz, CDCl$_3$) δ 7.86 (m, 2H), 7.36 (m, 2H), 3.91 (s, 3H), 2.58 (t, J=7.8, 2H), 1.62 (m, 2H), 1.39-1.15 (m, 16H), 0.88 (t, J=6.6, 3H). $^{13}$C NMR (75 MHz, CDCl$_3$) δ 167.50, 143.38, 133.23, 130.19, 129.64, 128.39, 127.05, 52.18, 35.90, 32.05, 31.54, 29.77, 29.71, 29.62, 29.48, 29.39, 26.11, 22.84, 14.27.

3-undecylbenzohydrazide (26b)

General procedure P was used to convert 26a (2.7 g, 9.3 mmol) to the title product as white solid (33% yield). $R_f$=0.32 (75% EtOAc in hexanes). $^1$H NMR (600 MHz, CDCl3) δ 7.65 (s, 1H), 7.59 (s, 1H), 7.55-7.51 (m, 1H), 7.33-7.31 (m, 2H), 2.62 (t, J=7.8, 2H), 1.64-1.56 (m, 2H), 1.38-1.16 (m, 16H), 0.87 (t, J=7.1, 3H). $^{13}$C NMR (151 MHz, CDCl$_3$) δ 169.11, 143.83, 132.72, 132.14, 128.68, 127.16, 124.08, 35.95, 32.04, 31.48, 29.78, 29.75, 29.69, 29.60, 29.46, 29.40, 22.81, 14.25.

N'-(1-cyanocyclopropanecarbonyl)-3-undecylbenzohydrazide (26c)

General procedure B was used to couple 26b (200 mg, 0.69 mmol) to 1-cyano-1-cyclopropanecarboxylic acid (77 mg, 0.69 mmol) to yield the title product as white solid (72% yield). $R_f$=0.60 (50% EtOAc in hexanes). $^1$H NMR (600 MHz, CDCl$_3$) δ 7.87-7.79 (m, 2H), 7.44-7.31 (m, 2H), 2.66 (t, J=7.8, 2H), 1.95 (s, 4H), 1.70-1.56 (m, 2H), 1.38-1.17 (m, 16H), 0.86 (t, J=6.6, 3H). $^{13}$C NMR (151 MHz, CDCl$_3$) δ 165.65, 164.34, 143.92, 132.90, 131.08, 128.74, 127.60, 124.67, 118.90, 35.91, 32.06, 32.05, 32.04, 32.03, 31.46, 29.80, 29.79, 29.78, 29.77, 29.76, 29.75, 29.74, 29.71, 29.60, 29.47, 29.46, 29.43, 22.82, 22.82, 22.81, 18.61, 14.25, 12.66.

1-(5-(3-undecylphenyl)-1,3,4-oxadiazol-2-yl)cyclopropanecarbonitrile (26d)

General procedure Q was used to convert 26c (189 mg, 0.49 mmol) to the title product as white solid (95% yield). $R_f$=0.39 (25% EtOAc in hexanes). $^1$H NMR (300 MHz, CDCl$_3$) δ 7.83 (d, J=7.4, 2H), 7.37 (dt, J=7.3, 9.4, 1H), 2.66 (t, J=7.8, 1H), 1.95 (s, 2H), 1.70-1.56 (m, 1H), 1.38-1.17 (m, J=16.8, 9H), 0.86 (t, J=6.6, 2H). $^{13}$C NMR (75 MHz, CDCl$_3$) δ 165.72, 162.24, 144.22, 132.41, 129.09, 126.87, 124.36, 123.00, 117.93, 77.59, 77.16, 76.74, 35.83, 31.97, 31.45, 29.70, 29.63, 29.53, 29.40, 29.32, 22.75, 19.26, 14.20, 7.16.

1-(5-(3-undecylphenyl)-1,3,4-oxadiazol-2-yl)cyclopropanecarboximidamide hydrochloride (26)

General procedure A was used to convert 26d (171 mg, 0.47 mmol) to the title product. $^1$H NMR (600 MHz, DMSO) δ 9.37 (s, 4H), 7.80 (s, 2H), 7.58-7.38 (m, 2H), 2.66 (s, 2H), 2.01-1.79 (m, 4H), 1.66-1.50 (m, 2H), 1.34-1.14 (m, 16H), 0.84 (s, 3H). $^{13}$C NMR (151 MHz, DMSO) δ 166.53, 163.99, 163.69, 143.53, 131.94, 129.19, 126.01, 123.88, 122.87, 34.62, 31.06, 30.68, 28.80, 28.76, 28.61, 28.48, 28.38, 21.88, 20.10, 16.72, 13.78.

Compound 27

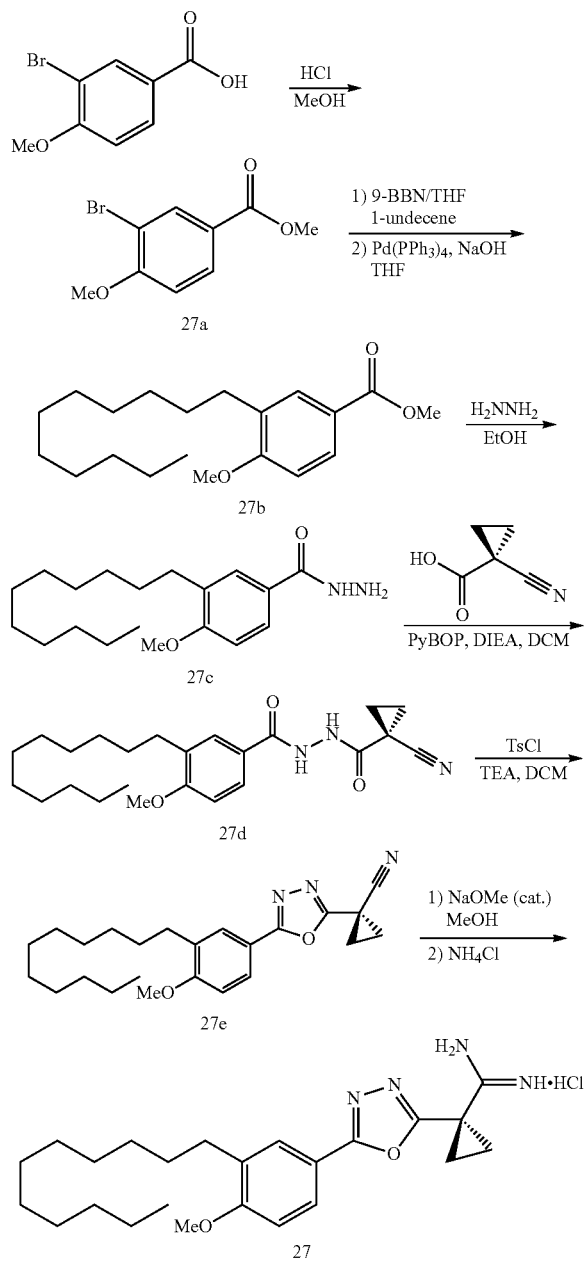

methyl 4-methoxy-3-undecylbenzoate (27b)

General procedure C was used to couple 1-undecene (0.42 mL, 2.02 mmol) and methyl 3-bromo-4-methoxybenzoate (330 mg, 1.35 mmol) to yield the title product as clear and colorless oil (56% yield). $R_f$=0.28 (10% EtOAc in hexanes). $^1$H NMR (600 MHz, CDCl$_3$) δ 7.88 (dd, J=2.2, 8.5, 1H), 7.81 (d, J=2.2, 1H), 6.83 (d, J=8.6, 1H), 3.88 (s, 3H), 3.86 (s, 3H), 2.60 (t, J=7.8, 2H), 1.61-1.50 (m, 2H), 1.35-1.20 (m, 16H), 0.88 (t, J=7.0, 3H). $^{13}$C NMR (151 MHz, CDCl$_3$) δ 167.32, 161.38, 131.43, 131.27, 129.37, 122.15, 109.62, 55.55, 51.90, 32.06, 30.15, 29.82, 29.78, 29.74, 29.72, 29.69, 29.65, 29.49, 22.83, 14.32, 14.25.

4-methoxy-3-undecylbenzohydrazide (27c)

General procedure P was used to convert 27b (240 mg, 0.75 mmol) to the title product as white solid (46% yield). $R_f$=0.27 (75% EtOAc in hexanes). $^1$H NMR (600 MHz, CDCl$_3$) δ 7.58 (dd, J=2.2, 8.5, 1H), 7.54 (d, J=2.1, 1H), 7.47 (s, 1H), 6.84 (d, J=8.5, 1H), 3.85 (s, 3H), 2.59 (t, J=7.8, 2H), 1.59-1.51 (m, 2H), 1.35-1.21 (m, 16H), 0.87 (t, J=7.0, 3H). $^{13}$C NMR (151 MHz, CDCl$_3$) δ 168.86, 160.53, 131.91, 128.61, 126.16, 124.49, 109.93, 55.58, 32.05, 30.26, 29.82, 29.78, 29.74, 29.70, 29.64, 29.48, 22.82, 14.25.

N'-(1-cyanocyclopropanecarbonyl)-4-methoxy-3-undecylbenzohydrazide (27d)

General procedure B was used to couple 27c (115 mg, 0.34 mmol) and 1-cyano-1-cyclopropanecarboxylic acid (38 mg, 0.34 mmol) to yield the title product as white solid (42% yield). $R_f$=0.52 (50% EtOAc in hexanes). $^1$H NMR (600 MHz, CDCl$_3$) δ 9.09 (s, 1H), 8.71 (s, 1H), 7.67 (dd, J=2.4, 8.5, 1H), 7.61 (d, J=2.3, 1H), 6.83 (d, J=8.6, 1H), 3.85 (s, 3H), 2.57 (t, J=7.8, 2H), 1.73 (dd, J=4.5, 8.4, 2H), 1.58 (dd, J=4.5, 8.3, 2H), 1.56-1.47 (m, 2H), 1.35-1.22 (m, 16H), 0.88 (t, J=7.0, 3H). $^{13}$C NMR (151 MHz, CDCl$_3$) δ 161.17, 132.07, 129.12, 126.95, 122.80, 118.96, 109.96, 55.62, 32.06, 30.24, 29.83, 29.79, 29.75, 29.75, 29.72, 29.64, 29.49, 29.49, 22.83, 18.54, 14.26, 12.66.

1-(5-(4-methoxy-3-undecylphenyl)-1,3,4-oxadiazol-2-yl)cyclopropanecarbontrile (27e)

General procedure Q was used to convert 27d (61 mg, 0.14 mmol) to the title product as white solid (86% yield). $R_f$=0.54 (25% EtOAc in hexanes). $^1$H NMR (600 MHz, CDCl$_3$) δ 7.84 (dd, J=2.3, 8.5, 1H), 7.79 (d, J=2.2, 1H), 6.91 (d, J=8.6, 1H), 3.88 (s, 3H), 2.66 (t, J=7.8, 2H), 1.94 (qd, J=2.1, 3.6, 4H), 1.63-1.53 (m, 2H), 1.39-1.19 (m, 16H), 0.87 (t, J=7.0, 3H). $^{13}$C NMR (151 MHz, CDCl$_3$) δ 165.87, 161.70, 160.72, 132.66, 128.50, 126.48, 118.13, 115.16, 110.48, 55.61, 32.02, 30.20, 29.79, 29.75, 29.72, 29.69, 29.61, 29.46, 22.80, 19.12, 14.23, 7.14.

1-(5-(4-methoxy-3-undecylphenyl)-1,3,4-oxadiazol-2-yl)cyclopropanecarboximidamide hydrochloride (27)

General procedure A was used to convert 27d (50 mg, 0.13 mmol) to the title product as yellow solid (55% yield). $^1$H NMR (600 MHz, DMSO) δ 9.24 (s, 4H), 7.54 (dd, J=2.4, 8.5, 2H), 7.18 (d, J=2.3, 1H), 3.79 (s, 3H), 2.67-2.32 (m, 2H), 1.96-1.63 (m, 4H), 1.60-0.97 (m, 18H), 0.78 (t, J=7.0, 3H). $^{13}$C NMR (151 MHz, DMSO) δ 166.40, 163.76, 162.93, 159.59, 131.05, 127.32, 125.94, 114.67, 110.94, 55.55, 30.88, 29.01, 28.75, 28.62, 28.58, 28.42, 28.29, 21.69, 19.91, 16.43, 13.60. LCMS: $t_R$=4.65; m/z=413.3. HRMS m/z calcd for $C_{24}H_{37}N_4O_2$ (M+H), 413.2917. found 413.2916.

Compound 28

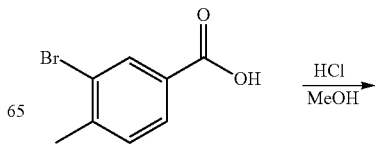

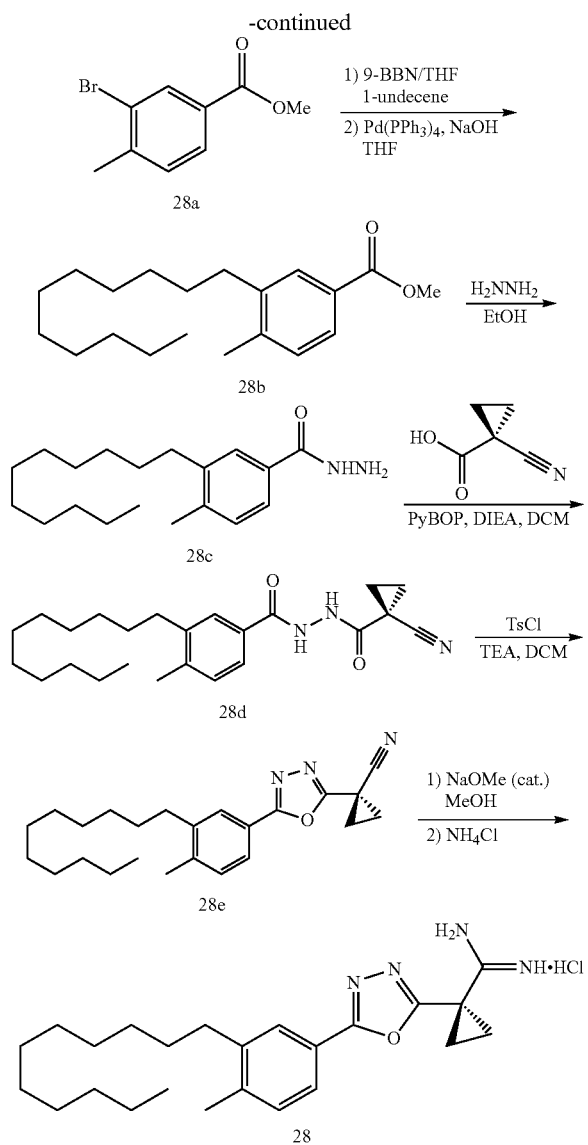

methyl 3-bromo-4-methylbenzoate (28a)

General procedure I was used to convert 3-bromo-4-methylbenzoic acid (500 mg, 2.3 mmol) to the title product as white solid (96% yield). $R_f$=0.49 (10% EtOAc in hexanes). $^1$H NMR (600 MHz, CDCl3) δ 8.19 (d, J=1.7, 1H), 7.86 (dd, J=1.7, 7.9, 1H), 7.28 (t, J=6.3, 1H), 3.90 (s, 3H), 2.44 (s, 3H). $^{13}$C NMR (151 MHz, CDCl$_3$) δ 165.98, 143.44, 133.57, 130.82, 129.57, 128.48, 124.91, 52.38, 23.33.

methyl 4-methyl-3-undecylbenzoate (28b)

General procedure C was used to couple 1-undecene (0.69 mL, 3.34 mmol) and 28a (516 mg, 2.23 mmol) to yield the title product as clear and colorless oil (57% yield). $R_f$=0.53 (10% EtOAc in hexanes). $^1$H NMR (300 MHz, CDCl$_3$) δ 7.80 (s, 1H), 7.75 (dd, J=1.6, 7.9, 1H), 7.18 (d, J=7.9, 1H), 3.89 (s, 3H), 2.70 (t, J=7.9, 2H), 2.35 (s, 3H), 1.74-1.47 (m, 2H), 1.46-1.13 (m, 16H), 0.88 (t, J=6.6, 3H). $^{13}$C NMR (75 MHz, CDCl$_3$) δ 167.58, 141.73, 141.48, 130.27, 130.00, 127.87, 127.10, 52.05, 33.35, 32.05, 30.30, 29.80, 29.68, 29.49, 22.83, 19.69, 14.27.

4-methyl-3-undecylbenzohydrazide (28c)

General procedure P was used to convert 28b (394 mg, 1.29 mmol) to the title product as white solid (73% yield). $R_f$=0.31 (75% EtOAc in hexanes). $^1$H NMR (300 MHz, CDCl$_3$) δ 7.77 (s, 1H), 7.55 (s, 1H), 7.45 (dd, J=1.1, 7.9, 1H), 7.16 (d, J=7.8, 1H), 2.59 (t, J=7.9, 2H), 2.32 (s, 3H), 1.62-1.47 (m, 2H), 1.38-1.20 (m, 16H), 0.87 (t, J=6.5, 3H). $^{13}$C NMR (75 MHz, CDCl$_3$) δ 169.05, 141.87, 140.47, 130.43, 130.24, 127.52, 124.10, 33.41, 32.02, 30.27, 29.78, 29.73, 29.65, 29.45, 22.80, 19.51, 14.24.

N'-(1-cyanocyclopropanecarbonyl)-4-methyl-3-undecylbenzohydrazide (28d)

General procedure B was used to couple 28c (289 mg, 0.95 mmol) and 1-cyano-1-cyclopropanecarboxylic acid (100 mg, 0.95 mmol) to yield the title product as white solid (67% yield). $R_f$=0.64 (50% EtOAc in hexanes). $^1$H NMR (300 MHz, CDCl$_3$) δ 9.38 (s, 1H), 9.20 (s, 1H), 7.61 (s, 1H), 7.53 (dd, J=1.5, 7.9, 1H), 7.12 (d, J=7.9, 1H), 2.54 (t, J=7.9, 2H), 2.30 (s, 3H), 1.66 (dd, J=4.6, 8.3, 2H), 1.50 (dd, J=4.6, 8.2, 4H), 1.39-1.17 (m, 16H), 0.87 (t, J=6.6, 3H). $^{13}$C NMR (75 MHz, CDCl$_3$) δ 165.90, 164.69, 141.86, 141.25, 130.39, 128.62, 128.02, 124.73, 118.87, 33.33, 31.99, 30.23, 29.82, 29.71, 29.61, 29.42, 22.76, 19.52, 18.50, 14.20, 12.60.

1-(5-(4-methyl-3-undecylphenyl)-1,3,4-oxadiazol-2-yl)cyclopropanecarbonitrile (28e)

General procedure Q was used to convert 28d (253 mg, 0.64 mmol) to the title product as white solid (95% yield). $R_f$=0.41 (25% EtOAc in hexanes). $^1$H NMR (300 MHz, CDCl$_3$) δ 7.78 (s, 1H), 7.72 (dd, J=1.6, 7.9, 1H), 7.23 (d, J=8.0, 1H), 2.56 (t, J=7.9, 2H), 2.35 (s, 3H), 1.94 (s, 4H), 1.68-1.47 (m, 2H), 1.47-1.15 (m, 16H), 0.86 (t, J=6.5, 3H). $^{13}$C NMR (75 MHz, CDCl$_3$) δ 165.84, 161.98, 142.38, 140.91, 130.89, 127.19, 124.35, 120.70, 118.00, 33.31, 31.96, 30.23, 29.67, 29.58, 29.39, 22.74, 19.60, 19.17, 14.18, 7.13.

1-(5-(4-methyl-3-undecylphenyl)-1,3,4-oxadiazol-2-yl)cyclopropanecarboximidamide hydrochloride (28)

General procedure A was used to convert 28e (229 mg, 0.60 mmol) to the title product as yellow solid (50% yield). $R_f$=0.23 (15% MeOH in CHCl$_3$). $^1$H NMR (600 MHz, DMSO) δ 9.34 (s, 4H), 7.84-7.57 (m, 2H), 7.34 (s, 1H), 2.67-2.56 (m, 2H), 2.21 (s, 3H), 1.97-1.76 (m, 4H), 1.60-1.40 (m, 2H), 1.40-1.09 (m, 16H), 0.83 (t, J=6.5, 3H). $^{13}$C NMR (151 MHz, DMSO) δ 166.59, 164.11, 163.52, 141.78, 140.22, 130.83, 126.38, 123.92, 120.62, 32.25, 31.13, 29.50, 28.86, 28.83, 28.71, 28.54, 21.94, 20.17, 18.93, 16.69, 13.83.

Compound 29

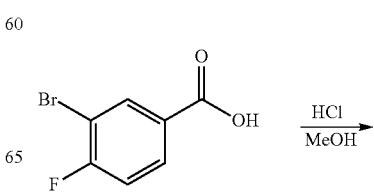

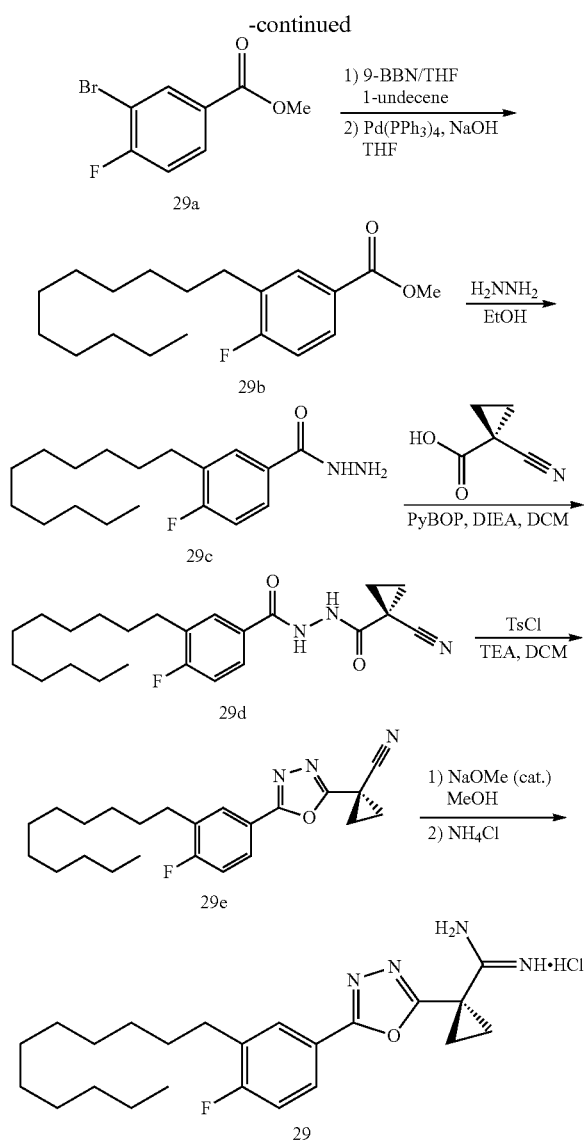

methyl 3-bromo-4-fluorobenzoate (29a)

General procedure O was used to convert 3-bromo-4-fluorobenzoic acid (500 mg, 2.28 mmol) to the title product as white solid (99% yield). $R_f$=0.36 (10% EtOAc in hexanes). $^1$H NMR (300 MHz, CDCl$_3$) δ 8.26 (dd, J=2.1, 6.7, 1H), 8.02-7.94 (m, 1H), 7.17 (t, J=8.4, 1H), 3.91 (s, 3H). $^{13}$C NMR (75 MHz, CDCl$_3$) δ 13C NMR (75 MHz, CDCl3) δ 165.13, 162.15 (d, J=254.4), 135.49, 130.90 (d, J=8.4), 127.79 (d, J=3.5), 116.61 (d, J=23.2), 109.41 (d, J=21.8), 52.64.

methyl 4-fluoro-3-undecylbenzoate (29b)

General procedure C was used to couple 1-undecene (0.53 mmol, 2.57 mmol) and 29a (527 mg, 2.26 mmol) to yield the title product as clear and colorless oil (26% yield). $R_f$=0.39 (10% EtOAc in hexanes). $^1$H NMR (600 MHz, CDCl$_3$) δ 7.90 (dd, J=2.0, 7.3, 1H), 7.86 (ddd, J=2.2, 4.9, 8.5, 1H), 7.04 (t, J=9.0, 1H), 3.91 (s, 3H), 2.65 (t, J=7.8, 2H), 1.67-1.55 (m, 2H), 1.36-1.18 (m, 16H), 0.88 (t, J=7.0, 3H). $^{13}$C NMR (151 MHz, CDCl$_3$) δ 166.61, 164.28 (d, J=252.5), 132.65 (d, J=6.8), 130.14 (d, J=17.2), 129.48 (d, J=9.4), 126.19 (d, J=3.2), 115.43 (d, J=23.59), 52.26, 32.06, 30.14, 30.13, 29.79, 29.76, 29.69, 29.55, 29.49, 29.44, 29.02, 29.01, 22.84, 14.26.

4-fluoro-3-undecylbenzohydrazide (29c)

General procedure P was used to convert 29b (179 mg, 0.58 mmol) to the title product as white solid (97% yield). $R_f$=0.42 (75% EtOAc in hexanes). $^1$H NMR (600 MHz, CDCl$_3$) δ 7.68-7.61 (m, 2H), 7.55 (ddd, J=2.3, 4.7, 8.4, 1H), 7.03 (t, J=8.9, 1H), 2.64 (t, J=7.8, 2H), 1.64-1.54 (m, 2H), 1.36-1.18 (m, 16H), 0.87 (t, J=7.0, 3H). $^{13}$C NMR (151 MHz, CDCl$_3$) δ 168.19, 163.45 (d, J=251.3), 130.55 (d, J=1.1), 130.00 (d, J=6.5), 128.62 (d, J=3.5), 126.31 (d, J=9.1), 115.66 (d, J=22.8), 32.04, 30.13, 30.12, 29.77, 29.74, 29.67, 29.53, 29.46, 29.44, 29.10, 29.08, 22.82, 14.25.

N'-(1-cyanocyclopropanecarbonyl)-4-fluoro-3-undecylbenzohydrazide (29d)

General procedure B was used to couple 29c (173 mg, 0.56 mmol) and 1-cyano-1-cyclopropanecarboxylic acid (62 mg, 0.56 mmol) to yield the title product as white solid (76% yield). $R_f$=0.68 (50% EtOAc in hexanes). $^1$H NMR (600 MHz, CDCl$_3$) δ 9.04 (s, 1H), 8.71 (s, 1H), 7.69 (dd, J=2.2, 7.0, 1H), 7.66-7.61 (m, 1H), 7.04 (t, J=8.9, 1H), 2.63 (t, J=7.8, 2H), 1.76 (dd, J=4.5, 8.3, 2H), 1.62 (q, J=4.5, 2H), 1.60-1.54 (m, 2H), 1.36-1.20 (m, 16H), 0.87 (t, J=7.0, 3H).

1-(5-(4-fluoro-3-undecylphenyl)-1,3,4-oxadiazol-2-yl)cyclopropanecarbonitrile (29e)

General procedure Q was used to convert 29d (171 mg, 0.43 mmol) to the title product as white solid (90% yield). $R_f$=0.44 (25% EtOAc in hexanes). $^1$H NMR (300 MHz, CDCl$_3$) δ 7.94-7.75 (m, 2H), 7.12 (t, J=8.9, 1H), 2.68 (t, J=7.6, 2H), 1.95 (s, 4H), 1.72-1.53 (m, 2H), 1.42-1.15 (m, 16H), 0.86 (t, J=6.4, 3H). $^{13}$C NMR (75 MHz, CDCl$_3$) δ 165.02, 163.52 (d, J=252.7), 162.33, 131.36 (d, J=17.3), 129.72 (d, J=6.3), 126.65 (d, J=9.0), 119.19 (d, J=3.4), 117.91, 116.35 (d, J=23.9), 162.33, 31.98, 30.10, 29.70, 29.63, 29.47, 29.41, 29.02, 22.76, 19.32, 14.21, 7.14.

1-(5-(4-fluoro-3-undecylphenyl)-1,3,4-oxadiazol-2-yl)cyclopropanecarboximidamide hydrochloride (29)

General procedure A was used to convert 29e (148 mg, 0.38 mmol) to the title product brown solid (30% yield). $^1$H NMR (600 MHz, DMSO) δ 9.32 (s, 4H), 8.01-7.77 (m, 2H), 7.46 (t, J=8.9, 1H), 2.66 (t, J=7.8, 2H), 1.95-1.81 (m, 4H), 1.61-1.53 (m, 2H), 1.35-1.15 (m, 16H), 0.90 (t, J=7.0, 3H). $^{13}$C NMR (151 MHz, DMSO) δ 166.49, 163.83, 163.32, 162.41 (d, J=250.2), 130.41 (d, J=16.5), 129.21 (d, J=5.9), 126.66 (d, J=10.0), 119.47 (d, J=2.4), 116.41 (d, J=24.6), 39.53, 31.13, 31.13, 29.44, 28.84, 28.81, 28.81, 28.78, 28.57, 28.54, 28.54, 28.45, 27.96, 21.95, 20.19, 16.71, 13.84.

Compound 30

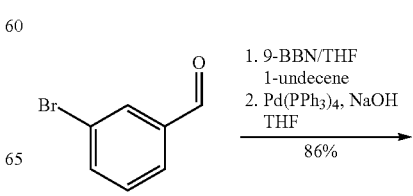

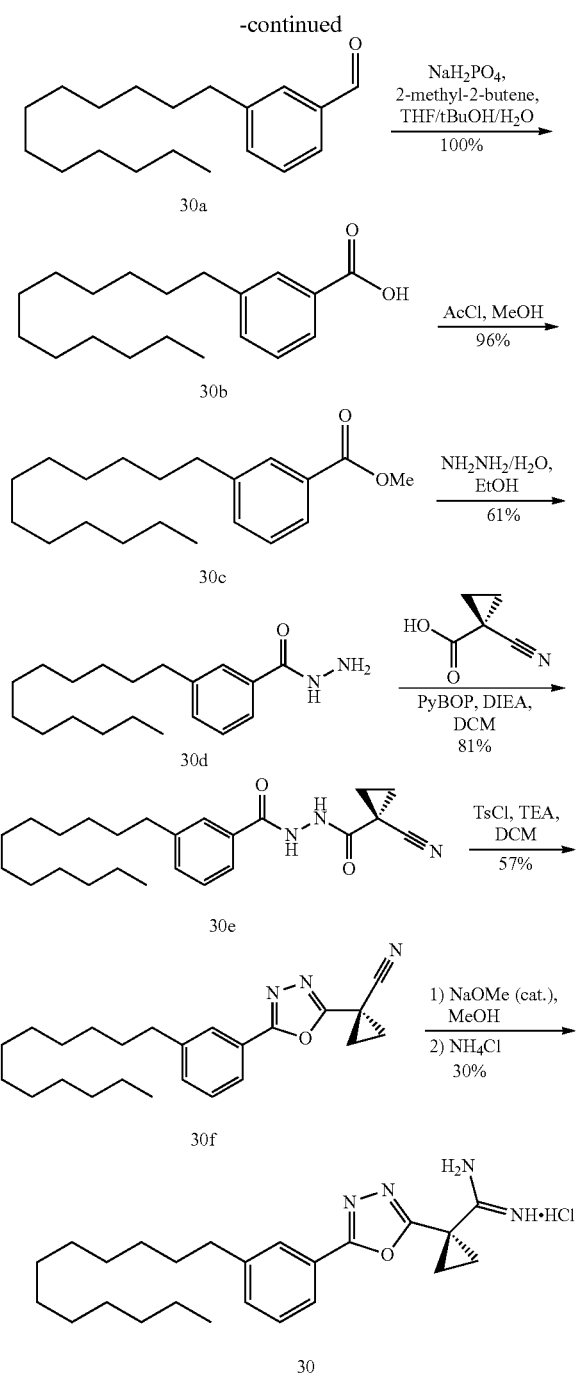

3-dodecylbenzaldehyde (30a)

General procedure C was used to convert 1-dodecene (38.6 mmol) (148 mg, 0.38 mmol) to the title product as an oil (58% yield). $^1$H NMR (300 MHz, Chloroform-d) δ 10.00 (s, 1H), 7.68 (dq, J=6.3, 1.8 Hz, 2H), 7.49-7.37 (m, 2H), 2.74-2.62 (m, 2H), 1.69-1.55 (m, 2H), 1.28 (m, 18H), 0.86 (d, J=7.5 Hz, 3H).

3-dodecylbenzoic acid (30b)

General procedure D was used to convert 30a (22.2 mmol) to the title product as white solid (100% yield).

methyl 3-dodecylbenzoate (30c)

15.5 mmol of acetyl chloride were added dropwise over 10 min to 12 mL ice-cold MeOH, and this solution was stirred 5 min. The solid 30b (5.2 mmol) was then added to the solution in one portion. This solution was heated to reflux with stirring for 2 h. At this point solid NaHCO$_3$ was added to neutralize the solution, which was then filtered through a finely fritted funnel. The solvent was evaporated from the filtrate, and 5.0 mmol of the product were isolated as an amber oil. $^1$H NMR (300 MHz, Chloroform-d) δ 7.89-7.80 (m, 2H), 7.35 (d, J=7.7 Hz, 2H), 3.91 (s, S3H), 2.64 (t, J=7.5 Hz, 2H), 1.32-1.14 (m, 20H), 0.88 (t, J=6.6 Hz, 3H).

3-dodecylbenzohydrazide (30d)

General procedure P was used to convert 30c (5 mmol) to the title product as white solid (58% yield). $^1$H NMR (300 MHz, DMSO-d6) δ 9.69 (bs, 1H), 7.66-7.59 (m, 2H), 7.33-7.26 (m, 2H), 2.52-2.45 (m, 2H), 1.97 (s, 2H), 1.25-1.10 (m, 20H), 0.82 (t, J=6.8 Hz, 3H).

N'-(1-cyanocyclopropanecarbonyl)-3-dodecylbenzohydrazide (30e)

General procedure A was used to couple 2.86 mmol of 30d to 2.86 mmol 1-cyanopropanecarboxylic acid. 1.6 mmol of the product were isolated (56% yield). $^1$H NMR (300 MHz, Chloroform-d) δ 8.88-8.78 (bs, 1H), 8.34-8.30 (s, 1H), 7.65-7.57 (m, 2H), 7.42-7.35 (m, 2H), 2.71-2.59 (m, 2H), 1.85-1.74 (m, 2H), 1.29-1.22 (m, 22H), 0.87 (t, J=7.0 Hz, 3H).

1-(5-(3-dodecylphenyl)-1,3,4-oxadiazol-2-yl)cyclopropanecarbonitrile (30f)

General procedure Q was used to convert 30e (1.6 mmol) to the title product as an oil. $^1$H NMR (300 MHz, Chloroform-d) δ 7.90-7.80 (m, 2H), 7.48-7.32 (m, 2H), 2.68 (t, J=7.5 Hz, 2H), 1.34-1.22 (m, 24H), 0.87 (t, J=6.6 Hz, 3H). $^{13}$C NMR (600 MHz, Chloroform-d) δ 162.21, 129.06, 126.88, 123.00, 119.46, 116.94, 31.93, 29.67; 29.59, 29.36, 19.21, 14.13.

1-(5-(3-dodecylphenyl)-1,3,4-oxadiazol-2-yl)cyclopropanecarboximidamide hydrochloride (30)

General procedure A was used to produce 30. $^1$H NMR (600 MHz, DMSO-d6) δ 9.31 (s, 2H), 9.16 (s, 2H), 7.82 (dd, J=6.8, 1.4 Hz, 2H), 7.55-7.46 (m, 2H), 2.69 (t, J=3 Hz, 2H), 1.64-1.58 (m, 2H), 1.32-1.2 (m, 22H), 0.87 (t, J=7.0 Hz, 3H). $^{13}$C NMR (600 MHz, DMSO-d6) δ 166.45, 164.20, 163.98, 143.80, 64.89, 40.06, 34.80, 31.26, 30.86, 28.99, 28.98, 28.97, 28.96, 28.88, 28.67, 28.57, 22.07, 20.43, 16.73, 15.15, 13.93.

Compound 31

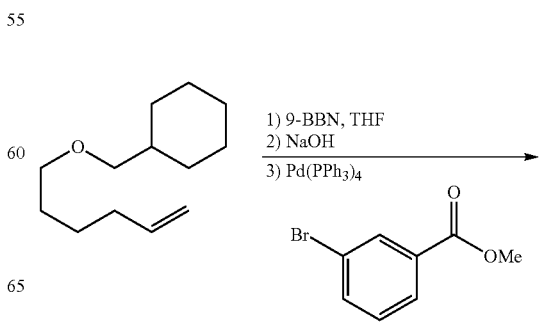

-continued

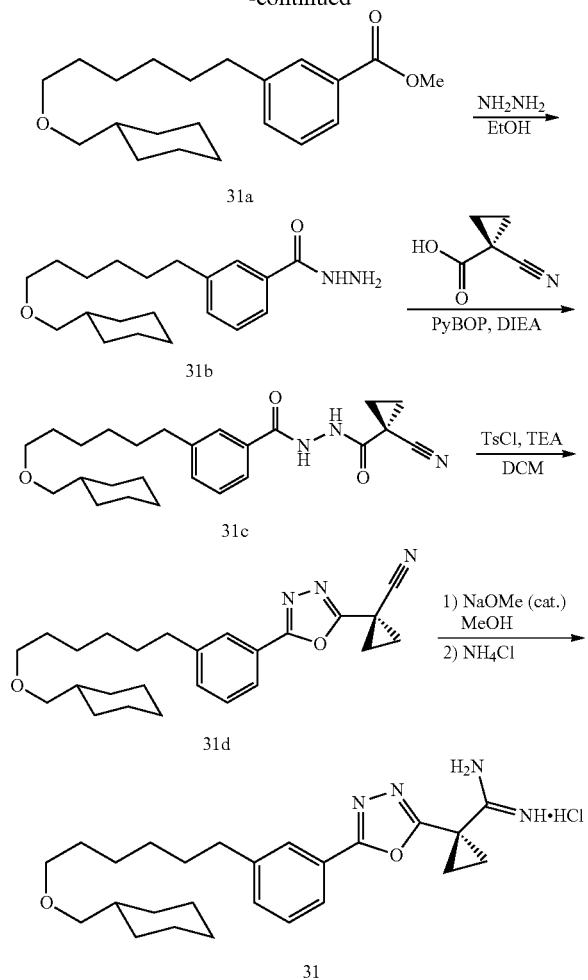

methyl 3-(6-(cyclohexylmethoxy)hexyl)benzoate (31a)

General procedure C was used to couple intermediate (0.38 g, 1.95 mmol) to 3-bromobenzoate (0.28 g; 1.36 mmol) to yield the title product as clear and colorless oil (94% yield). $R_f$=0.31 (10% EtOAc in hexanes). $^1$H NMR (300 MHz, CDCl$_3$) δ 7.88-7.81 (m, 2H), 7.38-7.31 (m, 2H), 3.91 (s, 3H), 3.36 (t, J=6.5, 2H), 3.18 (d, J=6.6, 2H), 2.57 (t, J=7.7, 2H), 1.86-1.04 (m, 17H), 0.99-0.76 (m, 2H). $^{13}$C NMR (75 MHz, CDCl$_3$) δ 167.45, 143.23, 133.21, 130.18, 129.61, 128.39, 127.07, 76.97, 71.12, 52.18, 38.16, 35.80, 31.44, 30.29, 29.75, 29.18, 26.80, 26.15, 26.02.

3-(6-(cyclohexylmethoxy)hexyl)benzohydrazide (31b)

General procedure P was used to convert 31a (405 mg, 1.22 mmol) to the title product as white solid (77% yield). $R_f$=0.18 (75% EtOAc in hexanes). $^1$H NMR (300 MHz, CDCl$_3$) δ 7.63 (s, 1H), 7.60-7.49 (m, 2H), 7.37-7.28 (m, 2H), 3.36 (t, J=6.5, 2H), 3.18 (d, J=6.6, 2H), 2.56 (t, J=7.7, 2H), 1.84-1.06 (m, 17H), 1.00-0.78 (m, 2H). $^{13}$C NMR (75 MHz, CDCl$_3$) δ 169.08, 143.68, 132.71, 132.14, 128.70, 127.14, 124.12, 76.94, 71.06, 38.12, 35.81, 31.38, 30.27, 29.71, 29.13, 26.77, 26.09, 25.99.

N'-(1-cyanocyclopropanecarbonyl)-3-(6-(cyclohexylmethoxy)hexyl)benzohydrazide (31c)

General procedure B was used to couple 31b (310 mg, 0.93 mmol) and 1-cyano-1-cyclopropanecarboxylic acid (104 mg, 0.93 mmol) to yield the title product as white solid (77% yield). $R_f$=0.57 (50% EtOAc in hexanes). $^1$H NMR (300 MHz, CDCl$_3$) δ 9.17 (s, 1H), 8.92 (s, 1H), 7.71-7.55 (m, 2H), 7.39-7.28 (m, 2H), 3.36 (t, J=6.5, 2H), 3.18 (d, J=6.6, 2H), 2.55 (t, J=7.7, 2H), 1.83-1.06 (m, 21H), 0.98-0.80 (m, 2H). $^{13}$C NMR (75 MHz, CDCl$_3$) δ 165.73, 164.39, 143.75, 132.88, 131.08, 128.76, 127.58, 124.73, 118.91, 76.93, 71.04, 38.11, 35.76, 31.34, 30.27, 29.69, 29.13, 26.77, 26.06, 25.99, 18.61, 12.63.

1-(5-(3-(6-(cyclohexylmethoxy)hexyl)phenyl)-1,3,4-oxadiazol-2-yl)cyclopropanecarbonitrile (31d)

General procedure Q was used to convert 31c (303 mg, 0.71 mmol) to the title product as white solid (52% yield). $R_f$=0.42 (25% EtOAc in hexanes). $^1$H NMR (300 MHz, CDCl$_3$) δ 7.84-7.76 (m, 2H), 7.43-7.29 (m, 2H), 3.34 (t, J=6.5, 2H), 3.15 (d, J=6.6, 2H), 2.61 (t, J=7.7, 2H), 1.94 (s, 4H), 1.81-1.01 (m, 17H), 0.97-0.76 (m, 2H). $^{13}$C NMR (75 MHz, CDCl$_3$) δ 165.64, 162.21, 144.04, 132.35, 129.06, 126.80, 124.34, 122.97, 117.88, 76.82, 70.95, 38.03, 35.69, 31.31, 30.15, 29.64, 29.07, 26.66, 26.03, 25.89, 19.20, 7.11.

1-(5-(3-(6-(cyclohexylmethoxy)hexyl)phenyl)-1,3,4-oxadiazol-2-yl)cyclopropanecarboximidamide hydrochloride (31)

General procedure A was used to convert 31d (151 mg, 0.37 mmol) to the title product as white solid (50% yield). $^1$H NMR (600 MHz, DMSO) δ 9.34 (s, 4H), 7.89-7.68 (m, 2H), 7.59-7.33 (m, 2H), 3.20 (t, J=6.5, 2H), 3.02 (d, J=6.6, 2H), 2.55 (t, J=7.7, 2H), 2.04-0.98 (m, 21H), 0.96-0.75 (m, 2H). $^{13}$C NMR (151 MHz, DMSO) δ 166.39, 163.86, 163.56, 143.37, 131.86, 129.11, 125.91, 123.79, 122.75, 75.44, 69.78, 37.16, 34.50, 30.54, 29.25, 28.80, 28.08, 25.86, 25.20, 25.05, 19.98, 16.67.

Compound 32

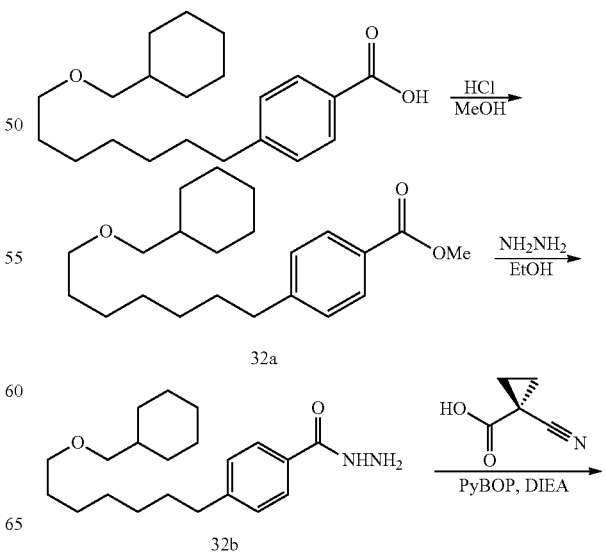

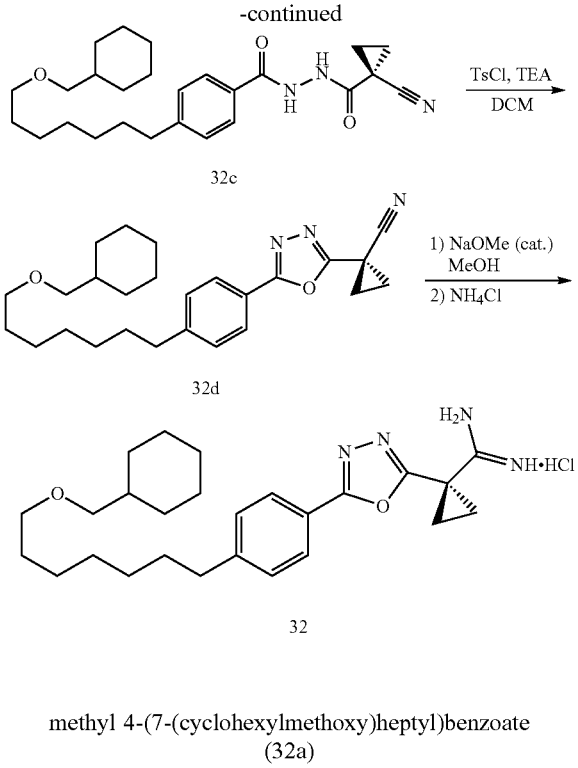

methyl 4-(7-(cyclohexylmethoxy)heptyl)benzoate (32a)

General procedure O was used to convert 4-(7-(cyclohexylmethoxy)heptyl)benzoic acid (263 mg, 0.79 mmol) to the title product as clear and colorless oil (66% yield). $R_f$=0.43 (10% EtOAc in hexanes). $^1$H NMR (300 MHz, CDCl$_3$) δ 7.94 (d, J=7.7, 2H), 7.23 (d, J=7.9, 2H), 3.83 (s, 3H), 3.36 (t, J=6.6, 2H), 3.18 (d, J=6.6, 2H), 2.57 (t; J=7.7, 2H), 1.90-1.05 (m, 19H), 1.01-0.78 (m, 2H). $^{13}$C NMR (75 MHz, CDCl$_3$) δ 167.36, 148.58, 129.74, 128.55, 127.70, 76.98, 71.17, 52.08, 38.15, 36.09, 31.19, 30.29, 29.81, 29.40, 29.30, 26.79, 26.20, 26.01.

4-(7-(cyclohexylmethoxy)heptyl)benzohydrazide (32b)

General procedure P was used to convert 32a (180 mg, 0.52 mmol) to the title product as white solid (62% yield). $R_f$=0.21 (75% EtOAc in hexanes). $^1$H NMR (300 MHz, CDCl3) δ 8.06 (s, 1H), 7.66 (d, J=8.1, 2H), 7.19 (d, J=8.1, 2H), 3.34 (t, J=6.6, 2H), 3.16 (d, J=6.6, 2H), 2.55 (t, J=7.7, 2H), 1.81-1.04 (m, 19H), 0.98-0.73 (m, 2H). $^{13}$C NMR (75 MHz, CDCl$_3$) δ 168.75, 147.26, 129.99, 128.71, 126.99, 76.89, 71.09, 38.05, 35.87, 31.16, 30.21, 29.73, 29.34, 29.21, 26.71, 26.14, 25.93.

N'-(1-cyanocyclopropanecarbonyl)-4-(7-(cyclohexylmethoxy)heptyl)benzohydrazide (32c)

General procedure B was used to convert 32b (111 mg, 0.32 mmol) to the title product as white solid (46% yield). $R_f$=0.66 (50% EtOAc in hexanes). $^1$H NMR (300 MHz, CDCl$_3$) δ 9.26 (s, 1H), 9.11 (s, 1H), 7.73 (d, J=8.2, 2H), 7.20 (d, J=8.2, 2H), 3.36 (t, J=6.6, 2H), 3.18 (d, J=6.6, 2H), 2.54 (t, J=7.7, 2H), 1.85-1.04 (m, 23H), 1.01-0.79 (m, 2H). $^{13}$C NMR (75 MHz, CDCl$_3$) δ 165.61, 164.59, 148.24, 128.83, 128.44, 127.58, 118.87, 76.94, 71.14, 38.11, 35.98, 31.18, 30.26, 29.79, 29.39, 29.29, 26.76, 26.20, 25.98, 18.58, 12.62.

1-(5-(4-(7-(cyclohexylmethoxy)heptyl)phenyl)-1,3,4-oxadiazol-2-yl)cyclopropanecarbonitrile (32d)

General procedure Q was used to convert 32c (71 mg, 0.16 mmol) to the title product as white solid (94% yield). $R_f$=0.32 (25% EtOAc in hexanes). $^1$H NMR (300 MHz, CDCl$_3$) δ 7.93 (d, J=8.3, 2H), 7.30 (d, J=8.2, 2H), 3.36 (t, J=6.6, 2H), 3.17 (d, J=6.6, 2H), 2.59 (t, J=7.7, 2H), 1.94 (s, 4H), 1.85-1.02 (m, 19H), 1.00-0.80 (m, 2H). $^{13}$C NMR (75 MHz, CDCl$_3$) δ 165.72, 162.10, 147.80, 129.27, 127.02, 120.57, 117.98, 76.93, 71.11, 38.11, 36.05, 31.12, 30.25, 29.77, 29.35, 29.24, 26.74, 26.17, 25.96, 19.24, 7.17.

1-(5-(4-(7-(cyclohexylmethoxy)heptyl)phenyl)-1,3,4-oxadiazol-2-yl)cyclopropanecarboximidamide hydrochloride (32)

General procedure A was used to convert 32d (63 mg, 0.15 mmol) to the title product as yellow solid (48% yield). $^1$H NMR (600 MHz, DMSO) δ 9.27 (s, 4H), 7.82 (d, J=8.2, 2H), 7.34 (d, J=8.2, 2H), 3.23 (t, J=6.6, 2H), 3.12 (d, J=6.6, 2H), 2.68-2.30 (m, 2H), 2.00-0.92 (m, 23H), 0.92-0.70 (m, 2H). $^{13}$C NMR (151 MHz, DMSO) δ 166.22, 163.73, 163.33, 146.56, 128.94, 126.20, 120.15, 75.33, 69.69, 37.07, 34.62, 30.13, 29.16, 28.72, 28.15, 25.76, 25.18, 24.96, 19.90, 16.56.

Compound 33

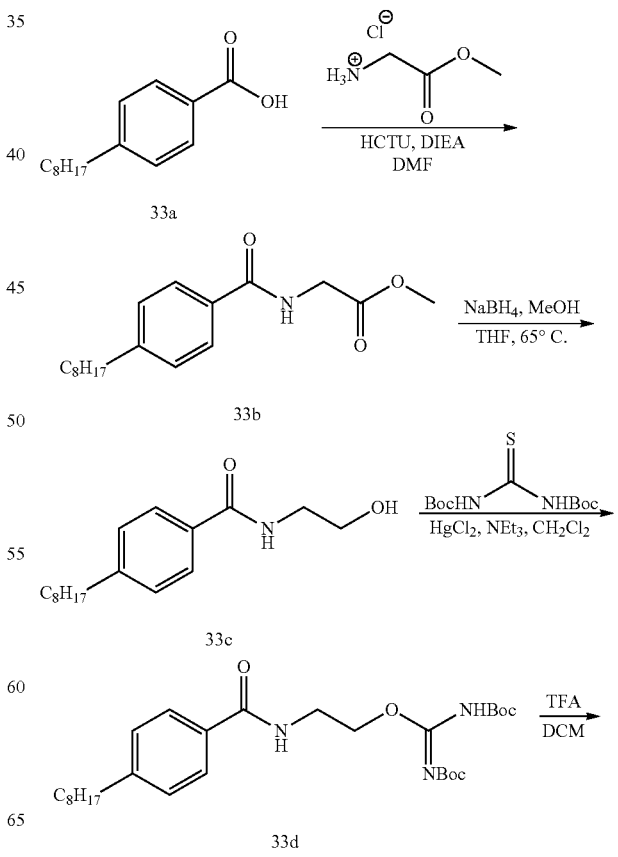

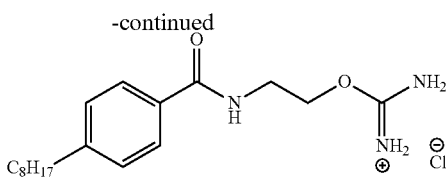

methyl 2-(4-octylbenzamido)acetate (33b)

General procedure Q was used to convert 33a (250 mg, 1.067 mmol) to the title product (93% yield). $^1$H NMR (500 MHz, CDCl$_3$) δ 7.65 (d, J=8.2 Hz, 2H), 7.16 (d, J=8.2 Hz, 2H), 4.16 (d, J=5.1 Hz, 2H), 3.71 (s, 3H), 2.62-2.50 (m, 2H), 1.54 (tt, J=9.1, 6.5 Hz, 2H), 1.33-1.08 (m, 10H), 0.80 (d, J=7.0 Hz, 3H); $^{13}$C NMR (101 MHz, CDCl$_3$) δ 170.6, 167.7, 147.0, 130.9, 128.4, 127.2, 52.2, 41.6, 35.8, 31.8, 31.2, 29.4, 29.2, 29.2, 22.6, 14.1.

N'-(2-hydroxyethyl)-4-octylbenzamide (33c)

Sodium borohydride (0.245 g, 6.47 mmol) was added to 33b (0.395 g, 1.293 mmol) dissolved in THF (20 mL) and the suspension was stirred at 65° C. for 15 min. Methanol (10 mL, 247 mmol) was added and the reaction went clear over 20 min. The solvent was removed under vacuum and the crude product was dissolved in ethyl acetate, washed with water, brine, and dried over sodium sulfate. Purification by silica gel column chromatography (50/50 EtOAc/Hexanes) yielded the final product (185 mg, 58% yield). $^1$H NMR (500 MHz, CDCl$_3$) δ 7.67 (d, J=8.2 Hz, 1H), 7.17 (d, J=8.0 Hz, 2H), 6.98-6.82 (m, 1H), 3.77 (t, J=5.0 Hz, 2H), 3.57 (q, J=5.2 Hz, 2H), 3.27 (s, 1H), 2.60 (t, J=7.8 Hz, 2H), 1.57 (q, J=7.5, 7.0 Hz, 2H), 1.39-1.08 (m, 10H), 0.86 (t, J=6.8 Hz, 2H); $^{13}$C NMR (126 MHz, CDCl$_3$) δ 168.8, 147.2, 131.5, 128.7, 127.1, 62.3, 42.9, 35.9, 31.9, 31.3, 29.5, 29.3, 29.3, 22.7, 14.2, 14.2.

Compound (33d)

Triethylamine (0.078 mL, 0.559 mmol) was added to a solution of N,N'-bisbocthiourea (49.8 mg, 0.180 mmol) and 33c (50 mg, 0.180 mmol) in dichloromethane (10 mL). The reaction mixture was cooled to 0° C., mercuric chloride (53.8 mg, 0.198 mmol) was added, and the reaction stirred for 1 h. The reaction was then warmed to r.t. and stirred overnight. TLC analysis showed the disappearance of the bisbocthiourea and the formation of a new spot. The reaction mixture was filtered over a pad of celite and the filtrate was transferred to a separatory funnel. The organic layer was washed with water, brine, and dried over sodium sulfate. Purification was performed via preparative TLC (35/65 EtOAc/hexanes) to yield the product as a clear oil (28%, 26 mg). $^1$H NMR (500 MHz, CDCl$_3$) δ 10.45 (s, 1H), 7.75 (d, J=8.2 Hz, 1H), 7.40-7.29 (m, 1H), 7.13 (d, J=8.2 Hz, 1H), 4.44 (t, J=5.1 Hz, 2H), 3.78 (q, J=5.2 Hz, 2H), 2.56 (t, J=7.7 Hz, 2H), 1.59-1.49 (m, 2H), 1.49-1.40 (m, 18H), 1.29-1.13 (m, 10H), 0.80 (t, J=6.9 Hz, 3H); $^{13}$C NMR (126 MHz, CDCl$_3$) δ 167.0, 159.2, 146.7, 131.5, 128.4, 127.3, 67.8, 38.5, 35.8, 31.8, 31.2, 29.4, 29.2, 28.0, 28.0, 22.6, 14.1.

2-(2-(4-octylbenzamido)ethyl)isouronium chloride (33)

General procedure I was used to convert 33d to the title product as white solid (65% yield). $^1$H NMR (500 MHz, CD$_3$OD) δ 8.01 (d, J=8.1 Hz, 2H), 7.53 (d, J=8.2 Hz, 2H), 5.15 (t, J=9.8 Hz, 2H), 4.30 (t, J=9.8 Hz, 2H), 2.84-2.74 (m, 2H), 1.75-1.59 (m, 2H), 1.46-1.22 (m, 10H), 0.91 (t, J=7.0 Hz, 3H); $^{13}$C NMR (126 MHz, CD$_3$OD) δ 174.0, 154.6, 131.0, 130.9, 128.3, 119.2, 74.3, 47.3, 37.1, 33.0, 32.1, 30.5, 30.3, 30.3, 23.7, 14.4.

Compound 34

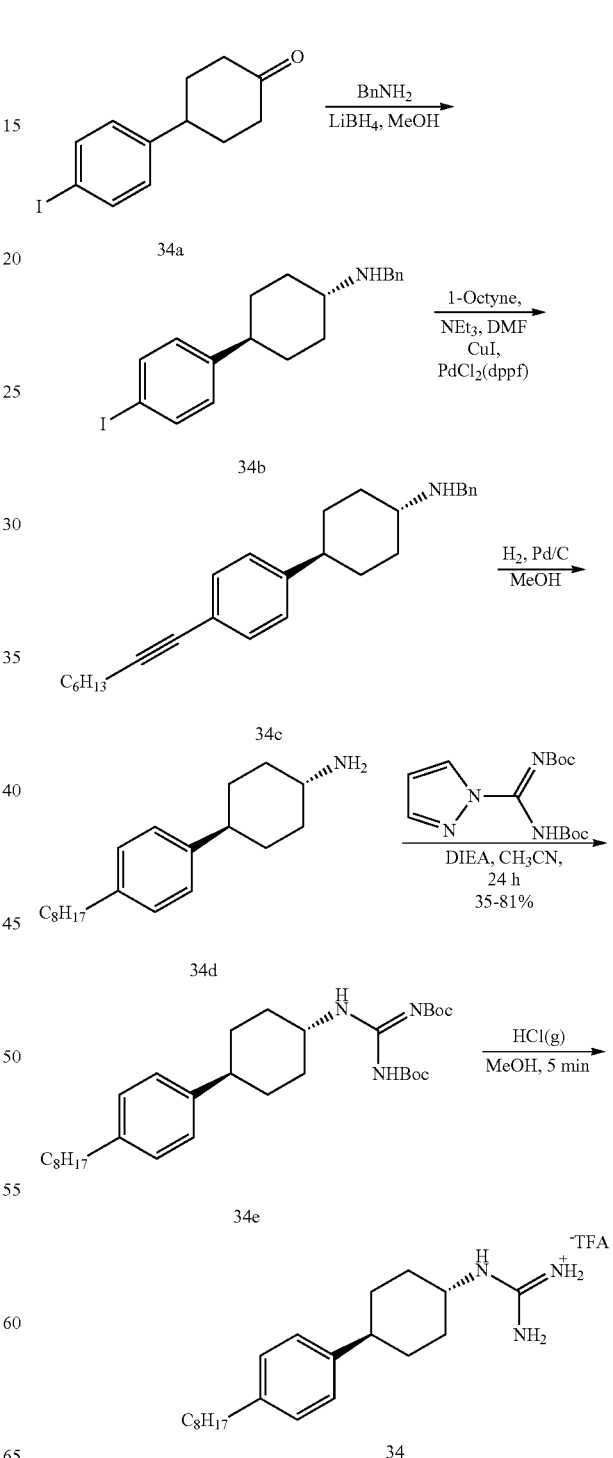

N-benzyl-4-(4-iodophenyl)cyclohexanamine (34b)

34a (250 mg, 0.833 mmol) and benzylamine (0.455 mL, 4.16 mmol) were stirred at r.t. together in methanol (10 mL) for 1 h. The solution was chilled to −78° C. and lithium borohydride (2.5 M solution in THF, 0.458 mL, 0.916 mmol) was added dropwise. After 2 hours, the reaction was warmed to r.t. and stirred for 12 h. The reaction was quenched with saturated $NaHCO_3$ and extracted 3× with EtOAc, washed with saturated $NaHCO_3$, brine, and dried over $Na_2SO_4$. The residue was purified by column chromatography on silica gel (70/30 hexanes/EtOAc) to give the title compound as a colorless oil (295 mg, 91% yield). $^1H$ NMR (500 MHz, $CDCl_3$) δ 7.61 (d, J=8.1 Hz, 2H), 7.50-7.32 (m, 4H), 7.32-7.22 (m, 1H), 6.96 (d, J=8.1 Hz, 2H), 3.88 (s, 2H), 2.65-2.54 (m, 1H), 2.54-2.39 (m, 1H), 2.16-2.06 (m, 2H), 1.97-1.84 (m, 2H), 1.53-1.39 (m, 2H), 1.37-1.22 (m, 2H); $^{13}C$ NMR (126 MHz, $CDCl_3$) δ 146.9, 140.9, 137.5, 129.1, 128.6, 128.2, 127.1, 91.1, 56.0, 51.3, 43.8, 33.8, 33.0.

N-benzyl-4-(4-(oct-1-yn-1-yl)phenyl)cyclohexanamine (34c)

General procedure M was used to convert 34b (550 mg, 1.406 mmol) to the title product as a colorless oil (368 mg, 70% yield). $^1H$ NMR (500 MHz, $CDCl_3$) δ 7.46-7.20 (m, 7H), 7.11 (d, J=7.8 Hz, 2H), 3.85 (s, 2H), 2.61-2.43 (m, 2H), 2.38 (t, J=7.1 Hz, 2H), 2.15-2.02 (m, 2H), 1.97-1.84 (m, 2H), 1.66-1.54 (m, 2H), 1.52-1.38 (m, 4H), 1.37-1.17 (m, 6H), 0.98-0.80 (m, 3H); $^{13}C$ NMR (126 MHz, CDCl3) δ 146.6, 140.9, 131.6, 128.5, 128.2, 127.0, 126.8, 121.7, 89.8, 80.6, 56.1, 51.3, 44.1, 33.8, 32.9, 31.5, 28.9, 28.7, 22.7, 19.5, 14.2.

(1S,4S)-4-(4-octylphenyl)cyclohexanamine (34d)

Pearlman's catalyst (27.7 mg, 0.099 mmol) was added to a two neck flask containing 34c (368 mg, 0.985 mmol) dissolved in methanol (10 mL). The reaction was stirred at r.t. for 12 h under hydrogen. The reaction was filtered over a pad of celite and the filtrate collected. The organic solvent was removed under reduced pressure and washed with diethyl ether to yield the title compound as a colorless oil (198 mg, 70% yield). $^1H$ NMR (400 MHz, $CDCl_3$) δ 7.10 (s, 4H), 2.79-2.64 (m, 1H), 2.59-2.51 (m, 2H), 2.44 (tt, J=12.1, 3.5 Hz, 1H), 2.01-1.83 (m, 4H), 1.65-1.43 (m, 4H), 1.40-1.15 (m, 10H), 0.87 (t, J=6.6 Hz, 3H); $^{13}C$ NMR (126 MHz, $CDCl_3$) δ 144.3, 140.6, 128.4, 128.4, 126.7, 126.7, 50.5, 43.3, 37.2, 36.1, 35.6, 33.3, 32.6, 32.0, 31.6, 29.6, 29.5, 29.4, 22.8, 14.2; HRMS (ESI+) m/z calcd for $C_{20}H_{33}N$ $[M+H]^+$ 287.2613. found 288.2691.

Compound (34e)

This compound was synthesized using general procedure K (22% yield). $^1H$ NMR (500 MHz, $CDCl_3$) δ 11.57 (s, 1H), 8.26 (d, J=8.3 Hz, 1H), 7.10 (s, 4H), 4.13-4.02 (m, 1H), 2.60-2.52 (m, 2H), 2.45 (tt, J=12.1, 3.4 Hz, 1H), 2.21-2.13 (m, 2H), 1.94-1.86 (m, 2H), 1.67-1.53 (m, 6H), 1.52-1.48 (m, 18H), 1.41-1.21 (m, 10H), 0.88 (t, J=6.5 Hz, 3H); $^{13}C$ NMR (126 MHz, $CDCl_3$) δ 164.0, 155.6, 153.4, 143.9, 140.8, 128.6, 128.4, 126.7, 83.0, 79.2, 48.9, 43.2, 35.6, 33.5, 33.4, 32.9, 32.0, 31.6, 29.6, 29.5, 29.3, 28.4, 28.2, 22.8, 14.2.

1-((1R,4R)-4-(4-octylphenyl)cyclohexyl)guanidinium chloride (34)

This compound was synthesized using general procedure 1 (35% yield). $^1H$ NMR (400 MHz, $CD_3OD$) δ 7.20-6.94 (m, 4H), 3.49-3.30 (m, 1H), 2.58-2.42 (m, 3H), 2.16-2.03 (m, 2H), 1.98-1.87 (m, 2H), 1.69-1.50 (m, 4H), 1.50-1.37 (m, 2H), 1.36-1.19 (m, 10H), 0.92-0.83 (m, 3H); $1^{13}C$ NMR (126 MHz, $CD_3OD$) δ 156.4, 143.5, 140.5, 128.1, 126.3, 50.4, 42.8, 35.2, 32.7, 32.6, 31.8, 31.5, 29.4, 29.4, 29.3, 29.2, 29.0, 22.4, 13.1; HRMS (ESI+) m/z calcd for $C_{21}H_{36}N_3$ $[M]^+$330.2909. found 330.2928.

Compound 35

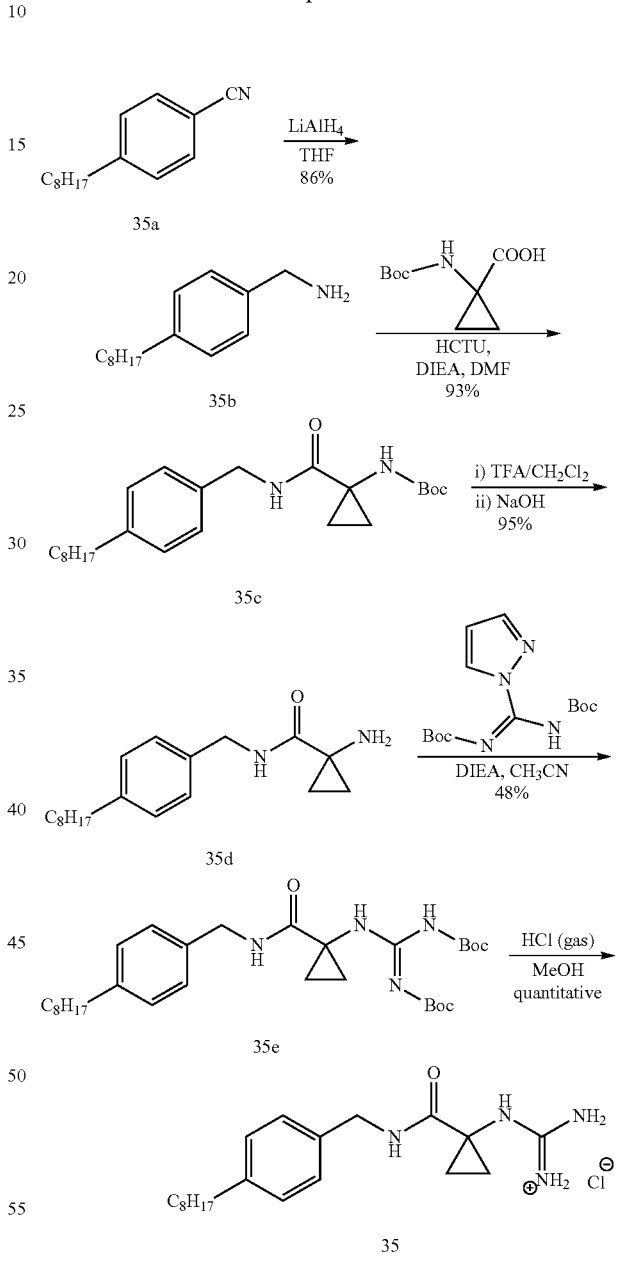

(4-octylphenyl)methanamine (35b)

A solution of 35a (102 mg, 0.474 mmol) in THF (2 mL) was added dropwise to a suspension of lithium aluminum hydride (54 mg, 1.42 mmol) in THF (2 mL) cooled to 0° C. The reaction mixture was warmed to r.t. and stirred for 1 h. At this time, TLC showed complete consumption of starting material. The reaction was cooled to 0° C. and diluted with 5 mL diethyl ether. It was quenched carefully by dropwise addition of 60 μL water, 60 μL 15% NaOH solution and finally 0.18 mL water. The solution was warmed to r.t. and stirred for 30 min. The inorganic precipitates were filtered through a pad of celite. The filtrate was extracted 3× with diethyl ether, washed with brine, dried over Na$_2$SO$_4$, filtered, and concentrated under reduced pressure to provide the title compound (89 mg, 86% yield) as a colorless oil. $^1$H NMR (400 MHz, CDCl$_3$) δ 7.22 (d, J=7.9 Hz, 2H), 7.15 (d, J=8.0 Hz, 2H), 3.84 (s, 2H), 2.59 (t, J=8.0 Hz, 2H), 1.71-1.54 (m, 2H), 1.38-1.24 (m, 10H), 0.88 (t, J=6.8 Hz, 3H); $^{13}$C NMR (101 MHz, CDCl$_3$) δ 146.0, 141.5, 128.5, 127.0, 46.3, 35.6, 31.9, 31.6, 29.5, 29.3, 29.2, 22.7, 14.1.

tert-butyl (1-((4-octylbenzyl)carbamoyl)cyclopropyl)carbamate (35c)

General procedure L was used to convert 35b (89 mg, 0.406 mmol) to the title product (152 mg, 93% yield). $^1$H NMR (400 MHz, CDCl$_3$) δ 7.14 (d, J=7.8 Hz, 2H), 7.07 (d, J=7.8 Hz, 2H), 5.99 (br s, 1H), 4.37 (d, J=5.5 Hz, 2H), 2.53 (t, J=7.7 Hz, 2H), 1.65-1.47 (m, 4H), 1.41-1.18 (m, 19H), 1.05-0.90 (m, 2H), 0.84 (t, J=6.8 Hz, 3H); $^{13}$C NMR (101 MHz, CDCl$_3$) δ 172.1, 171.1, 142.0, 135.5, 128.6, 127.4, 80.3, 60.3, 43.5, 35.5, 31.8, 31.5, 29.4, 29.2, 28.2, 22.6, 21.0, 14.1, 14.0; HRMS (ESI+) m/z calcd for C$_{24}$H$_{39}$N$_2$O$_3$ [M+H]$^+$ 403.2961. found 403.2938.

1-amino-N-(4-octylbenzyl)cyclopropanecarboxamide (35d)

This compound was synthesized using general procedure 1 (109 mg, 95% yield). $^1$H NMR (400 MHz, CDCl$_3$) δ 8.00 (br s, 1H), 7.21 (d, J=8.0 Hz, 2H), 7.14 (d, J=8.0 Hz, 2H), 4.41 (d, J=5.9 Hz, 2H), 2.65-2.51 (m, 2H), 1.63-1.57 (m, 2H), 1.47 (q, J=4.1 Hz, 2H), 1.35-1.19 (m, 10H), 0.88 (t, J=6.9 Hz, 3H), 0.81 (q, J=4.1 Hz, 2H); $^{13}$C NMR (101 MHz, CDCl$_3$) δ 174.9, 142.0, 135.9, 128.6, 127.7, 43.5, 35.6, 35.5, 31.9, 31.6, 29.5, 29.3, 29.2, 22.7, 19.4, 14.1; HRMS (ESI+) m/z calcd for C$_{19}$H$_{31}$N$_2$O [M+H]$^+$ 303.2436. found 303.2412.

Compound (35e)

This compound was synthesized using general procedure H (48% yield). The residue was purified by preparative TLC (85/15 hexanes/EtOAc) to give the title compound (95 mg, 48%) as a white solid. $^1$H NMR (500 MHz, CDCl$_3$) δ 11.42 (br s, 1H), 8.67 (br s, 1H), 7.36 (t, J=5.4 Hz, 1H), 7.25 (d, J=8.0 Hz, 2H), 7.16 (d, J=8.0 Hz, 2H), 4.45 (d, J=5.7 Hz, 2H), 2.70-2.48 (m, 2H), 1.70-1.64 (m, 2H), 1.64-1.56 (m, 2H), 1.50 (d, J=2.7 Hz; 18H), 1.37-1.25 (m, 10H), 1.13-1.06 (m, 2H), 0.90 (t, J=7.0 Hz, 3H); $^{13}$C NMR (126 MHz, CDCl$_3$) δ 171.0, 163.2, 157.0, 153.0, 141.9, 135.6, 128.6, 127.5, 83.7, 79.6, 43.7, 36.2, 35.6, 31.9, 31.5, 29.5, 29.4, 29.2, 28.3, 28.0, 28.0, 22.7, 17.3, 14.1; HRMS (ESI+) m/z calcd for C$_{30}$H$_{49}$N$_4$O$_5$ [M+H]$^+$ 545.3703. found 545.3714.

amino((1-((4-octylbenzyl)carbamoyl)cyclopropyl)amino)methaniminium chloride (35)

This compound was synthesized using general procedure J (18.8 mg, 99% yield) as a white solid. $^1$H NMR (500 MHz, CD$_3$OD) δ 8.20 (br s, 1H), 7.23 (d, J=8.0 Hz, 2H), 7.14 (d, J=8.0 Hz, 2H), 4.41 (s, 2H), 2.64-2.54 (m, 2H), 1.65 (q, J=4.4 Hz, 2H), 1.63-1.54 (m, 2H), 1.36-1.26 (m, 10H), 1.22 (d, J=3.3 Hz, 2H), 0.91 (t, J=7.0 Hz, 3H); $^{13}$C NMR (126 MHz, CD$_3$OD) δ 172.5, 159.6, 143.0, 137.3, 129.5, 128.5, 44.4, 36.5, 36.3, 33.0, 32.8, 30.6, 30.4, 30.3, 23.7, 18.6, 14.4; HRMS (ESI+) m/z calcd for C$_{20}$H$_{33}$N$_4$O [M+H]$^+$ 345.2649. found 345.2670.

Compound 36

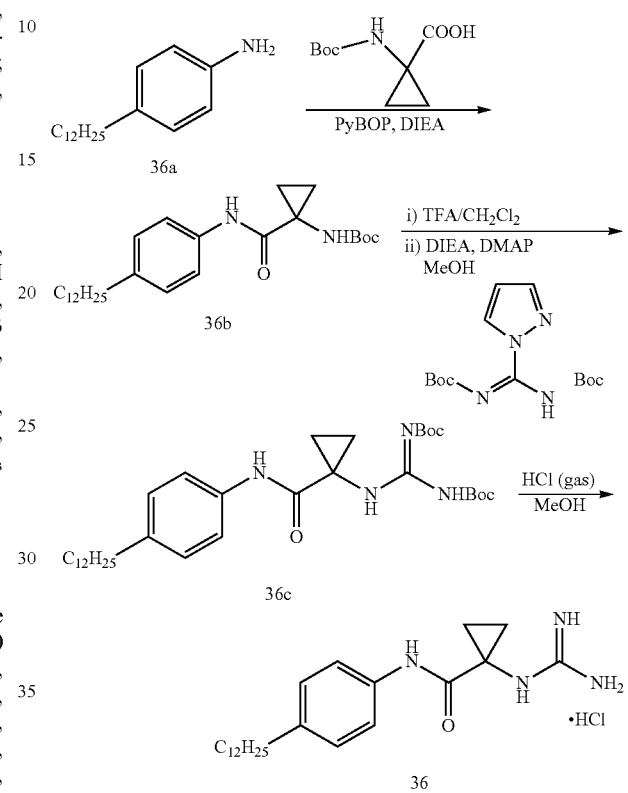

tert-butyl (1-((4-dodecylphenyl)carbamoyl)cyclopropyl)carbamate (36b)

General procedure B was used to couple 4-dodecylaniline (250 mg, 0.96 mmol) and 1-((tert-butoxycarbonyl)amino) cyclopropanecarboxylic acid (193 mg, 0.96 mmol) to yield the title product. 52%. White solid. R$_f$=0.70 (40% EtOAc in hexanes). $^1$H NMR (300 MHz, CDCl$_3$) δ 8.42 (s, 1H), 7.37 (d, J=8.4, 2H), 7.09 (d, J=8.4, 2H), 5.64 (s, 1H), 2.54 (t, J=7.5, 2H), 1.61 (dd, J=4.6, 7.7, 2H), 1.46 (s, 9H), 1.26 (m, 18H), 1.04 (dd, J=4.6, 7.7, 2H), 0.88 (t, J=6.7, 3H). $^{13}$C NMR (75 MHz, CDCl$_3$) δ 170.53, 156.36, 139.16, 135.73, 128.99, 120.16, 81.16, 36.59, 35.59, 32.15, 31.76, 29.91, 29.76, 29.59, 29.50, 28.51, 22.92, 18.01, 14.36.

Compound (36c)

General procedure E was used to deprotect 36b (220 mg, 0.50 mmol). General procedure H was used to couple deprotected 36b and N,N'-Di-Boc-1H-pyrazole-1-carboxamidine to yield the title product as white solid (39% yield). R$_f$=0.70 (25% EtOAc in hexanes). $^1$H NMR (300 MHz, CDCl$_3$) δ 11.30 (s, 1H), 10.68 (s, 1H), 8.82 (s, 1H), 7.46 (d, J=8.4, 2H), 7.09 (d, J=8.4, 2H), 2.54 (t, J=7.5, 2H), 1.61-1.44 (m, 20H), 1.24 (s, 18H), 1.07 (dd, J=5.2, 7.7, 2H), 0.87 (t, J=6.7, 3H). $^{13}$C NMR (75 MHz, CDCl$_3$) δ 168.46, 162.69, 157.69, 153.00, 138.55, 136.53, 128.84, 119.76, 84.23, 80.29, 37.74, 35.61, 32.13, 31.81, 29.87, 29.73, 29.56, 29.46, 28.50, 28.21, 22.90, 16.01, 14.33.

N-(4-dodecylphenyl)-1-guanidinocyclopropanecarboxamide hydrochloride (36)

General procedure J was used to yield the title product as white solid. $^1$H NMR (500 MHz, DMSO) δ 9.68 (d, J=10.3, 2H), 8.53 (d, J=8.1, 2H), 7.52 (t, J=9.3, 2H), 7.11 (t, J=9.4, 2H), 2.50 (m, 2H), 1.55 (s, 2H), 1.23 (m, 18H), 1.14 (s, 2H), 0.92-0.78 (m, 3H). $^{13}$C NMR (126 MHz, DMSO) δ 169.14, 158.57, 138.23, 136.71, 128.52, 121.42, 35.60, 35.00, 31.74, 31.45, 29.47, 29.31, 29.16, 29.04, 22.55, 18.23, 14.42.

Compound 37

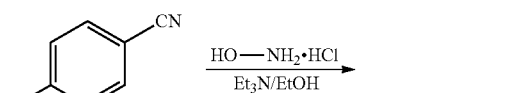

37a

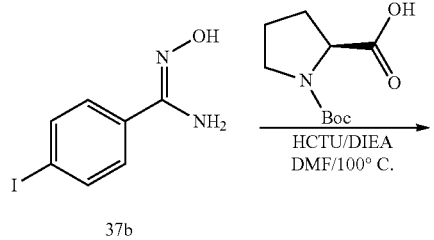

37b

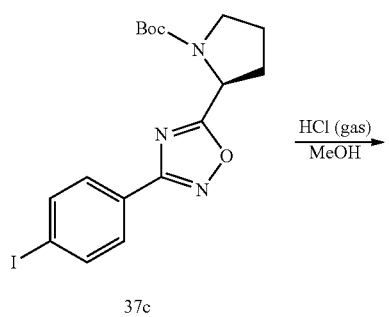

37c

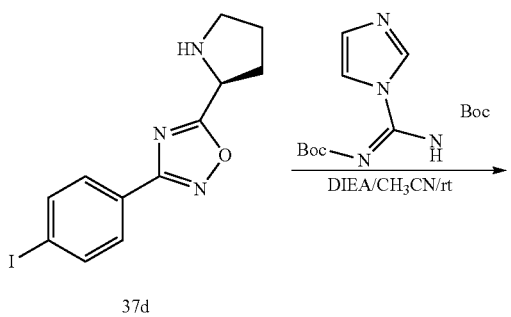

37d

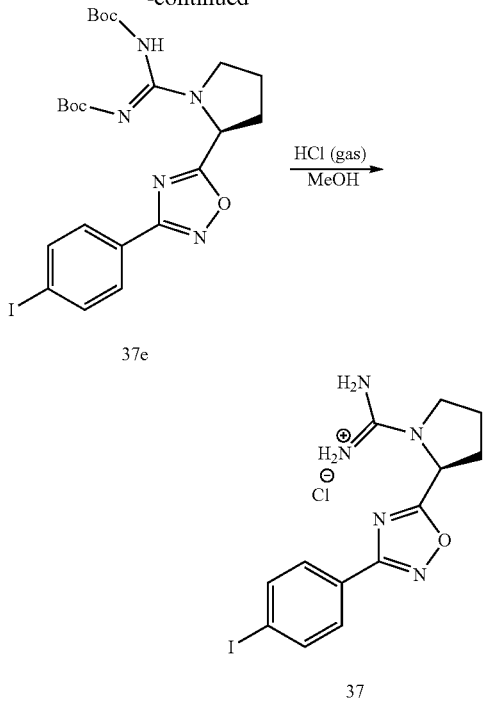

(Z)—N'-hydroxy-4-iodobenzimidamide (37b)

General procedure F was used to convert 37a (0.5 g, 2.18 mmol) to the title product as white solid (333 mg, 58% yield). $^1$H NMR (500 MHz, CDCl$_3$) δ 7.74 (d, J=8.6 Hz, 2H), 7.36 (d, J=8.6 Hz, 2H), 4.82 (s, 1H); $^{13}$C NMR (126 MHz, CDCl$_3$) δ 152.17, 137.96, 132.11, 127.58, 96.24.

(S)-tert-butyl-2-(3-(4-iodophenyl)-1,2,4-oxadiazol-5-yl)pyrrolidine-1-carboxylate (37c)

DIEA (0.4 mL, 2.29 mmol) was added to a solution of (S)-1-(tert-butoxycarbonyl)pyrrolidine-2-carboxylic acid (328 mg, 1.53 mmol) and (Z)—N'-hydroxy-4-iodobenzimidamide 37b (333 mg, 1.27 mmol) in DMF (4 mL). HCTU (790 mg, 1.91 mmol) was then added to the resulting mixture at r.t. and stirred at 100° C. for 3 hours. At this time, TLC showed complete conversion of starting material. The solution was partitioned between ethyl acetate and LiBr aqueous solution. The aqueous solution was extracted with ethyl acetate and the combined organic layers were washed with brine, dried over Na$_2$SO$_4$ and concentrated via vacuum. The residue was purified by silica gel column chromatography (15%, ethyl acetate/hexanes) to yield 27 (63 mg, 11%) as an oil. $^1$H NMR (500 MHz, CDCl$_3$) δ 7.84-7.69 (m, 4H), 5.24-4.88 (m, 1H), 3.73-3.37 (m, 2H), 2.45-1.87 (m, 4H), 1.51-1.13 (m, 9H); $^{13}$C NMR (126 MHz, CDCl$_3$) δ 180.96, 167.79, 153.49, 138.16, 128.96, 126.22, 98.00, 80.50, 53.81, 46.40, 32.42, 28.43, 28.19, 23.75; HRMS (ESI+): Calcd for C$_{17}$H$_{20}$N$_3$O$_3$INa [M+Na]: 464.0447. Found: 464.0405.

(S)-3-(4-iodophenyl)-5-pyrrolidin-2-yl-1,2,4-oxadiazole (37d)

General procedure I was used to convert 27 (214 mg, 0.49 mmol) to the title product as an oil (130 mg, 79% yield). $^1$H NMR (400 MHz, CDCl$_3$) δ 7.79 (s, 4H), 4.53 (dd, J=8.2, 5.5

Hz, 1H), 3.23-3.02 (m, 2H), 2.34-2.25 (m, 2H), 2.19-2.06 (m, 1H), 2.03-1.81 (m, 1H); $^{13}$C NMR (101 MHz, CDCl$_3$) δ 182.32, 167.68, 138.12, 129.08, 126.39, 97.93, 54.41, 46.99, 31.23, 25.45.

(S,E)-tert-butyl(((tert-butoxycarbonyl)amino)(2-(3-(4-iodophenyl)-1,2,4-oxadiazol-5-yl-pyrrolidin-1-yl)methylene)carbamate (37e)

General procedure K was used to convert 37d (63 mg, 0.19 mmol) to the title product (29 mg, 27% yield). $^1$H NMR (500 MHz, CDCl$_3$) δ 7.78 (d, J=2.8 Hz, 4H), 5.58 (dd, J=7.5, 4.6 Hz, 1H), 3.93-3.68 (m, 2H), 2.43 (dd, J=12.8, 6.9 Hz, 1H), 2.22-2.13 (m, 2H), 2.02 (q, J=6.6 Hz, 1H), 1.53-1.32 (m, 18H); $^{13}$C NMR (126 MHz, CDCl$_3$) δ 179.12, 167.57, 161.80, 153.46, 150.15, 137.85, 128.85, 126.04, 97.71, 82.08, 79.41, 55.15, 49.28, 31.41, 27.93, 22.47; MS: Calcd for $C_{23}H_{31}IN_5O_5$ [M+H]: 584.1370. Found: 584.15.

(S)-amino(2-(3-(4-iodophenyl)-1,2,4-oxadiazol-5-yl)pyrrolidin-1-yl)methaniminium chloride (37)

General procedure J was used to convert 37e (29 mg, 0.05 mmol) to the title product as white solid (20 mg, 95% yield). $^1$H NMR (400 MHz, Methanol-d$_4$) δ 7.94 (d, J=7.7 Hz, 2H), 7.84 (d, J=7.8 Hz, 2H), 5.49 (s, 1H), 3.86-3.63 (m, 2H), 2.57 (d, J=42.8 Hz, 2H), 2.20 (d, J=53.7 Hz, 2H); $^{13}$C NMR (101 MHz, Methanol-d$_4$) δ 179.21, 169.09, 157.00, 139.52, 129.92, 127.06, 98.97, 56.62, 49.28, 32.91, 24.44; HRMS (ESI+): Calcd for $C_{13}H_{15}N_5OI$ [M+H]: 384.0321. Found: 384.0313.

Compound 38

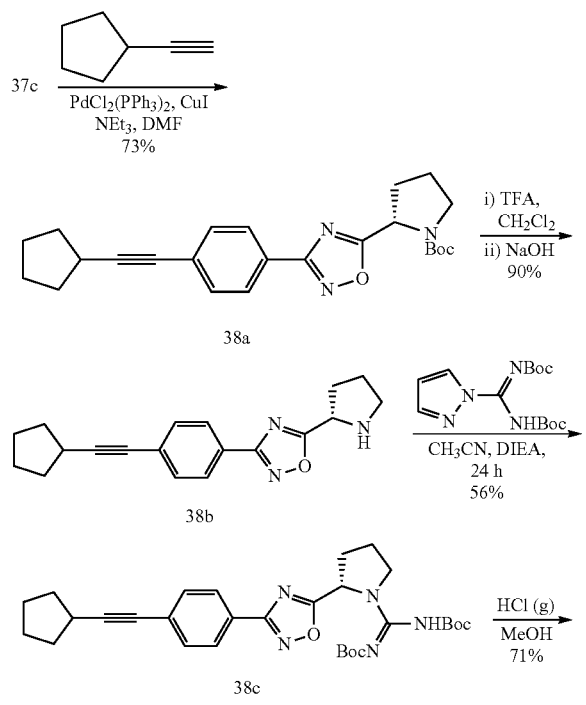

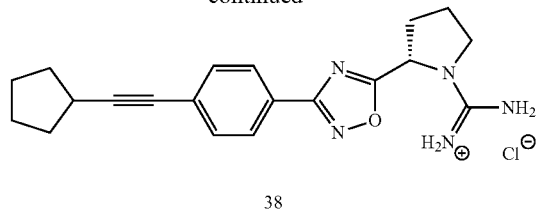

(S)-tert-butyl 2-(3-(4-(cyclopentylethynyl)phenyl)-1,2,4-oxadiazol-5-yl) pyrrolidine-1-carboxylate (38a)

General procedure M was used to convert 37c (0.675 g, 1.530 mmol) to the title product (73% yield). $^1$H NMR (500 MHz, CDCl$_3$) δ 8.06-7.89 (m, 2H), 7.56-7.39 (m, 2H), 5.30-5.17 (m, 1H, minor rotamer), 5.10-4.99 (m, 1H, major rotamer), 3.78-3.69 (m, 1H, major rotamer), 3.69-3.65 (m, 1H, minor rotamer), 3.61-3.53 (m, 1H, major rotamer) 3.53-3.46 (m; 1H, minor rotamer), 2.92-2.80 (m, 1H), 2.47-2.30 (m, 1H), 2.22-2.09 (m, 2H), 2.06-1.95 (m, 3H), 1.84-1.67 (m, 4H), 1.68-1.56 (m, 2H), 1.47 (s, 3H), 1.30 (s, 6H); $^{13}$C NMR (126 MHz, CDCl$_3$, mixture of rotamers) δ 180.7 (major), 180.4 (minor), 168.0 (major), 154.3 (minor), 153.5 (major), 131.9 (major), 131.8 (minor), 127.2 (minor), 127.2 (major), 125.7 (minor), 125.4 (major), 97.3 (major), 97.1 (minor), 80.4 (major), 80.3 (minor), 79.8 (minor), 79.7 (major), 53.8 (major), 46.6 (minor), 46.3 (major), 33.8 (major), 32.4 (major), 31.5 (minor), 30.8 (major), 28.4 (minor), 28.1 (major), 25.1 (major), 24.3 (minor), 23.7 (major).

(S)-3-(4-(cyclopentylethynyl)phenyl)-5-(pyrrolidin-2-yl)-1,2,4-oxadiazole (38b)

This compound was synthesized using general procedure I. It was used for the following step without further purification and characterization.

(S,E)-tert-butyl (((tert-butoxycarbonyl)amino)(2-(3-(4-(cyclopentylethynyl)phenyl)-1,2,4-oxadiazol-5-yl)pyrrolidin-1-yl)methylene)carbamate (38c)

This compound was synthesized using general procedure K. $^1$H NMR (500 MHz; CDCl$_3$) δ 10.16 (br s, 1H), 8.04-7.96 (m, 2H), 7.52-7.44 (m, 2H), 5.59 (dd, J=7.8, 4.6 Hz, 1H), 3.94-3.85 (m, 1H), 3.85-3.73 (m, 1H), 2.91-2.79 (m, 1H), 2.51-2.37 (m, 1H), 2.30-2.11 (m, 2H), 2.09-1.95 (m, 3H), 1.84-1.67 (m, 4H), 1.65-1.56 (m, 2H), 1.55-1.31 (m, 18H); $^{13}$C NMR (126 MHz, CDCl$_3$) δ 179.0, 171.0, 167.9, 161.9, 153.5, 150.3, 131.8, 127.2, 125.4, 97.2, 82.2, 79.7, 60.3, 55.3, 49.4, 33.8, 30.8, 29.7, 28.1, 25.1, 24.0.

(S)-amino(2-(3-(4-(cyclopentylethynyl)phenyl)-1,2,4-oxadiazol-5-yl)pyrrolidin-1-yl)methaniminium chloride (38)

This compound was synthesized using general procedure J. $^1$H NMR (500 MHz, CD$_3$OD) δ 8.06-7.93 (m, 2H), 7.57-7.40 (m, 2H), 5.56-5.34 (dd, J=7.9, 1.8 Hz, 1H), 3.88-3.72 (td, J=9.3, 2.6 Hz, 1H), 3.69-3.58 (m, 1H), 2.96-2.84 (m, 1H), 2.65-2.54 (m, 1H), 2.53-2.43 (m, 1H), 2.31-2.19 (m, 1H), 2.17-1.97 (m, 3H), 1.88-1.77 (m, 2H), 1.76-1.61 (m, 4H).

Compounds 39-41

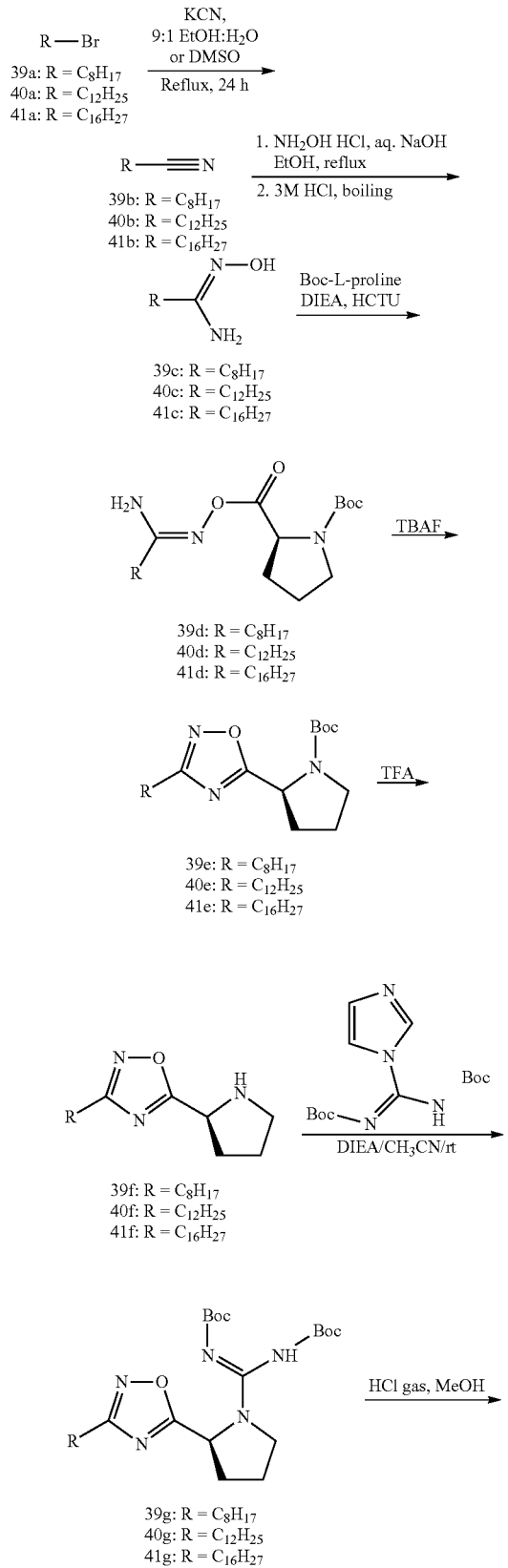

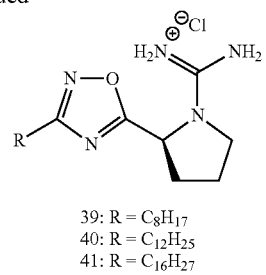

39: R = C₈H₁₇
40: R = C₁₂H₂₅
41: R = C₁₆H₂₇

Compound 39 nonanenitrile (39b)

Potassium cyanide (0.829 g, 12.74 mmol) was added to a round bottom flask containing DMSO (5 mL). The mixture was stirred and heated to 60° C. 1-Bromooctane 39a (2.0 mL, 11.58 mmol) was added dropwise to the flask and the reaction mixture was heated overnight. The reaction was cooled, diluted with water, washed with ether, 6N HCl, water and brine, and dried over sodium sulfate. The reaction was purified on a silica column with 86% hexane: 14% ethyl acetate to yield nonanenitrile 39b (0.323 g, 20%) a clear yellow liquid. $^1$H NMR (400 MHz, CDCl$_3$), δ 2.32 (t, J=7.1, 2H), 1.64 (dt, J=15.3, 7.2 Hz, 2H), 1.42 (dd, J=10.1, 4.8 Hz, 2H), 1.27 (dd, J=5.7, 4.4 Hz, 8H), 0.86 (t, J=6.9 Hz, 3H); $^{13}$C NMR (400 MHz, CDCl3) δ 119.83, 31.66, 28.93, 28.69, 28.62, 25.34, 22.56, 17.08, 14.01.

N'-hydroxylnonanimidamide (39c)

Hydroxylamine hydrochloride (0.998 g, 14.36 mmol) was dissolved in ethanol (7 mL) in a round bottom flask. 3M NaOH (4.8 mL, 14.36 mmol) was added to the flask. Nonanenitrile 2a (1.00 g, 7.18 mmol) dissolved in ethanol (7 mL) was added to the reaction mixture. The mixture was refluxed at 80° C. for 24 hours. At this time 2a was still visible in the reaction mixture by thin layer chromatography. An additional equivalent of hydroxylamine hydrochloride (0.50 g, 7.18 mmol) and 3M NaOH (2.4 mL, 3.59 mmol) was added to the reaction mixture. After an additional 5 hours of refluxing, a small amount of 2a was still visible by TLC and a final equivalent of hydroxylamine hydrochloride (0.50 g, 7.18 mmol) and 3M NaOH (2.4 mL, 3.59 mmol) were added to the flask. The reaction refluxed overnight. A final TLC indicated that 2a was not present in the mixture. The reaction was cooled to r.t., and solvent was removed under reduced pressure. The residue was dissolved in excess 3M HCl (2.63 mL, 7.90 mmol) and heated to 90° C. The reaction solution was cooled and insoluble material was filtered. The filtrate was extracted with DCM. The aqueous layer was adjusted to pH 8 using 3M NaOH to produce a white precipitate. The precipitate was filtered to yield N'-hydroxylnonanimidamide 39c (0.831 g, 67%) as a white solid; $^1$H NMR (400 MHz, MeOD) δ 2.13-2.02 (m, 2H), 1.56 (dd, J=14.7, 7.2 Hz, 2H), 1.41-1.21 (m, 11H), 0.90 (t, J=6.9 Hz, 3H); $^{13}$C NMR (400 MHz, MeOD) δ 157.75, 33.00, 31.79, 30.43, 30.36, 30.19, 28.34, 23.71, 14.43; HRMS (ESI+): Calcd for C9H20N2O [M+H]: 173.1648. Found: 173.1659.

(S)-tert-butyl 2-(3-octyl-1,2,4-oxadiazol-5-yl)pyrrolidine-1-carboxylate (39e)

Synthesized using general procedure L from N'-hydroxylnonamiidamide 39c (0.50 g, 2.90 mmol) to yield the product as white solid (512 mg, 50%); $^1$H NMR (400 MHz, CDCl$_3$) δ 5.16-4.90 (m, 1H), 3.71-3.58 (m, 1H), 3.55-3.39 (m, 1H), 2.68 (t, J=7.5 Hz, 2H), 2.41-2.22 (m, 1H), 2.10-2.00 (m, 2H), 2.00-1.90 (m, 1H), 1.77-1.64 (m, 2H), 1.42 (s, 3H), 1.37-1.17 (m, 19H), 0.85 (t, J=6.7 Hz, 3H); $^{13}$C NMR (400 MHz, CDCl3) δ 180.22, 170.65, 153.42, 80.25, 53.67, 46.29, 32.37, 31.76, 31.42, 29.12, 29.08, 28.10, 27.03, 25.93, 24.28, 23.64, 22.60, 14.06; HRMS (ESI+): Calcd for C19H33N3O3 [M+Na]: 374.48. Found: 374.2429.

(S)-3-octyl-5-(pyrrolidin-2-yl)-1,2,4-oxadiazole (39f)

39e (20 mg, 0.059 mmol) was dissolved in DCM (3 mL). TFA (0.52 mL, 6.80 mmol) was added to the solution and the reaction was stirred at r.t. for 6 hours. The solution was dissolved with diethyl ether and neutralized with 2M NaOH. The aqueous layer was extracted with diethyl ether. The combined organic layers were washed with brine and dried over Na$_2$SO$_4$. The solvent was removed under reduced pressure to yield the title product (14 mg, 85%), a yellow oil; $^1$H NMR (400 MHz, CDCl$_3$) δ 4.46 (s, 1H), 3.22-3.11 (m, 1H), 3.11-2.99 (m. 1H), 2.73-2.66 (m, 2H), 2.54-2.49 (m, 1H), 2.33-2.16 (m, 1H), 2.05 (dt, 19.6, 6.3 Hz, 1H), 1.90 (qd, J=12.9, 6.2 Hz, 2H), 1.72 (dt, J=15.4, 7.6 Hz, 2H), 1.39-1.18 (m, 11H), 0.87 (t, J=6.8 Hz, 3H); $^{13}$C NMR (400 MHz, CDCl3) δ 181.50, 170.49, 54.23, 46.84, 31.78, 31.07, 29.68, 29.14, 29.13, 29.10, 26.94, 26.01, 25.35, 22.62, 14.08; HRMS (ESI+): Calcd for C14H25N3O [M+H]: 252.37. Found: 252.2084.

(S)-tert-butyl (((tert-butylcarbonyl)imino)(2-(3-octyl-1,2,4-oxadiazol-5-yl)pyrrolidin-1-yl)methyl)carbamate (39g)

Using general procedure K, 39e (14 mg, 0.056 mmol) was converted to title product as an oil (18 mg, 66%); $^1$H NMR (400 MHz, CDCl$_3$) δ 10.08 (s, 1H), 5.49 (dd, J=7.7, 4.5 Hz, 1H), 3.89-3.71 (m, 2H), 3.88-3.69 (m, 2H), 2.72-2.65 (m, 2H), 2.45-2.31 (m, 1H), 2.20-2.05 (m, 2H), 2.0 (dd, J=13.0, 6.5 Hz), 1H), 1.71 (dd, J=14.9, 7.3 Hz, 2H), 1.53-1.39 (m, 17H), 1.38-1.19 (m, 11H), 0.87 (dd, J=7.4, 6.3 Hz, 3H); $^{13}$C NMR (400 MHz, CDCl3) δ 178.50, 170.70, 162.00, 82.20, 79.43, 55.28, 49.40, 31.80, 31.22, 29.68, 29.12, 29.09, 29.07, 28.10, 26.92, 25.96, 22.62, 14.06; HRMS (ESI+): Calcd for C25H43N5O5 [M+H]: 494.33. Found: 494.3358.

(S)-amino(2-(3-octyl-1,2,4-oxadiazol-5-yl)pyrrolidin-1-yl)methaniminium chloride (39)

Using general procedure J, the title product was isolated as white solid (10 mg, 86%); $^1$H NMR (500 MHz, MeOD) δ 5.36 (dd, J=8.0, 1.5 Hz, 1H), 3.72 (td, J=9.3, 2.5 Hz, 1H), 3.58 (td, J=9.7, 7.3 Hz, 1H), 2.73)t, J=7.5 Hz, 2H), 2.51 (ddd, J=14.9, 10.1, 6.7 Hz, 1H), 2.38, (dd, J=13.0, 6.5 Hz, 1H), 2.26-2.15 (m, 1H), 2.07-1.95 (m, 1H), 1.78-1.65 (m, 2H), 1.43-1.24 (m, 11H), 0.90 (t, J=6.9 Hz, 3H); $^{13}$C NMR (500 MHz, MeOD) δ 178.52, 172.06, 157.02, 56.33, 48.92, 32.95, 32.64, 30.24, 30.04, 27.86, 26.60, 24.25, 23.67, 14.40; HRMS (ESI+): Calcd for C15H28ClN5O [M+H]: 294.42. Found 294.2292.

Compound 40 tridecanenitrile (40b)

Same procedure as 39b. Product was isolated as a white solid (0.38 g, 93%); $^1$H NMR (400 MHz, CDCl$_3$) δ 2.32 (dd, J=8.5, 5.8 Hz, 2H), 1.64 (dt, J=14.9, 7.2 Hz, 2H), 1.47-1.39 (m, 2H), 1.33-1.17 (m, 16H), 0.87 (t, J=6.9 Hz, 3H); $^{13}$C NMR (400 MHz, CDCl3) δ 119.85, 31.89, 29.58, 29.48, 29.32, 29.29, 28.75, 28.64, 25.35, 22.67; 17.10, 14.10.

N'-hydroxyltridecanimidamide (40c)

Hydroxylamine hydrochloride (213 mg, 3.07 mmol) was dissolved in 95% ethanol (20 mL) in a round bottom flask. 3M NaOH (1.02 mL, 3.07 mmol) and tridecanenitrile 40b (0.30 g, 1.54 mmol) dissolved in 95% ethanol (20 mL) were added to the flask. The reaction mixture was refluxed at 80° C. The reaction progress was monitored by TLC and additional equivalents of hydroxylamine and 3M NaOH were added to push the reaction to completion [2 equivalent increments×3 (hydroxylamine hydrochloride (213 mg, 3.07 mmol), 3M NaOH (1.02 mL, 3.07 mmol))]. The reaction was refluxed for a total of 3 days until additional hydroxylamine hydrochloride and 3M NaOH did not seem to push the reaction forward. The reaction mixture was cooled tor.t. and solvent was removed under reduced pressure. The white residue was purified on a silica column with 20% hexane: 80% ethyl acetate to yield N'-hydroxyltridecananimidamide 40c (186 mg, 53%), white solid; $^1$H NMR (400 MHz, MeOD) δ 2.19 (t, J=8.0 Hz, 1.5H, major diastereomer), 2.08 (t, J=8.0 Hz, 0.5H, minor diastereomer), 1.59 (dd, J=14.4, 7.3 Hz, 2H), 1.36-1.26 (m, 20H), 0.90 (t, J=6.9 Hz, 3H); $^{13}$C NMR (400 MHz, MeOD) δ 179.35, 36.54, 33.09, 30.77, 30.74, 30.65, 30.49, 30.47, 30.33, 28.35, 26.93, 23.73, 14.45; HRMS (ESI+): Calcd for C13H28N2O [M+H]: 228.37. Found: 229.2271.

(S)-tert-butyl 2-((((1-aminotridecylidene)amino)oxy)carbonyl)pyrrilidine-1-carboxylate (40d)

(Z)—N'-hydroxyltetradecanimidamide 40c (130 mg, 0.536 mmol), Boc-L-proline (115 mg, 0.536 mmol), and HCTU (222 mg, 0.536 mmol) were suspended in DCM (15 mL). DIEA (0.38 mL, 2.15 mmol) was added dropwise to the reaction mixture. The reaction mixture was stirred for 4 hours at r.t. and the solvent was removed under reduced pressure. The residue was purified on a silica column in 40-80% ethyl acetate in hexanes to yield 40d (188 mg, 80%), a yellow oil; $^1$H NMR (400 MHz, CDCl$_3$) δ 4.39-4.32 (m, 1H), 3.61-3.49 (m, 1H, 3.42-3.36 (m, 1H), 2.38-2.30 (m, 1H), 2.29-2.16 (m, 3H), 2.09-1.87 (m, 1H), 1.94-1.85 (m, 1H), 1.66-1.54 (m, 2H), 1.45-1.39 (m, 6H), 1.36-1.18 (m, 19H), 0.91-0.84 (m, 3H); $^{13}$C NMR (400 MHz, CDCl3) δ 170.64, 161.56, 155.30, 80.24, 59.11, 28.64, 47.00, 32.06, 31.22, 29.84, 29.78, 29.77, 29.73, 29.59, 29.49, 29.41, 29.21, 28.61, 28.37, 27.03, 24.90, 24.56, 23.82, 22.83, 14.27.

(S)-tert-butyl 2-(3-dodecyl-1,2,4-oxadiazol-5-yl)pyrrolidine-1-carboxylate (40e)

Synthesized using general procedure G to afford the title product as a yellow oil (107 mg, 93% yield). $^1$H NMR (500 MHz, CDCl$_3$) δ 5.04 (dd, J=70.03, 2.7 Hz, 1H), 3.70-3.59 (m, 1H), 3.55-3.46 (m, 1H), 2.70 (t, J=7.0 Hz, 2H), 2.38-2.27 (m, 1H), 2.14-2.02 (m, 2H), 1.97 (d, J=5.7 Hz, 1H), 1.76-1.67 (m, 2H), 1.59 (s, 2H), 1.45 (s, 3H), 1.35-1.12 (m, 28H), 0.88 (t, 6.7 Hz, 6H); $^{13}$C NMR (500 MHz, CDCl3) δ 180.42, 170.86, 153.63, 80.46, 53.87, 46.48, 32.56, 32.06, 29.85, 29.79, 29.77, 29.75, 29.61, 29.49, 29.36, 29.27, 29.07, 28.51, 28.29, 27.22, 26.12, 24.47, 23.82, 22.83, 14.27; HRMS (ESI+): Calcd for C23H41N3O3 [M+Na]: 430.3148. Found: 430.3002.

(S)-3-dodecyl-5-(pyrrolidin-2-yl)-1,2,4-oxadiazole (40f)

Using general procedure I, the title product was isolated as a yellow oil (43 mg, 114%); $^1$H NMR (400 MHz, CDCl$_3$) δ 4.45 (dd, J=8.1, 5.6 Hz, 1H), 3.15 (dt, J=9.9, 6.9 Hz, 1H), 3.09-3.01 (m, 1H), 2.71-2.66 (m, 2H), 2.30-2.20 (m, 2H), 2.09-1.98 (m, 1H), 1.96-1.79 (m, 2H), 1.76-1.66 (m, 2H), 1.37-1.19 (m, 20H), 0.86 (t, J=6.9 Hz, 3H); $^{13}$C NMR (400 MHz, CDCl3) δ 181.58, 170.62, 54.37, 46.98, 32.03, 31.20, 29.77; 29.75, 29.71, 29.58, 29.47, 29.32, 29.27, 27.09, 26.14, 25.48, 22.81, 14.25; HRMS (ESI+): Calcd for C18H33N3O [M+H]: 308.2624. Found: 308.2672.

(S)-tert-butyl (((tert-butylcarbonyl)imino)(2-(3-dodecyl-1,2,4-oxadiazol-5-yl)pyrrolidin-1-yl)methyl) carbamate (40g)

Using general procedure K, the title product was isolated as an oil (38 mg, 71%); $^1$H NMR (400 MHz, CDCl$_3$) δ 5.49 (dd, J=7.7, 4.5 Hz, 1H), 3.87-3.79 (m, 1H), 3.79-3.70 (m, 1H), 2.72-2.66 (m, 2H), 2.44-2.33 (m, 1H), 2.19-2.06 (m, 2H), 2.00 (d, J=6.6 Hz, 1H), 1.76-1.66 (m, 2H), 1.48 (d, J=17.9 Hz, 18H), 1.38-1.19 (m, 21H), 0.87 (t, =6.8 Hz, 3H); $^{13}$C NMR (400 MHz, CDCl3) δ 178.46, 170.69, 142.68, 128.94, 109.74, 82.16, 79.43, 55.24, 49.39, 31.89, 29.67, 29.62, 29.61, 29.59, 29.43, 29.32, 29.16, 29.08, 28.09, 27.96, 26.92, 25.95, 22.66, 14.09; HRMS (ESI+): Calcd for C29H51N5O5 [M+H]: 550.3895. Found: 550.3968.

(S)-amino(2-(3-dodecyl-1,2,4-oxadiazol-5-yl)pyrrolidin-1-yl)methaniminium chloride (40)

Using general procedure J, the title product was isolated as a white solid (22 mg, 92%); $^1$H NMR (500 MHz, MeOD) δ 5.36 (d, J=7.5 Hz, 1H), 3.71 (t, J=8.3 Hz, 1H), 3.58 (dd, J=16.8, 9.3 Hz, 1H), 2.72 (t, J=7.5 Hz, 2H), 2.56-2.46 (m, 1H), 2.38 (dd, J=12.4, 6.2 Hz, 1H), 2.23-2.17 (M, 1H), 2.06-1.96 (m, 1H), 1.76-1.69 (m, 2H), 1.45-1.22 (m, 20H), 0.90 (t, J=6.9 Hz, 3H); $^{13}$C NMR (500 MHz, MeOD) δ 178.53, 172.08, 157.04, 56.38, 33.07, 32.69, 30.75, 30.74, 30.70, 30.59, 30.49, 30.29, 30.06, 27.88, 26.64, 24.30, 23.73, 14.43; HRMS (ESI+): Calcd for C19H36N5O [M+H]: 350.2915. Found: 350.2909.

Compound 41 heptadecanenitrile (41b)

Same procedure as 39b. Product was isolated as a white solid (1.513 g, 92%). $^1$H NMR (400 MHz, CDCl$_3$) δ 2.32 (t, J=7.1 Hz, 2H), 1.69-1.59 (m, 2H), 1.42 (dd, J=14.7, 7.0 Hz, 2H), 1.26 (d, J=11.9 Hz, 24H), 0.87 (t, J=6.8 Hz, 3H); $^{13}$C NMR (400 MHz, CDCl3) δ 119.85, 31.91, 29.68, 29.67, 29.66, 29.64, 29.63, 29.58, 29.49, 29.35, 29.29, 28.75, 28.65, 25.36, 22.68, 17.11, 14.11.

N'-hydroxylheptadecanimidamide (41c)

Hydroxylamine hydrochloride (221 mg, 3.18 mmol) was dissolved in ethanol (10 mL) in a round bottom flask. 3M NaOH (1.06 mL, 3.18 mmol) was added to the flask. Heptadecanenitrile 41b (0.40 g, 1.59 mmol) was dissolved in ethanol (5 mL) and added to the reaction mixture. The reaction was refluxed at 80° C. for 30 hours. TLC analysis indicated that 41b was still present in the reaction mixture. An additional equivalent of hydroxylamine hydrochloride (110 mg, 1.59 mmol) and 3M NaOH (0.53 mL, 1.59 mmol) were added and the reaction was refluxed overnight. TLC indicated that 41b had been consumed. The solvent was removed under reduced pressure. The white residue was purified on a silica column with 50-80% ethyl acetate in hexanes to yield 41c (310 mg, 69%), a white solid; $^1$H NMR (400 MHz, CDCl$_3$) δ 2.31 (t, J=7.1 Hz, 2H), 1.64 (dt, J=14.9, 7.2 Hz, 2H), 1.48-1.38 (m, 2H), 1.33-1.22 (m, 30H), 0.86 (t, J=6.9 Hz, 3H); $^{13}$C NMR (400 MHz, CDCl3) δ 119.87, 32.01, 29.78, 29.77, 29.76, 29.74, 29.73, 29.68, 29.59, 29.45, 29.39, 28.85, 28.74, 25.46, 22.77, 17.17; HRMS (ESI+): Calcd for C17H36N2O [M+H]: 285.2823. Found: 285.2896.

(S)-tert-butyl 2-((((1-aminoheptadecylidene)amino) oxy)carbonyl)pyrrilidine-1-carboxylate (41d)

(Z)—N'-hydroxylheptadecanimidamide 41c (50 mg, 0.176 mmol), Boc-L-proline (38 mg, 0.176 mmol), and HCTU (73 mg, 0.176 mmol) were suspended in DCM (3 mL). DIEA (0.12 mL, 0.703 mmol) was added dropwise to the reaction mixture. The reaction mixture was stirred for 4 hours at r.t. and the solvent was removed under reduced pressure. The residue was purified on a silica column in 40-80% ethyl acetate in hexanes to yield 41d (48 mg, 57%), a yellow oil; $^1$H NMR (400 MHz, CDCl$_3$) δ 4.76 (s, 1H), 4.39-4.30 (m, 1H), 3.59-3.42 (m, 1H), 3.42-3.32 (m, 1H), 2.29-2.13 (m, 4H), 2.04-1.93 (m, 1H), 1.62-1.52 (m, 2H), 1.41 (d, J=15.9 Hz, 9H), 1.34-1.16 (m, 29H), 0.86 (t, J=8.6 Hz, 3H); $^{13}$C NMR (400 MHz, CDCl3) δ170.63, 170.60, 161.50, 158.91, 155.22, 154.09, 80.41, 80.17, 59.02, 58.58, 46.94, 46.46, 32.02, 31.17, 29.79, 29.77, 29.76, 29.75, 29.70, 29.56, 29.46, 29.38, 29.17, 28.56, 28.32, 27.16, 26.99, 24.51, 23.78, 22.79, 14.23; HRMS (ESI+): Calcd for C27H51N3O4 [M+H]: 482.39. Found: 482.3984.

(S)-tert-butyl 2-(3-hexadecyl-1,2,4-oxadiazol-5-yl) pyrrolidine-1-carboxylate (41e)

To a 0.1M solution of (S)-tert-butyl 2-((((1-aminoheptadecylidene)amino)oxy)carbonyl)pyrrilidine-1-carboxylate 41d (100 mg, 0.208 mmol) in THF (2.08 mL) was added a 1.0 M solution of TBAF in THF (0.21 mL, 0.208 mmol). The solution was stirred at r.t. for 1 hour. The solvent was removed under reduced pressure. The resulting residue was purified on a silica column using 10-40% ethyl acetate in hexanes to yield 41e (91 mg, 95%), a yellow oil; $^1$H NMR (400 MHz, CDCl$_3$) δ 5.12-4.96 (m, 1H), 3.69-3.58 (m, 1H), 3.57-3.43 (m, 1H), 2.70 (t, J=7.6 Hz, 2H), 2.39-2.24 (m, 1H), 2.11-2.01 (m, 2H), 1.99-1.92 (m, 1H), 1.77-1.66 (m, 2H), 1.44 (s, 3H), 1.38-1.14 (m, 35H), 0.87 (t, J=6.9 Hz, 3H); $^{13}$C NMR (400 MHz, CDCl3) δ 180.40, 170.83, 153.60, 80.44, 53.85, 46.73, 46.47, 32.55, 32.07, 31.60, 29.84, 29.80, 29.75, 29.61, 29.51, 29.36, 29.27, 28.50, 28.28, 27.22, 27.04, 26.27, 26.12, 23.82, 22.84, 14.28; HRMS (ESI+): Calcd for C27H49N3O3 [M+Na]: 486.377. Found: 486.3686.

(S)-3-hexadecyl-5-(pyrrolidin-2-yl)-1,2,4-oxadiazole (41f)

Using general procedure I, the title product was isolated as a yellow oil (63 mg, 95%), a yellow oil; $^1$H NMR (500

MHz, CDCl₃) δ 4.46 (dd, J=7.8, 5.8 Hz, 1H), 3.21-3.11 (m, 1H), 3.09-3.01 (m, 1H), 2.73-2.65 (m, 2H), 2.32-2.22 (m, 1H), 2.09-2.01 (m, 1H), 1.97-1.82 (m, 2H), 1.73 (dt, J=15.3, 7.7 Hz, 2H), 1.40-1.20 (m, 30H), 0.87 (t, J=7.0 Hz, 3H); ¹³C NMR (500 MHz, CDCl3) δ 181.68, 170.67, 54.42, 4701, 32.07, 31.23, 29.84, 29.82, 29.80, 29.79, 29.74, 29.60, 29.51, 29.35, 29.30, 27.12, 26.18, 25.51, 22.84, 14.26

(S)-tert-butyl (((tert-butylcarbonyl)imino)(2-(3-hexadecyl-1,2,4-oxadiazol-5-yl)pyrrolidin-1-yl)methyl)carbamate (41g)

Using general procedure J, the title product was isolated as an oil (12 mg, 51%); ¹H NMR (400 MHz, CDCl₃) δ 5.49 (dd, J=7.8, 4.5 Hz, 1H), 3.83 (dt, J=11.5, 7.1 Hz, 1H), 3.78-3.70 (m, 1H), 2.72-2.66 (m, 2H), 2.38 (dt, J=21.2, 7.9 Hz, 1H), 2.19-2.06 (m, 2H), 2.02-1.93 (m, 1H), 1.75-1.67 (m, 2H), 1.52-1.39 (m, 17H), 1.37-1.19 (m, 32H), 0.87 (t, J=6.8 Hz, 5H); ¹³C NMR (400 MHz, CDCl3) δ 178.44, 170.65, 161.99, 153.61, 82.09, 79.45, 55.24, 49.38, 37.05, 32.70, 31.88, 31.19, 30.00, 29.65, 29.61, 29.59, 29.42, 29.32, 29.15, 29.06, 28.06, 27.94, 27.52, 27.05, 26.90, 25.93, 23.88, 22.65, 19.69, 14.08; HRMS (ESI+): Calcd for C33H59N5O5 [M+H]: 606.4516. Found: 606.4581.

(S)-amino(2-(3-hexadecyl-1,2,4-oxadiazol-5-yl)pyrrolidin-1-yl)methaniminium chloride (41)

Using general procedure J, the title product was isolated as a white solid (11 mg, 66%); ¹H NMR (400 MHz, MeOD) δ 5.35 (d, J=7.5 Hz, 1H), 3.73-3.66 (m, 1H), 3.57 (dd, J=16.9, 9.5 Hz, 1H), 2.72 (t, J=7.5 Hz, 2H), 2.55-2.46 (m, 1H), 2.42-2.34 (m, 1H), 2.23-2.16 (m, 1H), 2.05-1.97 (m, 1H), 1.73 (dt, J=14.8, 7.8 Hz, 2H), 1.43-1.22 (m, 28H), 0.90 (t, J=6.9 Hz, 3H); ¹³C NMR (400 MHz, MeOD) δ 177.05, 170.58, 155.53, 65.46 (diethyl ether), 54.89, 47.46, 31.63, 31.21, 29.33, 29.31, 29.29, 29.26, 29.15, 29.03, 28.85, 28.62, 26.43, 25.17, 22.81, 22.29, 14.00 (diethyl ether), 12.99; HRMS (ESI+): Calcd for C23H44N5O [M+H]: 406.3546. Found: 406.3571.

Compounds 42-44

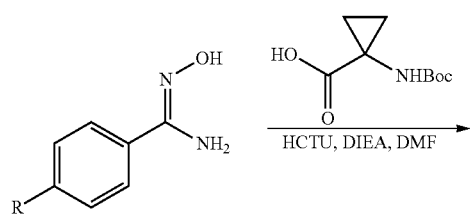

42a: R = C₈H₁₇
43a: R = C₁₁H₂₂
44a: R = C₁₂H₂₅

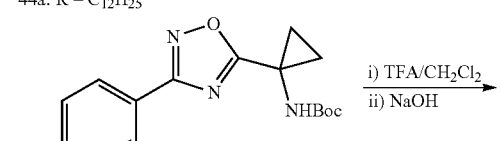

42b: R = C₈H₁₇
43b: R = C₁₁H₂₂
44b: R = C₁₂H₂₅

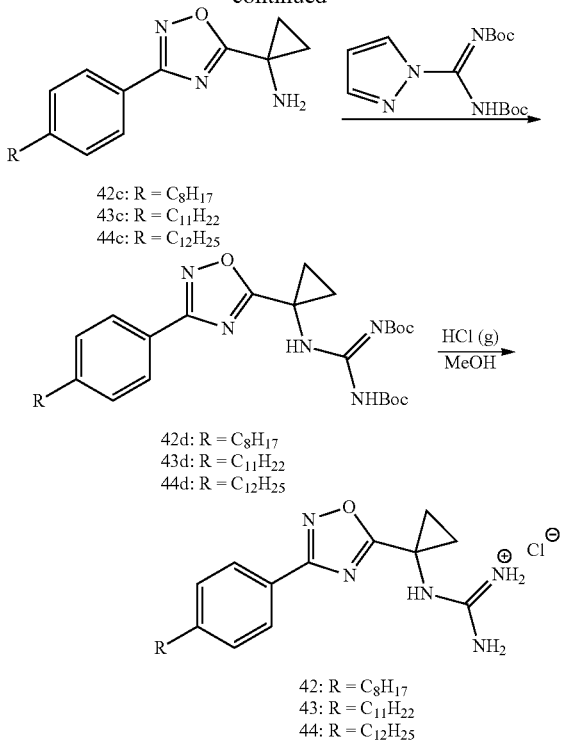

42c: R = C₈H₁₇
43c: R = C₁₁H₂₂
44c: R = C₁₂H₂₅

42d: R = C₈H₁₇
43d: R = C₁₁H₂₂
44d: R = C₁₂H₂₅

42: R = C₈H₁₇
43: R = C₁₁H₂₂
44: R = C₁₂H₂₅

Compound 42 tert-butyl (1-(3-(4-octylphenyl)-1,2,4-oxadiazol-5-yl)cyclopropyl)carbamate (42b)

This compound was synthesized using general procedure L (62% yield). ¹H NMR (400 MHz, CDCl₃) δ 7.91 (d, J=7.5 Hz, 2H), 7.24 (d, J=8.0 Hz, 2H), 5.53 (br s, 1H), 2.70-2.57 (m, 2H), 1.77-1.73 (m, 2H), 1.67-1.56 (m, 2H), 1.49-1.45 (m, 11H), 1.35-1.18 (m, 10H), 0.87 (t, J=7.2 Hz, 3H); ¹³C NMR (101 MHz, CDCl₃) δ 180.8, 168.5, 155.6, 146.3, 128.8, 127.4, 124.2, 80.5, 35.9, 31.9, 31.2, 30.9, 29.4, 29.3, 29.2, 28.3, 22.7, 19.6, 14.1; HRMS (ESI+) m/z calcd for C24H35N3NaO3 [M+Na]⁺ 436.2576. found 436.2530.

1-(3-(4-Octylphenyl)-1,2,4-oxadiazol-5-yl)cyclopropanamine (42c)

This compound was synthesized using general procedure 1 (99% yield). ¹H NMR (400 MHz, CDCl₃) δ 7.94 (d, J=8.2 Hz, 2H), 7.27 (d, J=8.0 Hz, 2H), 2.70-2.59 (m, 2H), 2.38 (br s, 2H), 1.69-1.55 (m, 2H), 1.54-1.46 (m, 2H), 1.36-1.19 (m, 12H), 0.87 (t, J=6.9 Hz, 3H); ¹³C NMR (101 MHz, CDCl₃) δ 183.8, 168.4, 146.4, 128.9, 127.3, 124.2, 35.9, 31.9, 31.8, 31.2, 29.4, 29.3, 29.2, 22.6, 19.8, 14.1; HRMS (ESI+) m/z calcd for C₁₉H₂₈N3O [M+H]+314.2232. found 314.2208.

Compound (42d)

This compound was synthesized using general procedure K (35% yield). ¹H NMR (500 MHz, CDCl₃) δ 11.50 (br s, 1H), 8.92 (br s, 1H), 7.86 (d, J=8.3 Hz, 2H), 7.18 (d, J=8.2 Hz, 2H), 2.57 (t, J=7.5 Hz, 2H), 1.79 (dd, J=5.5, 8.5 Hz, 2H), 1.60-1.53 (m, 2H), 1.51 (dd, J=5.5, 8.5 Hz, 2H), 1.45 (s, 9H), 1.32 (s, 9H), 1.26-1.12 (m, 10H), 0.80 (t, J=7.0 Hz, 3H); ¹³C NMR (126 MHz, CDCl$_3$) δ 180.1, 168.6, 163.3, 156.9, 153.2, 146.3, 128.8, 127.4, 124.3, 83.5, 79.6, 36.0, 31.9, 31.2, 30.7, 29.7, 29.4, 29.2, 28.2, 28.1, 22.7, 20.3, 14.1; HRMS (ESI+) m/z calcd for C$_{30}$H$_{46}$N$_5$O$_5$ [M+H]$^+$ 556.3499. found 556.3457.

amino((1-(3-(4-octylphenyl)-1,2,4-oxadiazol-5-yl)cyclopropyl)amino)methaniminium chloride (42)

This compound was synthesized using general procedure J (99% yield). $^1$H NMR (400 MHz, CD$_3$OD) δ 7.92 (d, J=8.2 Hz, 2H), 7.32 (d, J=8.2 Hz, 2H), 2.67 (t, J=7.6 Hz, 2H), 1.92 (dd, J=5.2, 8.4 Hz, 2H), 1.72-1.58 (m, 4H), 1.38-1.24 (m, 10H), 0.88 (t, J=6.9 Hz, 3H); $^{13}$C NMR (101 MHz, CD$_3$OD) δ 180.6, 169.9, 159.8, 148.2, 130.1, 128.3, 125.2, 36.9, 33.0, 32.5, 31.6, 30.5, 30.4, 30.3, 23.7, 21.1, 14.4; HRMS (ESI+) m/z calcd for C$_{20}$H$_{30}$N$_5$O [M+H]$^+$ 356.2445. found 356.2422.

Compound 43 tert-butyl (1-(3-(4-undecylphenyl)-1,2,4-oxadiazol-5-yl)cyclopropyl)carbamate (43b)

General procedure L was used to convert 43a (104 mg, 0.22 mmol) to the title product. 99%. White solid. R$_f$=0.60 (25% EtOAc in hexanes). $^1$H NMR (300 MHz, CDCl$_3$) δ 7.90 (d, J=7.8, 2H), 7.23 (d, J=7.8, 2H), 5.57 (s, 1H), 2.62 (t, J=7.5, 2H), 1.68-1.55 (m, 2H), 1.51-1.34 (m, 11H), 1.26 (m, 18H), 0.86 (t, J=6.6, 2H). $^{13}$C NMR (75 MHz, CDCl$_3$) δ 168.74, 155.89, 146.59, 129.02, 128.85, 127.57, 126.73, 124.39, 115.76, 80.75, 59.14, 36.16, 32.13, 31.44, 29.84, 29.79, 29.69, 29.56, 29.47, 28.47, 28.03, 24.30, 22.90, 19.96, 14.34, 13.89.

Compound (43d)

General procedure I was used to deprotect 43b (100 mg, 0.22 mmol). General procedure K was used to couple deprotected 43c and N,N'-Di-Boc-1H-pyrazole-1-carboxamidine (75 mg, 0.24 mmol) to yield the title product. 37%. White solid. R$_f$=0.38 (20% EtOAc in hexanes). $^1$H NMR (300 MHz, CDCl$_3$) δ 11.58 (s, 1H), 8.99 (s, 1H), 7.93 (d, J=8.2, 2H), 7.25 (d, J=8.2, 2H), 2.70-2.58 (t, J=2H), 1.87 (dd, J=5.3, 8.3, 2H), 1.70-1.46 (m, 13H), 1.39 (s, 9H), 1.27 (m, 16H), 0.87 (t, J=6.7, 3H). $^{13}$C NMR (75 MHz, CDCl$_3$) δ 180.28, 168.78, 163.55, 157.09, 153.41, 146.55, 129.02, 127.64, 124.48, 83.73, 79.83, 36.16, 32.13, 31.45, 30.93, 29.84, 29.70, 29.54, 29.46, 28.41, 28.30, 22.90, 20.55, 14.33.

1-(1-(3-(4-undecylphenyl)-1,2,4-oxadiazol-5-yl)cyclopropyl)guanidine hydrochloride (43)

General procedure J was used to deprotect 43d (49 mg, 0.008 mmol). The hydrochloride salt was prepared by the dropwise addition of 2 M HCl in ether to the purified guanidine. The ether was evaporated, reconstituted in ether, and again evacuated to dryness to yield the title product. 99%. Tan solid. $^1$H NMR (500 MHz, DMSO) δ 8.95 (s, 1H), 7.86 (d, J=8.2, 2H), 7.36 (d, J=8.2, 2H), 2.62 (t, J=7.6, 2H), 1.80 (s, 2H), 1.62 (s, 2H), 1.57 (s, 2H), 1.24 (m, 16H), 0.83 (t, J=5.9, 3H). $^{13}$C NMR (126 MHz, DMSO) δ 180.22, 168.21, 158.33, 146.84, 129.64, 127.41, 123.85, 35.49, 31.74, 31.09, 30.60, 29.44, 29.26, 29.16, 29.08, 22.55, 21.29, 14.42.

Compound 44 tert-butyl (1-(3-(4-dodecylphenyl)-1,2,4-oxadiazol-5-yl)cyclopropyl)carbamate (44b)

General procedure L was used to convert 44a (137 mg, 0.28 mmol) to the title product. 83%. White solid. R$_f$=0.65 (25% EtOAc in hexanes). $^1$H NMR (300 MHz, CDCl$_3$) δ 7.91 (d, J=7.7, 2H), 7.23 (d, J=8.0, 2H), 5.63 (s, 1H), 2.62 (t, J=7.7, 1H), 1.73 (s, 1H), 1.61 (m, 2H), 1.44 (s, 9H), 1.27 (m, 18H), 0.87 (t, J=6.6, 3H). $^{13}$C NMR (75 MHz, CDCl$_3$) δ 181.11, 168.74, 155.92, 146.56, 146.30, 129.01, 127.59, 124.41, 80.78, 36.17, 32.15, 31.46, 31.10, 29.88, 29.81, 29.71, 29.59, 29.49, 28.48, 28.04, 27.65, 22.92, 19.89, 14.36.

Compound (44d)

General procedure I was used to deprotect 44b (109 mg, 0.23 mmol). General procedure K was used to couple deprotected 44b and N,N'-Di-Boc-1H-pyrazole-1-carboxamidine to yield the title product. 11%. White solid. R$_f$=0.40 (20% EtOAc in hexanes). $^1$H NMR (300 MHz, CDCl$_3$) δ 11.57 (s, 1H), 9.00 (s, 1H), 7.93 (d, J=8.2, 2H), 7.25 (d, J=8.0, 2H), 2.64 (t, J=7.7, 2H), 1.87 (dd, J=5.3, 8.2, 2H), 1.58 (dd, J=5.3, 8.3, 2H), 1.52 (s, 9H), 1.39 (s, 9H), 1.27 (m, 18H), 0.87 (t, J=6.5, 3H). $^{13}$C NMR (75 MHz, CDCl$_3$) δ 157.09, 153.41, 146.57, 129.03, 127.64, 124.46, 83.75, 79.87, 36.17, 32.14, 31.47, 30.91, 29.86, 29.70, 29.57, 29.47, 28.41, 28.30, 22.91, 20.56, 14.34.

1-(1-(3-(4-dodecylphenyl)-1,2,4-oxadiazol-5-yl)cyclopropyl)guanidine hydrochloride (44)

General procedure J was used to deprotect 44d (17 mg, 0.003 mmol). The hydrochloride salt was prepared by the dropwise addition of 2 M HCl in ether to the purified guanidine. The ether was evaporated, reconstituted in ether, and again evacuated to dryness to yield the title product. 99%. $^1$H NMR (500 MHz, DMSO) δ 8.95 (s, 2H), 7.86 (s, 2H), 7.70 (s, 2H), 7.36 (s, 2H), 4.13 (s, 1H), 2.63 (s, 2H), 1.81 (s, 2H), 1.63 (s, 6H), 1.24 (m, 20H), 0.84 (s, 3H). $^{13}$C NMR (126 MHz, DMSO) δ 180.22, 168.22, 158.36, 146.84, 129.66, 127.43, 123.86, 35.52, 31.76, 31.10, 30.62, 29.47, 29.28, 29.17, 29.10, 22.57, 21.33, 14.44.

Compounds 46, 47, and 48

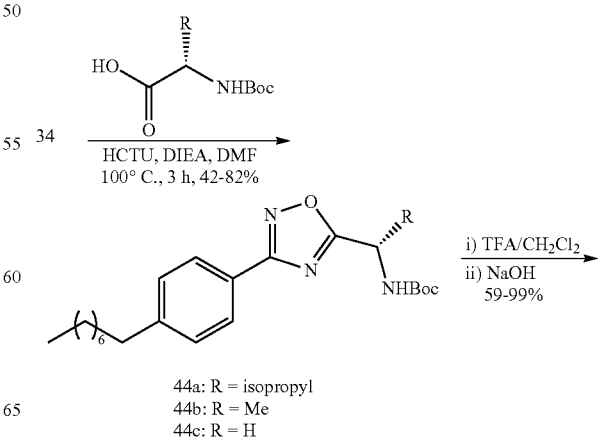

Scheme 4

44a: R = isopropyl
44b: R = Me
44c: R = H

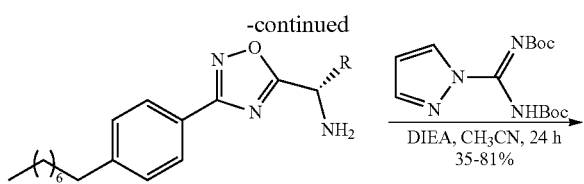

45a: R = isopropyl
45b: R = Me
45c: R = H

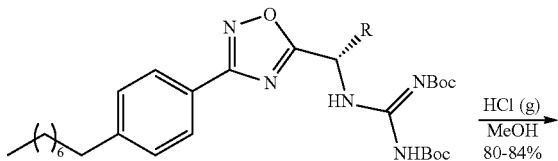

46a: R = isopropyl
46b: R = Me
46c: R = H

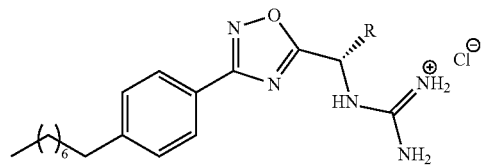

23: R = isopropyl
24: R = Me
25: R = H

Compound 46 tert-butyl ((3-(4-octylphenyl)-1,2,4-oxadiazol-5-yl)methyl)carbamate (46a)

This compound was synthesized using general procedure L (64% yield). $^1$H NMR (500 MHz, CDCl$_3$) δ 7.95 (d, J=8.1 Hz, 2H), 7.26 (d, J=8.0 Hz, 2H), 5.38 (br s, 1H), 4.61 (d, J=5.2 Hz, 2H), 2.64 (t, J=8.4 Hz, 2H), 1.66-1.56 (m, 2H), 1.46 (s, 9H), 1.36-1.19 (m, 10H), 0.86 (t, J=6.9 Hz, 3H); $^{13}$C NMR (126 MHz, CDCl$_3$) δ 176.4, 168.5, 155.6, 146.8, 129.0, 127.5, 123.9, 80.7, 37.3, 36.0, 32.0, 31.3, 29.5, 29.4, 29.3, 28.4, 22.7, 14.2.

(3-(4-octylphenyl)-1,2,4-oxadiazol-5-yl)methanamine (46b)

This compound was synthesized using general procedure 1 (91% yield). $^1$H NMR (500 MHz, CD$_3$OD) δ 8.08-7.92 (m, 2H), 7.34 (d, J=8.4 Hz, 2H), 4.86 (br s, 2H), 4.59 (s, 2H), 2.70-2.62 (m, 2H), 1.70-1.57 (m, 2H), 1.37-1.20 (m, 10H), 0.88 (t, J=7.0 Hz, 3H); $^{13}$C NMR (126 MHz, CD$_3$OD) δ 173.1, 168.5, 147.2, 128.9, 127.2, 123.4, 35.6, 34.9, 31.7, 31.1, 29.2, 29.1, 29.0, 22.4, 13.1.

Compound (46c)

This compound was synthesized using general procedure K (78% yield). $^1$H NMR (500 MHz, CDCl$_3$) δ 11.47 (br s, 1H), 8.99 (t, J=5.3 Hz, 1H), 7.99-7.95 (m, 2H), 7.28 (d, J=8.0 Hz, 2H), 4.95 (d, J=5.3 Hz, 2H), 2.64 (t, J=7.7 Hz, 2H), 1.67-1.58 (m, 2H), 1.52 (s, 9H), 1.49 (s, 9H), 1.35-1.19 (m, 10H), 0.86 (t, J=6.3 Hz, 3H); $^{13}$C NMR (126 MHz, CDCl$_3$) δ 175.4, 168.5, 163.2, 156.3, 153.1, 146.8, 129.0, 127.6, 123.8, 83.8, 79.9, 37.3, 36.1, 31.9, 31.3, 29.5, 29.3, 29.3, 28.3, 28.1, 22.7, 14.2.

amino(((3-(4-octylphenyl)-1,2,4-oxadiazol-5-yl)methyl)amino)methaniminium chloride (46)

This compound was synthesized using general procedure J (84% yield). $^1$H NMR (500 MHz, CD$_3$OD) δ 7.96 (d, J=8.2 Hz, 2H), 7.33 (d, J=8.2 Hz, 2H), 4.84 (s, 2H), 2.67 (t, J=7.6 Hz, 2H), 1.71-1.54 (m, 2H), 1.38-1.19 (m, 10H), 0.88 (t, J=7.0 Hz, 3H); $^{13}$C NMR (126 MHz, CD$_3$OD) δ 175.5, 168.4, 158.1, 147.0, 128.8, 127.1, 123.7, 37.4, 35.5, 31.7, 31.1, 29.2, 29.1, 29.0, 22.4, 13.1; HRMS (ESI+) m/z calcd for C$_{18}$H$_{28}$N$_5$O [M+H]$^+$ 330.2294. found 330.2269.

Compound 47

(S)-tert-butyl (1-(3-(4-octylphenyl)-1,2,4-oxadiazol-5-yl)ethyl)carbamate (47a)

This compound was synthesized using general procedure L (82% yield). $^1$H NMR (500 MHz, CDCl$_3$) δ 7.96 (d, J=8.0 Hz, 2H), 7.26 (d, J=8.0 Hz, 2H), 5.29 (br s, 1H), 5.22-5.03 (m, 1H), 2.64 (t, J=8.0 Hz, 2H), 1.68-1.53 (m, 5H), 1.45 (s, 9H), 1.36-1.17 (m, 10H), 0.86 (t, J=7.1 Hz, 3H); $^{13}$C NMR (126 MHz, CDCl$_3$) δ 180.0, 168.4, 154.9, 146.7, 129.0, 127.5, 124.0, 80.5, 44.3, 36.0, 31.9, 31.3, 29.5, 29.3, 29.3, 28.4, 22.7, 20.2, 14.2.

(S)-1-(3-(4-octylphenyl)-1,2,4-oxadiazol-5-yl)ethanamine (47b)

This compound was synthesized using general procedure 1 (89% yield). $^1$H NMR (500 MHz, CDCl$_3$) δ 8.06-7.89 (m, 2H), 7.35-7.19 (m, 2H), 4.33 (q, J=6.9 Hz, 1H), 2.70-2.55 (m, 2H), 1.81 (br s, 2H), 1.66-1.52 (m, 5H), 1.36-1.17 (m, 10H), 0.86 (t, J=7.0 Hz, 3H); $^{13}$C NMR (126 MHz, CDCl$_3$) δ 183.0, 168.3, 146.6, 129.0, 127.5, 124.2, 45.0, 36.0, 32.0, 31.3, 29.5, 29.4, 29.3, 22.7, 21.8, 14.2.

Compound (47c)

This compound was synthesized using general procedure K (81% yield). $^1$H NMR (500 MHz, CDCl$_3$) δ 11.50 (br s, 1H), 8.97 (d, J=8.1 Hz, 1H), 8.00-7.92 (m, 2H), 7.30-7.23 (m, 2H), 5.82-5.72 (m, 1H), 2.70-2.55 (m, 2H), 1.71-1.36 (m, 5H), 1.51 (s, 9H), 1.47 (s, 9H), 1.36-1.10 (m, 10H), 0.86 (t, J=7.0 Hz, 3H); $^{13}$C NMR (126 MHz, CDCl$_3$) δ 179.2, 168.5, 163.4, 155.7, 153.1, 146.7, 129.0, 127.6, 124.0, 83.7, 79.7, 43.8, 36.0, 32.0, 31.3, 29.5, 29.3, 28.3, 28.2, 22.7, 20.1, 14.2.

(S)-amino((1-(3-(4-octylphenyl)-1,2,4-oxadiazol-5-yl)ethyl)amino)methaniminium chloride (47)

This compound was synthesized using general procedure J (82% yield). $^1$H NMR (500 MHz, CD$_3$OD) δ 7.96 (d, J=8.1 Hz, 2H), 7.32 (d, J=8.0 Hz, 2H), 5.28-5.14 (m, 1H), 2.75-2.56 (m, 2H), 1.75 (d, J=6.9 Hz, 3H), 1.68-1.56 (m, 2H), 1.39-1.17 (m, 10H), 0.88 (t, J=6.8 Hz, 3H); $^{13}$C NMR (126 MHz, CD$_3$OD) δ 178.5, 168.4, 157.3, 147.0, 128.8, 127.1, 123.8, 45.2, 35.6, 31.7, 31.1, 29.2, 29.1, 29.0, 22.4, 18.0, 13.1; HRMS (ESI+) m/z calcd for C$_{19}$H$_{30}$N$_5$O [M+H]$^+$ 344.2450. found 344.2407.

Compound 48

(S)-tert-butyl (2-methyl-1-(3-(4-octylphenyl)-1,2,4-oxadiazol-5-yl)propyl)carbamate (48a)

This compound was synthesized using general procedure L (77% yield). $^1$H NMR (500 MHz, CDCl$_3$) δ 7.97 (d, J=8.1 Hz, 2H), 7.27 (d, J=8.1 Hz, 2H), 5.28-5.17 (m, 1H), 5.01-4.92 (m, 1H), 2.68-2.60 (m, 2H), 2.33-2.17 (m, 1H), 1.67-1.53 (m, 2H), 1.45 (s, 9H), 1.34-1.16 (m, 10H), 0.98 (d, J=6.8 Hz, 6H), 0.87 (t, J=6.9 Hz, 3H); $^{13}$C NMR (126 MHz, CDCl$_3$) δ 178.9, 168.3, 155.4, 146.7, 129.0, 127.5, 124.1, 80.4, 53.7, 36.0, 32.9, 31.9, 31.3, 29.5, 29.3, 28.4, 22.7, 18.7, 18.0, 14.2.

(S)-2-methyl-1-(3-(4-octylphenyl)-1,2,4-oxadiazol-5-yl)propan-1-amine (48b)

This compound was synthesized using general procedure I (59% yield). $^1$H NMR (500 MHz, CDCl$_3$) δ 8.01-7.92 (m, 2H), 7.30-7.19 (m, 2H), 4.00 (d, J=5.8 Hz, 1H), 2.61 (t, J=8.0 Hz, 2H), 2.23-2.11 (m, 1H), 1.73 (br s, 2H), 1.66-1.53 (m, 2H), 1.38-1.16 (m, 10H), 1.03-0.91 (m, 6H), 0.85 (t, J=7.0 Hz, 3H); $^{13}$C NMR (126 MHz, CDCl$_3$) δ 182.2, 168.1, 146.6, 129.0, 127.5, 124.2, 55.1, 36.0, 33.6, 31.9, 31.3, 29.5, 29.3, 22.7, 19.0, 17.9, 14.2.

Compound (48c)

This compound was synthesized using general procedure K (43% yield). $^1$H NMR (500 MHz, CDCl$_3$) δ 11.51 (br s, 1H), 9.05 (d, J=8.5 Hz, 1H), 7.98 (d, J=7.3 Hz, 2H), 7.26 (d, J=7.6 Hz, 2H), 5.59-5.55 (m, 1H), 2.64 (t, J=7.6 Hz, 2H), 2.43-2.35 (m, 1H), 1.66-1.57 (m, 2H), 1.52 (s, 9H), 1.44 (s, 9H), 1.34-1.19 (m, 10H), 1.05-0.99 (m, 6H), 0.86 (t, J=6.5 Hz, 3H); $^{13}$C NMR (126 MHz, CDCl$_3$) δ 178.2, 168.3, 163.4, 156.3, 153.2, 146.6, 129.0, 127.6, 124.2, 83.6, 79.6, 53.1, 36.0, 32.4, 31.9, 31.3, 29.5, 29.3, 29.3, 28.3, 28.2, 22.7, 18.6, 18.1, 14.2.

(S)-amino((2-methyl-1-(3-(4-octylphenyl)-1,2,4-oxadiazol-5-yl)propyl)amino)methaniminium chloride (48)

This compound was synthesized using general procedure J (80% yield). $^1$H NMR (500 MHz, CD$_3$OD) δ 7.96 (d, J=8.1 Hz, 2H), 7.32 (d, J=8.0 Hz, 2H), 5.08-4.99 (m, 1H), 2.65 (t, J=7.9 Hz, 2H), 2.51-2.40 (m, 1H), 1.68-1.56 (m, 2H), 1.38-1.19 (m, 10H), 1.07 (dd, J=15.1, 6.8 Hz, 6H), 0.87 (t, J=6.8 Hz, 3H); $^{13}$C NMR (126 MHz, CD$_3$OD) δ 177.4, 168.4, 157.9, 147.0, 128.9, 127.1, 123.7, 54.7, 35.6, 32.4, 31.7, 31.1, 29.2, 29.1, 29.0, 22.4, 17.6, 16.9, 13.1; HRMS (ESI+) m/z calcd for C$_{21}$H$_{34}$N$_5$O [M+H]$^+$ 372.2763. found 372.2773.

Compound 49

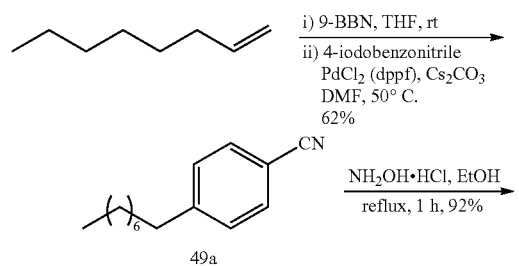
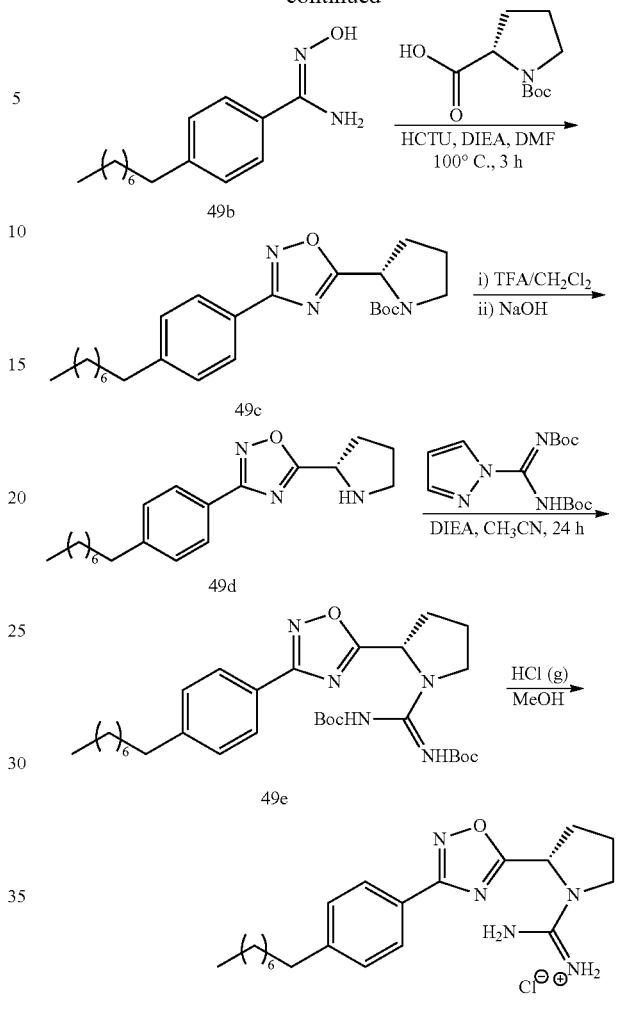

4-octylbenzonitrile (49a)

Oct-1-ene (3 mL, 19.2 mmol) was added to a round bottom flask containing THF (8 mL). 9-BBN (42 mL, 21.0 mmol) was added as a 0.5 M solution in THF and the solution stirred overnight at r.t. To the above borane solution was added a solution of 4-iodobenzonitrile (4 g, 17.5 mmol) in DMF (50 mL). The reaction mixture was degassed for 10 min by bubbling N$_2$ through the solution. Cs$_2$CO$_3$ (11.4 g, 34.9 mmol) and PdCl$_2$(dppf) (383 mg, 0.52 mmol) were added together. The reaction mixture was stirred at 70° C. for 10 h. It was poured into a solution of LiBr and extracted 3× with hexanes. The combined organic extracts were washed with brine, dried over Na$_2$SO$_4$, and concentrated under reduced pressure. The resulting residue was purified by column chromatography over silica gel (95/5 EtOAc/hexanes) to give the title compound (2.3 g, 62%) as a colorless oil. $^1$H NMR (500 MHz, CDCl$_3$) δ 7.54 (d, J=8.1 Hz, 2H), 7.26 (d, J=8.1 Hz, 2H), 2.64 (t, J=7.8 Hz, 2H), 1.69-1.53 (m, 2H), 1.36-1.18 (m, 10H), 0.86 (t, J=6.9 Hz, 3H); $^{13}$C NMR (126 MHz, CDCl$_3$) δ 148.7, 132.2, 129.3, 119.3, 109.6, 36.2, 32.0, 31.1, 29.5, 29.3, 29.2, 22.7, 14.2.

(Z)—N'-hydroxy-4-octylbenzimidamide (49b)

Triethylamine (3.9 mL, 27.8 mmol) and hydroxylamine hydrochloride (1.7 g, 24.5 mmol) were added to a solution of 49a (2.4 g, 11.1 mmol) in 95% ethanol (30 mL). The reaction mixture was refluxed for 2 h. The organic solvent was removed under reduced pressure and the residue was purified by column chromatography on silica gel (65/35 hexanes/EtOAc) to give the title compound (2.5 g, 92%) as a white solid. $^1$H NMR (500 MHz, CDCl$_3$) δ 9.32 (br s, 1H), 7.54 (d, J=8.1 Hz, 2H), 7.19 (d, J=8.0 Hz, 2H), 4.95 (br s, 2H), 2.61 (t, J=7.8 Hz, 2H), 1.66-1.55 (m, 2H), 1.38-1.18 (m, 10H), 0.89 (t, J=6.9 Hz, 3H); $^{13}$C NMR (126 MHz, CDCl$_3$) δ 152.8, 145.2, 129.8, 128.8, 125.9, 35.9, 32.0, 31.4, 29.6, 29.4, 29.3, 22.8, 14.2.

(S)-tert-butyl 2-(3-(4-octylphenyl)-1,2,4-oxadiazol-5-yl)pyrrolidine-1-carboxylate (49c)

This compound was synthesized using general procedure L (48% yield). $^1$H NMR (500 MHz, CDCl$_3$) δ 7.96 (d, J=7.8 Hz, 2H), 7.33-7.18 (m, 2H), 5.21-5.14 (m, 1H, minor rotamer), 5.07-5.01 (m, 1H, major rotamer), 3.75-3.67 (m, 1H, major rotamer), 3.67-3.61 (m, 1H, minor rotamer), 3.59-3.50 (m, 1H, major rotamer), 3.50-3.41 (m, 1H, minor rotamer), 2.66-2.58 (m, 2H), 2.44-2.25 (m, 1H), 2.20-2.05 (m, 2H), 2.05-1.89 (m, 1H), 1.68-1.54 (m, 2H), 1.44 (s, 3H), 1.37-1.16 (m, 16H), 0.85 (t, J=6.8 Hz, 3H); $^{13}$C NMR (126 MHz, CDCl$_3$, rotamers) δ 180.5 (major), 180.1 (minor), 168.5 (major), 154.3 (minor), 153.6 (major), 146.7 (major), 146.4 (minor), 129.0 (major), 128.9 (minor), 127.5 (minor), 127.5 (major), 124.4 (minor), 124.2 (major), 80.5 (major), 80.4 (minor), 53.9 (major), 46.7 (minor), 46.4 (major), 36.0 (major), 32.5 (major), 32.0 (major), 31.6 (minor), 31.3 (major), 29.5 (major), 29.3 (major), 29.2 (major), 28.5 (minor), 28.2 (major), 24.4 (minor), 23.8 (major), 22.7 (major), 14.2 (major).

(S)-3-(4-octylphenyl)-5-(pyrrolidin-2-yl)-1,2,4-oxadiazole (49d)

This compound was synthesized using general procedure 1 (82% yield). $^1$H NMR (500 MHz, CDCl$_3$) δ 8.01-7.87 (m, 2H), 7.25-7.18 (m, 2H), 4.46 (dd, J=8.3, 5.6 Hz, 1H), 3.20-3.09 (m, 1H), 3.09-2.94 (m, 1H), 2.60 (t, J=8.0 Hz, 2H), 2.34 (br s, 1H), 2.29-2.17 (m, 1H), 2.14-2.00 (m, 1H), 1.96-1.76 (m, 2H), 1.65-1.51 (m, 2H), 1.34-1.13 (m, 10H), 0.83 (t, J=7.0 Hz, 3H); $^{13}$C NMR (126 MHz, CDCl$_3$) δ 181.9, 168.2, 146.5, 128.9, 127.5, 124.2, 54.4, 46.9, 36.0, 31.9, 31.3, 31.2, 29.5, 29.3, 29.3, 25.4, 22.7, 14.2; HRMS (ESI+) m/z calcd for C$_{20}$H$_{30}$N$_3$O [M+H]$^+$ 328.2389. found 328.2354.

(S)-tert-butyl (((tert-butoxycarbonyl)imino)(2-(3-(4-octylphenyl)-1,2,4-oxadiazol-5-yl)pyrrolidin-1-yl)methyl)carbamate (49e)

This compound was synthesized using general procedure K (66% yield). $^1$H NMR (500 MHz, CDCl$_3$) δ 7.96 (d, J=8.2 Hz, 2H), 7.26 (d, J=8.0 Hz, 2H), 5.62-5.54 (m, 1H), 3.93-3.83 (m, 1H), 3.83-3.71 (m, 1H), 2.64 (t, J=7.9 Hz, 2H), 2.48-2.36 (m, 1H), 2.30-2.09 (m, 2H), 2.08-1.98 (m, 1H), 1.95-1.86 (m, 1H), 1.67-1.57 (m, 2H), 1.54-1.18 (m, 28H), 0.86 (t, J=7.0 Hz, 3H); $^{13}$C NMR (101 MHz, CDCl$_3$) δ 178.7, 168.3, 161.9, 153.5, 150.3, 146.5, 128.8, 127.4, 123.9, 82.2, 79.5, 55.3, 49.4, 35.9, 31.8, 31.2, 29.4, 29.2, 28.1, 23.9, 22.6, 14.1; HRMS (ESI+) m/z calcd for C$_{31}$H$_{48}$N$_5$O$_5$ [M+H]$^+$ 570.3655. found 570.3605.

(S)-amino(2-(3-(4-octylphenyl)-1,2,4-oxadiazol-5-yl)pyrrolidin-1-yl) methaniminium chloride (49)

This compound was synthesized using general procedure D (80% yield). $^1$H NMR (500 MHz, CD$_3$OD) δ 7.94 (d, J=8.2 Hz, 2H), 7.33 (d, J=8.2 Hz, 2H), 5.50-5.38 (m, 1H), 3.80-3.70 (m, 1H), 3.67-3.54 (m, 1H), 2.70-2.39 (m, 4H), 2.28-2.16 (m, 1H), 2.16-1.98 (m, 1H), 1.70-1.55 (m, 2H), 1.39-1.15 (m, 10H), 0.88 (t, J=6.9 Hz, 3H); $^{13}$C NMR (126 MHz, CD3OD) δ 177.5, 168.4, 155.8, 147.0, 128.8, 127.1, 123.6, 55.1, 35.5, 31.7, 31.4, 31.1, 29.2, 29.0, 28.9, 23.0, 22.4, 13.1; HRMS (ESI+) m/z calcd for C$_{21}$H$_3$ 2N$_5$O [M+H]$^+$ 370.2601. found 370.2607.

Compound 50

The synthesis of compound 50 ((R)-2-(3-(4-octylphenyl)-1,2,4-oxadiazol-5-yl)pyrrolidine-1-carboximidamide) is similar to the synthesis of 49 except that D-Boc-proline was used as starting material. Characterization of intermediates is shown below.

(R)-tert-butyl 2-(3-(4-octylphenyl)-1,2,4-oxadiazol-5-yl)pyrrolidine-1-carboxylate (50c)

This compound was synthesized using general procedure L (73% yield). $^1$H NMR (400 MHz, CDCl$_3$) δ 7.95 (d, J=7.9 Hz, 2H), 7.26 (d, J=8.0 Hz, 2H), 5.20-5.14 (m, 1H, minor rotamer), 5.07-5.00 (m, 1H, major rotamer), 3.76-3.65 (m, 1H, major rotamer), 3.65-3.59 (m, 1H, minor rotamer), 3.58-3.48 (m, 1H, major rotamer), 3.48-3.41 (m, 1H, minor rotamer), 2.63 (t, J=7.5 Hz, 2H), 2.44-2.25 (m, 1H), 2.21-2.04 (m, 2H), 2.02-1.87 (m, 1H), 1.69-1.53 (m, 2H), 1.44 (s, 3H), 1.34-1.15 (m, 16H), 0.85 (t, J=6.8 Hz, 3H); $^{13}$C NMR (101 MHz, CDCl$_3$, rotamers) δ 180.4 (major), 180.0 (minor), 171.0 (minor), 168.3 (major), 154.2 (minor), 153.5 (major), 146.5 (major), 146.3 (minor), 128.9 (major), 128.7 (minor), 127.4 (major), 127.3 (major), 124.2 (minor), 124.1 (major), 80.4 (major), 80.2 (minor), 60.3 (major), 53.8 (major), 46.6 (minor), 46.3 (major), 35.9 (major), 32.4 (major), 31.8 (major), 31.5 (minor), 31.2 (major), 29.4 (major), 29.2 (major), 29.2 (major), 28.4 (minor), 28.1 (major), 24.3 (minor), 23.7 (major), 22.6 (major), 21.0 (minor), 14.2 (minor), 14.1 (major); HRMS (ESI+) m/z calcd for C$_{25}$H$_{38}$N$_3$O$_3$ [M+H] 428.2913. found 428.2908.

(R)-3-(4-octylphenyl)-5-(pyrrolidin-2-yl)-1,2,4-oxadiazole (50d)

This compound was synthesized using general procedure 1 (99% yield). $^1$H NMR (500 MHz, CD$_3$OD) δ 7.97 (d, J=8.0 Hz, 2H), 7.32 (d, J=7.6 Hz, 2H), 4.65-4.44 (m, 1H), 3.34 (s, 1H), 3.12-3.18 (m, 2H), 2.67 (t, J=7.6 Hz, 2H), 2.35-2.31 (m, 1H), 2.18-2.14 (m, 1H), 2.05-1.91 (m, 2H), 1.68-1.62 (m, 2H), 1.38-1.25 (m, 10H), 0.90 (t, J=6.8 Hz, 3H); $^{13}$C NMR (126 MHz, CD$_3$OD) δ 182.8, 169.4, 148.0, 130.1, 128.4, 125.4, 55.3, 47.6, 36.9, 33.0, 32.4, 31.9, 30.6, 30.4, 30.4, 26.4, 23.7, 14.5; HRMS (ESI+) m/z calcd for C$_{20}$H$_{30}$N$_3$O [M+H]$^+$ 328.2389. found 328.2383.

(R)-tert-butyl (((tert-butoxycarbonyl)imino)(2-(3-(4-octylphenyl)-1,2,4-oxadiazol-5-yl)pyrrolidin-1-yl)methyl)carbamate (50e)

This compound was synthesized using general procedure K (55% yield). $^1$H NMR (500 MHz, CDCl$_3$) δ 10.10 (br s, 1H), 7.99 (d, J=8.2 Hz, 2H), 7.29 (d, J=8.2 Hz, 2H), 5.71-5.53 (m, 1H), 3.98-3.87 (m, 1H), 3.84-3.80 (m, 1H), 2.75-2.63 (m, 2H), 2.48-2.44 (m, 1H), 2.35-2.13 (m, 2H), 2.08-2.04 (m, 1H), 1.74-1.61 (m, 2H), 1.48 (s, 18H), 1.38-1.21 (m, 10H), 0.89 (t, J=7.0 Hz, 3H); $^{13}$C NMR (126 MHz, CDCl$_3$) δ 178.8, 168.4, 146.5, 129.6, 128.9, 127.5, 124.0, 82.2, 79.6, 55.3, 49.4, 36.0, 31.9, 31.4, 31.2, 29.7, 29.4, 29.2, 28.1, 23.9, 22.6, 14.1; HRMS (ESI+) m/z calcd for C$_{31}$H$_{48}$N$_5$O$_5$ [M+H]$^+$ 570.3655. found 570.3662.

(R)-amino(2-(3-(4-octylphenyl)-1,2,4-oxadiazol-5-yl)pyrrolidin-1-yl)methaniminium chloride (50)

This compound was synthesized using general procedure J (99% yield). $^1$H NMR (400 MHz, CD$_3$OD) δ 7.94 (d, J=7.8 Hz, 2H), 7.32 (d, J=7.9 Hz, 2H), 5.46-5.42 (m, 1H), 3.79-3.75 (m, 1H), 3.65-3.61 (m, 1H), 2.66 (t, J=7.5 Hz, 2H), 2.53-2.49 (m, 2H), 2.23-2.19 (m, 1H), 2.10-2.06 (m, 1H), 1.65-1.61 (m, 2H), 1.38-1.26 (m, 10H), 0.88 (t, J=6.7 Hz, 3H); $^{13}$C NMR (126 MHz, CD$_3$OD) δ 178.9, 169.7, 157.1, 148.4, 130.2, 128.5, 125.0, 56.6, 36.9, 33.0, 32.8, 32.4, 30.6, 30.4, 30.3, 24.4, 23.7, 14.5; HRMS (ESI+) m/z calcd for C$_{21}$H$_{32}$N$_5$O [M+H]$^+$ 370.2601. found 370.2596.

Compounds 51 and 52

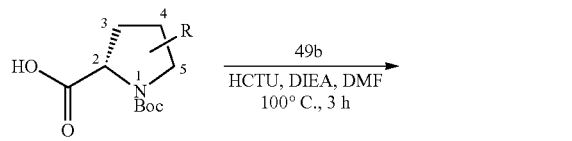

51a: R = (4R)-OH
52a: R = (3S)-OH

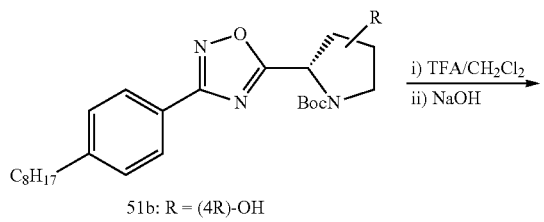

51b: R = (4R)-OH
52b: R = (3S)-OH

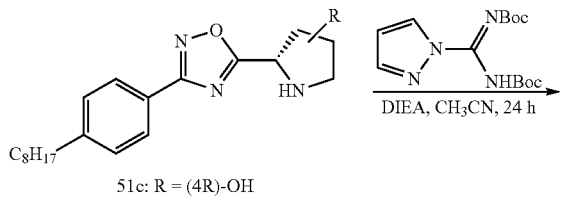

51c: R = (4R)-OH
52c: R = (3S)-OH

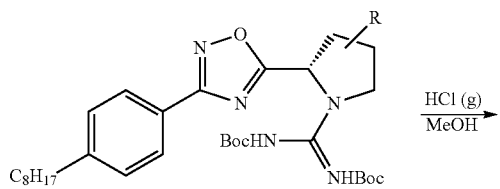

51d: R = (4R)-OH
52c: R = (3S)-OH

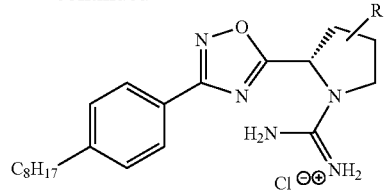

51: R = (4R)-OH
52: R = (3S)-OH (2S,4R)-tert-butyl 4-hydroxy-2-(3-(4-octylphenyl)-1,2,4-oxadiazol-5-yl)pyrrolidine-1-carboxylate (51b)

This compound was synthesized using general procedure L (63% yield). $^1$H NMR (500 MHz, CDCl$_3$) δ 7.99 (d, J=7.9 Hz, 2H), 7.31 (d, J=7.9 Hz, 2H), 5.42-5.30 (m, 1H, minor rotamer), 5.20-5.13 (m, 1H, major rotamer), 4.74-4.56 (m, 1H), 3.89-3.79 (m, 1H), 3.77-3.69 (m, 1H, major rotamer), 3.64-3.53 (m, 1H, minor rotamer), 2.74-2.61 (m, 2H), 2.59-2.40 (m, 1H), 2.38-2.28 (m, 1H), 1.74-1.58 (m, 2H), 1.56-1.16 (m, 19H), 0.90 (t, J=7.0 Hz, 3H); $^{13}$C NMR (126 MHz, CDCl$_3$, rotamers) δ 180.3 (major), 168.5 (major), 153.8 (major), 146.7 (major), 146.5 (minor), 129.0 (major), 128.8 (minor), 127.4 (major), 125.8 (minor), 123.9 (major), 81.0 (major), 80.8 (minor), 69.9 (minor), 69.3 (major), 54.8 (major), 52.6 (major), 40.9 (major), 40.2 (minor), 36.0 (major), 31.9 (major), 31.2 (major), 29.4 (major), 29.3 (major), 29.2 (major), 28.3 (minor), 28.1 (major), 22.7 (major), 14.1 (major).

(3R,5S)-5-(3-(4-octylphenyl)-1,2,4-oxadiazol-5-yl)pyrrolidin-3-ol (51c)

This compound was synthesized using general procedure 1 (80% yield). $^1$H NMR (500 MHz, CDCl$_3$) δ 7.89 (d, J=8.2 Hz, 2H), 7.19 (d, J=8.2 Hz, 2H), 4.79-4.63 (m, 1H), 4.57-4.43 (m, 1H), 3.22-3.10 (m, 1H), 3.08-2.95 (m, 1H), 2.77 (br s, 2H), 2.56 (t, J=7.7 Hz, 2H), 2.35-2.18 (m, 2H), 1.63-1.48 (m; 2H), 1.33-1.10 (m, 10H), 0.80 (t, J=6.9 Hz, 3H); $^{13}$C NMR (126 MHz, CDCl$_3$) δ 181.3, 168.3, 146.6, 128.9, 127.4, 124.0, 72.2, 55.4, 53.0, 40.7, 36.0, 31.9, 31.2, 29.4, 29.3, 29.2, 22.7, 14.1.

tert-butyl (((tert-butoxycarbonyl)imino)((2S,4R)-4-hydroxy-2-(3-(4-octylphenyl)-1,2,4-oxadiazol-5-yl)pyrrolidin-1-yl)methyl)carbamate (51d)

This compound was synthesized using general procedure K (53% yield). $^1$H NMR (500 MHz, CDCl$_3$) δ 7.99 (d, J=8.3 Hz, 2H), 7.29 (d, J=8.3 Hz, 2H), 5.83 (t, J=8.2 Hz, 1H), 4.72-4.59 (m, 1H), 4.05 (dd, J=12.5, 3.5 Hz, 1H), 3.85-3.69 (m, 1H), 2.67 (t, J=7.6 Hz, 2H), 2.63-2.53 (m, 1H), 2.45-2.32 (m, 1H), 1.74-1.60 (m; 2H), 1.47 (s, 18H), 1.39-1.24 (m, 10H), 0.90 (t, J=7.0 Hz, 3H); $^{13}$C NMR (126 MHz,) δ 178.5, 168.5, 154.1, 146.6, 128.9, 127.5, 124.0, 69.3, 58.0, 53.7, 40.0, 36.0, 31.9, 31.2, 29.7, 29.4, 29.2, 28.1, 22.7, 14.1.

amino((2S,4R)-4-hydroxy-2-(3-(4-octylphenyl)-1,2,4-oxadiazol-5-yl)pyrrolidin-1-yl)methaniminium chloride (51)

This compound was synthesized using general procedure J as a white solid (79% yield). $^1$H NMR (500 MHz, CD$_3$OD)

δ 8.01-7.93 (m, 2H), 7.41-7.31 (m, 2H), 5.66-5.54 (m, 1H), 4.67-4.58 (m, 1H), 3.96-3.85 (m, 1H), 3.65-3.58 (m, 1H), 2.74-2.61 (m, 3H), 2.58-2.49 (m, 1H), 1.73-1.61 (m, 2H), 1.42-1.24 (m, 10H), 0.91 (t, J=7.0 Hz, 3H); $^{13}$C NMR (126 MHz, CD$_3$OD) δ 178.9, 169.8, 157.7, 148.4, 130.2, 128.4, 124.9, 69.8, 57.1, 54.9, 41.1, 36.9, 33.0, 32.4, 30.5, 30.4, 30.3, 23.7, 14.5; HRMS (ESI+) m/z calcd for C$_{21}$H$_{32}$N$_5$O$_2$ [M+H]$^+$ 386.2556. found 386.2596.

Compound 52

(2S,3S)-tert-butyl-3-hydroxy-2-(3-(4-octylphenyl)-1,2,4-oxadiazol-5-yl)pyrrolidine-1-carboxylate (52b)

DIEA (0.1 mL, 1.05 mmol) was added to a solution of (2S,3S)-1-(tert-butoxycarbonyl)-3-hydroxypyrrolidine-2-carboxylic acid 5 (163 mg, 0.70 mmol) and (Z)—N'-hydroxy-4-octylbenzimidamide 4 (146 mg, 0.58 mmol) in DMF (3 mL). HCTU (366 mg, 0.88 mmol) was then added to the resulting mixture at r.t. and stirred at 100° C. for 3 hours. At this time, TLC showed complete conversion of starting material. The solution was partitioned between ethyl acetate and LiBr aqueous solution. The aqueous solution was extracted with ethyl acetate and the combined organic layers were washed with brine, dried over Na$_2$SO$_4$ and concentrated via vacuum. The residue was purified by silica gel column chromatography (15%, ethyl acetate/hexanes) to yield 52b (113 mg, 46%) as a yellow oil. $^1$H NMR (500 MHz, CDCl$_3$) δ 7.95 (d, J=8.0 Hz, 2H), 7.28 (d, J=8.0 Hz, 2H), 4.96 (s, 1H), 4.56 (s, 1H), 3.82-3.68 (m, 2H), 2.69-2.59 (m, 2H), 2.35-2.27 (m, 1H), 2.07-2.00 (m, 1H), 1.66-1.58 (m, 2H), 1.46 (s, 3H), 1.36-1.21 (m, 16H), 0.87 (t, J=7.0 Hz, 3H); $^{13}$C NMR (126 MHz, CDCl$_3$) δ 178.34, 168.60, 153.96, 146.91, 129.10, 128.98, 127.54, 123.92, 80.96, 76.11, 62.47, 44.46, 36.09, 32.22, 31.98, 31.33, 29.55, 29.39, 29.35, 28.52, 28.26, 22.77, 14.21.

(2S,3S)-2-(3-(4-octylphenyl)-1,2,4-oxadiazol-5-yl)pyrrolidin-3-ol (52c)

TFA (0.1 mL, 1.16 mmol) was added to a solution of (2S,3S)-tert-butyl-3-hydroxy-2-(3-(4-octylphenyl)-1,2,4-oxadiazol-5-yl)pyrrolidine-1-carboxylate 6 (50 mg, 0.11 mmol) in CH$_2$Cl$_2$ (0.6 mL). The reaction mixture was then stirred at r.t. overnight. At this time, TLC showed complete conversion of starting material. The organic solvent was removed under reduced pressure. Some water was added to the flask then the aqueous solution was adjusted to pH 14 by adding 10% NaOH solution. The resulting solution was then extracted with ether and the combined organic layers were washed with brine, dried over Na$_2$SO$_4$, filtered, and concentrated via vacuum to provide 52c (23 mg, 59%) as a clear oil without further purification. $^1$H NMR (500 MHz, CDCl$_3$) δ 7.97 (d, J=8.0 Hz, 2H), 7.27 (d, J=7.4 Hz, 2H), 4.70 (s, 1H), 3.35 (s, 1H), 2.74-2.52 (m, 2H), 2.43-2.17 (m, 3H), 1.97 (s, 1H), 1.72-1.49 (m, 2H), 1.43-1.13 (m, 10H), 0.87 (t, J=6.9 Hz, 3H); $^{13}$C NMR (126 MHz, CDCl$_3$) δ 179.44, 168.41, 146.80, 129.04, 127.58, 123.97, 76.52, 63.27, 45.08, 36.10, 34.37, 32.00, 31.34, 29.57, 29.41, 29.37, 22.79, 14.23; HRMS (ESI+): Calcd for C$_{20}$H$_{30}$N$_3$O$_2$ [M+H]: 344.2338. Found: 344.2338.

(E)-tert-butyl(((tert-butoxycarbonyl)amino)((2S,3S)-3-hydroxy-2-(3-(4-octylphenyl)-1,2,4-oxadiazol-5-yl)pyrrolidin-1-yl)methylene)carbamate (52d)

This compound was synthesized using general procedure K to yield 52d (32 mg, 89%). $^1$H NMR (500 MHz, CDCl$_3$) δ 7.95 (d, J=8.2 Hz, 2H), 7.25 (d, J=7.9 Hz, 2H), 5.52 (s, 1H), 4.64 (s, 1H), 4.06-3.86 (m, 2H), 2.63 (t, J=7.1 Hz, 2H), 2.38-2.30 (m, 1H), 2.17-2.05 (m, 1H), 1.68-1.57 (m, 2H), 1.49-1.40 (m, 18H), 1.33-1.23 (m, 10H), 0.87 (t, J=7.0 Hz, 3H); $^{13}$C NMR (101 MHz, CDCl$_3$) δ 177.10, 168.84, 147.17, 129.34, 127.95, 124.17, 75.14, 63.85, 47.41, 36.42, 32.32, 31.67, 30.16, 29.89, 29.71, 29.70, 28.54, 23.11, 14.56; HRMS (ESI+): Calcd for C$_{31}$H$_{48}$N$_5$O$_6$ [M+H]: 586.3604. Found: 586.3569.

amino((1S,3S)-3-hydroxy-2-(3-(4-octylphenyl)-1,2,4-oxadiazol-5-yl)pyrrolidin-1-yl)methaniminium chloride (52)

This compound was synthesized using general procedure J as a white solid (4.5 mg, 52% yield). $^1$H NMR (500 MHz, Methanol-d$_4$) δ 7.97 (d, J=8.2 Hz, 2H), 7.36 (d, J=8.2 Hz, 2H), 5.24 (s, 1H), 4.80 (d, J=3.2 Hz, 1H), 3.85-3.82 (m, 2H), 2.70 (t, J=7.2 Hz, 2H), 2.30-2.14 (m, 2H), 1.72-1.60 (m, 2H), 1.44-1.22 (m, 10H), 0.91 (t, J=6.9 Hz, 3H); $^{13}$C NMR (126 MHz, Methanol-d$_4$) δ 176.65, 169.74, 157.51, 148.36, 130.07, 128.38, 124.74, 75.96, 64.08, 47.34, 36.84, 32.98, 32.48, 32.40, 30.51, 30.35, 30.30, 23.67, 14.39; HRMS (ESI+): Calcd for C$_{21}$H$_{32}$N$_5$O$_2$ [M+H]: 386.2556. Found: 386.2576.

Compound 53

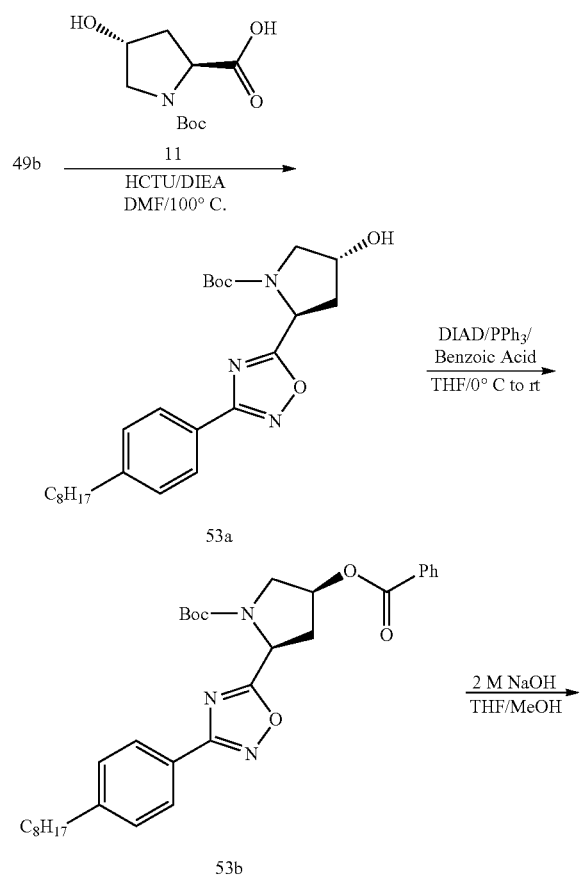

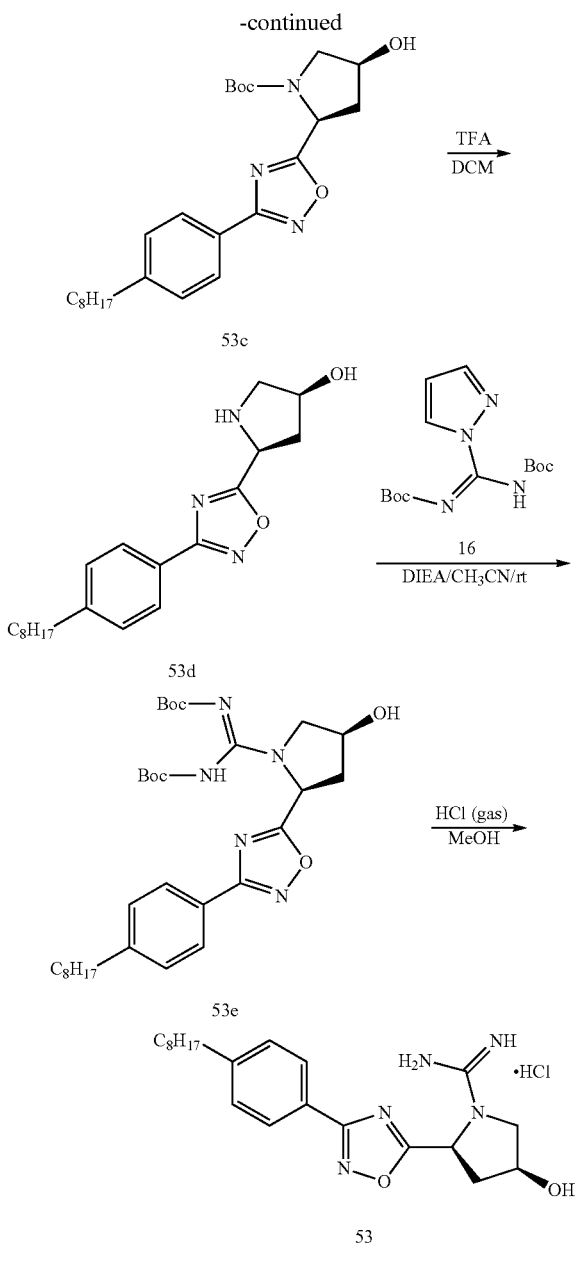

(2S,4R)-tert-butyl-4-hydroxy-2-(3-(4-octylphenyl)-1,2,4-oxadiazol-5-yl)pyrrolidine-1-carboxylate (53a)

This compound was synthesized using general procedure L to yield 53a (500 mg, 77%) as an oil. $^1$H NMR (500 MHz, CDCl$_3$) δ 7.96 (d, J=7.9 Hz, 2H), 7.28 (d, J=8.0 Hz, 2H), 5.23 (t, J=7.8 Hz, 1H), 4.66-4.61 (m, 1H), 3.88-3.63 (m, 2H), 2.70-2.60 (m, 2H), 2.53-2.43 (m, 1H), 2.37-2.21 (m, 1H), 1.65-1.59 (m, 2H), 1.44 (s, 3H), 1.34-1.21 (m, 16H), 0.87 (t, J=7.0 Hz, 3H); $^{13}$C NMR (126 MHz, CDCl$_3$) δ 180.39, 168.61, 153.96, 146.82, 129.09, 127.51, 124.06, 81.11, 69.40, 54.89, 52.69, 41.04, 36.09, 31.98, 31.34, 29.56, 29.41, 29.35, 28.22, 22.78, 14.22; HRMS (ESI+): Calcd for C$_{25}$H$_{37}$N$_3$O$_4$Na [M+Na]: 466.2681. Found: 466.2646.

(2S,4S)-tert-butyl-4-(benzoyloxy)-2(3(4-octylphenyl)-1,2,4-oxadiazol-5-yl)pyrrolidine-1-carboxylate (53b)

PPh$_3$ (112 mg, 0.43 mmol), benzoic acid (52 mg, 0.43 mmol), and (2S,4R)-tert-butyl-4-hydroxy-2-(3-(4-octylphenyl)-1,2,4-oxadiazol-5-yl)pyrrolidine-1-carboxylate 53a were added to THF (1.0 mL) at r.t. The solution was cooled to 0° C. and DIAD (0.08 mL, 0.43 mmol) was added dropwise. The solution was warmed to r.t. and stirred overnight. At this time, TLC showed conversion of starting material. The organic solvent was removed under reduced pressure, the residue was purified by silica gel column chromatography (15%, ethyl acetate/hexanes) to yield 53b (120 mg, 75%) as an oil. $^1$H NMR (500 MHz, CDCl$_3$) δ 7.93 (d, J=7.8 Hz, 2H), 7.77 (d, J=7.6 Hz, 1H), 7.71 (d, J=7.5 Hz, 1H), 7.36 (t, J=7.9 Hz, 1H), 7.24 (t, J=7.8 Hz, 2H), 7.13 (t, J=7.0 Hz, 2H), 5.65 (s, 1H), 5.28 (d, J=8.3 Hz, 1H), 4.00-3.80 (m, 2H), 2.80-2.63 (m, 4H), 1.67-1.60 (m, 2H), 1.51 (s, 3H), 1.39 (s, 6H), 1.37-1.23 (m, 10H), 0.87 (t, J=6.9 Hz, 3H); $^{13}$C NMR (126 MHz, CDCl$_3$) δ 179.74, 168.48, 165.70, 154.03, 153.44, 146.56, 133.16, 129.66, 129.38, 128.98, 128.84, 128.27, 127.43, 124.08, 81.13, 73.60, 72.38, 53.43, 53.08, 52.56, 37.96, 37.26, 36.02, 31.95, 31.34, 29.53, 29.34, 29.30, 28.46, 28.27, 22.74, 14.20; HRMS (Mixed+): Calcd for C$_{32}$H$_{41}$N$_3$O$_5$Na [M+Na]: 570.2944. Found: 570.2903.

(2S,4S)-tert-butyl-4-hydroxy-2-(3-(4-octylphenyl)-1,2,4-oxadiazol-5-yl)pyrrolidine-1-carboxylate (53c)

(2S,4S)-tert-butyl-4-(benzoyloxy)-2-(3-(4-octylphenyl)-1,2,4-oxadiazol-5-yl)pyrrolidine-1-carboxylate 53b (85 mg, 0.16 mmol) was dissolved in equal parts of methanol (0.38 mL) and THF (0.38 mL) and 2 M NaOH (0.15 mL, 2 M) and stirred for 30 min at r.t. under nitrogen. The solution was partitioned between ethyl acetate and water. The aqueous solution was extracted with ethyl acetate and the combined organic layers were washed with brine, dried over Na$_2$SO$_4$, and concentrated via vacuum to yield 53c (66 mg, 95%) as an oil. $^1$H NMR (500 MHz, CDCl$_3$) δ 7.92 (d, J=8.0 Hz, 2H), 7.27 (d, J=8.3 Hz, 2H), 5.11 (d, J=9.1 Hz, 1H), 4.51 (s, 1H), 3.87-3.63 (m, 2H), 2.64 (t, J=7.5 Hz, 2H), 2.59-2.50 (m, 1H), 2.35-2.25 (m, 1H), 1.66-1.57 (m, 2H), 1.43 (s, 3H), 1.37-1.19 (m, 16H), 0.86 (t, J=7.0 Hz, 3H); $^{13}$C NMR (126 MHz, CDCl$_3$) δ 181.51, 168.14, 153.47, 147.11, 129.11, 129.00, 127.52, 123.37, 81.18, 70.60, 55.99, 52.43, 39.65, 36.06, 31.95, 31.31, 29.53, 29.34, 29.33, 28.25, 22.75, 14.20; HRMS (ESI+): Calcd for C$_{25}$H$_{37}$N$_3$O$_4$Na [M+Na]: 466.2681. Found: 466.2637.

(2S,4S)-2-(3-(4-octylphenyl)-1,2,4-oxadiazol-5-yl)pyrrolidin-4-ol (53d)

This compound was synthesized using general procedure I to provide 53d (187 mg, 48%) as an oil without further purification. $^1$H NMR (500 MHz, CDCl$_3$) δ 7.92 (d, J=8.1 Hz, 2H), 7.25 (d, J=7.6 Hz, 2H), 4.66 (d, J=6.6 Hz, 1H), 4.53 (s, 1H), 3.91 (s, 2H), 3.27 (s, 2H), 2.67-2.60 (m, 2H), 2.56-2.50 (m, 1H), 2.29 (d, J=13.8 Hz, 1H), 1.62 (p, J=7.5 Hz, 2H), 1.38-1.19 (m, 10H), 0.87 (t, J=6.9 Hz, 3H); $^{13}$C NMR (126 MHz, CDCl$_3$) δ 181.11, 168.25, 146.96, 129.07, 127.57, 123.70, 71.95, 55.98, 53.15, 40.19, 36.10, 31.99, 31.32, 29.56, 29.40, 29.36, 22.78, 14.22; HRMS (Mixed+): Calcd for C$_{20}$H$_{30}$N$_3$O$_2$ [M+H]: 344.2338. Found: 344.2315.

(E)-tert-butyl (((tert-butoxycarbonyl)amino)((2S,4S)-4-hydroxy-2-(3-(4-octylphenyl)-1,2,4-oxadiazol-5-yl)pyrrolidin-1-yl)methylene)carbamate (53e)

This compound was synthesized using general procedure K to yield 53e (81 mg, 79%). $^1$H NMR (500 MHz, CDCl$_3$) δ 7.96 (d, J=8.2 Hz, 2H), 7.26 (d, J=8.2 Hz, 2H), 5.81 (t, J=8.2 Hz, 1H), 4.63 (s, 1H), 4.02 (dd, J=12.5 Hz, 1H), 3.79-3.70 (m, 1H), 2.69-2.59 (m, 2H), 2.57 (dd, J=13.3, 7.7 Hz, 1H), 2.41-2.29 (m, 1H), 1:62 (p, J=7.5 Hz, 2H), 1.45 (s, 18H), 1.35-1.20 (m, 10H), 0.87 (t, J=6.9 Hz, 3H); $^{13}$C NMR (100 MHz, CDCl$_3$) δ 167.91, 147.06, 129.09, 129.01, 127.60, 123.45, 77.73, 58.50, 54.05, 36.11, 32.01, 31.36, 29.85, 29.58, 29.39, 28.23, 28.14, 22.81, 14.25; HRMS (ESI+): Calcd for C$_{31}$H$_{48}$N$_5$O$_6$ [M+H]: 586.3604. Found: 586.3603.

amino((1S,4S)-4-hydroxy-2-(3-(4-octylphenyl)-1,2,4-oxadiazol-5-yl)pyrrolidin-1-yl)methaniminium chloride (53)

This compound was synthesized using general procedure J to yield 53 (1.2 mg, 22%) as white solid. $^1$H NMR (500 MHz, Methanol-d$_4$) δ 7.94 (d, J=8.2 Hz, 2H), 7.33 (d, J=8.1 Hz, 2H), 5.39 (dd, J=7.5, 1.8 Hz, 1H), 4.61 (s, 1H), 3.77 (dd, J=10.9, 4.3 Hz, 1H), 3.66-3.55 (m, 1H), 2.73-2.58 (m, 4H), 1.70-1.58 (m, 2H), 1.40-1.21 (m, 10H), 0.89 (t, J=6.9 Hz, 3H); $^{13}$C NMR (126 MHz, Methanol-d$_4$) δ 179.49, 169.61, 148.15, 130.07, 128.38, 125.25, 70.22, 64.42, 57.32, 56.12, 41.26, 36.83, 32.98, 32.40, 30.51, 30.34, 30.29, 23.70, 14.36; HRMS (ESI+): Calcd for C$_{21}$H$_{32}$N$_5$O$_2$ [M+]: 386.2556. Found: 386.2548.

Compounds 54-55

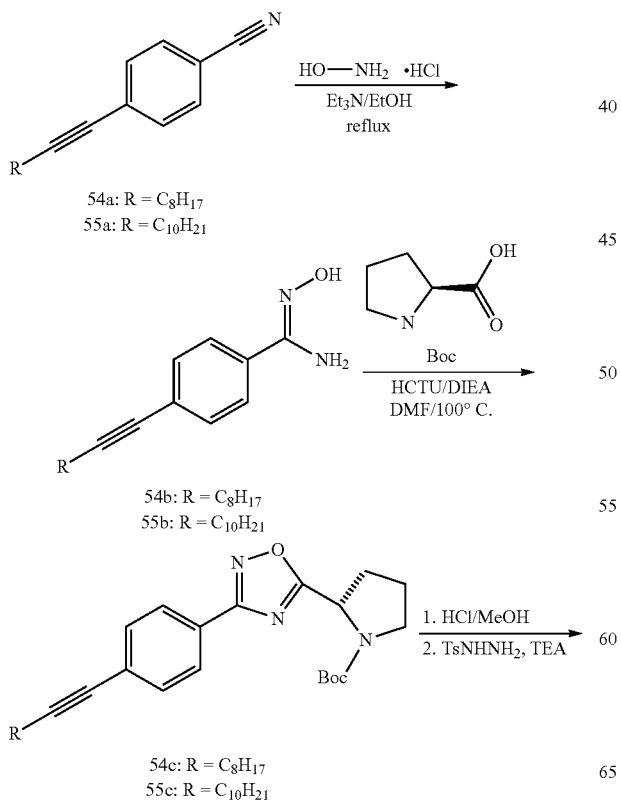

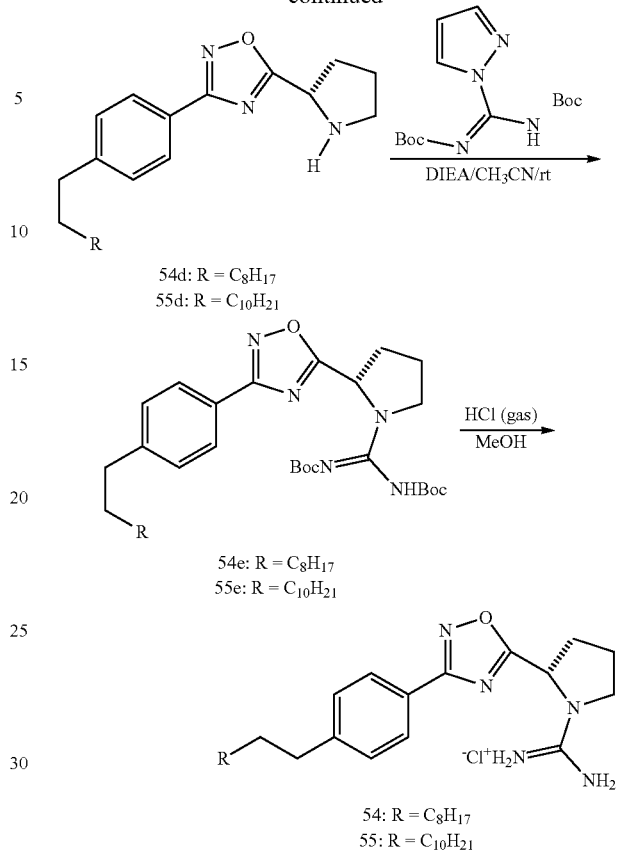

Compound 54

4-(dec-1-yn-1-yl)-N'-hydroxybenzimidamide (54b)

Synthesized using general procedure F. $^1$H NMR (400 MHz, Chloroform-d): δ 7.57-7.53 (m, 2H), 7.41 (d, J=8.4 Hz, 2H), 4.86 (s, 2H), 2.41 (t, J=7.1 Hz, 2H), 1.61 (p, J=7.1 Hz, 2H), 1.51-1.38 (m, 3H), 1.36-1.22 (m, 11H), 0.91-0.86 (m, 2H).

(S)-tert-butyl-2-(3-(4-(dec-1-yn-1-yl)phenyl)-1,2,4-oxadiazol-5-yl)pyrrolidine-1-carboxylate (54c)

Synthesized using general procedure L. $^1$H NMR (500 MHz, Chloroform-d): δ 8.00 (d, J=8.1 Hz, 2H), 7.48 (t, J=9.3 Hz, 2H), 5.20 (d, J=7.3 Hz, 0.5H), 5.06 (dd, J=8.1, 3.5 Hz, 1H), 3.71 (dq, J=15.1, 8.5, 6.4 Hz, 1H), 3.63-3.44 (m, 1H), 2.52-2.31 (m, 2H), 2.15 (dp, =14.7, 7.6, 6.7 Hz, 3H), 2.05-1.95 (m, 1H), 1.75 (s, OH), 1.62 (p, J=7.2 Hz, 2H), 1.45 (d, J=10.8 Hz, 5H), 1.30 (d, J=11.0 Hz, 12H), 0.89 (t, J=6.9 Hz, 3H).

(S)-3-(4-decylphenyl)-5-(pyrrolidin-2-yl)-1,2,4-oxadiazole (54d)

Through a solution of the N-Boc protected amines 54 compound in methanol, hydrochloric acid gas was bubbled for 5 min or until complete consumption of starting material was observed. The reaction mixture was concentrated under reduced pressure and triturated with diethyl ether to yield the corresponding free amine hydrochloride salts, which were used in the next reaction without further purification. To a solution of the alkyne (1 equiv) in DME (20 vol/wt) were added 4-methylbenzenesulfonohydrazide (10 equiv) and TEA (5 equiv). The resulting reaction mixture was refluxed overnight, until complete consumption of starting alkyne was observed. The reaction was quenched by addition of water. The product was extracted using Et₂O, the organics were combined, dried over anhydrous sodium sulfate, and concentrated under reduced pressure to yield a pale yellow oil which was purified by flash chromatography over silica gel to yield corresponding product as a colorless oil. ¹H NMR (500 MHz, Chloroform-d) δ 7.91 (d, J=8.2 Hz, 2H), 7.21 (d, J=8.2 Hz, 2H), 4.48 (s, 1H), 4.05 (q, J=7.1 Hz, 1H), 3.99 (t, J=6.7 Hz, 1H), 3.16 (q, J=8.1, 7.0 Hz, 2H), 3.09-2.96 (m, 2H), 2.65-2.54 (m, 3H), 2.30-2.20 (m, 2H), 2.07 (ddd, J=18.8, 7.5, 5.2 Hz, 2H), 1.56 (dq, J=12.1, 6.1, 4.8 Hz, 4H), 1.33-1.11 (m, 14H), 0.81 (t, J=7.0 Hz, 3H).

(S)-tert-butyl(((tert-butoxycarbonyl)amino)(2-(3-(4-decylphenyl)-1,2,4-oxadiazol-5-yl)pyrrolidin-1-yl)methylene)carbamates (54e)

Synthesized using general procedure K. ¹H NMR (500 MHz, Chloroform-d) δ 7.90 (d, J=8.1 Hz, 2H), 7.24-7.16 (m, 3H), 5.52 (s, 1H), 3.81 (s, 1H), 3.73 (s, 1H), 2.58 (t, J=7.7 Hz, 2H), 2.36 (s, 1H), 2.11 (s, 2H), 1.96 (s, 1H), 1.56 (s, 2H), 1.41 (d, J=21.5 Hz, 14H), 1.21 (d, J=26.9 Hz, 18H), 0.80 (t, J=6.8 Hz, 3H).

(S)-amino(2-(3-(4-decylphenyl)-1,2,4-oxadiazol-5-yl)pyrrolidin-1-yl)methaniminium chloride (54)

Synthesized using general procedure J. ¹H NMR (400 MHz, Methanol-d₄) δ 7.92 (d, J=7.7 Hz, 2H), 7.30 (d, J=7.8 Hz, 2H), 5.44 (s, OH), 3.68 (d, J=57.0 Hz, 2H), 2.64 (t, J=7.5 Hz, 2H), 2.50 (d, J=38.7 Hz, 1H), 2.13 (d, J=53.3 Hz, 0H), 1.62 (s, 2H), 1.41-1.08 (m, 13H), 0.86 (t, J=6.7 Hz, 3H). ¹³C NMR (101 MHz, CD₃OD): δ 177.41, 168.24, 155.66, 146.86, 128.73, 127.01, 123.53, 55.11, 35.44, 31.62, 31.38, 30.97, 29.26, 29.12, 29.00, 28.87, 23.00, 22.30, 13.04.

Compound 55

4-(dodec-1-yn-1-yl)-N'-hydroxybenzimidamide (55b)

Synthesized using general procedure F. ¹H NMR (500 MHz, Chloroform-d): δ 7.53-7.41 (m, 2H), 7.39-7.26 (m, 2H), 4.80 (s, 2H), 2.34 (t, J=7.1 Hz, 2H), 1.53 (p, J=7.2 Hz, 2H), 1.42-1.31 (m, 3H), 1.22 (d, J=13.5 Hz, 17H), 0.81 (t, J=6.9 Hz, 3H).

(S)-tert-butyl-2-(3-(4-(dodec-1-yn-1-yl)phenyl)-2,4-oxadiazol-5-yl)pyrrolidine-1-carboxylate (55c)

Synthesized using general procedure L. ¹H NMR (500 MHz, Chloroform-d): δ 7.99 (d, J=8.1 Hz, 2H), 7.48 (dd, J=12.4, 6.0 Hz, 2H), 5.20 (d, J=7.9 Hz, 0.5H), 5.06 (dd, J=8.0, 3.5 Hz, 1H), 3.80-3.63 (m, 1H), 3.61-3.44 (m, 1H), 2.42 (q, J=11.2, 9.1 Hz, 2H), 2.15 (dd, J=12.8, 8.7 Hz, 2H), 2.00 (d, J=11.8 Hz, 1H), 1.62 (p, J=7.2 Hz, 2H), 1.57 (s, 6H), 1.45 (d, J=11.8 Hz, 5H), 1.37-1.19 (m, 14H), 0.88 (t, J=6.9 Hz, 3H).

(S)-3-(4-dodecylphenyl)-5-(pyrrolidin-2-yl)-1,2,4-oxadiazole (55d)

Same procedure for the synthesis of compound 54d. ¹H NMR (500 MHz, Chloroform-d) δ 7.91 (d, J=8.2 Hz, 2H), 7.21 (d, J=8.2 Hz, 3H), 4.48 (s, 1H), 4.05 (q, J=7.1 Hz, 1H), 3.99 (t, J=6.7 Hz, 0H), 3.16 (q, J=8.1, 7.0 Hz, 2H), 3.09-2.96 (m, 2H), 2.65-2.54 (m, 3H), 2.30-2.20 (m, 2H), 2.07 (ddd, J=18.8, 7.5, 5.2 Hz, 2H), 1.95-1.74 (m, 9H), 1.56 (dq, J=12.1, 6.1, 4.8 Hz, 4H), 1.33-1.11 (m, 16H), 0.81 (t, J=7.0 Hz, 4H).

(S)-tert-butyl(((tert-butoxycarbonyl)amino)(2-(3-(4-decylphenyl)-1,2,4-oxadiazol-5-yl)pyrrolidin-1-yl)methylene)carbamates (55e)

Synthesized using general procedure K. ¹H NMR (500 MHz, Chloroform-d): δ 7.90 (d, J=8.1 Hz, 2H), 7.24-7.16 (m, 2H), 5.52 (s, 1H), 3.81 (s, 1H), 3.73 (s, 1H), 2.58 (t, J=7.7 Hz, 2H), 2.36 (s, 1H), 2.11 (s, 2H), 1.96 (s, 1H), 1.56 (s, 2H), 1.41 (d, J=21.5 Hz, 16H), 1.21 (d, J=26.9 Hz, 18H), 0.80 (t, J=6.8 Hz, 3H).

(S)-amino(2-(3-(4-dodecylphenyl)-1,2,4-oxadiazol-5-yl)pyrrolidin-1-yl)methaniminium chloride (55)

Synthesized using general procedure J. ¹H NMR (400 MHz, Methanol-d₄) δ 7.94 (d, J=8.1 Hz, 2H), 7.34 (d, J=8.1 Hz, 2H), 5.43 (dd, J=7.8, 1.6 Hz, 1H), 3.77 (td, J=9.2, 2.5 Hz, 1H), 3.66-3.56 (m, 1H), 3.30 (p, J=1.6 Hz, 9H), 2.72-2.64 (m, 2H), 2.61-2.43 (m, 2H), 2.29-2.02 (m, 1H), 1.75-1.56 (m, 1H), 1.41-1.22 (m, 23H), 0.89 (t, J=6.8 Hz, 3H). ¹³C NMR (101 MHz, CD₃OD) δ 177.41, 168.25, 155.63, 146.93, 129.21, 128.26, 127.05, 126.89, 123.52, 55.65, 35.42, 31.64, 31.00, 29.30, 28.87, 22.91, 22.31.

Compound 56

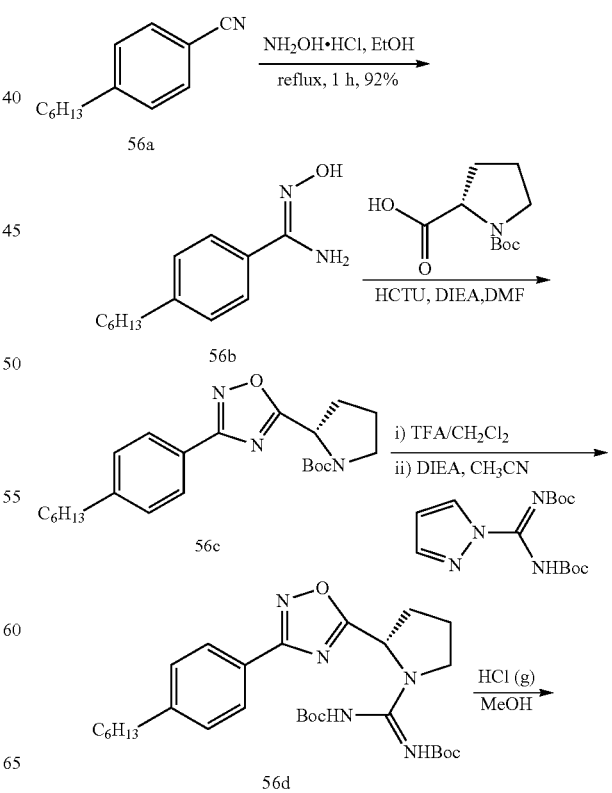

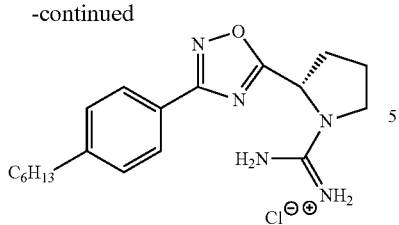

56

4-(n-hexyl)-N'-hydroxybenzimidamide (56b)

Using general procedure F, product 56b was isolated as a white solid. $^1$H NMR (400 MHz, Chloroform-d): δ 7.59-7.55 (m, 2H), 7.41 (d, J=8.4 Hz, 2H), 4.86 (s, 2H), 2.47 (t, J=7.1 Hz, 2H), 1.61 (m, J=7.1 Hz, 1H), 1.51-1.38 (m, 2H), 1.36-1.22 (m, 9H), 0.91-0.86 (m, 2H).

(S)-tert-butyl 2-(3-(4-hexylphenyl)-1,2,4-oxadiazol-5-yl)pyrrolidine-1-carboxylate (56c)

Synthesized using general procedure L. $^1$H NMR (500 MHz, Chloroform-d) δ 7.90 (d, J=7.9 Hz, 2H), 7.27-7.13 (m, 2H), 5.12 (d, J=7.6 Hz, 1H), 4.98 (dd, J=8.1, 3.5 Hz, 1H), 3.71-3.54 (m, 1H), 3.44 (dq, J=38.8, 9.1, 8.2 Hz, 1H), 3.12 (s, 1H), 2.58 (t, J=7.6 Hz, 2H), 2.15-1.99 (m, 2H), 1.99-1.85 (m, 1H), 1.81 (s, 1H), 1.39 (s, 9H), 1.20 (d, J=21.5 Hz, 9H), 0.80 (t, J=6.9 Hz, 3H). $^{13}$C NMR (101 MHz, Chloroform-d) δ 180.42, 168.33, 153.53, 146.55, 128.90, 128.76, 127.35, 124.03, 80.40, 53.78, 46.58, 46.31, 35.94, 32.37, 31.90, 31.47, 31.22, 29.26, 28.36, 28.12.

(S)-tert-butyl (((tert-butoxycarbonyl)amino)(2-(3-(4-hexylphenyl)-1,2,4-oxadiazol-5-yl)pyrrolidin-1-yl)methylene)carbamate (56d)

Through a solution of the N-Boc protected amine 56c in methanol, hydrochloric acid gas was bubbled for 5 min or until complete consumption of starting material was observed. The reaction mixture was concentrated under reduced pressure and triturated with diethyl ether to yield the corresponding free amine hydrochloride salts, which were used in the next reaction without further purification. DIEA (3 equiv) was added to a solution of the corresponding amine hydrochloric acid salt and the reagent (Z)-tert-butyl (((tert-butoxycarbonyl)imino)(1H-pyrazol-1-yl)methyl)carbamate (1.05 equiv) in acetonitrile (20 vol/wt). The resulting reaction mixture was then stirred at r.t. until complete conversion of the starting material was observed. The organic solvent was removed under reduced pressure and the resulting residue was purified by column chromatography over silica gel to yield the pure product. $^1$H NMR (400 MHz, Chloroform-d) δ 7.89 (d, J=8.1 Hz, 2H), 7.19 (d, J=8.0 Hz, 2H), 5.52 (dd, J=7.7, 4.5 Hz, 1H), 4.10-3.95 (m, OH), 3.81 (dt, J=11.4, 7.3 Hz, 1H), 3.76-3.63 (m, 1H), 2.57 (t, J=7.7 Hz, 2H), 2.03-1.88 (m, 1H), 1.55 (m, J=7.6 Hz, 2H), 1.38 (s, 9H), 1.30-1.06 (m, 18H), 0.80 (t, J=6.6 Hz, 3H).

(S)-amino(2-(3-(4-hexylphenyl)-1,2,4-oxadiazol-5-yl)pyrrolidin-1-yl)methaniminium chloride (56)

Synthesized using general procedure J. $^1$H NMR (400 MHz, Methanol-d$_4$) δ 7.92 (d, J=8.1 Hz, 2H), 7.30 (d, J=8.1 Hz, 2H), 5.44 (d, J=7.1 Hz, 2H), 3.61 (q, J=9.2 Hz, 2H), 2.70-2.62 (m, 2H), 2.13 (dd, J=57.6, 6.6 Hz, 2H), 1.70-1.55 (m, 4H), 1.39-1.16 (m, 9H), 0.91-0.83 (m; 3H). HRMS: Calculated for $C_{19}H_{28}N_5O^+$ [M$^+$]=342.2288. Found 342.2296.

Compound 57

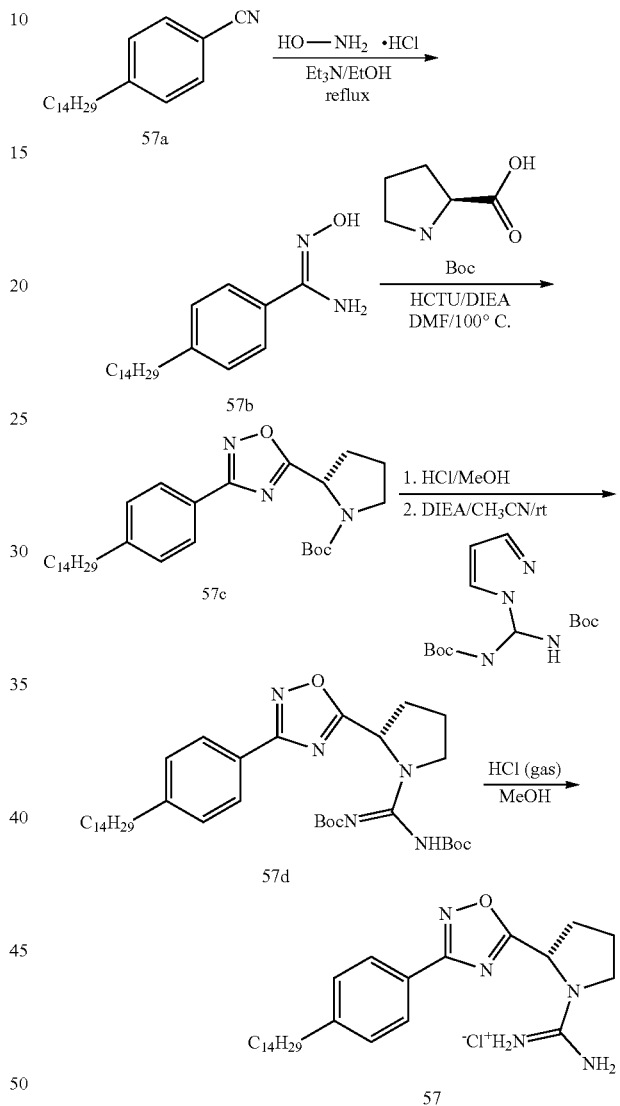

N'-hydroxy-4-tetradecylbenzimidamide (57b)

Synthesized using general procedure F. $^1$H NMR (400 MHz, Chloroform-d): δ 7.57-7.53 (m, 2H), 7.41 (d, J=8.4 Hz, 2H), 4.86 (s, 2H), 2.62 (s, 2H), 2.41 (t, J=7.1 Hz, 2H), 1.61 (p, J=7.1 Hz, 2H), 1.51-1.38 (m, 3H), 1.36-1.22 (m, 11H), 0.91-0.86 (m, 3H).

(S)-tert-butyl 2-(3-(4-tetradecylphenyl)-1,2,4-oxadiazol-5-yl)pyrrolidine-1-carboxylate (57c)

Synthesized using general procedure L to give the title product (0.082 g, 53%). $^1$H NMR (500 MHz, Chloroform-d) δ 7.90 (d, J=7.9 Hz, 2H), 7.27-7.13 (m, 2H), 5.12 (d, J=7.6

Hz, 0H), 4.98 (dd, J=8.1, 3.5 Hz, 1H), 3.71-3.54 (m, 1H), 3.44 (dq, J=38.8, 9.1, 8.2 Hz, 1H), 3.12 (s, OH), 2.58 (t, J=7.6 Hz, 2H), 2.39-2.19 (m, 1H), 2.15-1.99 (m, 2H), 1.99-1.85 (m, 1H), 1.81 (s, OH), 1.65-1.47 (m, 3H), 1.39 (s, 2H), 1.20 (d, J=21.5 Hz, 19H), 0.80 (t, J=6.9 Hz, 3H). $^{13}$C NMR (101 MHz, CDCl$_3$) δ 180.42, 168.33, 153.53, 146.55, 128.90, 128.76, 127.35, 124.03, 80.40, 53.78, 46.58, 46.31, 35.94, 32.37, 31.90, 31.47, 31.22, 29.68, 29.65, 29.63, 29.56, 29.46, 29.34, 29.26, 28.36, 28.12.

(S)-tert-butyl (((tert-butoxycarbonyl)amino)(2-(3-(4-tetradecylphenyl)-1,2,4-oxadiazol-5-yl)pyrrolidin-1-yl)methylene)carbamate (57d)

DIEA (3 equiv) was added to a solution of the corresponding amine hydrochloric acid salt and the reagent (Z)-tert-butyl (((tert-butoxycarbonyl)imino)(1H-pyrazol-1-yl)methyl)carbamate (1.05 equiv) in acetonitrile (20 vol/wt). The resulting reaction mixture was then stirred at r.t. until complete conversion of the starting material was observed. The organic solvent was removed under reduced pressure and the resulting residue was purified by column chromatography over silica gel to yield the pure product. $^1$H NMR (400 MHz, Chloroform-d) δ 7.89 (d, J=8.1 Hz, 2H), 7.19 (d, J=8.0 Hz, 2H), 5.52 (dd, J=7.7, 4.5 Hz, 1H), 4.10-3.95 (m, OH), 3.81 (dt, J=11.4, 7.3 Hz, 1H), 3.76-3.63 (m, 1H), 2.57 (t, J=7.7 Hz, 2H), 2.45-2.25 (m, 1H), 2.25-2.03 (m, 1H), 2.03-1.88 (m, 1H), 1.55 (p, J=7.6 Hz, 3H), 1.38 (s, 18H), 1.30-1.06 (m, 18H), 0.80 (t, J=6.6 Hz, 3H).

(S)-amino(2-(3-(4-tetradecylphenyl)-1,2,4-oxadiazol-5-yl)pyrrolidin-1-yl)methaniminium chloride (57)

Synthesized using general procedure J. $^1$H NMR (400 MHz, Methanol-d$_4$) δ 7.92 (d, J=8.1 Hz, 2H), 7.30 (d, J=8.1 Hz, 2H), 5.44 (d, J=7.1 Hz, 2H), 3.75 (t, J=8.3 Hz, 2H), 3.61 (q, J=9.2 Hz, 2H), 2.70-2.62 (m, 3H), 2.60-2.39 (m, 4H), 2.13 (dd, J=57.6, 6.6 Hz, 2H), 1.70-1.55 (m, 4H), 1.39-1.16 (m, 26H), 0.91-0.83 (m, 3H). $^{13}$C NMR (101 MHz, cd$_3$od) δ 177.41, 168.24, 155.65, 146.86, 128.71, 127.00, 123.53, 55.04, 35.44, 31.64, 31.31, 30.98, 29.35, 29.33, 29.32, 29.29, 29.25, 29.12, 29.04, 28.89, 22.94, 22.31, 13.04.

Compound 58

Synthesized following the scheme for the synthesis of compound 49.

(S)-amino(2-(3-(3-octylphenyl)-1,2,4-oxadiazol-5-yl)pyrrolidin-1-yl)methaniminium chloride (58)

Synthesized using general procedure J to yield title product as white solid. $^1$H NMR (400 MHz, CD$_3$OD) δ 7.88-7.81 (m, 2H), 7.45-7.34 (m, 2H), 5.48-5.40 (m, 1H), 3.81-3.73 (m, 1H), 3.68-3.55 (m, 1H), 2.72-2.64 (m, 2H), 2.62-2.41 (m, 2H), 2.28-2.17 (m, 1H), 2.15-2.02 (m, 1H), 1.69-1.58 (m, 2H), 1.39-1.19 (m, 10H), 0.91-0.83 (m, 3H); $^{13}$C NMR (101 MHz, CD$_3$OD) δ 177.5, 168.4, 155.7, 143.7, 131.5, 128.7, 126.8, 126.0, 124.4, 55.1, 35.3, 31.6, 31.3, 31.2, 29.1, 29.0, 28.9, 22.9, 22.3, 13.0.

Compound 59

Synthesized following the scheme for the synthesis of compound 49.

(R)-tert-butyl 3-(3-(4-octylphenyl)-1,2,4-oxadiazol-5-yl)pyrrolidine-1-carboxylate (59c)

Synthesized using general procedure L to yield title product (500 mg, 77%) as an oil. $^1$H NMR (500 MHz, CDCl$_3$) δ 7.95 (d, J=8.2 Hz, 2H), 7.25 (d, J=7.7 Hz, 2H), 3.93-3.37 (m, 5H), 2.68-2.57 (m, 2H), 2.36 (dq, J=12.0, 6.9 Hz, 2H), 1.61 (p, J=7.4 Hz, 2H), 1.46 (s, 9H), 1.34-1.18 (m, 10H), 0.86 (t, J=6.9 Hz, 3H); $^{13}$C NMR (126 MHz, CDCl$_3$) δ 179.31, 168.48, 154.27, 146.67, 128.99, 127.45, 124.04, 79.85, 49.46, 45.14, 36.67, 36.03, 31.93, 31.29, 29.69, 29.51, 29.33, 29.31, 28.56, 22.73, 14.18; HRMS (ESI+): Calcd for C$_{25}$H$_{37}$N$_3$O$_3$Na [M+Na]: 450.2732. Found: 450.2695.

(R)-3-(4-octylphenyl)-5-(pyrrolidin-3-yl)-1,2,4-oxadiazole (59d)

Synthesized using general procedure I to yield title product (110 mg, 79%) as an oil. $^1$H NMR (400 MHz, CDCl$_3$) δ 7.95 (d, J=8.2 Hz, 2H), 7.25 (d, J=8.4 Hz, 2H), 3.57 (ddd, J=12.7, 9.1, 6.3 Hz, 1H), 3.29 (d, J=5.9 Hz, 2H), 3.25-3.16 (m, 1H), 3.06-2.96 (m, 1H), 2.67-2.57 (m, 2H), 2.34-2.08 (m, 3H), 1.68-1.55 (m, 2H), 1.27 (d, J=19.6 Hz, 10H), 0.86 (t, J=6.8 Hz, 3H); $^{13}$C NMR (101 MHz, CDCl$_3$) δ 182.09, 168.38, 146.55, 128.97, 127.45, 124.27, 52.64, 47.53, 37.35, 36.04, 32.01, 31.95, 31.30, 29.79, 29.53, 29.35, 29.33, 22.75, 14.18; HRMS (ESI+): Calcd for C$_{23}$H$_{34}$N$_2$O$_2$ [M+H]: 370.2620. Found: 370.2586.

(R,Z)-tert-butyl (((tert-butoxycarbonyl)imino)(3-(3-(4-octylphenyl)-1,2,4-oxadiazol-5-yl)pyrrolidin-1-yl)methyl)carbamate (59e)

Synthesized using general procedure K to yield title product (16 mg, 8%). $^1$H NMR (400 MHz, CDCl$_3$) δ 7.96 (d, J=8.3 Hz, 2H), 7.27 (d, J=8.2 Hz, 2H), 4.05 (s, 2H), 3.87-3.68 (m, 3H), 2.69-2.62 (m, 2H), 2.45 (dt, J=13.4, 6.5 Hz, 2H), 1.61-1.61 (m, 2H), 1.50 (s, 18H), 1.28 (d, J=22.8 Hz, 10H), 0.92-0.83 (m, 3H); $^{13}$C NMR (101 MHz, CDCl$_3$) δ 178.63, 171.27, 168.62, 154.41, 146.80, 129.07, 127.57, 124.03, 77.36, 65.99, 60.53, 36.12, 32.01, 31.74, 31.35, 29.85, 29.58, 29.41, 29.38, 28.32, 25.43, 22.80, 21.18, 15.42, 14.35, 14.26, 14.23, 11.57, 1.16; HRMS (ESI+): Calcd for C$_{31}$H$_{48}$N$_5$O$_5$ [M+H]: 570.3655. Found: 570.3690.

(R)-amino(3-(3-(4-octylphenyl)-1,2,4-oxadiazol-5-yl)pyrrolidin-1-yl)methaniminium chloride (59)

Synthesized using general procedure J to yield title product (8 mg, 72%) as white solid. $^1$H NMR (400 MHz, Methanol-d$_4$) δ 7.98 (d, J=8.0 Hz, 2H), 7.37 (d, J=8.0 Hz, 2H), 4.13-3.87 (m, 3H), 3.74-3.65 (m, 2H), 2.75-2.62 (m, 3H), 2.53 (s, 1H), 1.72-1.64 (m, 2H), 1.45-1.24 (m, 10H), 0.92 (t, J=6.8 Hz, 3H); $^{13}$C NMR (101 MHz, Methanol-d$_4$) δ 180.30, 169.63, 156.41, 148.18, 130.11, 128.33, 125.18, 51.38, 47.73, 37.35, 36.83, 32.98, 32.41, 30.57, 30.51, 30.34, 30.30, 23.68, 14.39; MS: Calcd for C$_{21}$H$_{32}$N$_5$O [M+]: 370.2606. Found: 370.30.

Compound 60

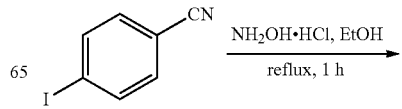

-continued

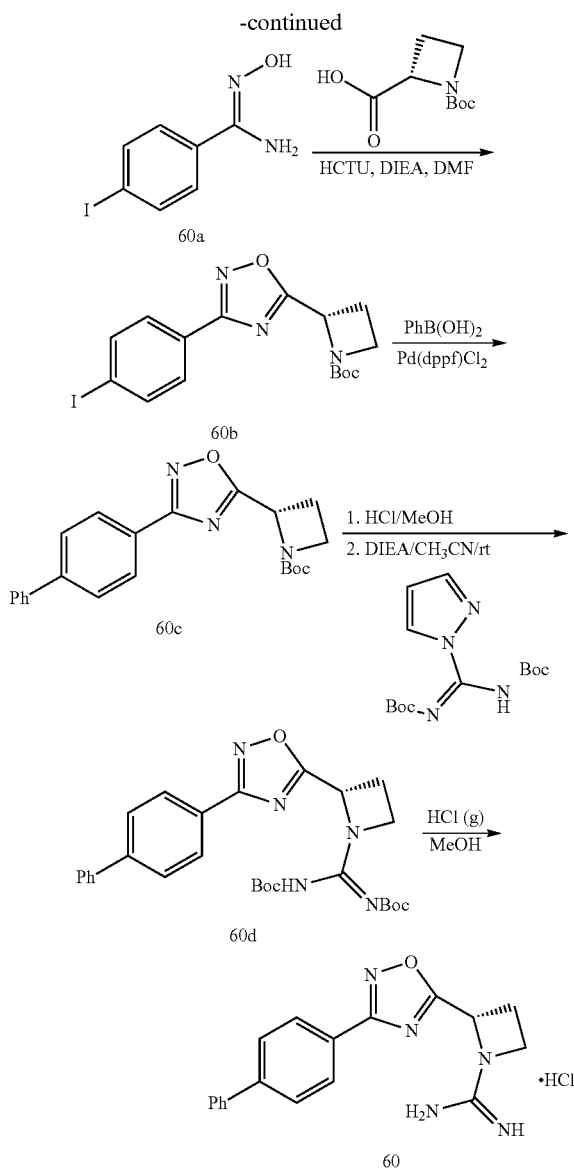

(S)-tert-butyl 2-(3-(4-iodophenyl)-1,2,4-oxadiazol-5-yl)azetidine-1-carboxylate (60b)

Synthesized using general procedure L to yield title product (0.5 g, 71% yield). $^1$H NMR (400 MHz, Chloroform-d) δ 7.84 (s, 4H), 5.42 (dd, J=8.6, 5.9 Hz, 1H), 4.29-4.16 (m, 1H), 4.06 (q, J=8.4 Hz, 1H), 2.72 (ddt, J=14.7, 9.1, 4.2 Hz, 1H), 2.55 (tt, J=11.7, 6.0 Hz, 1H), 1.36 (s, 9H). $^{13}$C NMR (101 MHz, cdcl$_3$) δ 184.06, 178.59, 167.95, 138.10, 128.95, 98.00, 80.67, 38.59, 28.14, 21.83.

(S)-tert-butyl 2-(3-([1,1'-biphenyl]-4-yl)-1,2,4-oxadiazol-5-yl)azetidine-1-carboxylate (60c)

Phenyl Boronic Acid (0.034 g, 0.3 mmol) and Cs$_2$CO$_3$ (0.084 g, 0.26 mmol) were added to a round bottom flask containing (S)-tert-butyl-2-(3-(4-iodophenyl)-1,2,4-oxadiazol-5-yl)azetidine-1-carboxylate (0.100 g, 0.234 mmol) in DMF (3 mL) under nitrogen. The reaction mixture was degassed for 30 min by passing N$_2$ to remove oxygen. To the above solution was added Pd(dppf)Cl$_2$ (0.034 g, 0.047 mmol) and the brown reaction mixture was stirred at 80° C. for 18 hours. The reaction mixture was poured into a solution of LiBr and extracted with ethyl acetate (3×20 mL). The combined organic solution was washed with ammonium chloride, brine, dried over Na$_2$SO$_4$, filtered, and concentrated under reduced pressure. The resulting residue was purified by flash chromatography over silica gel to provide the title product as colorless oil (0.08 g, 91% yield). $^1$H NMR (400 MHz, Chloroform-d) δ 8.17 (d, J=8.1 Hz, 2H), 7.72 (d, J=8.2 Hz, 2H), 7.65 (d, J=7.6 Hz, 2H), 7.47 (t, J=7.7 Hz, 2H), 7.43-7.32 (m, 1H), 5.44 (dd, J=8.7, 5.8 Hz, 1H), 4.28-4.17 (m, 1H), 4.12-4.01 (m, 1H), 2.73 (dtd, J=11.7, 8.9, 5.9 Hz, 1H), 2.58 (ddd, J=11.5, 9.2, 5.9 Hz, 1H), 1.37 (s, 11H). $^{13}$C NMR (101 MHz, Chloroform-d) δ 178.38, 168.33, 140.11, 128.90, 127.93, 127.52, 127.14, 104.99, 80.66, 59.60, 46.04, 28.17, 21.88, -7.90.

(S)-tert-butyl((2-(3-([1,1'-biphenyl]-4-yl)-1,2,4-oxadiazol-5-yl)azetidin-1-yl)((tert-butoxycarbonyl)imino)methyl)carbamate (60d)

Prepared by following the synthesis for 57d (91% yield). $^1$H NMR (400 MHz, Chloroform-d) δ 8.17-8.12 (m, 2H), 7.73-7.67 (m, 2H), 7.65-7.60 (m, 3H), 7.50-7.42 (m, 3H), 7.40-7.33 (m, 1H), 4.63 (d, J=7.1 Hz, 1H), 4.19 (td, J=9.4, 5.6 Hz, 1H), 4.14-4.06 (m, 1H), 2.95-2.74 (m, 1H), 2.57 (ddt, J=15.0, 11.2, 5.5 Hz, 2H), 1.47 (d, J=21.7 Hz, 18H). $^{13}$C NMR (101 MHz, Chloroform-d) δ 168.29, 144.03, 140.08, 128.94, 128.88, 127.97, 127.93, 127.62, 127.47, 127.12, 127.09, 125.28, 60.35, 34.63, 31.56, 29.67, 28.04, 25.25, 22.63, 22.61, 22.40, 21.02, 19.09, 14.17, 14.10, 11.41.

(S)-(2-(3-([1,1'-biphenyl]-4-yl)-1,2,4-oxadiazol-5-yl)azetidin-1-yl)(amino) methaniminium chloride (60)

Synthesized using general procedure J. 85% yield. $^1$H NMR (400 MHz, Chloroform-d) δ 8.17 (d, J=8.1 Hz, 2H), 7.72 (d, J=8.2 Hz, 2H), 7.65 (d, J=7.6 Hz, 2H), 7.47 (t, J=7.7 Hz, 2H), 7.43-7.36 (m, 1H), 5.44 (dd, J=8.7, 5.8 Hz, 1H), 4.31-4.15 (m, 1H), 4.13-3.99 (m, 1H), 2.73 (dtd, J=11.7, 8.9, 5.9 Hz, 1H), 2.58 (ddd, J=11.5, 9.2, 5.9 Hz, 2H). $^{13}$C NMR (101 MHz, Chloroform-d) δ 178.38, 168.33, 140.11, 128.90, 127.93, 127.52, 127.14, 125.44, 104.99, 80.66, 28.17, 21.88. HRMS: Calculated for $C_{18}H_{18}N_5O^+$ [M$^+$]=320.1506. Found 320.1497

Compounds 61-63

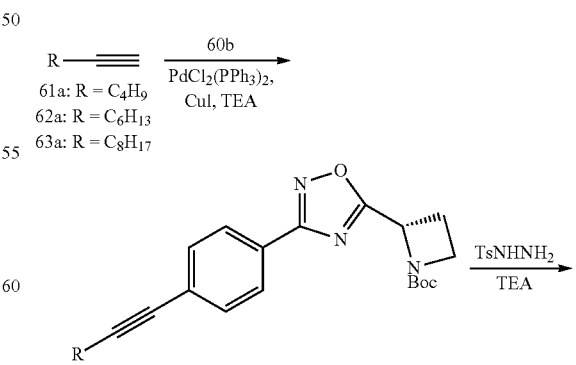

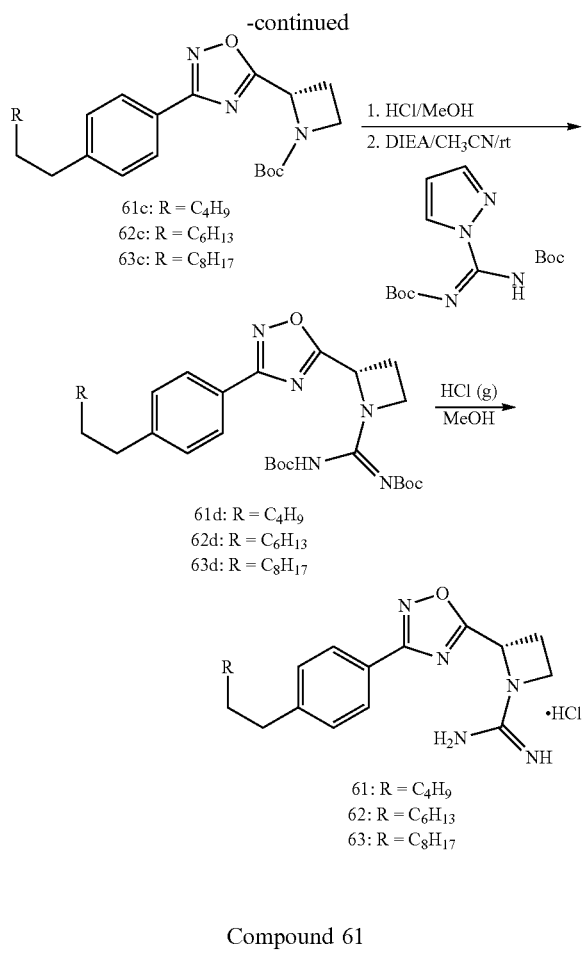

Compound 61

(S)-tert-butyl-2-(3-(4-(hex-1-yn-1-yl)phenyl)-1,2,4-oxadiazol-5-yl)azetidine-1-carboxylate (61b)

Synthesized using general procedure M. 94% yield. $^1$H NMR (400 MHz, Chloroform-d) δ 8.02 (d, J=8.1 Hz, 2H), 7.48 (d, J=8.1 Hz, 2H), 4.56 (s, 1H), 4.22 (td, J=9.4, 5.6 Hz, 1H), 2.9 (p, J=9.4 Hz, 2H), 1.57 (q, J=7.2 Hz, 2H), 1.50-1.44 (m, 9H), 1.40-1.21 (m, 8H), 0.98-0.83 (m, 3H).

(S)-tert-butyl 2-(3-(4-hexylphenyl)-1,2,4-oxadiazol-5-yl)azetidine-1-carboxylate (61c)

Synthesized using general procedure N. 89% yield. $^1$H NMR (400 MHz, Chloroform-d) δ 8.02-7.96 (m, 2H), 7.36-7.24 (m, 2H), 5.32 (dd, J=8.8, 5.7 Hz, 1H), 4.12 (td, J=8.6, 5.9 Hz, 1H), 4.01 (td, J=8.6, 6.2 Hz, 1H), 2.72-2.55 (m, 2H), 2.46 (ddt, J=11.7, 9.1, 6.0 Hz, 2H), 1.52 (m, 8H), 1.40-1.24 (m, 9H), 0.89-0.81 (m, 3H). $^{13}$C NMR (101 MHz, cdcl$_3$) δ 178.14, 168.51, 146.55, 131.91, 128.86, 127.38, 127.21, 123.96, 80.50, 35.91, 31.62, 31.53, 31.12, 30.83, 28.87, 28.11, 22.59, 22.52, 21.83, 14.05, 14.01.

(S)-tert-butyl(((tert-butoxycarbonyl)imino)(2-(3-(4-hexylphenyl)-1,2,4-oxadiazol-5-yl)azetidin-1-yl)methyl)carbamate (61d)

Synthesized using general procedures I and K. 58% yield. $^1$H NMR (400 MHz, Chloroform-d) δ 8.00-7.94 (m, 2H), 7.32-7.20 (m, 2H), 5.38 (dd, J=8.8, 5.7 Hz, 1H), 4.17 (td, J=8.6, 5.9 Hz, 1H), 4.01 (td, J=8.6, 6.2 Hz, 1H), 2.75-2.58 (m, 2H), 2.51 (ddt, J=11.7, 9.1, 6.0 Hz, 2H), 1.60 (m, 8H), 1.40-1.24 (m, 18H), 0.89-0.81 (m, 3H).

(S)-amino(2-(3-(4-hexylphenyl)-1,2,4-oxadiazol-5-yl)azetidin-1-yl)methaniminium chloride (61)

Synthesized using general procedure J. 73% yield. $^1$H NMR (400 MHz, Methanol-d$_4$) δ 8.02-7.86 (m, 2H), 7.40-7.26 (m, 2H), 5.83 (dd, J=9.4, 5.3 Hz, 1H), 4.36 (td, J=8.8, 6.3 Hz, 1H), 4.26 (ddd, J=9.3, 8.3, 5.9 Hz, 1H), 3.05 (dtd, J=11.6, 9.4, 6.2 Hz, 2H), 2.75-2.56 (m, 2H), 1.72-1.55 (m, 2H), 1.40-1.22 (m, 8H), 0.87 (td, J=7.2, 2.7 Hz, 3H). $^{13}$C NMR (101 MHz, CD$_3$OD) δ 176.75, 168.41, 157.14, 146.94, 128.74, 127.02, 123.52, 57.01, 49.48, 35.43, 31.39, 30.95, 28.56, 26.71, 22.21, 21.54, 12.96. HRMS: Calculated for C$_{18}$H$_{26}$N$_5$O$^+$ [M$^+$]=328.2132. Found 328.2743

Compound 62

(S)-tert-butyl-2-(3-(4-(oct-1-yn-1-yl)phenyl)-1,2,4-oxadiazol-5-yl)azetidine-1-carboxylate (62b)

Synthesized using general procedure M. 88% yield. $^1$H NMR (400 MHz, Chloroform-d) δ 8.01 (d, J=8.1 Hz, 2H), 7.50 (d, J=8.1 Hz, 2H), 4.60 (s, 1H), 4.19 (td, J=9.4, 5.6 Hz, 1H), 2.8 (p, J=9.4 Hz, 2H), 1.61 (q, J=7.2 Hz, 2H), 1.50-1.44 (m, 9H), 1.40-1.21 (m, 10H), 0.98-0.83 (m, 3H). $^{13}$C NMR (101 MHz, Chloroform-d) δ 179.00, 168.16, 155.86, 131.97, 127.30, 127.20, 125.23, 93.26, 80.19, 80.10, 31.33, 28.60, 28.57, 28.31, 25.70, 22.54, 19.48, 14.05.

(S)-tert-butytyl,2-(3-(4-octylphenyl)-1,2,4-oxadiazol-5-yl)azetidine-1-carboxylate (62c)

Synthesized using general procedure N. 92% yield. $^1$H NMR (400 MHz, CDCl$_3$) δ $^{13}$C NMR (101 MHz, CDCl$_3$) $^1$H NMR (400 MHz, Chloroform-d) δ 7.97 (d, J=8.2 Hz, 2H), 7.38-7.15 (m, 2H), 4.60 (s, 1H), 4.19 (td, J=9.4, 5.6 Hz, 1H), 2.8 (p, J=9.4 Hz, 2H), 2.72-2.40 (m, 2H), 1.83-1.61 (m, 3H), 1.42 (s, 9H), 1.33-1.19 (m, 10H), 1.18 (t, J=6.9 Hz, 3H). $^{13}$C NMR (101 MHz, Chloroform-d) δ 179.01, 168.17, 155.87, 131.97, 127.31, 127.21, 125.23, 93.27, 80.21, 80.11, 31.33, 28.60, 28.57, 28.32, 25.71, 22.54, 19.49, 14.05, -7.29.

(S)-tert-butyl(((tert-butoxycarbonyl)imino)(2-(3-(4-octylphenyl)-1,2,4-oxadiazol-5-yl)azetidin-1-yl)methyl)carbamate (62d)

Synthesized using general procedures I and K. 75% yield. $^1$H NMR (400 MHz, Chloroform-d) δ 7.99 (d, J=8.2 Hz, 2H), 7.40-7.15 (m, 2H), 4.63 (s, 1H), 4.20 (td, J=9.4, 5.6 Hz, 1H), 2.85 (p, J=9.4 Hz, 2H), 2.75-2.40 (m, 2H), 1.86-1.57 (m, 3H), 1.45 (s, 18H), 1.36-1.19 (m, 10H), 0.88 (t, J=6.9 Hz, 3H).

(S)-amino(2-(3-(4-octylphenyl)-1,2,4-oxadiazol-5-yl)azetidin-1-yl)methaniminium chloride (62)

Synthesized using general procedure J. 89% yield. $^1$H NMR (400 MHz, Methanol-d$_4$) δ 7.98 (d, J=8.2 Hz, 2H), 7.34 (d, J=8.2 Hz, 2H), 5.83 (dd, J=9.3, 5.2 Hz, 1H), 4.37 (q, J=8.6 Hz, 1H), 4.27 (q, J=8.7 Hz, 1H), 3.16-2.96 (m, 2H), 2.74-2.54 (m, 2H), 1.64 (q, J=7.3 Hz, 2H), 1.42-1.17 (m, 10H), 0.93-0.83 (m, 3H). $^{13}$C NMR (101 MHz, CD$_3$OD) δ 176.77, 168.41, 157.13, 146.97, 128.76, 127.01, 123.52, 57.02, 49.47, 35.44, 31.59, 31.02, 29.11, 28.96, 28.90, 22.29, 21.55, 13.01. HRMS: Calculated for $C_{20}H_{30}N_5O^+$ [M+]=356.2445. Found 356.2458 Compound 63:

(S)-tert-butyl-2-(3-(4-(decyn-1-yl)phenyl)-1,2,4-oxadiazol-5-yl)azetidine-1-carboxylate (63b)

Synthesized using general procedure M. 87% yield. $^1$H NMR (500 MHz, Chloroform-d) δ 8.02 (d, J=8.1 Hz, 2H), 7.36-7.30 (m, 2H), 5.35 (s, 1H), 3.87 (d, J=18.7 Hz, 1H), 2.83-2.64 (m, 1H), 2.59-2.50 (m, 2H), 1.63 (h, J=7.1, 6.6 Hz, 2H), 1.52 (s, 9H), 1.29 (d, J=27.6 Hz, 15H), 0.88 (t, J=7.0 Hz, 3H). $^{13}$C NMR (126 MHz, CDCl$_3$) δ 180.65, 179.45, 168.38, 146.54, 128.88, 128.76, 128.72, 127.44, 124.03, 117.02, 110.21 55.34, 35.96, 31.89, 31.20, 29.59, 29.56, 29.49, 29.47, 29.31, 29.26, 14.10, 11.89.

(S)-tert-butyl,2-(3-(4-decylphenyl)-1,2,4-oxadiazol-5-yl)azetidine-1-carboxylate (63c)

Synthesized using general procedure N. 95% yield. $^1$H NMR (500 MHz, Chloroform-d) δ 8.01 (d, J=8.2 Hz, 2H), 7.31-7.26 (m, 2H), 5.15 (s, 1H), 3.77 (d, J=18.7 Hz, 1H), 2.87-2.69 (m, 1H), 2.69-2.60 (m, 2H), 2.48-2.33 (m, 2H), 1.63 (h, J=7.1, 6.6 Hz, 2H), 1.52 (s, 9H), 1.29 (d, J=27.6 Hz, 17H), 0.88 (t, J=7.0 Hz, 3H). $^{13}$C NMR (126 MHz, CDCl$_3$) δ 180.65, 179.45, 168.38, 146.54, 128.88, 128.76, 128.72, 127.44, 124.03, 55.34, 35.96, 31.89, 31.20, 29.59, 29.56, 29.49, 29.47, 29.31, 29.26, 26.74, 22.67, 14.10, 11.89.

(S)-tert-butyl(((tert-butoxycarbonyl)imino)(2-(3-(4-decylphenyl)-1,2,4-oxadiazol-5-yl)azetidin-1-yl)methyl)carbamate (63d)

Synthesized using general procedures I and K. 81% yield. $^1$H NMR (400 MHz, Methanol-d$_4$) δ 8.01 (d, J=8.2 Hz, 2H), 7.37 (t, J=6.7 Hz, 2H), 5.91 (dd, J=9.1, 5.2 Hz, 1H), 4.42 (q, J=8.2 Hz, 1H), 4.37-4.27 (m, 1H), 3.23-2.97 (m, 2H), 2.84-2.53 (m, 2H), 1.68 (s, 2H), 1.61 (s, 18H), 1.48-1.17 (m, 14H), 1.00-0.79 (m, 3H). $^{13}$C NMR (101 MHz, CD$_3$OD) δ 178.15, 169.78, 158.54, 148.28, 130.14, 128.43, 124.92, 58.42, 50.95, 49.00, 47.34, 36.83, 33.02, 32.36, 30.65, 30.52, 30.40, 30.27, 29.34, 23.69, 22.97, 14.45.

(S)-amino(2-(3-(4-decylphenyl)-1,2,4-oxadiazol-5-yl)azetidin-1-yl)methaniminium chloride (63)

Synthesized using general procedure J. 80% yield. $^1$H NMR (400 MHz, Methanol-d$_4$) δ 8.01 (d, J=8.2 Hz, 2H), 7.37 (t, J=6.7 Hz, 2H), 5.91 (dd, J=9.1, 5.2 Hz, 1H), 4.42 (q, J=8.2 Hz, 1H), 4.37-4.27 (m, 1H), 3.23-2.97 (m, 2H), 2.84-2.53 (m, 2H), 1.68 (s, 2H), 1.48-1.17 (m, 14H), 1.00-0.79 (m, 3H). $^{13}$C NMR (101 MHz, CD$_3$OD) δ 178.15, 169.78, 158.54, 148.28, 130.14, 128.43, 124.92, 58.42, 50.95, 49.00, 36.83, 33.02, 32.36, 30.65, 30.52, 30.40, 30.27, 23.69, 22.97, 14.45. HRMS: Calculated for $C_{22}H_{34}N_5O^+$ [M+]=384.2758. Found 384.2764.

Compound 64

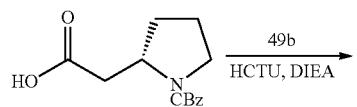

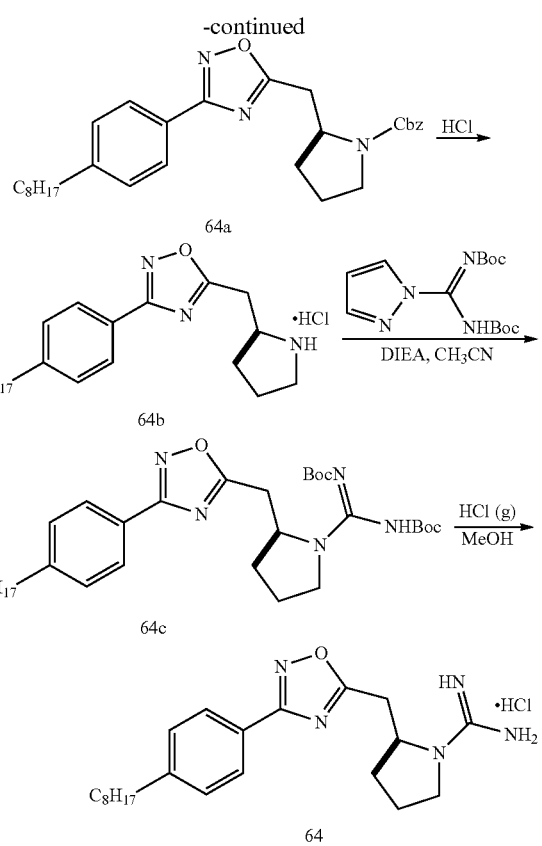

(S)-benzyl 2-((3-(4-octylphenyl)-1,2,4-oxadiazol-5-yl)methyl)pyrrolidine-1-carboxylate (64a)

Synthesized using general procedure L to give 64a (0.33 g, 0.694 mmol, 54% yield). $^1$H NMR (400 MHz, CDCl$_3$) δ 7.97 (d, J=7.2 Hz, 2H), 7.46-7.18 (m, 7H), 5.13 (d, J=13.6 Hz, 2H), 4.51-4.29 (m, 1H), 3.56-3.39 (m, 3H), 3.30 (dd, J=14.7, 3.9 Hz, 1H), 3.22-3.08 (m, 1H), 3.02 (dd, J=14.6, 8.8 Hz, 1H), 2.72-2.60 (m, 2H), 2.18-2.00 (m, 1H), 1.98-1.73 (m, 3H), 1.63 (p, J=7.4 Hz, 2H), 1.41-1.20 (m, 11H), 0.94-0.81 (m, 3H). $^{13}$C NMR (101 MHz, CDCl$_3$) δ 176.98, 176.82, 168.28, 154.81, 146.50, 146.40, 136.79, 128.87, 128.46, 127.92, 127.82, 127.34, 124.18, 67.06, 66.77, 55.53, 55.10, 46.92, 46.61, 35.93, 31.84, 31.23, 30.96, 30.54, 29.97, 29.42, 29.23, 29.22, 23.58, 22.64, 14.09. HRMS: Calculated for $C_{29}H_{38}N_3O_3$ [M+H]=476.2835. Found 476.2916.

(S)-2-((3-(4-octylphenyl)-1,2,4-oxadiazol-5-yl)methyl)pyrrolidin-1-ium chloride (64b)

Synthesized using general procedure J to yield a white solid (0.136 g, 0.4 mmol, 82% yield). $^1$H NMR (500 MHz, CD$_3$OD) δ 7.96 (d, J=8.2 Hz, 2H), 7.34-7.18 (m, 3H), 4.70 (s, 3H), 3.87 (p, J=7.1 Hz, 1H), 3.37 (dd, J=15.8, 7.1 Hz, 1H), 3.30-3.20 (m, 3H), 3.15 (ddd, J=10.8, 8.3, 6.3 Hz, 2H), 2.67-2.60 (m, 3H), 2.16 (ddt, J=15.1, 7.3, 3.9 Hz, 2H), 2.05-1.82 (m, 4H), 1.76-1.55 (m, 5H), 1.40-1.18 (m, 10H), 0.88 (t, J=7.0 Hz, 3H). $^{13}$C NMR (126 MHz, CD$_3$OD) δ 176.77, 168.28, 146.60, 128.90, 128.40, 127.89, 127.39, 123.89, 56.40, 53.44, 50.63, 45.86, 35.94, 31.86, 31.31, 31.22, 30.87, 29.43, 29.27, 29.24, 24.31, 22.66, 14.10. HRMS: Calculated for $C_{21}H_{32}N_3O^+$ [M+$^+$]=342.2540. Found 342.2545.

(S)-tert-butyl(((tert-butoxycarbonyl)amino)(2-((3-(4-octylphenyl)-1,2,4-oxadiazol-5-yl)methyl)pyrrolidin-1-yl)methylene)carbamate (64c)

Synthesized using general procedure K. 92% yield. $^1$H NMR (400 MHz, CDCl$_3$) δ 8.05-7.89 (m, 2H), 7.32-7.16 (m, 2H), 4.94-4.58 (m, 1H), 3.64 (ddd, J=11.6, 8.9, 6.4 Hz, 2H), 3.49 (d, J=10.3 Hz, 1H), 3.12 (dd, J=15.2, 8.4 Hz, 1H), 2.63 (dd, J=8.6, 6.8 Hz, 2H), 2.07-1.69 (m, 3H), 1.71-1.52 (m, 3H), 1.45 (s, 18H), 1.38-1.16 (m, 14H), 0.85 (t, J=7.4, 5.9, 1.9 Hz, 3H). $^{13}$C NMR (101 MHz, CDCl$_3$) δ 176.86, 168.23, 146.32, 128.80, 127.38, 124.24, 56.45, 49.98, 35.92, 31.83, 31.55, 31.22, 30.54, 30.28, 29.41, 29.21, 28.10, 22.62, 14.09, 14.06. HRMS: Calculated for $C_{32}H_{50}N_5O_5$ [M+H] =584.3734. Found 584.3807.

(S)-amino(2-((3-(4-octylphenyl)-1,2,4-oxadiazol-5-yl)methyl)pyrrolidin-1-yl) methaniminium chloride (64)

Synthesized using general procedure J. 71% yield. $^1$H NMR (400 MHz, CD$_3$OD) δ 8.05-7.89 (m, 2H), 7.32-7.16 (m, 2H), 4.94-4.58 (m, 1H), 3.64 (ddd, J=11.6, 8.9, 6.4 Hz, 2H), 3.49 (d, J=10.3 Hz, 1H), 3.12 (dd, J=15.2, 8.4 Hz, 1H), 2.63 (dd, J=8.6, 6.8 Hz, 2H), 2.07-1.69 (m, 3H), 1.71-1.52 (m, 3H), 1.38-1.16 (m, 14H), 0.85 (t, J=7.4, 5.9, 1.9 Hz, 3H). $^{13}$C NMR (101 MHz, CD$_3$OD) δ 176.86, 168.23, 146.32, 128.80, 127.38, 124.24, 121.32, 56.45, 49.98, 35.92, 31.83, 31.55, 31.22, 30.54, 30.28, 29.21, 28.10, 22.62, 14.09, 14.06. HRMS: Calculated for $C_{22}H_{34}N_5O^+$ [M$^+$]=384.2758. Found 384.2779.

Compound 65

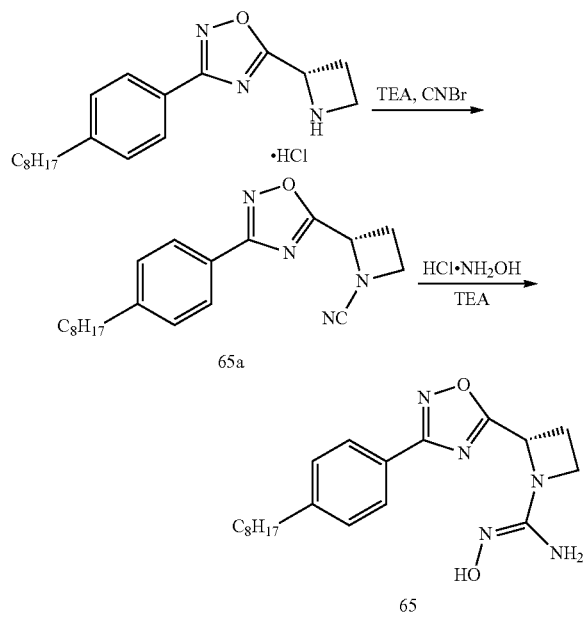

(S)-2-(3-(4-octylphenyl)-1,2,4-oxadiazol-5-yl)azetidine-1-carbonitrile (65a)

To a solution of amine hydrochloride (0.05 g, 0.143 mmol) in CH$_2$Cl$_2$ (2 mL) was added TEA (0.58 mL, 0.058 mmol) and the solution was cooled to −10° C. using an ice-salt bath. To this solution was added cyanogen bromide (2M soln, 0.357 mL, 0.714 mmol) and the resulting reaction mixture was warmed to r.t. over the course of 1 hour. The reaction was then quenched by addition of water and extracted with (3×10 mL) CH$_2$Cl$_2$, dried over MgSO$_4$, and concentrated under reduced pressure to yield a pale yellow oil which was purified by flash chromatography over silica gel to yield (0.057 g, 80%) of 65a as a clear oil. $^1$H NMR (400 MHz, Chloroform-d) δ 8.03-7.95 (m, 2H), 7.32-7.26 (d, J=8.3 Hz, 2H), 5.67-5.53 (t, J=7.8 Hz, 1H), 4.42-4.24 (m, 1H), 2.96-2.76 (q, J=7.7 Hz, 1H), 2.73-2.61 (m, 2H), 1.78-1.52 (dq, J=18.4, 10.9, 9.2 Hz, 2H), 1.38-1.17 (m, 11H), 0.91-0.67 (t, 3H). $^{13}$C NMR (101 MHz, Chloroform-d) δ 175.39, 168.86, 147.00, 129.67, 128.50, 128.29, 128.23, 127.41, 126.50, 123.38, 114.94, 59.27, 54.68, 35.95, 31.16, 29.20, 23.92, 22.61, 13.74. HRMS: Calculated for $C_{20}H_{27}N_4O$ [M+H]=338.2107. Found 338.2096.

(S)—N'-hydroxy-2-(3-(4-octylphenyl)-1,2,4-oxadiazol-5-yl)azetidine-1-carboximidamide (65)

Synthesized using general procedure F to yield the oxime product 65 (0.009 g, 27%) as a pale yellow colored oil, which solidified to an off white crystalline solid on standing. $^1$H NMR (400 MHz, Chloroform-d) δ 7.96-7.93 (m, 2H), 7.31-7.26 (d, J=8.1 Hz, 1H), 5.46-5.20 (m, OH), 3.97-3.85 (td, J=8.6, 3.7 Hz, 1H), 2.97-2.83 (ddd, J=16.7, 11.4, 8.7 Hz, 1H), 2.77-2.61 (m, 3H), 1.71-1.57 (m, 3H), 1.40-1.17 (m, 11H), 0.93-0.81 (m, 3H). HRMS: Calculated for $C_{20}H_{30}N_5O_2$ [M+H]=372.2321. Found 372.2405.

Compound 66

Synthesized using the scheme for compound 49.

tert-butyl 3-(3-(4-octylphenyl)-1,2,4-oxadiazol-5-yl)azetidine-1-carboxylate (66c)

Starting with 49b and following general procedure L, the title compound was prepared in 95% yield. $^1$H NMR (400 MHz, Chloroform-d) δ 7.96 (d, J=8.4 Hz, 2H), 7.30-7.15 (m, 3H), 4.45-4.24 (m, 4H), 4.02 (s, OH), 2.69-2.59 (m, 2H), 2.36 (s, 1H), 1.62 (m, J=7.6 Hz, 2H), 1.45 (s, 9H), 1.35-1.18 (m, 10H), 0.86 (q, J=7.1, 6.6 Hz, 3H). $^{13}$C NMR (101 MHz, Chloroform-d) δ 178.74, 168.58, 155.88, 146.68, 129.78, 128.92, 127.50, 127.37, 123.81, 80.14, 35.93, 31.82, 31.16, 29.39, 29.22, 29.19, 28.31, 25.74, 22.61, 21.48, 14.05.

tert-butyl(((tert-butoxycarbonyl)amino)(3-(3-(4-octylphenyl)-1,2,4-oxadiazol-5-yl)azetidin-1-yl)methylene) carbamate (66e)

Synthesized using general procedures I and K. 65% yield. $^1$H NMR (400 MHz, Chloroform-d) δ 7.99-7.94 (m, 2H), 7.30-7.25 (m, 2H), 4.44-4.23 (m, 4H), 4.13-3.96 (m, 1H), 2.72-2.56 (m, 2H), 1.62 (p, J=7.6 Hz, 3H), 1.45 (s, 18H), 1.36-1.16 (m, 11H), 0.95-0.73 (m, 3H). $^{13}$C NMR (101 MHz, Chloroform-d) δ 178.74, 168.58, 155.88, 146.68, 129.78, 128.92, 127.50, 127.37, 123.81, 80.14, 35.93, 31.82, 31.16, 29.39, 29.22, 29.19, 28.31, 25.74, 22.61, 21.48, 14.05.

amino(3-(3-(4-octylphenyl)-1,2,4-oxadiazol-5-yl)azetidin-1-yl)methaniminium chloride (66)

Synthesized using general procedure J. 73% yield. $^1$H NMR (400 MHz, Methanol-d$_4$) δ 7.98 (d, J=8.1 Hz, 2H), 7.34 (d, J=8.1 Hz, 2H), 4.64 (t, J=8.8 Hz, 2H), 4.52-4.44 (m, 2H), 4.39 (dt, J=14.4, 7.2 Hz, 1H), 2.68 (t, J=7.6 Hz, 2H), 1.64 (q, J=7.1 Hz, 3H), 1.42-1.20 (m, 10H), 0.88 (t, J=6.7 Hz, 3H). $^{13}$C NMR (101 MHz, CD$_3$OD) δ 178.60, 168.40, 146.79, 128.70, 126.94, 123.74, 54.39, 35.41, 31.56, 30.99, 29.09, 28.92, 28.88, 25.73, 22.25, 12.98. HRMS: Calculated for C$_{20}$H$_{30}$N$_5$O$^+$ [M$^+$]=356.2445. Found 356.2437

Compound 67

Synthesized using the scheme for compound 49.

tert-butyl 3-(3-(4-decylphenyl)-1,2,4-oxadiazol-5-yl)azetidine-1-carboxylate (67c)

Synthesized using general procedure L. $^1$H NMR (400 MHz, Chloroform-d) δ 8.01-7.96 (m, 2H), 7.51-7.45 (m, 2H), 4.42-4.25 (m, 4H), 4.02 (tt, J=8.9, 6.1 Hz, 1H), 2.49-2.33 (m, 2H), 1.67-1.54 (m, 2H), 1.45 (s, 9H), 1.36-1.16 (m, 14H), 0.87 (td, J=6.0, 5.3, 2.5 Hz, 3H). $^{13}$C NMR (101 MHz, Chloroform-d) δ 178.99, 168.18, 155.86, 131.96, 128.92, 127.20, 126.27, 93.26, 31.80, 29.15, 29.07, 28.91, 28.59, 28.31, 25.73, 22.62, 19.47, 14.06.

tert-butyl(((tert-butoxycarbonyl)amino)(3-(3-(4-decylphenyl)-1,2,4-oxadiazol-5-yl)azetidin-1-yl)methylene)carbamate (67e)

Synthesized using general procedures I and K. 85% yield. $^1$H NMR (400 MHz, Chloroform-d) δ 8.02-7.95 (m, 2H), 7.56-7.49 (m, 2H), 4.42-4.25 (m, 4H), 4.02 (m, 1H), 2.49-2.33 (m, 2H), 1.67-1.54 (m, 2H), 1.45 (s, 18H), 1.36-1.16 (m, 14H), 0.87 (td, J=6.0, 5.3, 2.5 Hz, 3H).

amino(3-(3-(4-decylphenyl)-1,2,4-oxadiazol-5-yl)azetidin-1-yl)methaniminium chloride (67)

Synthesized using general procedure. 59% yield. $^1$H NMR (400 MHz, Methanol-d$_4$) δ 8.00 (d, J=8.6 Hz, 2H), 7.48 (d, J=8.5 Hz, 2H), 4.63 (t, J=8.8 Hz, 2H), 4.46 (dd, J=8.5, 5.7 Hz, 1H), 4.39 (ddt, J=11.8, 5.6, 2.7 Hz, 1H), 3.29 (p, J=1.6 Hz, 1H), 2.71-2.62 (m, 1H), 2.42 (t, J=7.0 Hz, 1H), 2.22 (dt, J=12.3, 6.1 Hz, 1H), 1.66-1.53 (m, 2H), 1.39-1.23 (m, 12H), 0.88 (td, J=5.9, 5.0, 2.1 Hz, 3H). $^{13}$C NMR (101 MHz, cd$_3$od) δ 178.87, 167.97, 156.86, 131.60, 128.71, 126.86, 126.03, 92.59, 79.57, 54.39, 31.61, 31.56, 29.24, 29.10, 28.99, 28.93, 28.90, 28.85, 28.77, 28.55, 28.32, 25.74, 22.28, 22.27, 18.62, 14.01, 13.00.

Compounds 68-69

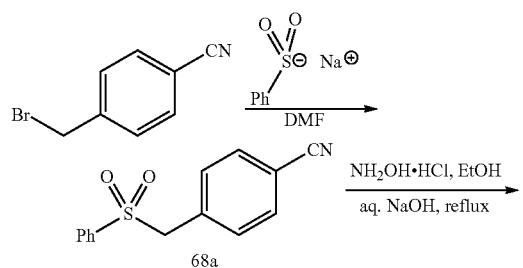

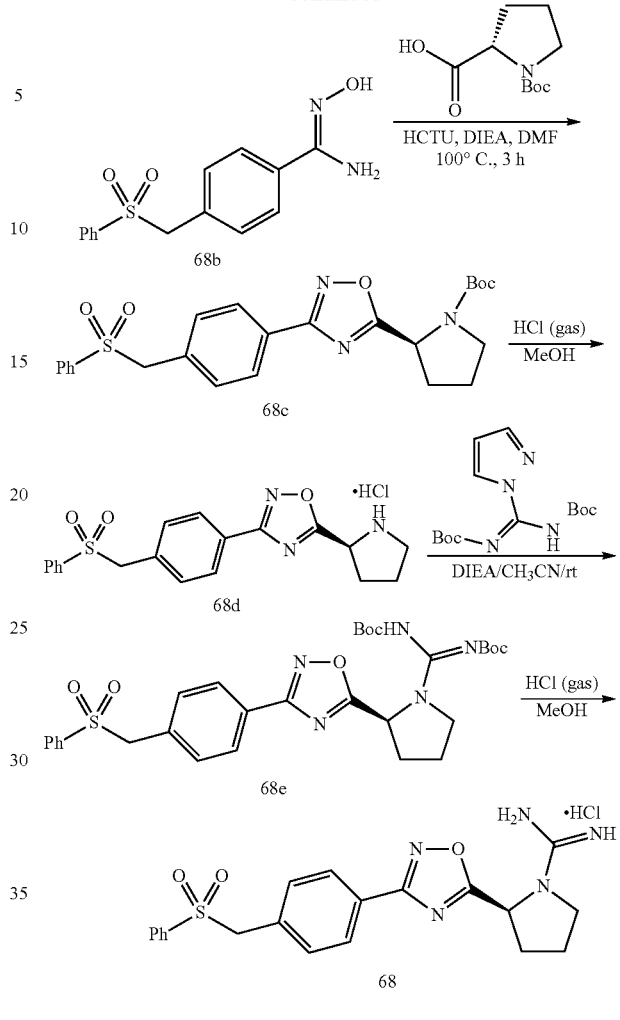

Compound 68

4-((phenylsulfonyl)methyl)benzonitrile (68a)

Sodium benzenesulfinate (523 mg, 3.19 mmol) was slurried in DMF (10 mL) and heated to 60° C. 4-(bromomethyl)nitrile (500 mg, 2.55 mmol) was added slowly. The reaction solution was heated for 2 hours. The reaction was cooled to r.t. and water was added to produce a white precipitate. The solid was filtered and dried under vacuum overnight to produce 68a (586 mg, 89%) as a white solid. $^1$H NMR (400 MHz, DMSO) δ 7.79-7.66 (m, 5H), 7.59 (t, 7.7 Hz, 2H), 7.33 (d, 8.5 Hz, 2H), 4.84 (s, 2H); $^{13}$C NMR (400 MHz, CDCl3) δ 138.45, 134.85, 134.54, 132.55, 132.34, 129.70, 128.47, 118.96, 111.60, 60.60, 39.95.

(Z)—N'-hydroxyl-4-((phenylsulfonyl)methyl)benzimideamide (68b)

In a round bottom flask flushed with nitrogen, hydroxylamine hydrochloride (216 mg, 3.11 mmol) was dissolved in 15 mL of 190 proof ethanol. 4-((phenylsulfonyl)methyl)benzonitrile 68a (200 mg, 0.777 mmol) was added to the flask in one portion. TEA (0.65 mL, 4.66 mmol) was added to the flask dropwise. The reaction was heated at 80° C. overnight. The reaction mixture was cooled to r.t. and filtered to produce 68b (160 mg, 71%), a white solid. ¹H NMR (400 MHz, DMSO) δ 7.68-7.63 (m, 3H), 7.54-7.49 (m, 4H), 7.16-7.12 (m, 2H), 4.51 (s, 2H), 2.13 (s, 1H); ¹³C NMR (400 MHz, CDCl3) δ154.75, 139.43, 135.06, 132.15, 130.19, 129.68, 127.20, 62.66; HRMS (ESI+): Calcd for C14H14N2O3S [M+H]: 291.0175. Found: 291.0788.

(S)-tert-butyl 2-(3-(4-((phenylsulfonyl)methyl)phenyl)-1,2,4-oxadiazol-5-l)pyrrolidine-1-carboxylate (68c)

(Z)—N'-hydroxyl-4-((phenylsulfonyl)methyl)benzimideamide 68b (77 mg, 0.265 mmol) and Boc-L-proline (74 mg, 0.345 mmol) were placed in a nitrogen flushed round bottom flask and dissolved in DMF (10 mL). DIEA (0.12 mL, 0.658 mmol) was added dropwise to the solution followed by HCTU (143 mg, 0.345 mmol) in one portion. The reaction mixture was heated to 110° C. for 6 hours. At this time, TLC showed complete consumption of 68b. The solution was cooled to r.t., and partitioned between ethyl acetate and a saturated LiBr aqueous solution. The aqueous solution was extracted with ethyl acetate. The combined organic layers were washed with brine, dried over Na₂SO₄, and concentrated under reduced pressure. The residue was purified on a silica column with 67% hexane: 33% ethyl acetate to yield 68c (57 mg, 46%), a white solid; ¹H NMR (400 MHz, CDCl₃) δ 7.96 (d, J=7.9 Hz, 2H), 7.63 (dd, J=18.8, 6.9 Hz, 3H), 7.46 (d, J=7.2 Hz, 2H), 7.18 (dd, J=21.1, 7.7 Hz, 2H), 5.11 (dd, J=50.2, 6.0 Hz, 1H), 4.35 (s, 2H), 3.73-3.62 (m, 1H), 3.59-3.42 (m, 1H), 2.45-2.31 (m, 1H), 2.19-2.07 (m, 2H), 2.04-1.95 (m, 1H), 1.45 (s, 3H), 1.28 (s, 6H) 0.89-0.74 (m, 2H); ¹³C NMR (400 MHz, CDCl3) δ 181.01, 167.89, 153.60, 137.91, 134.02, 131.25, 129.14, 128.72, 127.70, 127.29, 80.57, 65.94, 62.78, 53.90, 46.77, 46.46, 32.48, 31.61, 28.50, 28.26, 24.48, 23.81, 15.38.

(S)-2-(3-(4-((phenylsulfonyl)methyl)phenyl)-1,2,4-oxadiazol-5-yl)pyrrodilin-1-ium chloride (68d)

Synthesized using general procedure J to yield 68d (20 mg, 58%) as a white solid; ¹H NMR (400 MHz, MeOD) δ7.98 (d, J=8.3 Hz, 2H), 7.72-7.65 (m, 3H), 7.52 (t, J=7.8 Hz, 2H), 7.31 (d, J=8.3 Hz, 2H), 5.19 (t, J=7.7 Hz, 1H), 4.59 (s, 2H), 3.62-3.48 (m, 2H), 2.65 (dt, J=13.5, 6.8 Hz, 1H), 2.41 (dd, J=13.4, 7.6 Hz, 1H), 2.32-2.19 (m, 2H); ¹³C NMR (400 MHz, MeOD) δ 176.21, 169.36, 139.47, 135.17, 133.97, 132.95, 130.25, 129.64, 128.44, 127.42, 62.62, 55.60, 47.44, 34.54, 30.22, 26.64, 26.02, 24.51

(S)-tert-butyl (((tert-butylcaronyl)imino)(2-(3-(4-((phenylsulfonyl)methyl)phenyl)-1,2,4-oxadiazol-5-yl)pyrrolidin-1-yl)methyl)carbamate (68e)

Synthesized using general procedure K to yield 68e (16 mg, 53%), a white solid; ¹H NMR (400 MHz, CDCl₃) δ 8.01-7.90 (m, 2H), 7.70-7.55 (m, 3H), 7.46 (t, J=7.8 Hz, 2H), 7.18 (d, J=8.3 Hz, 2H), 5.60 (dd, J=7.9, 4.5 Hz, 1H), 4.36 (s, 2H), 3.89 (dt, J=11.3, 7.2 Hz, 1H), 3.84-3.73 (m, 1H), 2.44 (dt, J=16.4, 8.0 Hz, 2H), 2.29-2.12 (m, 3H), 2.08-1.97 (m, 2H), 1.55-1.38 (m, 18H), 1.33-1.05 (m, 12H), 0.95-0.71 (m, 16H); ¹³C NMR (400 MHz, CDCl₃) δ 167391, 137.79, 134.05, 131.35, 129.17, 128.79, 127.83, 103.53, 62.87, 49.60, 29.85, 29.58, 28.26.

(S)-amino-(2-(3-(4-((phenylsulfonyl)methyl)phenyl)-1,2,4-oxadiazol-5-yl)pyrrolidin-1-yl)methaniminimum chloride (68)

Synthesized using general procedure J to yield 68 (4 mg, 33%), a white solid; ¹H NMR (400 MHz, MeOD) δ 7.95 (d, J=7.8 Hz, 2H), 7.70 (t, J=9.6 Hz, 3H), 7.55 (t, J=7.7 Hz, 2H), 7.41 (s, 1H), 7.31 (d, J=8.0 Hz, 2H), 5.44 (d, J=7.36 Hz, 1H), 4.60 (s, 2H), 3.84-3.70 (m, 1H), 3.70-3.56 (m, 1H), 2.62-2.52 (m, 1H), 2.52-2.44 (m, 1H), 2.27-2.17 (m, 1H), 2.16-2.04 (m, 1H); ¹³C NMR (400 MHz, MeOD) δ 177.77, 167.78, 155.63, 138.02, 133.74, 132.32, 131.45, 128.83, 128.24, 126.91, 126.36, 61.19, 55.07, 31.32, 22.90.

Compound 69

Synthesized following the scheme for compound 68.

(S)-tert-butyl 2-(3-(4-((phenylsulfonyl)methyl)phenyl)-1,2,4-oxadiazol-5-l)azetidine-1-carboxylate (70c)

(76 mg, 59%), a white solid; ¹H NMR (400 MHz, CDCl₃) δ 7.98 (d, 8.1 Hz, 2H), 7.64 (d, J=7.9 Hz, 2H), 7.59 (d, J=7.6 Hz, 1H), 7.45 (t, J=7.7 Hz, 2H), 7.19 (d, J=8.0 Hz, 2H), 5.41 (dd, J=8.7, 5.8 Hz, 1H), 4.36 (s, 2H), 418 (td, J=8.6, 5.9 Hz, 1H), 4.04 (dd, J=14.8, 8.5 Hz, 1H), 2.77-2.66 (m, 1H), 2.59-2.46 (m, 1H), 1.35 (s, 9H), 0.89-0.76 (m, 1H); ¹³C NMR (400 MHz, CDCl₃) δ 178.70, 168.06, 137.72, 134.03, 131.44, 131.41, 129.14, 128.70, 127.73, 127.17, 80.77, 62.75, 28.26, 21.94.

(S)-2-(3-(4-((phenylsulfonyl)methyl)phenyl)-1,2,4-oxadiazol-5-yl)azetidin-1-ium chloride (69d)

(16 mg, 64%), a white solid; ¹H NMR (400 MHz, MeOD) δ 8.00 (d, J=8.3 Hz, 2H), 7.73-7.65 (m, 3H), 7.52 (dd, J=8.0, 7.6 Hz, 2H), 7.32 (d, J=8.3 Hz, 2H), 5.83 (t, J=8.5 Hz, 1H), 4.60 (s, 2H), 4.37-4.26 (m, 1H), 4.18 (dd, J=9.9, 6.3 Hz, 1H), 3.17-3.00 (m, 2H); ¹³C NMR (400 MHz, MeOD) δ175.61, 169.61, 139.46, 135.17, 133.97, 132.96, 130.26, 129.63, 128.45, 127.46, 62.63, 54.24, 46.09, 25.34.

(S)-tert-butyl (((tert-butoxycarbonyl)amino)(2-(3-(4-((phenylsulfonyl)methyl)phenyl)-1,2,4-oxadiazol-5-yl)azetidin-1-yl)methylene)carbamate (69e)

In a nitrogen flushed round bottom, 69d (16 mg, 0.041 mmol) and (Z)-tert-butyl (((tert-butoxycarbonyl)imino)(1H-pyrazol-1-yl)methyl)carbamate 7 (14 mg, 0.045 mmol) were dissolved in acetonitrile (2 mL). DIEA (0.036 mL, 0.204 mmol) was added dropwise to the solution. The reaction was stirred under nitrogen, at r.t. for 1 week. The solvent was removed under reduced pressure. The residue was purified on a silica column with 5-40% ethyl acetate in hexanes to yield 69e (19 mg, 78%), a white solid; ¹H NMR (400 MHz, CDCl₃) δ 7.99 (d, J=8.4 Hz, 2H), 7.64 (t, J=8.2 Hz, 3H), 7.47 (t, J=7.6 Hz, 2H), 7.20 (d, J=7.9 Hz, 2H), 6.10-5.99 (m, 1H), 4.71-4.63 (m, 1H), 4.37 (s, 2H), 4.26-4.18 (m, 1H), 2.92-2.83 (m, 1H), 2.64-2.52 (m, 1H), 1.53-1.03 (m, 24H), 0.86 (s, 4H); ¹³C NMR (400 MHz, CDCl₃) δ 131.44, 129.20, 128.78, 127.86, 62.84, 28.19.

(S)-amino-(2-(3-(4-((phenylsulfonyl)methyl)phenyl)-1,2,4-oxadiazol-5-yl)azedtidin-1-yl)methaniminimum chloride (69)

(S)-tert-butyl (((tert-butoxycarbonyl)amino)(2-(3-(4-((phenylsulfonyl)methyl)phenyl)-1,2,4-oxadiazol-5-yl)azetidin-1-yl)methylene)carbamate 69e (9 mg, 0.015 mmol) was dissolved in methanol (15 mL). HCl gas was bubbled through the solution for 5 min. The acidic solution was stirred for an additional 10 min. Reaction progress was monitored by TLC. Once 69e had been consumed, the solvent was removed under reduced pressure. The remaining white residue was washed with diethyl ether to yield 69 a brown solid; $^1$H NMR (400 MHz, MeOD) δ 7.98 (t, J=8.9 Hz, 2H), 7.69 (t, J=15.6 Hz, 3H), 7.55 (d, J=7.7 Hz, 2H), 7.31 (t, J=7.2 Hz, 2H), 5.90-5.77 (m, 1H), 4.60 (s, 2H), 4.41-4.33 (m, 1H), 4.29-4.21 (m, 1H), 3.47 (t, J=7.0 Hz, 4H, diethyl ether), 3.11-3.00 (m, 1H), 2.69-2.59 (m, 1H), 1.17 (t, J=7.0 Hz, 7H, diethyl ether).

Compound 70

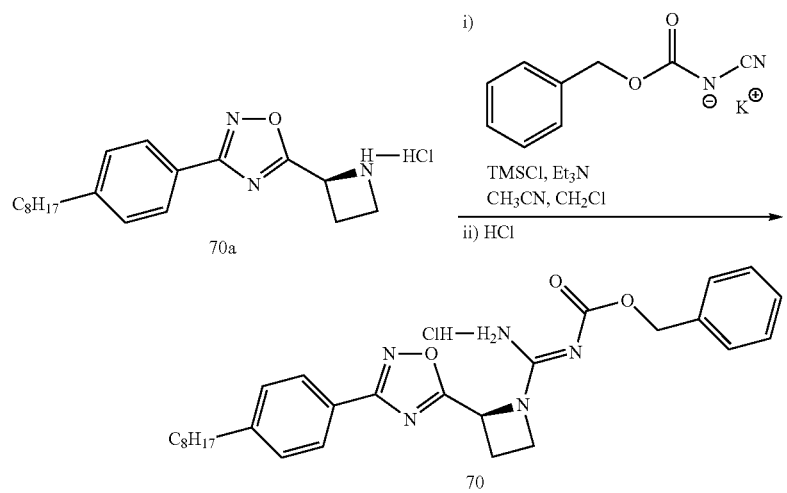

(S,E)-benzyl (amino(2-(3-(4-octylphenyl)-1,2,4-oxadiazol-5-yl)azetidin-1-yl)methylene)carbamate hydrochloride (70)

To a solution of Looper's reagent (1.1 equiv) in dry acetonitrile was added 1 M chlorotrimethylsilane in dichloromethane (1.1 equiv) and the solution was stirred at r.t. for 10 min. In a separate flask, 70a (1.0 equiv) was dissolved in dry acetonitrile, triethylamine was added (1.1 equiv), and this solution was added to the solution containing Looper's reagent. The mixture was stirred for 2 hours at r.t. and then extracted into ethyl acetate, washing with saturated NaHCO$_3$ solution, water, and brine. The organic layer was dried over sodium sulfate, filtered, and evaporated to dryness. The residue was reconstituted in ethyl acetate and HCl gas was bubbled through for 30 min to provide 70 as a white solid (75% yield). $^1$H NMR (400 MHz, CDCl$_3$) δ 8.67 (br s, 2H), 7.83 (d, J=7.8 Hz, 2H), 7.35-7.21 (m, 5H), 7.11 (d, J=7.7 Hz, 2H), 6.51 (br s, 1H), 5.13 (s, 2H), 4.65 (br s, 1H), 4.49 (br s, 1H), 2.93-2.73 (m, 1H), 2.67-2.42 (m, 3H), 1.55 (m, 2H), 1.26 (m, 10H), 0.91-0.79 (t, J=7.0 Hz, 3H); $^{13}$C NMR (101 MHz, CDCl$_3$) δ 175.6, 168.3, 154.0, 147.2, 134.3, 129.1, 128.7, 128.7, 128.2, 127.5, 123.0, 110.1, 77.5, 77.2, 76.8, 69.0, 36.0, 31.9, 31.2, 29.5, 29.4, 29.3, 22.7, 14.2; HRMS (ESI+) m/z calcd for C$_{28}$H$_{36}$N$_5$O$_3$ [M-Cl]$^+$: 490.2818. found 490.2827.

Compound 71

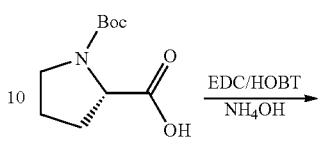

-continued

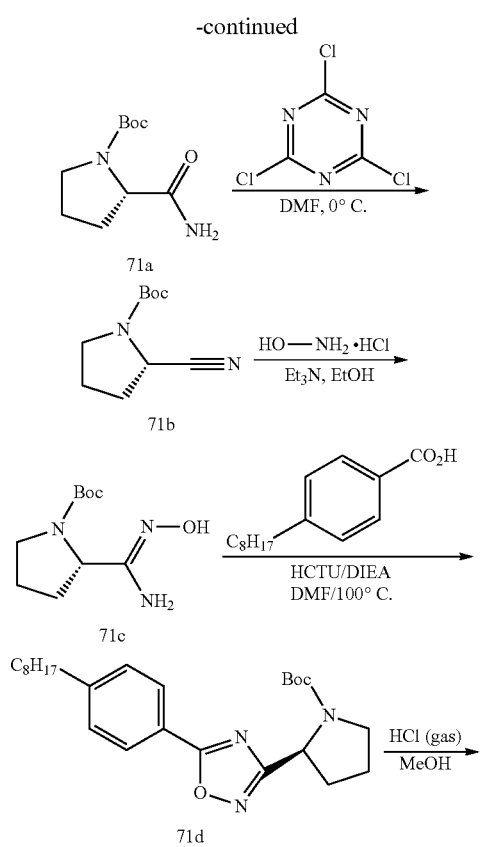

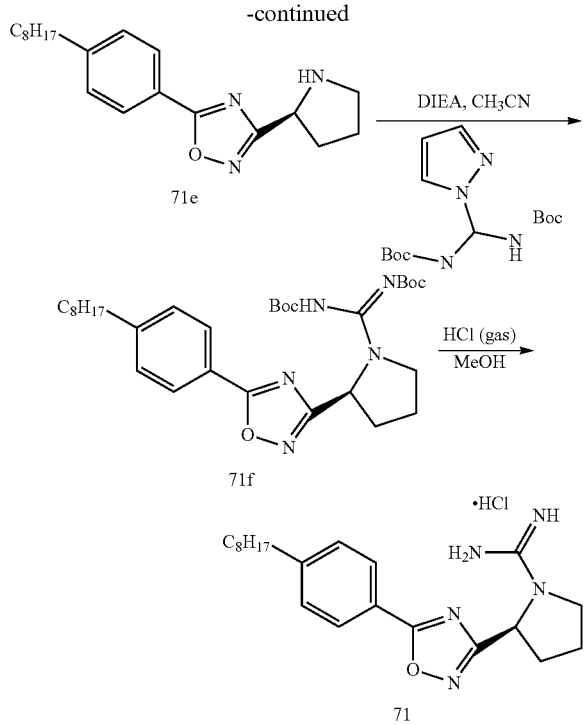

(S)-tert-butyl 2-carbamoylpyrrolidine-1-carboxylate (71a)

To a solution of 1-(tert-butoxycarbonyl)pyrrolidine-2-carboxylic acid (0.2 g, 0.93 mmol) in THF (13 mL), HOBT (142 mg, 0.93 mmol) was added followed by EDC (205 mg, 1.07 mmol). After stirring at r.t. for 6 hours, concentrated ammonium hydroxide (0.3 mL, 6.50 mmol) was added and the reaction mixture was stirred for 16-60 hours. Once reaction showed by TLC to be at completion, the organic solvent was removed under reduced pressure and the residue was diluted with ethyl acetate. The organic layer was washed with sodium bicarbonate solution and brine, dried over sodium sulfate, and concentrated to afford final product 71a (87 mg, 43%) as an oil. $^1$H NMR (500 MHz, CDCl$_3$) δ 4.17 (d, J=62.9 Hz, 1H), 3.35 (d, J=67.9 Hz, 2H), 2.26-1.98 (m, 2H), 1.92-1.75 (m, 2H), 1.39 (s, 9H); $^{13}$C NMR (126 MHz, CDCl$_3$) δ 175.15, 154.61, 80.33, 59.67, 47.15, 31.12, 28.37, 24.52. HRMS (ESI+): Calcd for C$_{10}$H$_{19}$N$_2$O$_3$ [M+H]: 215.1395. Found: 215.1389.

(S)-tert-butyl 2-cyanopyrrolidine-1-carboxylate (71b)

To a solution of (S)-tert-butyl 2-carbamoylpyrrolidine-1-carboxylate 71a (86 mg, 0.40 mmol) in DMF (2 mL) at 0° C., 2,4,6-trichloro-1,3,5-triazine (104 mg, 0.56 mmol) was added. After stirring for one hour at 0° C., the reaction mixture was quenched with a cold 0.5 M NaOH solution. The mixture was then extracted with ethyl acetate. Organic layers were combined and washed with water and brine twice, dried over Na$_2$SO$_4$, and concentrated via vacuum. The crude reside was purified by silica gel column chromatography (15% ethyl acetate/hexane to yield 71b (56 mg, 71%) as an oil. $^1$H NMR (500 MHz, CDCl$_3$) δ 4.56-4.39 (m, 1H), 3.58-3.22 (m, 2H), 2.28-1.94 (m, 4H), 1.47 (d, J=16.4 Hz, 9H); $^{13}$C NMR (126 MHz, CDCl$_3$) δ 153.09, 119.23, 81.50, 47.27, 45.79, 31.74, 28.39, 23.89; HRMS (ESI+): Calcd for C$_{10}$H$_{17}$N$_2$O$_2$ [M+H]: 197.1290. Found: 197.1287.

(S,Z)-tert-butyl 2-(N'-hydroxycarbamimidoyl)pyrrolidine-1-carboxylate (71c)

Synthesized using general procedure F to yield 71c (60 mg, 95%) as a solid. $^1$H NMR (500 MHz, CDCl$_3$) δ 5.28 (s, 1H), 4.55 (d, J=61.9 Hz, 1H), 3.56-3.22 (m, 2H), 2.41-1.68 (m, 4H), 1.45 (s, 9H); $^{13}$C NMR (126 MHz, CDCl$_3$) δ 154.73, 80.37, 56.82, 47.15, 29.83, 28.54, 27.57, 24.73; HRMS (ESI+): Calcd for C$_{10}$H$_{20}$N$_3$O$_3$ [M+H]: 230.1504. Found: 230.1492.

(S)-tert-butyl 2-(5-(4-octylphenyl)-1,2,4-oxadiazol-3-yl)pyrrolidine-1-carboxylate (71d)

DIEA (0.08 mL, 0.45 mmol) was added to a solution of 4-octylbenzoic acid (59 mg, 0.25 mmol) and (S,Z)-tert-butyl 2-(N'-hydroxycarbamimidoyl)pyrrolidine-1-carboxylate 71c (69 mg, 0.30 mmol) in DMF (1.3 mL). HCTU (156 mg, 0.38 mmol) was then added to the resulting mixture at r.t. and stirred at 100° C. for 3 hours. At this time, TLC showed complete conversion of starting material. The solution was partitioned between ethyl acetate and LiBr aqueous solution. The aqueous solution was extracted with ethyl acetate and the combined organic layers were washed with brine, dried over Na$_2$SO$_4$, and concentrated via vacuum. The residue was purified by silica gel column chromatography (25%, ethyl acetate/hexanes) to yield 71d (25 mg, 19%) as an oil. $^1$H NMR (400 MHz, CDCl$_3$) δ 8.02 (d, J=7.7 Hz, 2H), 7.32 (d, J=7.8 Hz, 2H), 4.99 (d, J=4.3 Hz, 1H), 3.73-3.52 (m, 2H), 2.68 (t, J=7.6 Hz, 2H), 2.32 (s, 1H), 2.19-2.04 (m, 2H), 1.96 (d, J=5.8 Hz, 1H), 1.69-1.59 (m, 2H), 1.46 (s, 3H), 1.37-1.22 (m, 16H), 0.91-0.85 (m, 3H); $^{13}$C NMR (101 MHz, CDCl3) δ 164.58, 156.00, 129.28, 128.24, 79.95, 77.36, 53.53, 46.59, 36.23, 32.56, 32.00, 31.26, 29.86, 29.56, 29.40, 29.37, 28.63, 28.44, 23.55, 22.81, 14.24; HRMS (ESI+): Calcd for C$_{25}$H$_{38}$N$_3$O$_3$ [M+H]: 428.2913. Found: 428.2918.

(S)-5-(4-octylphenyl)-3-(pyrrolidin-2-yl)-1,2,4-oxadiazole (71e)

Hydrogen chloride gas is passed through a solution of (S)-tert-butyl 2-(5-(4-octylphenyl)-1,2,4-oxadiazol-3-yl)pyrrolidine-1-carboxylate 38 (25 mg 0.06 mmol) in methanol (5 mL) for 5 min. The organic solvent was then removed under reduced pressure. The residue was washed with ether 3× and then extracted with ether, water, and 2 M NaOH. Organic layers were combined and washed with brine, dried over Na$_2$SO$_4$, and concentrated via vacuum to yield 71e (17 mg, 89%). $^1$H NMR (400 MHz, Methanol-d$_4$) δ 8.11 (d, J=8.4 Hz, 2H), 7.47 (d, J=8.5 Hz, 2H), 5.02 (t, J=7.7 Hz, 1H), 3.63-3.46 (m, 2H), 2.78-2.72 (m, 2H), 2.62 (dtd, J=12.8, 7.8, 5.2 Hz, 2H), 2.47-2.18 (m, 3H), 1.75-1.63 (m, 2H), 1.41-1.26 (m, 10H), 0.94-0.87 (m, 3H); $^{13}$C NMR (101 MHz, Methanol-d$_4$) δ 178.70, 168.58, 150.98, 130.64, 129.32, 122.14, 55.82, 47.19, 36.97, 32.99, 32.27, 30.50, 30.34, 30.30, 30.13, 24.53, 23.69, 14.40; HRMS (ESI+): Calcd for C$_{20}$H$_3$ON$_3$O [M+H]: 328.2388. Found: 328.2386.

(S,E)-tert-butyl (((tert-butoxycarbonyl)amino)(2-(5-(4-octylphenyl)-1,2,4-oxadiazol-3-yl)pyrrolidin-1-yl)methylene)carbamate (71f)

Synthesized using general procedure K to yield 71f (8 mg, 19%). $^1$H NMR (400 MHz, CDCl$_3$) δ 8.02 (d, J=8.4 Hz, 2H), 7.31 (d, J=8.5 Hz, 2H), 5.37 (s, 1H), 3.78 (s, 2H), 2.71-2.65 (m, 2H), 2.38-2.29 (m, 1H), 2.08 (ddt, J=45.5, 12.7, 7.0 Hz, 3H), 1.67-1.60 (m, 2H), 1.49 (s, 18H), 1.34-1.25 (m, 10H), 0.90-0.85 (m, 3H); $^{13}$C NMR (101 MHz, CDCl$_3$) δ 170.60, 166.89, 161.65, 129.09, 128.23, 122.89, 77.16, 54.75, 49.39, 36.05, 31.80, 31.03, 30.84, 29.66, 29.40, 29.36, 29.18, 29.17, 28.15, 27.99, 27.95, 22.60, 14.03; HRMS (ESI+): Calcd for C$_{31}$H$_{48}$N$_5$O$_5$ [M+H]: 570.3655. Found: 570.3659.

(S)-amino(2-(5-(4-octylphenyl)-1,2,4-oxadiazol-3-yl)pyrrolidin-1-yl)methaniminium chloride (71)

Synthesized using general procedure J to yield the title product (1.5 mg, 28%) as white solid. $^1$H NMR (400 MHz, Methanol-d$_4$) δ 8.05 (d, J=6.9 Hz, 2H), 7.43 (d, J=7.2 Hz, 2H), 5.29 (d, J=7.3 Hz, 1H), 3.74-3.69 (m, 1H), 3.65-3.53 (m, 1H), 2.73 (t, J=7.8 Hz, 2H), 2.52-2.39 (m, 2H), 2.19 (s, 2H), 1.70-1.63 (m, 2H), 1.32 (d, J=20 Hz, 10H), 0.93-0.86 (m, 3H); $^{13}$C NMR (126 MHz, Methanol-d$_4$) δ 178.25, 171.14, 156.91, 150.62, 130.55, 129.20, 122.45, 56.29, 36.96, 33.00, 32.35, 32.31, 30.51, 30.36, 30.31, 24.09, 23.70, 14.41; HRMS (ESI+): Calcd for C$_{21}$H$_{32}$N$_5$O [M+H]: 370.2606. Found: 370.2617.

Compound 72

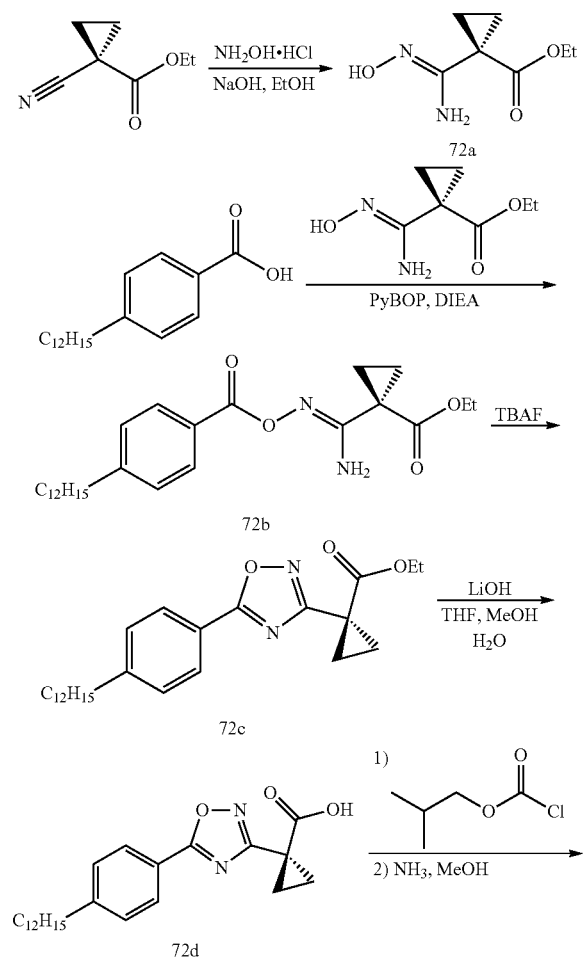

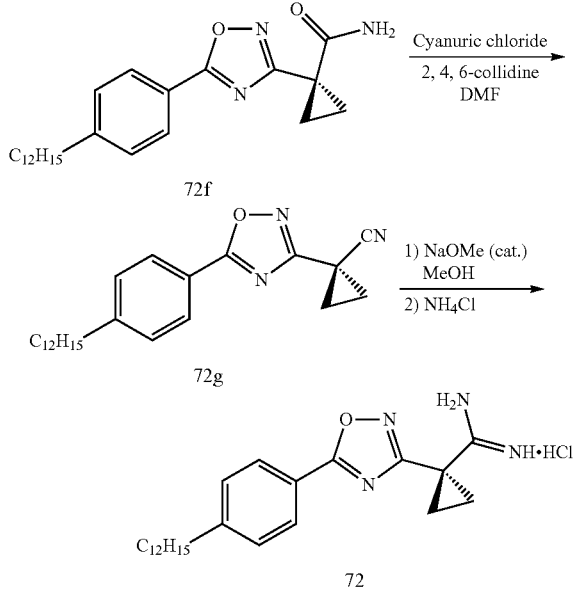

(Z)-ethyl 1-(N'-hydroxycarbamimidoyl)cyclopropanecarboxylate (72a)

Sodium hydroxide (0.33 g, 8.26 mmol) and hydroxylamine hydrochloride (0.55 g, 7.91 mmol) were stirred in EtOH (7.19 mL, 1 M) at r.t. for 2 h. The mixture was filtered through a fine frit and ethyl 1-cyano-1-cyclorpropanecarboxylate (1.0 g, 7.19 mmol) was added and the reaction heated to 50° C. overnight. The mixture was then cooled to r.t., evaporated to a white solid, and immediately purified by flash chromatography. 46%. White solid. R$_f$=0.37 (75% EtOAc in hexanes). $^1$H NMR (300 MHz, CDCl$_3$) δ 5.01 (s, 2H), 4.11 (q, 7.1, 2H), 1.37 (dd, J=4.2, 7.2, 2H), 1.29 (dd, J=4.0, 7.1, 2H), 1.20 (t, J=7.1, 3H). $^{13}$C NMR (75 MHz, CDCl$_3$) δ 172.40, 152.34, 61.41, 25.02, 15.65, 14.11.

(Z)-ethyl 1-(N'-((4-dodecylbenzoyl)oxy)carbamimidoyl)cyclopropanecarboxylate (72b)

General procedure B was used to couple 72a (0.23 g, 1.35 mmol) and 4-dodecylbenzoic acid (0.39 g, 1.35 mmol) to yield the title product as a white solid (54% yield). R$_f$=0.27 (25% EtOAc in hexanes). $^1$H NMR (300 MHz, CDCl$_3$) δ 7.88 (d, J=8.2, 2H), 7.17 (d, J=8.2, 2H), 5.61 (s, 2H), 4.08 (q, J=7.1, 2H), 2.40 (t, J=7.7, 2H), 1.60-1.44 (m, 6H), 1.28-1.18 (m, 21H), 0.82 (t, J=6.6, 3H). $^{13}$C NMR (75 MHz, CDCl$_3$) δ 171.76, 163.88, 157.45, 148.49, 129.38, 128.41, 126.86, 61.39, 35.92, 31.83, 31.05, 29.56, 29.49, 29.38, 29.27, 29.19, 28.67, 24.83, 22.60, 16.60, 14.03, 13.99.

ethyl 1-(5-(4-dodecylphenyl)-1,2,4-oxadiazol-3-yl)cyclopropanecarboxylate (72c)

General procedure G was used to convert 72b (325 mg, 0.73 mmol) to the title product. 84%. R$_f$=0.56 (20% EtOAc in hexanes). $^1$H NMR (300 MHz, CDCl$_3$) δ 7.98 (d, J=8.2, 2H), 7.26 (d, J=8.2, 2H), 4.16 (q, J=7.1, 2H), 2.62 (t, J=7.7, 2H), 1.68 (dd, J=4.3, 7.6, 2H), 1.64-1.54 (m, 2H), 1.50 (dd, J=4.3, 7.6, 2H), 1.36-1.12 (m, 21H), 0.82 (t, J=6.6, 3H). $^{13}$C NMR (75 MHz, CDCl$_3$) δ 175.61, 170.94, 169.68, 148.39, 129.09, 128.07, 121.61, 61.58, 36.04, 31.91, 31.09, 29.63, 29.56, 29.45, 29.35, 29.22, 22.68, 21.27, 16.65, 14.09.

1-(5-(4-dodecylphenyl)-1,2,4-oxadiazol-3-yl)cyclopropanecarboxylic acid (72d)

To a mixture of 72c (261 mg, 0.61 mmol) and LiOH (3.0 equiv) were added THF (2 mL), ᵗBuOH (2 mL), and H₂O (2 mL). The mixture was stirred at r.t. for 4 h. The mixture was diluted with EtOAc (100 mL) and washed with 1 M HCl (3×10 mL). The organic layer was washed with brine, dried over MgSO₄, evaporated to a white solid, and carried on crude.

1-(5-(4-dodecylphenyl)-1,2,4-oxadiazol-3-yl)cyclopropanecarboxamide (72e)

Crude acid 72d (244 mg, 0.61 mmol) was dissolved in CH₂Cl₂ (0.3 M) at 0° C. and treated with TEA (3.0 equiv) and then isobutyl chloroformate (1.1 equiv). The mixture turned turbid after the addition and was warmed to r.t. After 1 h at r.t., the mixture was treated with 2 M NH₃ in MeOH (2.0 equiv) and stirred 8 h. The mixture was then evaporated and taken on crude.

1-(5-(4-dodecylphenyl)-1,2,4-oxadiazol-3-yl)cyclopropanecarbonitrile (72f)

The crude amide 72e (168 mg, 0.42 mmol) was dissolved in DMF (0.1 M) and 2,4,6-collidine (8 equiv) at 0° C. and then treated with cyanuric chloride (3.15 equiv) and warmed to r.t. The reaction turned a deep red color and was stirred for 12 h. The mixture was then extracted with EtOAc (20×volume of DMF) and washed 3× with saturated NaHCO₃ (10× the volume of DMF), 3× with 1 M HCl (10× the volume of DMF), and 1× with brine (10× the volume of DMF). The organic layer was then dried with MgSO₄, evaporated to a yellow oil, and immediately purified with flash chromatography to yield the title compound. 31% (over 3 steps). R$_f$=0.34 (15% EtOAc in hexanes). $^1$H NMR (300 MHz, CDCl₃) δ 7.98 (d, J=8.3, 2H), 7.31 (d, J=8.4, 2H), 2.67 (t, J=7.7, 2H), 1.84 (s, 4H), 1.70-1.56 (m, 2H), 1.43-1.19 (m, 18H), 0.87 (t, J=6.7, 3H). $^{13}$C NMR (75 MHz, CDCl₃) δ 176.78, 168.09, 149.17, 129.32, 128.30, 121.03, 119.08, 36.18, 32.00, 31.15, 29.73, 29.64, 29.53, 29.45, 29.31, 22.78, 18.29, 14.22, 7.87.

1-(5-(4-dodecylphenyl)-1,2,4-oxadiazol-3-yl)cyclopropanecarboximidamide hydrochloride (72)

General procedure A was used to convert 72f (71 mg, 0.19 mmol) to the title product. 20%. Yellow solid. R$_f$=0.42 (15% MeOH in CHCl₃). $^1$H NMR (600 MHz, DMSO) δ 9.27 (s, 4H), 7.77 (d, J=8.2, 2H), 7.28 (d, J=8.2, 2H), 2.58 (t, J=7.6, 2H), 1.86-1.44 (m, 6H), 1.41-0.95 (m, 18H), 0.83 (t, J=6.6, 2H). $^{13}$C NMR (151 MHz, DMSO) δ 175.28, 169.33, 166.96, 148.58, 129.38, 127.74, 124.37, 34.97, 31.10, 30.30, 28.82, 28.61, 28.51, 28.40, 21.90, 20.93, 15.87, 13.81.

Compound 73

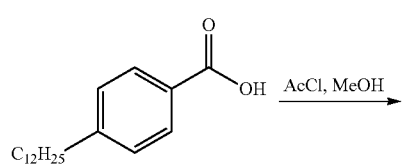

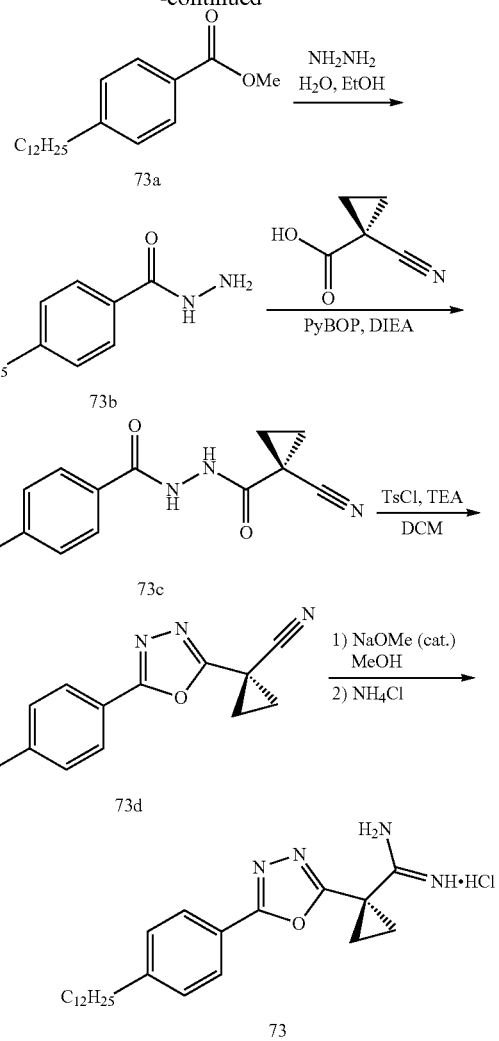

methyl 4-dodecylbenzoate (73a)

General procedure I was used to convert 4-dodecylbenzoic acid (1.2 g, 4.13 mmol) to the title product. 95%. Clear and colorless oil. R$_f$=0.45 (5% EtOAc in hexanes). $^1$H NMR (600 MHz, CDCl₃) δ 7.94 (d, J=8.1, 2H), 7.23 (d, J=8.1, 2H), 3.89 (s, 3H), 2.61 (t, J=7.7, 2H), 1.67-1.55 (m, 2H), 1.37-1.17 (m, 18H), 0.88 (t, J=7.0, 3H). $^{13}$C NMR (151 MHz, CDCl₃) δ 167.31, 148.62, 129.73, 128.54, 127.75, 60.68, 36.14, 32.05, 31.25, 29.76, 29.68, 29.58, 29.47, 29.37, 29.33, 22.81, 14.23.

4-dodecylbenzohydrazide (73b)

General procedure J was used to convert 73a (1.2 g, 3.94 mmol) to the title product. 42%. White solid. R$_f$=0.31 (75% EtOAc in hexanes). $^1$H NMR (300 MHz, CDCl₃) δ 7.65 (d, J=8.2, 2H), 7.22 (d, J=8.3, 2H), 4.92 (s, 2H), 2.62 (t, J=7.7, 2H), 1.66-1.54 (m, 2H), 1.37-1.17 (m, 18H), 0.86 (t, J=6.6, 3H). $^{13}$C NMR (75 MHz, CDCl₃) δ 168.92, 147.51, 130.12, 129.74, 128.86, 127.00, 36.00, 32.04, 31.73, 31.32, 29.77, 29.70, 29.59, 29.48, 29.38, 22.79, 14.24.

N'-(1-cyanocyclopropanecarbonyl)-4-dodecylbenzohydrazide (73c)

General procedure B was used to couple 73b (250 mg, 0.82 mmol) and 1-cyano-1-cyclopropanecarboxylic acid (91 mg, 0.82 mmol) to yield the title product. 71%. White solid. $R_f$=0.57 (50% EtOAc in hexanes). $^1$H NMR (300 MHz, CDCl$_3$) δ 7.73 (d, J=8.3, 2H), 7.19 (d, J=8.3, 2H), 2.55 (t, J=7.7, 2H), 1.68 (dd, J=4.6, 8.3, 2H), 1.64-1.48 (m, 4H), 1.41-1.18 (m, 18H), 0.87 (t, J=6.7, 3H). $^{13}$C NMR (75 MHz, CDCl$_3$) δ 165.68, 164.69, 148.31, 128.83, 128.44, 127.60, 118.89, 36.02, 32.02, 31.25, 29.76, 29.57, 29.45, 29.39, 22.79, 18.56, 14.23, 12.64.

1-(5-(4-dodecylphenyl)-1,3,4-oxadiazol-2-yl)cyclopropanecarbonitrile (73d)

General procedure K was used to convert 73c (230 mg, 0.58 mmol) to the title product. 75%. White solid. $R_f$=0.46 (25% EtOAc in hexanes). $^1$H NMR (300 MHz, CDCl$_3$) δ 7.91 (d, J=8.3, 2H), 7.29 (d, J=8.3, 2H), 2.64 (t, J=7.7, 2H), 1.93 (s, 4H), 1.73-1.50 (m, 2H), 1.48-1.16 (m, 18H), 0.85 (t, J=6.2, 3H). $^{13}$C NMR (75 MHz, CDCl$_3$) δ 165.64, 162.07, 147.79, 129.21, 126.96, 120.53, 117.91, 36.03, 31.95, 31.14, 29.67, 29.60, 29.49, 29.38, 29.27, 22.72, 19.17, 14.16, 7.14.

1-(5-(4-dodecylphenyl)-1,3,4-oxadiazol-2-yl)cyclopropanecarboximidamide hydrochloride (73)

General procedure A was used to convert 73d (164 mg, 0.43 mmol) to the title product. 46%. Tan solid. $R_f$=0.36 (15% MeOH in CHCl$_3$). $^1$H NMR (600 MHz, DMSO) δ 9.39 (d, J=11.1, 4H), 7.91 (d, J=7.5, 2H), 7.42 (d, J=7.6, 2H), 2.66 (t, J=7.1, 2H), 1.96-1.81 (m, 4H), 1.64-1.54 (m, 2H), 1.33-1.19 (m, 18H), 0.85 (t, J=6.7, 3H). $^{13}$C NMR (151 MHz, DMSO) δ 166.68, 164.11, 163.69, 146.93, 129.22, 126.53, 120.55, 34.97, 31.20, 30.51, 28.94, 28.91, 28.88, 28.72, 28.62, 28.50, 22.01, 20.26, 16.81, 13.88.

(S)-2-(3-(4-octylphenyl)-1,2,4-oxadiazol-5-YL)pyrrolidine-1-carboximidamide ("SLR080811") drives a SphK1-dependent increase in S1P in mice Materials and Methods Sphk1-/- [5] and Sphk2-/- [4] mice were gifts from Dr. Richard Proia (NIH/NIDDK). C57BL/6j mice were from Jackson Laboratories (Bar Harbor, Me.). The plasmid encoding diacylglycerol kinase alpha and was a gift from Dr. Kaoru Goto (Yamagata University School of Medicine, Yamagata, Japan). Adult mouse kidney fibroblast cultures were a gift from Dr. Amandeep Bajwa (University of Virginia). Deuterated (D7) S1P, S1P, sphingosine, C17 S1P and C17 sphingosine were purchased from Avanti Polar Lipids (Alabaster, Ala., USA).

Kinase Assays

SphK activity was measured by a scintillation proximity assay as previously described [1], the disclosure of which is incorporated herein. Briefly, recombinant SphK1 or SphK2 were expressed in Sf9 insect cells, crude homogenates were prepared and incubated in 96 well FlashPlates (Perkin-Elmer) in a buffer containing D-erythro-sphingosine and γ-[33P]ATP. The [33P]S1P product, which adheres to the plate wall, was quantified by scintillation counting. To assay ceramide kinase or diacylglycerol kinases, the recombinant proteins were incubated with γ-[32P]ATP and substrate (C6 ceramide or 1-Ohexadecyl-2-acetyl-sn-glycerol, respectively) and the lipid product, after recovery by organic extraction, was resolved by thin layer chromatography, detected by autoradiography, and quantified by liquid scintillation counting. These assays were performed with and without a fixed concentration of inhibitor and its effect on KM and Vmax determined.

Sample Preparation

Sample preparation protocols were from Shaner et al. [2], the disclosure of which is incorporated herein, with minor modifications. Cell pellets (2-4×106 cells), whole blood (20 μl) or plasma (50 μl) was mixed with 2 ml of a methanol:chloroform solution (3:1) and transferred to a capped glass vial. Suspensions were supplemented with 10 μl of internal standard solution containing 10 pmoles each of C17 S1P or deuterated (D7) S1P, C17 sphingosine or deuterated (D7) sphingosine and an undecyl analogue of compound 1a [3,4]. The mixture was placed in a bath sonicator for 10 min and incubated at 48° C. for 16 hours. The mixture was then cooled to ambient temperature and mixed with 200 μl of 1M KOH in methanol. The samples were again sonicated and incubated a further 2 hours at 37° C. Samples were then neutralized by the addition of 20 μl of glacial acetic acid and transferred to 2 ml microcentrifuge tubes. Samples were then centrifuged at 12,000×g for 12 min at 4° C. The supernatant fluid was collected in a separate glass vial and evaporated under a stream of nitrogen gas. Immediately prior to LC-MS analysis, the dried material was dissolved in 0.3 ml of methanol and centrifuged at 12,000×g for 12 min at 4° C. Fifty μl of the resulting supernatant fluid was analyzed.

LC/MS Protocol

Analyses were performed by Liquid Chromatography-ESI Mass Spectrometry (LC-MS) using a triple quadrupole mass spectrometer (AB-Sciex 4000 Q-Trap) coupled to a Shimadzu LC-20AD LC system. A binary solvent gradient with a flow rate of 1 ml/min was used to separate sphingolipids and drugs by reverse phase chromatography using a Supelco Discovery C18 column (50 mm×2.1 mm, 5 μm bead size). Mobile phase A consisted of water: methanol: formic acid (79:20:1) while mobile phase B was methanol: formic acid (99:1). The run started with 100% A for 0.5 min. Solvent B was then increased linearly to 100% B in 5.1 min and held at 100% for 4.3 min. The column was finally re-equilibrated to 100% A for 1 min. Natural sphingolipids were detected using multiple reaction monitoring (MRM) protocols previously described [24], the disclosure of which is incorporated herein, as follows: C17S1P (366.4→250.4); S1P (380.4→264.4); dihydroS1P (382.4→266.4); deuterated (D7)C18S1P (387.4→271.3); C17sphingosine (286.4→250.3); sphingosine (300.5→264.4); sphinganine (302.5→260.0), deuterated (D7) sphingosine (307.5→271.3). Fragmentation of compound (S)-2-(3-(4-octylphenyl)-1,2,4-oxadiazol-5-YL)pyrrolidine-1-carboximidamide was analyzed by direct infusion of a 1 μM solution in methanol:formic acid (99:1) and it was found that the transition (371.1→140.1) in positive mode provided the most intense signal at the following voltages, DP: 76; EP: 10; CE: 29; CXP: 10. All analytes were analyzed simultaneously using the aforementioned MRMs. Retention times for all analytes under our experimental conditions were between 5.1 and 5.6 min. Ceramide (16:0) was measured in positive mode by monitoring the m/z 264.4 product ion and using a Supelco Supelcosil LC-NH2 column (50 mm×2.1 mm, 3 μm bead size) as previously described [2]. Quantification was carried out by measuring peak areas using commercially available software (Analyst 1.5.1).

Cell Culture

U937 cells were grown in RPMI 1640 media supplemented with L-glutamate, 10% fetal bovine serum (FBS) and 1% penicillin/streptomycin at 37° C. in an atmosphere containing 5% CO2 [12]. SKOV3 cells were grown in McCoy's 5a media supplemented with 10% FBS and penicillin/streptomycin at 37° C. in an atmosphere containing 5% CO2. Mouse kidney fibroblast were grown in DMEM low glucose media with 10% FBS. Twenty-four hours before adding inhibitors, the growth media was replaced with media containing 0.5% FBS.

Cell Viability Assay

U937 cells were plated in 96 well plates at a density of 60-80,000 cells per well. Cells were treated with the indicated concentration of compounds for 24 hours. Cell viability was assessed using TACS™ MTT assay according to the manufacturer's protocol (R&D System, Minneapolis, Minn.). Briefly, 10 μl of MTT reagent was added to 100 μl of cell culture medium and the plate was incubated at 37° C. for 4 hours, followed by incubation with 100 μl of Detergent Reagent at r.t. for 2 hours. Absorbance was measured at a wavelength of 570 nm.

Generation of F2 Hybrid Mice

Sphk1−/− and Sphk2−/− mice were mated and 15 (5 male, 10 female) of the resulting F1 heterozygotes were intercrossed to yield a cohort of F2 hybrid mice. Mice were genotyped at weaning (P21) and the various genotypes were found at the expected Mendelian ratios except for the embryonic lethal double null genotype [5]. After 12-14 hours of fasting, blood was obtained from F2 mice from retro-orbital sinuses under light isofluorane anesthesia. Aliquots of whole blood and plasma were processed for LC-MS analysis of S1P levels as described above.

Pharmacokinetic Analysis

Groups of 8-12 week old mice (strain: C57BL/6j) were injected (intraperitoneal route) with either SLR080811 (dose: 10 mg/kg) or an equal volume of vehicle (2% solution of hydroxypropyl-3-cyclodextrin (Cargill Cavitron 82004)). After injection, animals were bled at the specified time points (ASAP time points were 1-2 min after dosing). Whole blood was processed immediately for LC-MS analysis as described above. Animal protocols were approved prior to experimentation by the University of Virginia's School of Medicine Animal Care and Use Committee.

Inhibitor Design Strategy

In the course of our previous studies of amidine-based SphK1 inhibitors [3,6] designed to generate compounds with longer half-lives, we reasoned that compounds containing amidine or amide might be rapidly hydrolyzed in vivo. Therefore, we synthesized compound SLR080811 (Table 3), which retained the pyrrolidine ring of our SphK1 inhibitor compound 1a [4] while replacing the carboximidamide group with the more stable guanidine isostere. Further, the amide in compound 1a is replaced by an oxadiazole group. SLR080811 was evaluated at recombinant SphKs, other lipid kinases, in whole cells and finally, in wild type and SphK null mice.

TABLE 3

Chemical structure and inhibitory constants of SLR080811 and 1a

| Compound | SphK1 $K_i$ (μM) | SphK2 $K_i$ (μM) |
|---|---|---|
| 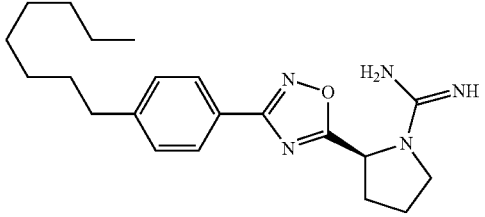<br>SLR080811 | 12 | 1.3 |
| 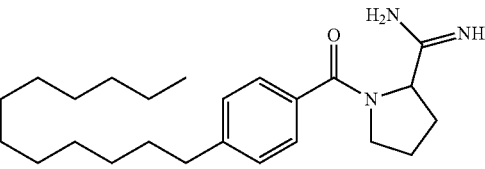<br>1a | 0.1 | 1.5 |

Evaluation of SLR080811 In Vitro

SLR080811, prepared as the HCl salt, was tested first at recombinant SphK1 and SphK2 using a broken cell assay (see Methods). In these assays, SLR080811 was found to have inhibitory constants ($K_i$) of 1.3 and 12 μM for SphK2 and SphK1, respectively (Table 3). Further, SLR080811 was found to be competitive with sphingosine, but not with ATP. Because SLR080811 is a sphingosine analog, we tested SLR080811 as an inhibitor of related lipid kinases including ceramide kinase and DGKα. At a concentration of 3 μM, no inhibition of either enzyme was observed (data not shown). We characterized SLR080811 in detail because of its SphK2-selectivity that, although modest (10-fold), is unusual in our carboximidamide series. We chose human leukemia U937 cells for the evaluation of SphK2 inhibitors because they exhibit high SphK1 and SphK2 activities, can be cultured with ease, and more importantly, these cells have been used in the past by us and other authors [7] to test SphK1 inhibitors enabling comparisons of the effects of inhibitors. We first treated U937 cultures with either vehicle or SLR080811 and measured the intracellular levels of S1P, sphinganine 1-phosphate (dhS1P), sphingosine (Sph), sphinganine (dhSph) and SLR080811. We observed that treatment of U937 cells with SLR080811, but not vehicle, resulted in decreased amounts of phosphorylated sphingolipids S1P and dhS1P (FIGS. 1a and 1c) and the concomitant increase of the corresponding non-phosphorylated precursors sphingosine and sphinganine (FIGS. 1b and 1d). The data in FIGS. 1a and 1c indicate that the $IC_{50}$ values of SLR080811 are less than the its $K_i$ (1.3 μM) determined at recombinant SphK2. In addition to sphingolipids, we also measured the intracellular concentration of SLR080811. As shown in FIG. 1e, (S)-2-(3-(4-octylphenyl)-1,2,4-oxadiazol-5-YL)pyrrolidine-1-carboximidamide accumulates inside U937 cells in a concentration dependent manner, which might explain its potent effect on the levels of intracellular sphingolipids shown in FIG. 1.

Figure 2:
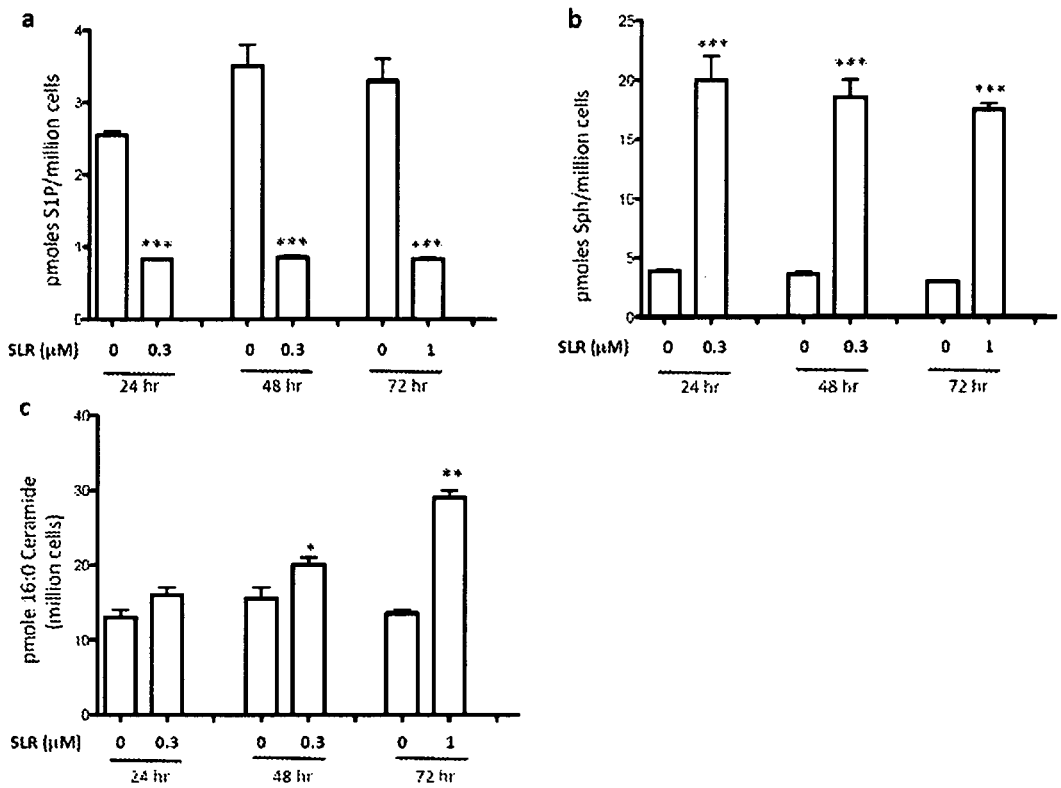
FIG. 2 exemplifies cultured U937 cells that were treated with vehicle or (S)-2-(3-(4-octylphenyl)-1,2,4-oxadiazol-5-YL)pyrrolidine-1-carboximidamide (SLR080811) (1 μM) for different times as indicated. Cells were harvested by centrifugation, lysed and the amounts of sphingolipids and SLR080811 in the lysates were measured by LC-MS as described in the Methods section. Amounts are expressed as the number of pmoles per million cells. The graphs are: a: S1P; b: sphingosine; c: C16:0-ceramide. Data are presented as means±SD of three independent experiments. $*p<0.05$, $p<0.01$, $*p<0.001$ (Student t-test, compared with the control (no compound treatment)).

Treatment of human Jurkat T leukemia cells or human SKOV3 ovarian cancer cells with SLR080811 for 2 hours also resulted in decreased S1P (data not shown). In U937 cells, the effect of SLR080811 on intracellular sphingolipids was observed as early as 20 min after SLR080811 e exposure (data not shown) and persisted for at least 72 hours as documented in FIGS. 2a and 2b. We also quantified one of the prominent ceramide species (C16:0) in these cells and found that this ceramide was significantly elevated, but only at the 48 and 72 hour time points (FIG. 2c).

Figure 3:
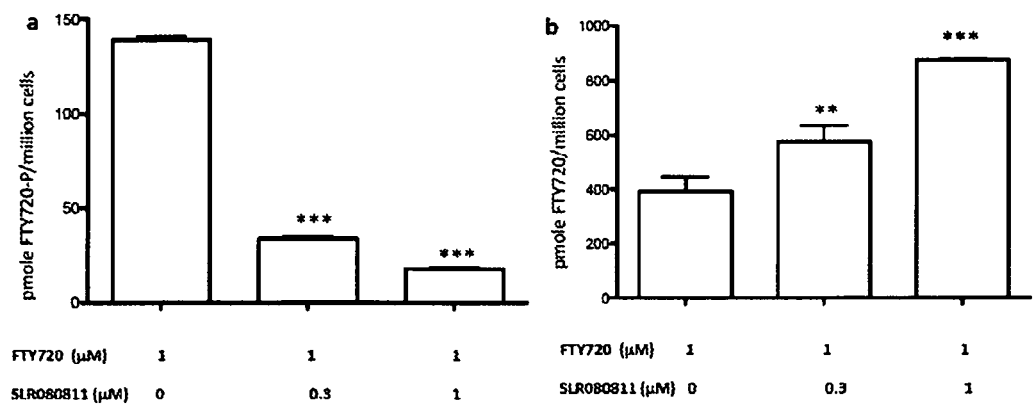
FIG. 3 exemplifies levels of FTY720-P and FTY720 in U397 cells treated with FTY720 and (S)-2-(3-(4-octylphenyl)-1,2,4-oxadiazol-5-YL)pyrrolidine-1-carboximidamide (SLR080811). Cultured U937 cells were exposed to 1 μM of FTY720 and two concentrations of SLR080811 as indicated in the figure. After 2 hours of exposure, cells were harvested by centrifugation, lysed and the amounts of FTY720 and phospho-FTY720 were measured by LC-MS as described in the Methods section. The graphs are: a: accumulation of FTY720-P; b: accumulation of FTY720. Amounts are expressed as the number of pmoles per million cells. Drug and FTY720 concentrations on X axis refer to the concentration of these molecules in the culture medium. Data are presented as means±SD of three independent experiments. $*p<0.05$, $p<0.01$, $*p<0.001$ (one-way ANOVA; and Bonferroni's multiple comparison test, compared with the control (no compound treatment)).
Figure 4:
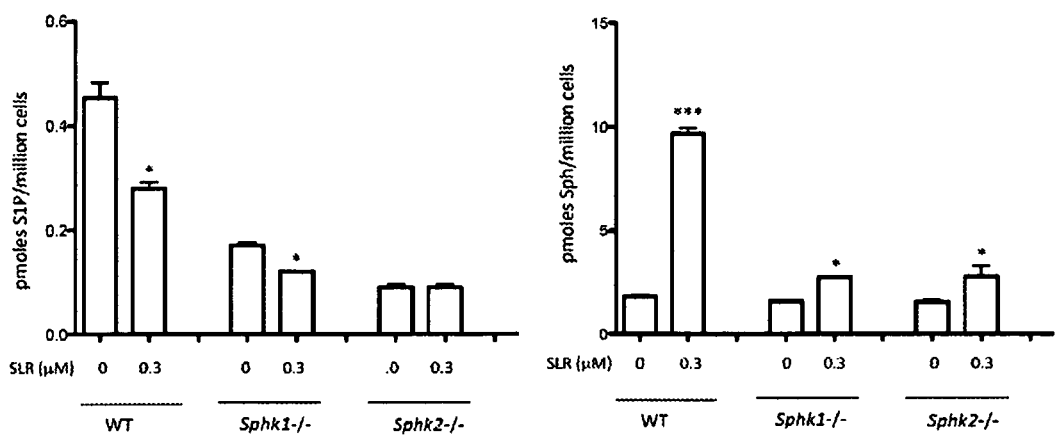
FIG. 4 exemplifies the selectivity of (S)-2-(3-(4-octylphenyl)-1,2,4-oxadiazol-5-YL)pyrrolidine-1-carboximidamide (SLR080811) inhibition: WT, Sphk1−/− and Sphk2−/− adult mouse kidney fibroblast were exposed to 1 μM SLR080811 for 2 hours. Cells were harvested by centrifugation, lysed and sphingolipids were measured by LC-MS as described in Example 5. The graphs are: (a) S1P; and (b) sphingosine. Data are presented as means±SD of three independent experiments. $*p<0.05$, $***p<0.001$ (Student t-test, compared with the control (no inhibitor)).

The most obvious explanation for the decline in U937 cell-associated S1P and dhS1P in response to SLR080811 is decreased synthesis, but it is conceivable that the decline was somehow the result of increased metabolism via, for example, S1P phosphatase or S1P lyase, or increased S1P export. To discriminate between these possibilities, we used FTY720, an SphK2-selective substrate [8, 9]. We observed that treatment of U937 cells with SLR080811 impaired their ability to convert FTY720 into FTY720-phosphate. As shown in FIG. 3, we observed much lower levels of intracellular FTY720-phosphate in SLR080811-treated cells that, as expected, correlated with correspondingly higher levels of FTY720. This suggests that the reduction of intracellular S1P levels in U937 cells produced by SLR080811 is due to SphK2 inhibition rather than the alternative mechanisms mentioned above. To evaluate further the selectivity of SLR080811 in vitro, we used SphK1 null and SphK2 null mouse kidney fibroblasts. Because the wild type fibroblasts derived from adult mouse kidney have both SphK1 and SphK2 activity (not shown), null cells are a useful model for testing compound selectivity. We found that SLR080811 reduces the levels of intracellular S1P in both wild type and SphK1 null cells but not in SphK2 null cells (FIG. 4a). This suggests SphK2, but not SphK1, is a target for SLR080811. However, the effect of SLR080811 on sphingosine levels was not selective for SphK2. As shown in FIG. 4b, both SphK1 null and SphK2 null fibroblasts exhibited increased concentrations of sphingosine on treatment with SLR080811 suggesting that other mechanisms may be at play in the regulation of these sphingolipids. Finally, we tested whether the effects of SLR080811 on U937 cells included cell toxicity. In general, we found that SLR080811 has no obvious cytotoxic effects on U397 cells.

Figure 5:
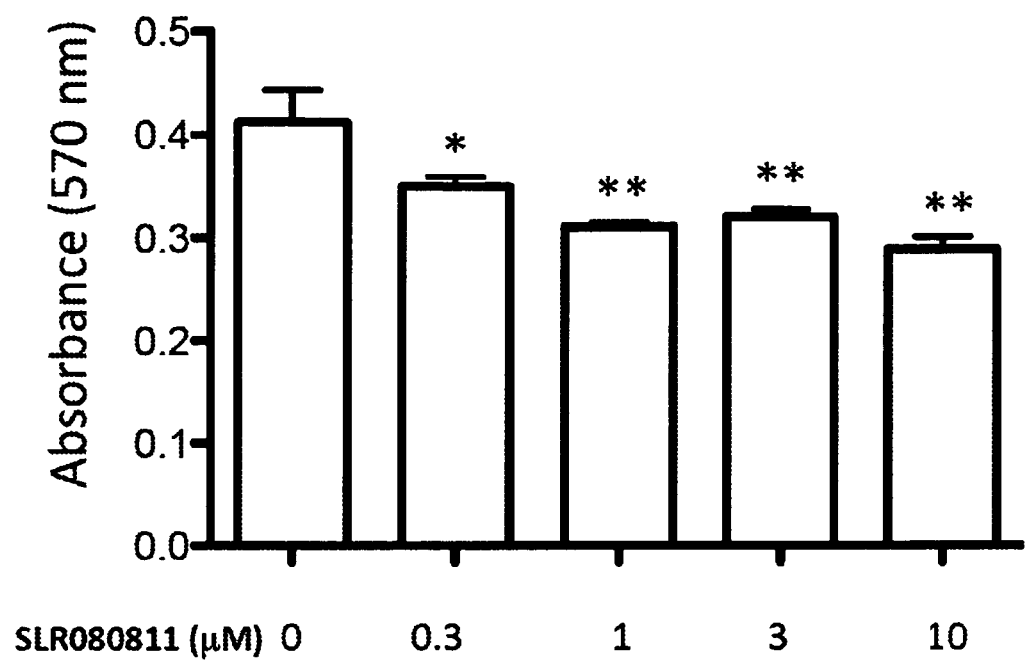
FIG. 5 exemplifies the viability of U937 cells treated with: (a) (S)-2-(3-(4-octylphenyl)-1,2,4-oxadiazol-5-YL)pyrrolidine-1-carboximidamide (SLR080811). U937 cells were exposed to various concentrations of compounds for 24 hours as indicated. The viability of the cells was measured by MTT assay as described in the Methods section. Viability is directly proportional to the amount of formazan dye produced by live cells as measured by absorbance at 570 nm. Data are presented as means±SD of three independent experiments. $*p<0.05$, $**p<0.01$ (one-way ANOVA, and Bonferroni's multiple comparison post test, compared with the control (no inhibitor)).

For example, cultures grew normally in medium containing up to 3 μM SLR080811 and there were no signs of cell growth inhibition (data not shown). Further, we investigated the effect of SLR080811 on U397 cells using a standard assay that correlates cell viability with their redox potential (MTT assay, see Methods section). We found that (SLR080811 had a slight cytotoxic effect that is apparent even at the lowest concentration tested but was not concentration dependent (FIG. 5).

Evaluation of SLR080811 In Vivo: Isotype Selectivity and Pharmacokinetics

As an extension of our experiments in vitro, we sought to evaluate the sphingosine kinase isotype selectivity of SLR080811 in vivo. To this end, we injected groups of SphK1 null, SphK2 null, and wild type mice with a single intraperitoneal dose of SLR080811 and analyzed the blood levels of S1P. We observed (FIG. 6a) that SphK1 null mice exhibit reduced levels of blood S1P after injection whereas in SphK2 null animals the blood levels of S1P did not change. This result once again suggests that SLR080811 is a selective inhibitor of SphK2. Levels of S1P in SphK1-null mice reached a nadir between 2 and 4 hours after injection and slowly returned to pre-treatment levels at approximately 24 hours. In addition to S1P, we also measured the blood levels of SLR080811. The kinetics of SLR080811 approximate that of S1P in the sense that we observed an early SLR080811 peak at 1 h, rather than 2 h (FIG. 6b) as in the case of S1P, and then a slow disappearance of the compound over the subsequent 24 h.

Figure 6:
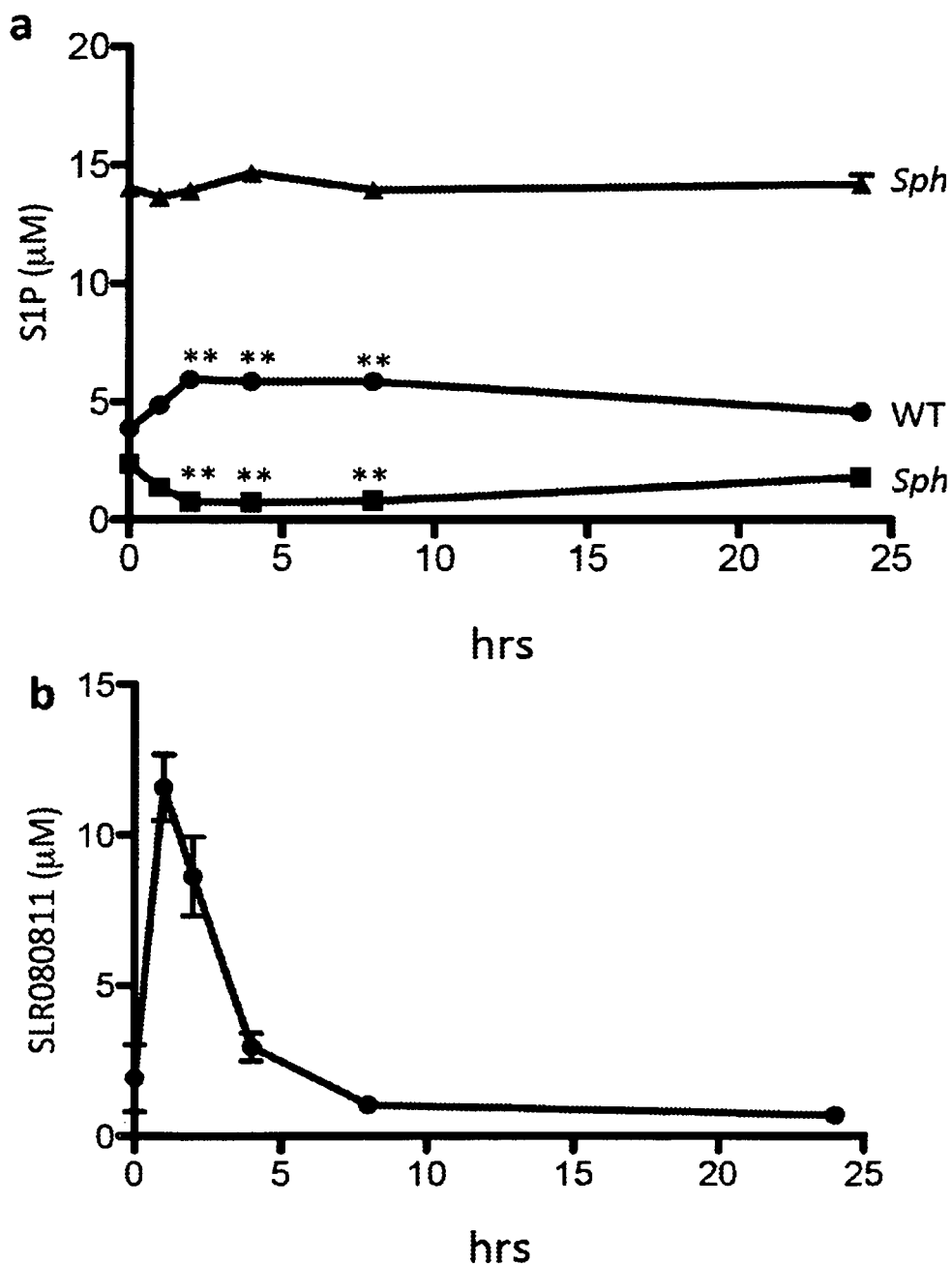
FIG. 6 exemplifies S1P and (S)-2-(3-(4-octylphenyl)-1,2,4-oxadiazol-5-YL)pyrrolidine-1-carboximidamide (SLR080811) levels in the blood of mice injected with SLR080811. Wild type or Sphk1 null or Sphk2 null mice were administered SLR080811 (dose: 10 mg/kg, intraperitoneal route). Blood samples were drawn at times 0, 1, 2, 4, 8 and 24 hours post injection. Levels of: (a) S1P; and (b) SLR080811 in WT mice in blood samples were measured by LC-MS. Data are presented as means±SD of 3-5 mice per group. $*p<0.05$, $**p<0.01$ (repeated measures two way ANOVA, and Bonferroni's multiple comparison test compared to ASAP time point after injection of the compound (time 0)).
Figure 7:
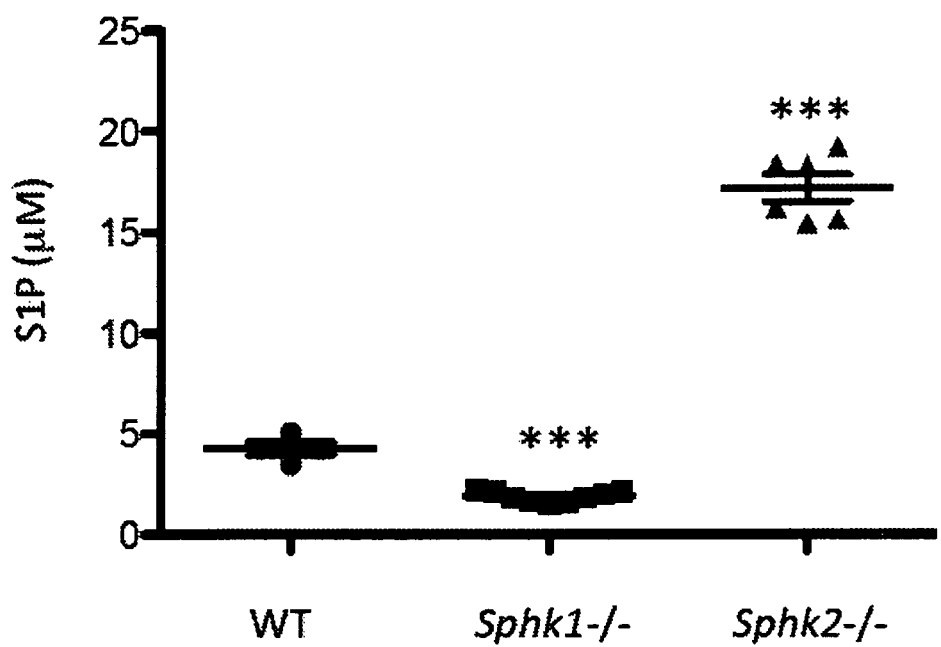
FIG. 7 exemplifies S1P levels in age-matched WT, Sphk1- and Sphk2-littermates. Blood were drawn from wild type; Sphk1 and SphK2 null mice and the S1P levels were measured by LCMS as described in the Methods section. Data shown are independent measurements of whole blood from 4 WT, 9 Sphk1$^{-/-}$ and 6 Sphk2$^{-/-}$ mice. The null mice were either heterozygous or wild type at the other. SphK locus. $***p<0.001$ (one-way ANOVA, and Bonferroni's multiple comparison test, compared with WT).

The effect of SLR080811 in wild type mice was to increase, rather than decrease, the levels of S1P (FIG. 6a). To investigate this seemingly paradoxical result, we generated a cohort of age-matched Sphk1 Sphk2 F2 hybrid mice (see Methods) and measured the blood S1P levels in SphK1 wild type, SphK2 null; SphK1 null, SphK2 wild type and SphK1 wild type, SphK2 wild type mice. These mice constitute a genetically homogeneous population whose levels of blood S1P that should be less influenced by genetic variation than the parent strains. In this population we observed, as shown in FIG. 7, the same pattern of blood S1P levels: high S1P in SphK2 null animals, lower S1P levels in wild type animals and, as has been reported, low levels of S1P in SphK1 null animals [5]. Thus it appears that SLR080811, by inhibiting SphK2, mimics the effect of lack of functional Sphk2 alleles.

Figure 8:
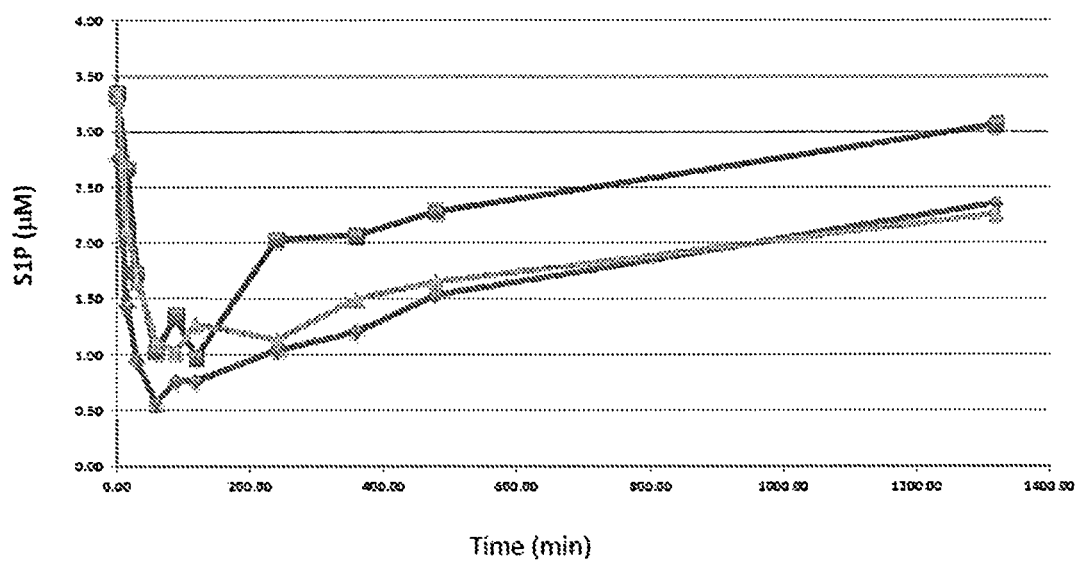
FIG. 8 exemplifies S1P levels in whole blood from three rats (SD, male, 450 μm) injected (10 mpk IP) with SLP7111228 (Compound 64). S1P was measured by LC-MS. Time points ASAP, 15 min, 30 min, 60 min, 90 min, 2 hr, 4 hr, 6 hr, 22 hr.

Compound 64 of the invention (SLP7111228) is a potent, selective inhibitor of SphK1. To learn the effect of administering SLP7111228 on blood S1P levels, we injected three male Sprague Dawley rats with this compound at a dose of 10 mg/kg using the intraperitoneal inject for administration. At the times indicated in FIG. 8, we drew blood from the tail vein of the rats and measured S1P using standard, published [2,4]methods. As documented in FIG. 8, administration of SLP7111228 resulted in a rapid decrease in the concentration of S1P in blood with S1P levels reaching a nadir at about 90 minutes after injection and remaining below normal levels for 12-24 hours. Thus, unlike SphK2 selective inhibitors, SphK1 selective inhibitors decrease blood S1P levels in rats (FIG. 8) and mice [4].

REFERENCES

1. Kharel, Y., Mathews, T. P., Kennedy, A. J., Macdonald, T. L. and Lynch, K. R. (2011) A rapid assay for assessment of sphingosine kinase inhibitors and substrates. Anal. Biochem. 411, 230-235.
2. Shaner, R. L., Allegood, J. C., Park, H., Wang, E., Kelly, S., Haynes, C. A., Sullards, M. C., and Merrill, A. H. (2009) Quantitative analysis of sphingolipids for lipidomics using triple quadrupole and quadrupole linear ion trap mass spectrometers. J. Lipid Res. 50, 1692-1707.
3. Mathews, T. P., Kennedy, A. J., Kharel, Y., Kennedy, P. C., Nicoara, O., Sunkara, M., Morris, A. J., Wamhoff, B. R., Lynch, K. R. and Macdonald, T. L. (2010) Discovery, biological evaluation, and structure-activity relationship of amidine based sphingosine kinase inhibitors. J. Med. Chem. 53, 2766-2778

4. Kharel, Y., Mathews, T. P., Gellett, A. M., Tomsig, J. L., Kennedy, P. C., Moyer, M. L., Macdonald, T. L. and Lynch, K. R. (2011) Sphingosine kinase type 1 inhibition reveals rapid turnover of circulating sphingosine 1-phosphate. Biochem. J. 440, 345-353

5. Mizugishi, K., Yamashita, T., Olivera, A., Miller, G. F., Spiegel, S. and Proia, R. L. (2005) Essential role for sphingosine kinases in neural and vascular development. Mol. Cell. Biol. 25, 11113-11121.

6. Kennedy, A. J., Mathews, T. P., Kharel, Y., Field, S. D., Moyer, J. L., East, J. E., Houck, J. D., Lynch, K. R. and Macdonald, T. L. (2011) Development of amidine-based sphingosine kinase 1 nanomolar inhibitors and reduction of sphingosine 1-phosphate in human leukemia cells. J. Med. Chem. 54, 3524-3548.

7. Paugh, S. W., Paugh, B. S., Rahmani, M., Kapitonov, D., Almenara, J. A., Kordula, T., Milstien, S., Adams, J. K., Zipkin, R. E., Grant, S. and Spiegel, S. (2008) A selective sphingosine kinase 1 inhibitor integrates multiple molecular therapeutic targets in human leukemia. Blood 112, 1382-1391.

8. Billich, A., Bornancin, F., Dévay, P., Mechtcheriakova, D., Urtz, N. and Baumruker, T. (2003) Phosphorylation of the immunomodulatory drug FTY720 by sphingosine kinases. J. Biol. Chem. 278, 47408-47415.

9. Paugh, S. W., Payne, S. G., Barbour, S. E., Milstein, S. and Spiegel, S. (2003) The immunosuppressant FTY720 is phosphorylated by sphingosine kinase type 2. FEBS Lett. 554, 189-193.

The claimed invention is:

1. A compound that is selected from the group consisting of:

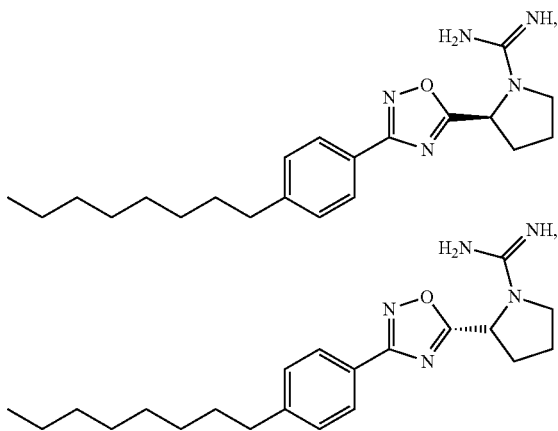

and pharmaceutically acceptable salts thereof.

2. A compound that is selected from the group consisting of:

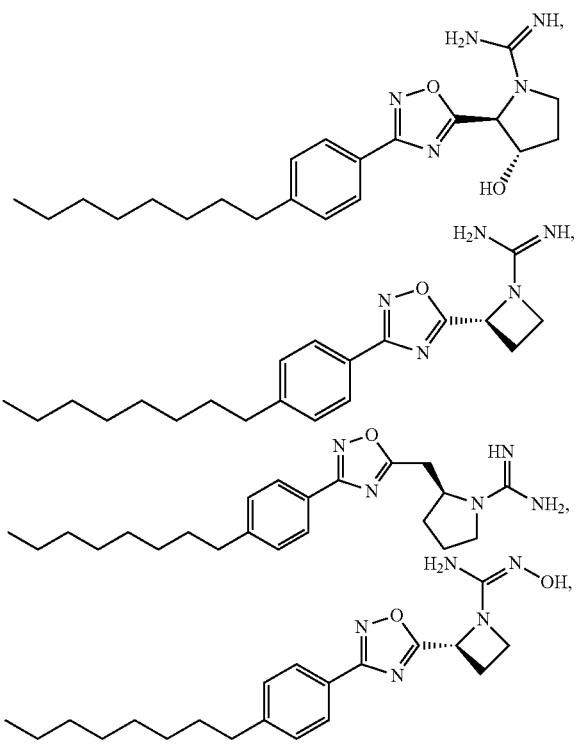

and pharmaceutically acceptable salts thereof.

3. A pharmaceutical composition comprising the compound of claim 1 or 2, and a pharmaceutically acceptable carrier.

4. A method for the treatment of a pathological condition or symptom in a mammal, wherein inhibition of the SphK1 enzyme or SphK2 enzyme, or both SphK1 and SphK2 enzymes is implicated and such inhibition is desired, comprising administering to said mammal an effective amount of the compound of claim 1 or 2.

5. The method of claim 4, wherein the pathological condition comprises age-related macular degeneration or diabetic retinopathy;
a hyperproliferative disorder;
cancer;
a hypertensive disease or disorder;
or an inflammatory disease or disorder, or fibrosis.

6. The method of claim 5, wherein the inflammatory disease or disorder is an inflammatory kidney disease selected from the group consisting of glomerulonephritis, glomerular injury, nephrotic syndrome, interstitial nephritis, lupus nephritis, Goodpasture's disease, Wegener's granulomatosis, renal vasculitis, IgA nephropathy, diabetic nephropathy, chronic allograft nephropathy and idiopathic glomerular disease.

* * * * *